US011926656B2

United States Patent
(12) United States Patent
Bu et al.

(10) Patent No.: US 11,926,656 B2
(45) Date of Patent: Mar. 12, 2024

(54) ANTIBODIES AND METHODS FOR THE DIAGNOSIS AND TREATMENT OF EPSTEIN BARR VIRUS INFECTION

(71) Applicants: The U.S.A., as represented by the Secretary, Department of Health and Human Services, Bethesda, MD (US); The Henry M. Jackson Foundation for the Advancement of Military Medicine, Inc., Bethesda, MD (US)

(72) Inventors: Wei Bu, Potomac, MD (US); Masaru Kanekiyo, Chevy Chase, MD (US); Michael Gordon Joyce, Washington, DC (US); Jeffrey I. Cohen, Silver Spring, MD (US)

(73) Assignees: The United States of America, as represented by the Secretary, Department of Health and Human Services, Bethesda, MD (US); The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 9 days.

(21) Appl. No.: 17/553,139

(22) Filed: Dec. 16, 2021

(65) Prior Publication Data

US 2022/0098284 A1 Mar. 31, 2022

Related U.S. Application Data

(62) Division of application No. 16/608,386, filed as application No. PCT/US2018/029463 on Apr. 25, 2018, now Pat. No. 11,236,151.

(60) Provisional application No. 62/490,023, filed on Apr. 25, 2017.

(51) Int. Cl.
*C07K 16/08* (2006.01)
*A61K 38/00* (2006.01)
*C07K 14/05* (2006.01)

(52) U.S. Cl.
CPC ............ *C07K 16/085* (2013.01); *C07K 14/05* (2013.01); *A61K 38/00* (2013.01); *C07K 2317/10* (2013.01); *C07K 2317/21* (2013.01); *C07K 2317/565* (2013.01)

(58) Field of Classification Search
CPC .................. C07K 16/085; C07K 14/05; C07K 2317/10; C07K 2317/21; C07K 2317/565; A61K 38/00
See application file for complete search history.

(56) References Cited

U.S. PATENT DOCUMENTS

2012/0108492 A1* 5/2012 Holers .................... A61P 31/22 530/300
2020/0190168 A1 6/2020 Bu et al.

OTHER PUBLICATIONS

Szakonyi G, Klein MG, Hannan JP, Young KA, Ma RZ, Asokan R, Holers VM, Chen XS. Structure of the Epstein-Barr virus major envelope glycoprotein. Nat Struct Mol Biol. Nov. 2006; 13(11):996-1001. Epub Oct. 29, 2006. (Year: 2006).*
Young KA, Herbert AP, Barlow PN, Holers VM, Hannan JP. Molecular basis of the interaction between complement receptor type 2 (CR2/CD21) and Epstein-Barr virus glycoprotein gp350. J Virol. Nov. 2008;82(22):11217-27. Epub Sep. 10, 2008. (Year: 2008).*
Tanner J, Whang Y, Sample J, Sears A, Kieff E. Soluble gp350/220 and deletion mutant glycoproteins block Epstein-Barr virus adsorption to lymphocytes. J Virol. Dec. 1988;62(12):4452-64. (Year: 1988).*
Bowie et al., "Deciphering the Message in Protein Sequences: Tolerance to Amino Acid Substitutions," *Science*, vol. 247:1306-1310, 2013.
Chen et al., "Human Monoclonal Antibodies Targeting the Haemagglutinin Glycoprotein can Neutralize H7N9 Influenza Virus," *Nat. Commun.*, vol. 6:6714, 2015.
Coghill et al., "High Levels of Antibody that Neutralize B-cell Infection of Epstein-Barr Virus that Bind EBV gp350 are Associated with a Lower Risk of Nasopharyngeal Carcinoma," *Clin. Cancer Res.*, vol. 22:3451-3457, 2016.
Collis et al., "Analysis of the Antigen Combining Site: Correlations Between Length and Sequence Composition of the Hypervariable Loops and the Nature of the Antigen," *J. Mol. Biol.*, vol. 325:337-354, 2003.
Dondelinger et al., "Understanding the Significance and Implications of Antibody Numbering and Antigen-Binding Surface/Residue Definition," *Front. Immunol.*, vol. 9:2278, (15 pages), 2018.
Herrman et al., "Epstein Barr Virus gp350 can Functionally Replace the Rhesus Lymphocryptovirus Major Membrane Glycoprotein and does not Restrict Infection of Rhesus Macaques," *J. Virol.*, vol. 90:1222-1230, 2016.
International Search Report and Written Opinion dated Jul. 25, 2018 for International Application No. PCT/US2018/029463.
International Preliminary Report on Patentability for International Application No. PCT/US2018/029463, dated Nov. 7, 2019, 13 pages.
Kanekiyo et al., "Rational Design of an Epstein-Barr Virus Vaccine Targeting the Receptor-Binding Site," *Cell*, vol. 162:1090-1100, 2015.

(Continued)

*Primary Examiner* — Rachel B Gill
(74) *Attorney, Agent, or Firm* — Klarquist Sparkman, LLP

(57) ABSTRACT

Antibodies and compositions of matter useful for the detection, diagnosis and treatment of Epstein Barr Virus (EBV) infection in mammals, and methods of using those compositions of matter for the detection, diagnosis and treatment of EBV infection are described. Also described are proteins, referred to as anti-gp350 antibody probes, and anti-gp350 B-cell probes, that maintain the epitope structure of the CR2-binding region of gp350, but do not bind CR2.

20 Claims, 23 Drawing Sheets

Specification includes a Sequence Listing.

(56) References Cited

OTHER PUBLICATIONS

Kussie et al., "A Single Engineered Amino Acid Substitution Changes Antibody Fine Specificity," *J. Immunol.*, vol. 152:146-152, 1994.

Ogembo et al., "A Chimeric EBV gp350/220-based VLP Replicates the Virion B-cell Attachment Mechanism and Elicits Long-Lasting Neutralizing Antibodies in Mice," *J. Transl. Med.*, vol. 13:50, (14 pages), 2015.

Sela-Culang et al., "The Structural Basis of Antibody-Antigen Recognition," *Front. Immunol.*, vol. 4:302, (13 pages), 2013.

Servat et al., "Identification of the Critical Attribute(s) of EBV gp350 Antigen Required for Elicitation of a Neutralizing Antibody Response in vivo," *Vaccine*, vol. 33:6771-6777, 2015.

Sirin et al., "AB-Bind: Antibody Binding Mutational Database for Computational Affinity Predictions," *Protein Sci.*, vol. 25:393-409, 2016.

Sitompuli et al., "Epitope Mapping of gp350/220 Conserved Domain of Epstein Barr Virus to Develop Nasopharyngeal Carcinoma (npc) Vaccine," *Bioinformation*, vol. 8:479-482, 2012.

Tanner et al., "Peptides Designed to Spatially Depict the Epstein-Barr Virus Major Virion Glycoprotein gp350 Neutralization of Epitope Elicit Antibodies that Block Virus-Neutralizing Antibody 72A1 Interaction with the Native gp350 Molecule," *J. Virol.*, vol. 89:4932-4941, 2015.

Tanner et al., "Construction and Characterization of a Humanized Anti-Epstein-Barr Virus gp350 Antibody with Neutralizing Activity in Cell Culture," *Cancers*, vol. 10:112, (18 pages), 2018.

Tsuchiya et al., "The Diversity of H3 Loops Determines the Antigen-Binding Tendencies of Antibody CDR Loops," *Protein Sci.*, vol. 25:815-825, 2016.

Weiss et al., "High Epstein-Barr Virus Load and Genomic Diversity are Associated with Generation of gp350-Specific Neutralizing Antibodies following Acute Infectious Mononucleosis," *J. Virol.*, vol. 91:e01562-16, 2016.

Winkler et al., "Changing the Antigen Binding Specificity by Single Point Mutations of an Anti-p24 (HIV-1) Antibody," *J. Immunol.*, vol. 165:4505-4514, 2000.

Zhao et al., "Immunization with Fc-Based Recombinant Epstein-Barr Virus gp350 Elicits Potent Neutralizing Humoral Immune Response in a BALB/c Mice Model," *Front. Immunol.*, vol. 9:932, 15 pages, 2018.

* cited by examiner

ANTIBODIES AND METHODS FOR THE DIAGNOSIS AND TREATMENT OF EPSTEIN BARR VIRUS INFECTION

CROSS-REFERENCE TO RELATED APPLICATIONS

This is a divisional application of U.S. application Ser. No. 16/608,386, filed Oct. 25, 2019, which is a national stage application under 35 U.S.C. § 371 and claims the benefit of PCT Application No. PCT/US2018/029463 having an international filing date of Apr. 25, 2018, which designated the United States, which PCT application claims the benefit of priority under 35 U.S.C. § 119(e) to U.S. Provisional Patent Application No. 62/490,023, filed Apr. 25, 2017. The entire disclosures of the above-listed applications are incorporated herein by reference.

REFERENCE TO SEQUENCE LISTING

This application contains a Sequence Listing submitted as an ASCII text file, created on Nov. 12, 2021, 279 KB. The information contained in this electronic file is hereby incorporated by reference in its entirety pursuant to 37 CFR § 1.52(e)(5).

FIELD OF THE INVENTION

The present invention is directed to compositions of matter useful for the diagnosis and treatment of Epstein Barr Virus infections in mammals and to methods of using those compositions of matter for the same.

BACKGROUND

Epstein-Barr-Virus (EBV) is a human herpes virus that infects over 90% of the population world-wide with a life-long persistence in its host. In most cases, primary infection occurs during early childhood and is usually asymptomatic. In contrast, if infection is retarded and happens during adolescence or adulthood, it is regularly symptomatic, causing a benign, normally self-limiting, lymphoproliferative syndrome termed infectious mononucleosis (IM) in up to 50% of cases. Although the disease is normally self-limiting, prolonged forms of chronic active EBV infection (CAEBV) with fatal outcome have been reported. EBV infection also significantly increases the risk of developing Hodgkin disease and other types of lymphoma later in life. EBV infection is also an independent risk factor for multiple sclerosis later in life. In addition, EBV is causally associated with a heterogeneous group of malignant diseases like nasopharyngeal carcinoma, gastric carcinoma, and various types of lymphoma, and the WHO classifies EBV as a class I carcinogen.

Besides the above described medical conditions caused by EBV, patients with primary or secondary immune defects, like transplant recipients, are at elevated risk for EBV-associated diseases because of the detrimental effect of immunosuppressive agents on the immune-control of EBV-infected B-cells. EBV-associated post-transplant lymphoproliferative disorder (PTLD) is an important form of post-transplant complications, occurring in up to 20% of organ recipients. Importantly, immunocompromised transplant recipients who are immunologically naive for EBV at the onset of immunosuppression are at a particular high risk of developing life-threatening EBV positive PTLD due to a primary EBV infection, e.g. often caused after transplantation via transmission of the virus through a donor organ due to the high prevalence of EBV. Due to impaired T-cell immunity that results from exposure to immunosuppressive drugs, these patients are unable to effectively prime EBV-specific T-cells that play a critical role in controlling proliferation of EBV-infected B-cells. In contrast, patients who are EBV-seropositive at transplant have a much lower risk for developing PTLD, demonstrating the essential role of EBV-specific T-cells in eliminating virally infected cells. In general, patients who are EBV-seronegative before transplantation are at a much higher risk to develop EBV-associated diseases, since transmission of donor EBV in transplanted organs or natural infection with the virus causes lymphoproliferative disease in EBV-seronegative recipients after transplantation. As with many virus-associated diseases a promising approach for diagnosing and/or treating virus infection and its consequences in the host is the use of antibodies that specifically recognize the virus. This is also true in the case of reducing the high risk of PTLD in seronegative patients by identifying them and treating them prior to the transplantation.

These EBV-associated diseases highlight the need for a better understanding of herpes viruses and their role in mammalian diseases. As part of this understanding, there is a great need for additional diagnostic and therapeutic agents capable of detecting the presence of EBV in a mammal and effectively inhibiting EBV infection and replication. Accordingly, it is an objective of the present invention to specifically identify EBV-associated polypeptides and to use that identification specificity to produce compositions of matter useful in the therapeutic treatment and diagnostic detection of EBV in mammals.

SUMMARY

The invention is in part based on a variety of antibodies to Epstein Barr virus (EBV) glycoprotein 350 (gp350 protein; viral envelope glycoprotein that initiates EBV infection by binding to the B cell surface receptor, CR2) and their use in the detection and diagnosis during active EBV infection. The inventors isolated monoclonal antibodies (mAbs) from macaque monkeys immunized with a gp350 nanoparticle vaccine. Characterization using multiple methods with active virus and gp350 revealed the mAbs of this disclosure (including those monoclonal antibodies produced by the B03, E04, D09, C02, H02, B04, B05, D06, D07, A03, and G12 clones) were EBV-specific, and have as much as 100-fold greater EBV neutralizing activity than 72A1, a murine antibody that targets the putative CR2-binding site on gp350 and is the most potent EBV-neutralizing antibody reported to date. Thus, the mAbs of this disclosure can recognize both cell-associated and secreted forms of native gp350 from infected cell culture and are therefore high value mAbs with potential uses in immunoassay development and as immunodiagnostic reagents for clinical sample and tissue confirmation of EBV, and treatment or prevention of EBV-associated diseases and disorders.

This disclosure provides an antibody which binds, preferably specifically, to an EBV gp350 protein. Optionally, the antibody is a monoclonal antibody, antibody fragment, chimeric antibody, humanized antibody, single-chain antibody or antibody that competitively inhibits the binding of an anti-EBV gp350 protein antibody to its respective antigenic epitope. The antibodies of this disclosure may optionally be produced in CHO cells or bacterial cells and preferably inhibit the growth or proliferation of or induce the death of a cell to which they bind. For diagnostic purposes, the antibodies of this disclosure may be detectably labeled, attached to a solid support, or the like, such as a lateral flow assay device which provides for point-of-care detection and/or diagnosis of EBV infection.

This disclosure also provides vectors comprising DNA encoding any of the herein described antibodies. Host cells comprising any such vector are also provided. By way of example, the host cells may be CHO cells, *E. coli* cells, or yeast cells. A process for producing any of the herein described antibodies is further provided and comprises culturing host cells under conditions suitable for expression of the desired antibody and recovering the desired antibody from the cell culture.

The disclosure also provides a composition of matter comprising an anti-EBV gp350 antibody as described herein, in combination with a carrier. Optionally, the carrier is a pharmaceutically acceptable carrier.

This disclosure also provides an article of manufacture comprising a container and a composition of matter contained within the container, wherein the composition of matter may comprise an anti-EBV gp350 antibody as described herein. The article may optionally comprise a label affixed to the container, or a package insert included with the container, that refers to the use of the composition of matter for the therapeutic treatment or diagnostic detection of an EBV infection.

This disclosure also provides the use of an anti-EBV gp350 polypeptide antibody as described herein, for the preparation of a medicament useful in the treatment of a condition which is responsive to the anti-EBV gp350 protein antibody.

This disclosure also provides any isolated antibody comprising one or more of the complementary determining regions (CDRs), including a CDR-L1, CDR-L2, CDR-L3, CDR-H1, CDR-H2, or CDR-H3 sequence disclosed herein, or any antibody that binds to the same epitope as such antibody.

This disclosure also provides a method for inhibiting the growth of a cell that expresses an EBV gp350 protein, including contacting the cell with an antibody that binds to the EBV gp350 protein, wherein the binding of the antibody to the EBV gp350 protein causes inhibition of the growth of the cell expressing the EBV gp350 protein. In these methods, the cell may be one or more of a B-lymphocyte and an epithelial cell. Binding of the antibody to the EBV gp350 protein causes death of the cell expressing the EBV gp350 protein. Optionally, the antibody is a monoclonal antibody, antibody fragment, chimeric antibody, humanized antibody, or single-chain antibody. Antibodies employed in the methods of this disclosure may optionally be conjugated to a growth inhibitory agent or cytotoxic agent such as a toxin. The antibodies employed in the methods of this disclosure may optionally be produced in CHO cells or bacterial cells.

This disclosure also provides a method of therapeutically treating a mammal having an EBV infection by administering to the mammal a therapeutically effective amount of an antibody that binds to the EBV gp350 protein, thereby resulting in the effective therapeutic treatment of the infection in the mammal. In these therapeutic methods, the antibody may be a monoclonal antibody, antibody fragment, chimeric antibody, humanized antibody, or single-chain antibody. Antibodies employed in these methods may optionally be conjugated to a growth inhibitory agent or cytotoxic agent such as a toxin. The antibodies employed in these methods of this disclosure may optionally be produced in CHO cells or bacterial cells.

This disclosure also provides is a method of determining the presence of an EBV gp350 protein in a sample suspected of containing the EBV gp350 protein, by exposing the sample to an antibody that binds to the EBV gp350 protein and determining binding of the antibody to the EBV gp350 protein in the sample, wherein the presence of such binding is indicative of the presence of the EBV gp350 protein in the sample. Optionally, the sample may contain cells (which may be fibroblasts, keratinocytes, or dendritic cells) suspected of expressing the EBV gp350 protein. The antibody employed in these methods may optionally be detectably labeled, attached to a solid support, or the like.

This disclosure also provides methods of diagnosing the presence of an EBV infection in a mammal, by detecting the level of an EBV gp350 protein in a test sample of tissue cells obtained from the mammal, wherein detection of the EBV gp350 protein in the test sample is indicative of the presence of EBV infection in the mammal from which the test sample was obtained.

This disclosure also provides methods of diagnosing the presence of an EBV infection in a mammal, by contacting a test sample comprising tissue cells obtained from the mammal with an antibody that binds to an EBV gp350 protein and detecting the formation of a complex between the antibody and the EBV gp350 protein in the test sample, wherein the formation of a complex is indicative of the presence of an EBV infection in the mammal Optionally, the antibody employed is detectably labeled, attached to a solid support, or the like. In these methods, the test sample of tissue cells may be obtained from an individual suspected of having a viral infection.

This disclosure also provides a method of treating or preventing an EBV infection-related disorder by administering to a subject in need of such treatment an effective amount of an antagonist of an EBV gp350 protein. The EBV infection-related disorder may be infectious mononucleosis (glandular fever), particular forms of cancer, such as Hodgkin's lymphoma, Burkitt's lymphoma, gastric cancer, nasopharyngeal carcinoma, and conditions associated with human immunodeficiency virus (HIV), such as hairy leukoplakia and central nervous system lymphomas, autoimmune diseases, including dermatomyositis, systemic lupus erythematosus, rheumatoid arthritis, Sjögren's syndrome, and multiple sclerosis, and post-transplant lymphoproliferative disorder (PTLD). In these methods, the antagonist of the EBV gp350 protein is an anti-EBV gp350 protein antibody of this disclosure. Effective treatment or prevention of the disorder may be a result of direct killing or growth inhibition of cells that express an EBV gp350 protein or by antagonizing the production of EBV gp350 protein.

This disclosure also provides methods of binding an antibody to a cell that expresses an EBV gp350 protein, by contacting a cell that expresses an EBV gp350 protein with the antibody of this disclosure under conditions which are suitable for binding of the antibody to the EBV gp350 protein and allowing binding therebetween. The antibody may be labeled with a molecule or compound that is useful for qualitatively and/or quantitatively determining the location and/or amount of binding of the antibody to the cell.

This disclosure also provides for the use of an EBV gp350 protein, a nucleic acid encoding an EBV gp350 protein, or a vector or host cell comprising that nucleic acid, or an anti-EBV gp350 protein antibody in the preparation of a medicament useful for (i) the therapeutic treatment or diagnostic detection of an EBV infection, or (ii) the therapeutic treatment or prevention of an EBV infection-related disorder.

This disclosure also provides a method for inhibiting the production of additional viral particles in an EBV-infected mammal or cell, wherein the growth of the EBV infected cell is at least in part dependent upon the expression of an EBV gp350 protein (wherein the EBV gp350 protein may be expressed either within the infected cell itself or a cell that produces polypeptide(s) that have a growth potentiating effect on the infected cells), by contacting the EBV gp350 protein with an antibody that binds to the EBV gp350 protein, thereby antagonizing the growth-potentiating activity of the EBV gp350 protein and, in turn, inhibiting the growth of the infected cell. Preferably the growth of the infected cell is completely inhibited. More preferably, binding of the antibody to the EBV gp350 protein induces the death of the infected cell. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

This disclosure also provides methods of treating a viral infection in a mammal, wherein the infection is at least in part dependent upon the expression of an EBV gp350 protein, by administering to the mammal a therapeutically effective amount of an antibody that binds to the EBV gp350 protein, thereby antagonizing the activity of the EBV gp350 protein and resulting in the effective therapeutic treatment of the infection in the mammal Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

This disclosure also provides a protein useful for identifying an anti-gp350 antibody, or an anti-gp350 B-cell. Such a protein comprises: a) a polypeptide sequence at least 80%, at least 85%, at least 90%, at least 95%, at least 97% or at least 99% identical to the amino acid sequence of the CR2-binding region of EBV gp350; or b) a polypeptide sequence at comprising at least 100, at least 150, at least 200, at least 250, at last 300, at least 350, at least 400, or at least 425 contiguous amino acids from the amino acid sequence of the CR2-binding region of EBV gp350; wherein the protein can bind an anti-gp350 antibody, or a B-cell expressing an anti-the gp350 B-cell receptor (BCR), wherein binding of the B-cell is through the BCR, and wherein the protein is unable to bind CR2. In certain aspects, at least one amino acid residue corresponding to amino acid Q122, P158, 1160, K161, W162, D163, N164, or D296, of SEQ ID NO:124 has been deleted, or has been substituted with one or more amino acid residues. In certain aspects, the amino acid sequence of the CR2-binding region comprises SEQ ID NO:125.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid Q122 of SEQ ID NO:124 has been deleted, or has been substituted with one or more amino acid residues. In certain aspects, the one or more amino acid residue is selected from the group consisting of methionine, leucine, isoleucine, glycine, alanine, valine, phenylalanine, tyrosine, tryptophan, lysine, arginine, histidine, glutamate, and aspartate. In certain aspects, the amino acid corresponding to amino acid Q122 of SEQ ID NO:124 has been substituted with asparagine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid P158 of SEQ ID NO:124 has been deleted, or has been substituted with one or more amino acid residues. In certain aspects, the one or more amino acid residues is selected from the group consisting of methionine, leucine, isoleucine, glycine, alanine, valine, phenylalanine, tyrosine, tryptophan, lysine, arginine, histidine, glutamate, and aspartate. In certain aspects, the amino acid corresponding to amino acid P158 of SEQ ID NO:124 has been substituted with arginine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid I160 of SEQ ID NO:124 has been deleted, or has been substituted with one or more amino acid residues. In certain aspects, the one or more amino acid residue is selected from the group consisting of serine, threonine, cysteine, proline, asparagine, glutamine, tyrosine, phenylalanine, tryptophan, glutamate, aspartate, arginine, glutamine, histidine and lysine. In certain aspects, the amino acid corresponding to amino acid I160 of SEQ ID NO:124 has been substituted with arginine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid W162 of SEQ ID NO:124 has been deleted, or has been substituted with one or more amino acid residues. In certain aspects, the one or more amino acid residue is selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine. In certain aspects, the amino acid corresponding to amino acid W162 of SEQ ID NO:124 has been substituted with alanine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D163 of SEQ ID NO:124 has been deleted, or has been substituted with one or more amino acid residues. In certain aspects, the one or more amino acid residue is selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine. In certain aspects, the amino acid corresponding to amino acid D163 of SEQ ID NO:124 has been substituted with asparagine. In certain aspects, at least one amino acid has been inserted between the amino acid corresponding to amino acid N164 of SEQ ID NO:124 and the amino acid corresponding to C165 of SEQ ID NO:124. In certain aspects, the at least one amino acid is selected from the group consisting of serine, threonine, cysteine, proline, asparagine, and glutamine. In certain aspects, a serine residue has been inserted between the amino acid corresponding to amino acid N164 of SEQ ID NO:124 and the amino acid corresponding to C165 of SEQ ID NO:124.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid N164 of SEQ ID NO:124 has been deleted, or has been substituted with one or more amino acid residues. In certain aspects, the one or more amino acid residue is selected from the group consisting of methionine, leucine, isoleucine, glycine, alanine, valine, phenylalanine, tyrosine, tryptophan, lysine, arginine, histidine, glutamate, serine, and aspartate. In certain aspects, the amino acid corresponding to amino acid N164 of SEQ ID NO:124 has been substituted with serine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has been deleted, or has been substituted with one or more amino acid residues. In certain aspects, the one or more amino acid residue is selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine. In certain aspects, the amino acid corresponding to amino acid D296 of SEQ ID NO:124 has been substituted with arginine. In certain aspects, the amino acid corresponding to amino acid I160 of SEQ ID NO:124 has been deleted, or has been substituted with at least one amino acid residue. In certain aspects, the at least one amino acid residue is selected from the group consisting of serine, threonine, cysteine, proline, asparagine, glutamine, tyrosine, phenylalanine, tryptophan, glutamate, aspartate, arginine, glutamine, histidine and lysine. In certain aspects, the amino acid corresponding to amino acid I160 of SEQ ID NO:124 has been substituted with arginine. In further aspects, the amino acid corresponding to amino acid P158 of SEQ ID NO:124 has been deleted, or has been substituted with at least one amino acid residue. In certain aspects, the at least one amino acid residue is selected from the group consisting of methionine, leucine, isoleucine, glycine, alanine, valine, phenylalanine, tyrosine, tryptophan, lysine, arginine, histidine, glutamate, and aspartate. In certain aspects, the amino acid corresponding to amino acid P158 of SEQ ID NO:124 has been substituted with arginine or asparagine. In certain aspects, the amino acid corresponding to amino acid I160 of SEQ ID NO:124, has been substituted with a threonine or an arginine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein one or more amino acids has been inserted between the amino acid corresponding to amino acid N164 of SEQ ID NO:124 and the amino acid corresponding to C165 of SEQ ID NO:124. Inc certain aspects, the one or more amino acids are selected from the group consisting of serine, threonine, cysteine, proline, asparagine, and glutamine In certain aspects, a serine residue has been inserted between the amino acid corresponding to amino acid N164 of SEQ ID NO:124 and the amino acid corresponding to C165 of SEQ ID NO:124.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acids corresponding to amino acids W162-N164 of SEQ ID NO:124 have been deleted, or have been substituted with one or more amino acid residues. In certain aspects, the one or more amino acid residue, is selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine. In certain aspects, the amino acids corresponding to amino acids W162-N164 of SEQ ID NO:124 have each been substituted with an alanine residue.

This disclosure also provides a protein having an amino acid sequence at least 85%, at least 90%, at least 95%, at least 97% or at least 999% identical to an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO:157, and SEQ ID NO:159. In certain aspects, the protein comprises an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO:157, and SEQ ID NO:159.

This disclosure also provides a nucleic acid molecule encoding a protein having an amino acid sequence at least 85%, at least 90%, at least 95%, at least 97% or at least 999% identical to an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO:157, and SEQ ID NO:159. In certain aspects, the nucleic acid molecule encodes a protein comprises an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO:157, and SEQ ID NO:159. In certain aspects, the nucleic acid molecule comprises a sequence selected from the group consisting of SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:146, SEQ ID NO:148, SEQ ID NO:150, SEQ ID NO:152, SEQ ID NO:154, SEQ ID NO:156, SEQ ID NO:158, and SEQ ID NO:160.

This disclosure also provides a method of identifying an anti-gp350 antibody, comprising contacting a protein of the invention with a solution comprising antibodies, and isolating antibodies that specifically bind to the protein. In certain aspects, the protein comprises a His-tag, an epitope tag, or a detectable label.

This disclosure also provides a method of identifying an anti-gp350 B-cell, comprising contacting a protein of the invention with a solution comprising B-cells, and isolating B-cells that specifically bind to the protein. In certain aspects, the protein comprises a His-tag, an epitope tag, or a detectable label.

Further embodiments will be evident to the skilled artisan upon a reading of the present specification.

This disclosure contains the following Sequences:

| SEQ ID NO | Description | Sequence |
|---|---|---|
| 1 | B03 clone Heavy Chain aa sequence | QVQLQESGPGLVKPAETLSLTCTVSGGSFSSYWWG<br>WIRQSPGKGLEWIGHISSGGNNYLNPSLKSRVTLSLD<br>TSKNQFSLKLNSVTAADSAVYYCARAPRIVVRGRYF<br>DQWGQGVLVTVSS |
| 2 | B03 clone Heavy Chain nucleotide sequence | caggtgcagctgcaggagtcgggcccaggactggtgaagcctgcggagaccct<br>gtccctcacctgcactgtctctggtggctctttcagcagttactggtggggctggatc<br>cgtcagtccccagggaagggactggagtggattgggcatatcagtagtggtggaa<br>acaactaccttaatccgtccctcaagagtcgagtcaccctgtcactagacacgtcca<br>agaaccagttctccctgaagctgaactctgtgaccgccgcggactcggccgtgtat<br>tactgtgccagagcccccgtattgttgttagaggccgatactttgaccaatggggc<br>cagggagtcctggtcaccgtctcctca |
| 3 | B03 clone Heavy Chain CDR1 | GGSFSSYW |
| 4 | B03 clone Heavy Chain CDR2 | ISSGGNN |
| 5 | B03 clone Heavy Chain CDR3 | APAPRIVVRGRYFDQW |
| 6 | B03 clone Kappa Chain aa sequence | DIQMTQSPSSLSASVGDTVTITCRASQGINIYLNWFQ<br>QRPGKAPKLLIYAATTLQSGVPSRFSGSGSGTDFTLTI<br>SSLQPEDFATYYCLQCESYPLTFGGGTKVEIK |
| 7 | B03 clone Kappa Chain nucleotide sequence | gacatccagatgacccagtctccatcctccctgtctgcatctgtaggagacactgtc<br>accatcacttgccgggcaagtcagggtatcaatatctacctgaattggtttcagcag<br>agaccagggaaagcccctaaactcctgatctatgctgcgaccactttacaaagtgg<br>ggtcccatcaagattcagcggcagtggatctgggacagatttcactctcaccatcag<br>cagcctgcagcctgaagatttcgcaacttattactgtctacagtgtgaaagttatccg<br>ctcactttcggcggagggaccaaggtggagatcaaa |
| 8 | B03 clone Kappa Chain CDR1 | QGINIY |
| 9 | B03 clone Kappa Chain CDR2 | AAT |
| 10 | B03 clone Kappa Chain CDR3 | LQCESYPLT |
| 11 | E04 clone Heavy Chain aa sequence | QVQLQESGPGLVKPSETLSLTCTVSGGSISGAYYYW<br>SWIRQPPGKGLDWIGYIYGSFGSAYYNPSLKSRATIS<br>KDTPKNQFSLKLSSVTAADTAVYYCARGRRLGYSN<br>WFDVWGPGVLVTVSS |
| 12 | E04 clone Heavy Chain nucleotide sequence | caggtgcaactgcaggagtcgggcccaggactggtgaagccttcggagaccctg<br>tccctcacctgcactgtctctggtggctccatcagcggtGCTTACtactactgg<br>agctggattcgacagcccccggggaagggactggactggattggatatatctatg<br>gaagttttgggagtgcctactacaacccctccctcaagagtcgagccaccatttcaa<br>aagacacgcccaagaaccagttctccctgaaactgagctctgtgaccgccgcgga<br>cacggccgtgtattactgtgcgagaggaaggcgactaggctattcgaactggttcg<br>atgtctggggcccgggagtcctggtcaccgtctcctca |
| 13 | E04 clone Heavy Chain CDR1 | GGSISGAYYY |
| 14 | E04 clone Heavy Chain CDR2 | IYGSFGSA |
| 15 | E04 clone Heavy Chain CDR3 | ARGRRLGYSNWFDVW |
| 16 | E04 clone Kappa Chain aa sequence | DIQMTQSPSSLSASVGDKVTITCRTSQDVSSYLAWY<br>QQKPGKAPQLLIYAASSLQSGVPSRFTGSGSGAEFTL<br>TISSLQPEDFASYYCQQYKNLPLTFGGGTKVEIK |
| 17 | E04 clone Kappa Chain nucleotide sequence | gacatccagatgacccagtctccatcttccctgtctgcatctgtaggagacaaagtc<br>accatcacttgtcggacaagtcaggacgttagcagttatttagcctggtatcagcag<br>aaaccagggaaagcccctcagctcctgatctatgctgcatccagtttgcaaagtgg<br>ggtcccatcaaggttcaccggcagtggatctggggcagaattcactctcaccatca<br>gcagccttcagcctgaagattttgcatcatattactgtcaacagtataaaaatctcccg<br>ctcactttcggcggagggaccaaagtggagatcaaa |
| 18 | E04 clone Kappa Chain CDR1 | QDVSSY |
| 19 | E04 clone Kappa Chain CDR2 | AAS |

-continued

| SEQ ID NO | Description | Sequence |
|---|---|---|
| 20 | E04 clone Kappa Chain CDR3 | QQYKNLPLT |
| 21 | D09 clone Heavy Chain aa sequence | QVQLQESGPGLVKPSETLSLTCDVSGGSFSGDFYWS WIRQPPGKGLDWIGNIHGSSAGTKYKPSLKSRVTISK DTSKNQFSLKLSSVTAADTAVYYCTRGPLSRIVAGF GRGINWFDVWGPGVLVTVSS |
| 22 | D09 clone Heavy Chain nucleotide sequence | caggtgcagctgcaggagtcgggcccaggactggtgaagccttcggagaccctg tccctcacctgcgatgtctctggtggctccttcagcggtgatTTCtactggagctg gatccgccagcccccagggaagggactggactggattgggaatatccatggcag cagtgcgggcaccaaatacaagccctccctcaagagtcgagtcaccatttcaaaa gacacgtccaagaaccagttctccctgaaactgagctctgtgaccgccgcggaca cggccgtctattactgtacgagaggccccccttagtaggatagtagctggttttggga gggggattaactggttcgatgtctggggcccgggagtcctggtcaccgtctcctca |
| 23 | D09 clone Heavy Chain CDR1 | GGSFSGDFY |
| 24 | D09 clone Heavy Chain CDR2 | IHGSSAGT |
| 25 | D09 clone Heavy Chain CDR3 | TRGPLSRIVAGFGRGINWFDVW |
| 26 | D09 clone Lambda Chain aa sequence | QPVLTQPTSLSASPGASVRLSCTLSSGINVGSYSIFWY QQKPGSPPRYLLFYFSDSSKHQGSGVPSRFSGSKDTS ANAGLLLISGLQSEDEADYYCAIWHSSASVLFGGGT RLTVL |
| 27 | D09 clone Lambda Chain nucleotide sequence | cagcctgtgctgacccagccaacctccctctcagcatctccgggagcatcagtcag actcagctgcaccttgagcagtggcatcaatgttggtagttacagcatattctggtac cagcagaagccagggagtcctccccggtaccttctgttctatttctcagactcaagta agcaccagggctctggagtccccagccgtttctctggatccaaggatacttcagcc aatgcagggcttttactgatctctgggctccagtctgaagatgaggctgactattact gtgccatatggcacagcagcgcttctgtgttattcggaggagggacccggctgaca gtacta |
| 28 | D09 clone Lambda Chain CDR1 | TLSSGINVGSYSIF |
| 29 | D09 clone Lambda Chain CDR2 | YFSDSSK |
| 30 | D09 clone Lambda Chain CDR3 | AIWHSSASVL |
| 31 | C02 clone Heavy Chain aa sequence | QLQLQESGPGLVKPSETLSLTCAVSGGSISGYYWSWI RQPPGKGPEWIGFIDGNTVGTNYNPSLKSRVTLSKDT SKNQFSLKVSSVTAADTAVYYCARKPLRRYFWFDV WGPGVLVTVSS |
| 32 | C02 clone Heavy Chain nucleotide sequence | cagctgcagctgcaggagtcgggcccaggactggtgaagccttcggagaccctg tccctcacctgcgctgtctctggtggctccatcagcggttactactggagttggattc gccagcccccagggaagggaccggagtggattgggtttattgatggtaatactgtg ggcaccaactacaacccctccctcaagagtcgagtcaccattcaaaagacacgtc caagaatcagttctccctgaaggtgagttctgtgaccgccgcggacacggccgtgt attactgtgcgaggaagccgctacgccgttatttctggttcgatgtctggggcccgg gagtcctggtcaccgtctcctca |
| 33 | C02 clone Heavy Chain CDR1 | GGSISGYY |
| 34 | C02 clone Heavy Chain CDR2 | IDGNTVGT |
| 35 | C02 clone Heavy Chain CDR3 | ARKPLRRYFWFDVW |
| 36 | C02 clone Lambda Chain aa sequence | QSVLTQPPSVSGDPGQRVTISCTGSSSNIGAGYYVYW YQQFPGTAPKLLIYQDNKRPSGVSDRFSGSKSGTSAS LTITGLQPGDEADYYCSAWDSSLSAVMFGRGTRLTV L |
| 37 | C02 clone Lambda Chain nucleotide sequence | cagtctgtgctgacgcagccgccctcagtgtctggggaccccgggcagagggtc accatctcgtgcactgggagcagctccaacatcgggGCGggttattatgtatact ggtaccagcagttcccaggaacggcccccaaactcctcatctatcaagataataag cgaccctcaggggtttctgaccgattctctggctccaagtctggtacctcagcctcc ctgaccatcactgggctccagcctggggatgaggctgattattactgctcagcatgg gatagcagcctgagtgctgttatgttcggaagaggcaccaggctgacagtacta |
| 38 | C02 clone Lambda Chain CDR1 | SSNIGAGYY |

-continued

| SEQ ID NO | Description | Sequence |
|---|---|---|
| 39 | C02 clone Lambda Chain CDR2 | QDN |
| 40 | C02 clone Lambda Chain CDR3 | SAWDSSLSAVM |
| 41 | H02 clone Heavy Chain aa sequence | QLQLQESGPGVVKPSETLSLTCTISGGSFSTYYWTWI RQPPGKGLEWVGYIGNGGRSLNYNPSLKSRITLSVD ASKNQFSLKVTSVTAADTAVYYCGRARGLRGNWFD VWGPGVLVTVSS |
| 42 | H02 clone Heavy Chain nucleotide sequence | caactgcagttgcaggagtcgggcccaggagtggtgaagccttcggagaccctgt ccctcacctgcactatctctggtggctccttcagtacttactactggacctggattcgc cagcccccagggaagggactggagtgggttgggtatatcggtaatggtggtcgta gcctcaactacaacccctccctcaagagtcgcatcaccctgtcagtagacgcgtcc aagaaccagttctccctgaaggtgacctctgtgaccgccgcggacacggccgtct attactgtgggagagccaggggactccgcggaaactggttcgatgtctggggccc gggagtcctggtcaccgtctcctca |
| 43 | H02 clone Heavy Chain CDR1 | GGSFSTYY |
| 44 | H02 clone Heavy Chain CDR2 | IGNGGRSL |
| 45 | H02 clone Heavy Chain CDR3 | GRARGLRGNWFDVW |
| 46 | H02 clone Lambda Chain aa sequence | QAALTQPPSVSGSPGQSVTISCTGTSSDIGGYNYVSW YQQHPGKAPKVMIYEVSKRPSGVSDRFSGSKSGNIA SLTISGLQAEDEADYYCSSYAGSNTFLFGGGTRLTVL |
| 47 | H02 clone Lambda Chain nucleotide sequence | caggctgccctgactcagcctccctctgtgtctgggtctcctggacagtcggtcacc atctcctgcactggaaccagcagtgacatcggtggttataactatgtctcctggtacc aacaacacccaggcaaagcccccaaagtcatgatttatgaggtcagtaagcggcc ctcaggggtctctgatcgcttctctggttccaaatctggcaacatagcctccctgacc atctctgggctccaggctgaggacgaggctgattattactgcagctcatatgcaggc agcaacactttcttattcggaggagggacccggctgacagtacta |
| 48 | H02 clone Lambda Chain CDR1 | SSDIGGYNY |
| 49 | H02 clone Lambda Chain CDR2 | EVS |
| 50 | H02 clone Lambda Chain CDR3 | SSYAGSNTFL |
| 51 | A03 clone Heavy Chain aa sequence | QVQLQESGPGLVKPSETLSLTCAVSGGSISSNYWSWI RQPPGKGLEWIGRIYGSGGSTDYNPSLKSRVTISTDT SKNQFSLKVSSVTAADTAVYYCARVRIQWVQLRGW FDVWGPGVLVTVSS |
| 52 | A03 clone Heavy Chain nucleotide sequence | caggtgcagctgcaggagtcgggcccaggactggtgaagccttcggagaccctg tccctcacctgcgctgtctctggtggctccatcagcagtaactactggagctggatc cgccagcccccagggaagggactggagtggattggacgtatctatggtagtggtg ggagcaccgactacaacccctccctcaagagtcgagtcaccatttcaacagacac gtccaagaaccagttctccctgaaggtgagctctgtgaccgccgcggacacggcc gtgtattactgtgcgagagtgcggatacagtgggtacagttgcgaggctggttcgat gtctggggcccgggagtcctggtcaccgtctcctca |
| 53 | A03 clone Heavy Chain CDR1 | GGSISSNYWS |
| 54 | A03 clone Heavy Chain CDR2 | IYGSGGST |
| 55 | A03 clone Heavy Chain CDR3 | ARVRIQWVQLRGWFDVW |
| 56 | A03 clone Kappa Chain aa sequence | YIQMTQSPSSLSASVGDTVTFTGPASQSFSSSLAWYQ QKPGKAPNLLIYSASSLQCGVRSRFSGSKSGTDFTLTI SSLQPEDIASYYCQQYYSYPFTFGPGTKLDIK |
| 57 | A03 clone Kappa Chain nucleotide sequence | Tacatacagatgacgcagtctccatcctccctgtctgcatctgtaggagacacagtc accttcactggccccgcaagtcagagctttagtagtagtttagcctggtatcagcag aaaccagggaaagcccctaacctcctgatctatagtgcatccagtttgcaatgtggg gttcgttcgaggttcagtggcagtaagtctgggacagatttcactctcaccatcagca gcctgcagcctgaagatattgctagttattactgtcaacagtattacagttatccattca ctttcggccccgggaccaaactggatatcaaa |

-continued

| SEQ ID NO | Description | Sequence |
|---|---|---|
| 58 | A03 clone Kappa Chain CDR1 | QSFSSS |
| 59 | A03 clone Kappa Chain CDR2 | SAS |
| 60 | A03 clone Kappa Chain CDR3 | QQYYSYPFT |
| 61 | B04 clone Heavy Chain aa sequence | QVQLQESGPGLVRPSETLSLTCAVSGGSISSNYWSWI<br>RQPPGKGLEWIGYISGSTGSTYQNPSLKSRVTVSKDT<br>SKNQFSLKLNSVTAADTAVYYCARSGRRGSSLDLW<br>GRGVLVTVSS |
| 62 | B04 clone Heavy Chain nucleotide sequence | Caggtgcagctgcaggagtcgggcccaggactggtgaggccttcggagaccct<br>atccctcacctgcgctgtctctggtggctccatcagcagtaactactggagctggatt<br>cgccagcccccagggaaggggctggagtggattgggtatatctctggtagtactg<br>ggagcacctaccagaacccctccctcaagagtcgagtcaccgtttcaaaagacac<br>gtctaagaaccagttctccctgaagctgaattctgtgaccgccgcggacacggccg<br>tgtattactgtgcgagaagtgggagaagaggcagctcattggatttgtggggccgg<br>ggagttctggtcaccgtctcctca |
| 63 | B04 clone Heavy Chain CDR1 | GGSISSNY |
| 64 | B04 clone Heavy Chain CDR2 | ISGSTGST |
| 65 | B04 clone Heavy Chain CDR3 | ARSGRRGSSLDLW |
| 66 | B04 clone Lambda Chain aa sequence | QSVLTQPPSVSGDPGQRVTISCTGSSSNIGAGYYVYW<br>YQQFPGTAPKLLIYQDNKRPSGVSDRFSGSKSGTSAS<br>LTITGLQPGDEADYYCSAWDSSLSAVFFGGGTRLTV<br>L |
| 67 | B04 clone Lambda Chain nucleotide sequence | cagtctgtgctgacgcagccgccctcagtgtctggggaccccgggcagagggtc<br>accatctcgtgcactgggagcagctccaacatcgggGCGggttattatgtatact<br>ggtaccagcagttcccaggaacggcccccaaactcctcatctatcaagataataag<br>cgaccctcaggggtttctgaccgattctctggctccaagtctggtacctcagcctcc<br>ctgaccatcactgggctccagcctggggatgaggctgattattactgctcagcatgg<br>gatagcagcctgagtgctgtgttcttcggaggagggacccggctgacagtacta |
| 68 | B04 clone Lambda Chain CDR1 | SSNIGAGYY |
| 69 | B04 clone Lambda Chain CDR2 | QDN |
| 70 | B04 clone Lambda Chain CDR3 | SAWDSSLSAVF |
| 71 | B05 clone Heavy Chain aa sequence | QLQESGPGLVKPSETLSLTCTVSGGSISDTYRWSWIR<br>QSPGKGLEWIAYIYGTTTSTNYNPSLKSRLTISKDTS<br>KNQFSLNLRSVTAADTAVYYCARGDSGGRSAHVFH<br>FWGQGLRVTVSS |
| 72 | B05 clone Heavy Chain nucleotide sequence | cagctgcaggagtcgggcccaggactggtgaagccttcggagaccctgtccctca<br>cctgcactgtctctggtggctccatcagcgatacttacCGGtggagctggattcgc<br>cagtccccagggaagggactggagtggattgcctacatctatggtactactacgag<br>caccaactacaacccctccctcaagagtcgactcaccatttcaaaagacacgtcca<br>agaaccagttctccttgaacctgaggtctgtgaccgccgcggacacggccgtgtat<br>tactgtgcgagaggggatagcggtggccggtcagcgcatgtttttcatttctggggc<br>caagggctcagggtcaccgtctcttca |
| 73 | B05 clone Heavy Chain CDR1 | GGSISDTYR |
| 74 | B05 clone Heavy Chain CDR2 | IYGTTTST |
| 75 | B05 clone Heavy Chain CDR3 | ARGDSGGRSAHVFHFW |
| 76 | B05 clone Lambda Chain aa sequence | QSVLTQPPSVFGDPGQRITISCTGSSSNIGAGYYVYW<br>YQQFPGTAPKLLIYQDNKRPSGVSDRFSGSKSGSSAS<br>LTITGLQPGDEADYYCSAWDSSLSVRVFGGGTRLTV<br>L |
| 77 | B05 clone Lambda Chain nucleotide sequence | cagagtgttctgacgcagccgccctcagtgtttggggaccccgggcagaggatca<br>ccatctcgtgcactgggagcagctccaacatcgggGCGggttattatgtatactg<br>gtaccagcagttcccaggaacggcccccaaactcctcatctatcaagataataagc<br>gaccctcaggggtttctgaccgattttctggctccaagtctggttcctcagcctccct<br>gaccatcactgggctccagcctggggatgaggctgattattactgctcagcatggg<br>atagcagcctgagtgtacgggttttcggaggagggacccggctgacagtacta |

-continued

| SEQ ID NO | Description | Sequence |
|---|---|---|
| 78 | B05 clone Lambda Chain CDR1 | SSNIGAGYY |
| 79 | B05 clone Lambda Chain CDR2 | QDN |
| 80 | B05 clone Lambda Chain CDR3 | SAWDSSLSVRV |
| 81 | D06 clone Heavy Chain aa sequence | EVQLVESGGGLVQPGGSLRLSCAASGFTFSSYGMN WVRQAPGKGLEWVSFITNTGKTTYYADSVRGRFTIS RDNAKKSVSLQMSSLRAEDTAVYYCTRGRGRHGWS SGVFDFWGQGLRVTVS |
| 82 | D06 clone Heavy Chain nucleotide sequence | Gaggtgcaactggtggagtctggaggaggcttggtccagcctggagggtccctg agactctcctgtgcagcctctggattcaccttcagtagttacggcatgaactgggtcc gccaggctccgggaaaggggctggagtgggtctcattcattactaacactggtaaa accacatactacgctgactctgtgaggggccgattcaccatctccagagacaacgc caagaagtcggtgtctctacaaatgagtagcctgagagccgaggacacggccgtc tattactgtactaggggaagaggtagacacggctggtccagtggtgtttttgatttctg gggccaaggtctcagggtcaccgtctcttc |
| 83 | D06 clone Heavy Chain CDR1 | GFTFSSYG |
| 84 | D06 clone Heavy Chain CDR2 | ITNTGKTT |
| 85 | D06 clone Heavy Chain CDR3 | TGRGRHGWSSGVFDFW |
| 86 | D06 clone Lambda Chain aa sequence | QSVLTQPPSVFGDPGQRITISCTGSSSNIGAGYYVYW YQQFPGTAPKLLIYQDNKRPSGVSDRFSGSKFGSSAS LTITGVQRGDEGDYYCSAWDSSLSVRVLGGGTRLTV L |
| 87 | D06 clone Lambda Chain nucleotide sequence | cagtctgttctgacgcagccgccctcagtgttcggggaccccgggcagaggatca ccatttcgtgcactgggagcagctccaacatcgggGCGggttattatgtatactg gtaccagcagttcccaggaacggcccccaaactcctcatctatcaagataataagc gaccctcaggggtttctgaccgattctctggctccaagtttggttcctcagcctccct gaccatcactggggtccagcgtggggatgagggtgattattactgctcagcatggg atagcagcctgagtgtacgggttttgggaggagggacccggctgacagtacta |
| 88 | D06 clone Lambda Chain CDR1 | SSNIGAGYY |
| 89 | D06 clone Lambda Chain CDR2 | QDN |
| 90 | D06 clone Lambda Chain CDR3 | SAWDSSLSVRV |
| 91 | D07 clone Heavy Chain aa sequence | EVQLVESGGGLVQPGGSLRLSCVASGFTFSDRYIDW VRQAPGKGLEWVSTISTGSGDTALYSDSVKGRFTISR DNAKNTLYLQMNSLRAEDTAVYYCARHSGTFYTHF DYWGQGVLVTVSS |
| 92 | D07 clone Heavy Chain nucleotide sequence | gaagtgcagttggtggagtctgggggaggcttggtacagccggggggtccctg agactctcctgtgtagcctctggattcaccttcagtgaccgctacatagactgggtcc gccaggctccagggaagggcctggagtgggtctcaactattagcactggtAGT ggtgataccgcattgtactcagactctgtcaagggccgattcaccatctccagagac aacgccaagaacacactgtatctgcaaatgaacagcctgagagccgaagacacg gctgtctattactgtgcgagacatagtggtactttttacacccactttgactactgggg ccagggagtcctggtcaccgtctcctca |
| 93 | D07 clone Heavy Chain CDR1 | GFTFSDRY |
| 94 | D07 clone Heavy Chain CDR2 | ISTGSGDTA |
| 95 | D07 clone Heavy Chain CDR3 | ARHSGTFYTHFDYW |
| 96 | D07 clone Kappa Chain aa sequence | DIQMTQSPSSLSASVGDTVTFTCRASRSISSWLAWYQ QKPGRAPKVLIYKASSLQSGVPSRFSGSGSGTDFTLTI SSLQSEDFATYYCQQYSSRPPTFGQGTKVEIR |
| 97 | D07 clone Kappa Chain nucleotide sequence | Gacatccagatgacccagtctccatcctccctgtctgcatctgtaggagacacagt caccttcacctgccgggcgagtcggagtattagcagctggttagcctggtatcagc agaaaccagggagagcccctaaagtcctgatctataaggcgtccagtttgcaaagt |

-continued

| SEQ ID NO | Description | Sequence |
|---|---|---|
| | | ggggttccttcaaggttcagcggcagtggatctgggacagacttcactctcaccatc<br>agcagcctacagtctgaagattttgcaacatattattgtcaacagtatagtagtcgcc<br>ctccgacgttcggccaagggaccaaggtggaaatcaga |
| 98 | D07 clone Kappa Chain CDR1 | RSISSW |
| 99 | D07 clone Kappa Chain CDR2 | KAS |
| 100 | D07 clone Kappa Chain CDR3 | QQYSSRPPT |
| 101 | G12 clone Heavy Chain aa sequence | QVQLQESGPGLLKPSETLSLTCAVSGGSFSSFWWSW<br>LRQPPEKGLEWIGEINGDSGSTNYNPSLKSRVTISKD<br>ASKNQFSLKLTSVTAADTAVFYCARVRRILRSLDVW<br>GRGVLVTVSS |
| 102 | G12 clone Heavy Chain nucleotide sequence | Caggtgcagctgcaggagtcgggcccaggactgctgaagccttcggagaccct<br>gtccctcacctgcgctgtctctggtggctccttcagtagtttctggtggagctggctc<br>cgccagcccccagaaaagggactggagtggattggggagatcaatggtgatagt<br>gggagcaccaactacaacccctccctcaagagtcgagtcaccatttcaaaagacg<br>cgtccaagaaccagttctccctgaaactgacctctgtgaccgccgcggacacggc<br>cgtttttactgtgcgagagttcggcgaattctgaggtcattggatgtctggggccgg<br>ggagttctggtcaccgtctcctca |
| 103 | G12 clone Heavy Chain CDR1 | GGSFSSFW |
| 104 | G12 clone Heavy Chain CDR2 | INGDSGST |
| 105 | G12 clone Heavy Chain CDR3 | ARVRRILRSLDVW |
| 106 | G12 clone Kappa Chain aa sequence | DIQMTQSPFSLFAFVGDRVTITCQASQGISHLLAWYQ<br>QKPGKAPKLLIYSASTLQSGVPSRFSGSGFGTEFTLTI<br>SSLQPEDFATYYCQQHNSYPRTFGQGTKVEIK |
| 107 | G12 clone Kappa Chain nucleotide sequence | Gacatccagatgacccagtctccttttttccttgtttgcatttgtaggagacagagtcac<br>catcacttgccaagccagtcagggtattagccacttgttagcttggtatcagcagaa<br>accagggaaagcccctaagctccttatttattctgcatccactttgcaaagtggggtc<br>ccatcaaggttcagcggcagtggatttgggacggaattcactctcaccatcagcag<br>cctgcagcctgaagattttgcaacttattactgtcaacagcataatagttaccctcgga<br>cgttcggccaagggaccaaggtggaaatcaaa |
| 108 | G12 clone Kappa Chain CDR1 | QGISHL |
| 109 | G12 clone Kappa Chain CDR2 | SAS |
| 110 | G12 clone Kappa Chain CDR3 | QQHNSYPRT |
| 111 | Macaque HC backbone Nucleotide sequence | tcgcgcgttt cggtgatgac ggtgaaaacc tctgacacat gcagctcccg<br>gagacggtca cagcttgtct gtaagcggat gccgggagca gacaagcccg<br>tcagggcgcg tcagcgggtg ttggcgggtg tcggggctgg cttaactatg<br>cggcatcaga gcagattgta ctgagagtgc accatatgcg gtgtgaaata<br>ccgcacagat gcgtaaggag aaaataccgc atcagattgg<br>ctattggcca ttgcatacgt tgtatccata tcataatatg tacatttata<br>ttggctcatg tccaacatta ccgccatgtt gacattgatt attgactagt<br>tattaatagt aatcaattac ggggtcatta gttcatagcc catatatgga<br>gttccgcgtt acataactta cggtaaatgg cccgcctggc tgaccgccca<br>acgacccccg cccattgacg tcaataatga cgtatgttcc catagtaacg<br>ccaataggga ctttccattg acgtcaatgg gtggagtatt tacggtaaac<br>tgcccacttg gcagtacatc aagtgtatca tatgccaagt acgcccccta<br>ttgacgtcaa tgacggtaaa tggcccgcct ggcattatgc ccagtacatg<br>accttatggg actttcctac ttggcagtac atctacgtat tagtcatcgc<br>tattaccatg gtgatgcggt tttggcagta catcaatggg cgtggatagc<br>ggtttgactc acggggattt ccaagtctcc accccattga cgtcaatggg<br>agtttgtttt ggcaccaaaa tcaacgggac tttccaaaat gtcgtaacaa<br>ctccgcccca ttgacgcaaa tgggcggtag gcgtgtacgg tgggaggtct<br>atataagcag agctcgttta gtgaaccgtc agatcgcctg gagacgccat<br>ccacgctgtt ttgacctcca tagaagacac cgggaccgat ccagcctcca<br>tcggctcgca tctctccttc acgcgcccgc cgccctacct gaggccgcca<br>tccacgccgg ttgagtcgcg ttctgccgcc tcccgcctgt ggtgcctcct<br>gaactgcgtc cgccgtctag gtaagtttaa agctcaggtc gagaccgggc<br>ctttgtccgg cgctcccttg gagcctacct agactcagcc ggctctccac<br>gctttgcctg accctgcttg ctcaactcta gttaacggtg gagggcagtg<br>tagtctgagc agtactcgtt gctgccgcgc gcgccaccag acataatagc<br>tgacagacta acagactgtt cctttccatg ggtcttttct gcagtcaccg<br>tcgtcgacac gtgtgatcag atatcgcggc cgctctagac caccatggga<br>tggtcatgta tcatcctttt tctagtagca actgcaaccg gtgtacattc<br>ccaggtgcag ctggtgcagc tgcacgagtc gggcccagga ctggtgaagc |

-continued

| SEQ ID NO | Description | Sequence |
|---|---|---|
| | | cttcggagac cctgtccctc acctgcgctg tctctggtgg ctctatcagc |
| | | agtagctact ggagctggat ccgccaggcc ccagggaagg gactggagtg |
| | | gattgggtat gtctatggta gtggtcgtga caccaacgac aacccctccc |
| | | tcaagagtcg agtcaccctg tcagtagaca cgtccaagaa ccagctctcc |
| | | ctgaagctga gatctgtgac cgccgcggac acggccgtgt attactgtgc |
| | | gagcagcggc tggcctcctg ggttggacta ctggggccag ggagtcacgg |
| | | tcaccgtctc ctcagctagc accaagggcc ctagtgtgtt tcctctggcc |
| | | cctagcagca gaagcacatc tgaatctaca gccgccctgg gctgcctggt |
| | | gaaagattac ttccccgagc ccgtgaccgt gtcttggaat agcggctctc |
| | | tgaccagcgg cgtgcacaca tttccagctg tgctgcagag |
| | | cagcggcctg tattctctga gcagcgtggt gacagtgcca agcagctctc |
| | | tgggcaccca gacctacgtg tgcaacgtga accacaagcc cagcaacacc |
| | | aaggtggaca agcgggtgga aatcaagacc tgtggcggcg gaagcaagcc |
| | | tcctacctgt cctccttgta ccagccctga actgctgggc ggacctagcg |
| | | tgttcctgtt cccccaaag cccaaggaca ccctgatgat cagcagaacc |
| | | cccgaagtga cctgcgtggt ggtggatgtg tcccaggaag atcccgacgt |
| | | gaagttcaat tggtacgtga acggcgccga ggtgcaccat gcccagacaa |
| | | agcccagaga gacacagtac aacagcacct accgggtggt gtctgtgctg |
| | | accgtgacac accaggactg gctgaacggc aaagagtaca catgcaaggt |
| | | gtccaacaag gccctgcctg cccccatcca gaaaaccatc agcaaggaca |
| | | agggccagcc cagagaacct caggtgtaca cactgccccc |
| | | cagcagagag gaactgacca agaatcaggt gtccctgacc tgtctggtga |
| | | aaggcttcta ccccagcgac atcgtggtgg aatgggagtc tagcggacag |
| | | cccgagaaca cctacaagac cacccctcca gtgctggata gcgacggcag |
| | | ctacttcctg tacagcaagc tgaccgtgga caagagcaga tggcagcagg |
| | | gcaacgtgtt cagctgctct gtgatgcacg aggccctgca caaccactac |
| | | acccagaagt ctctgagcct gagccccgga aagtgatgat gaacacgtgg |
| | | gatccagatc tgctgtgcct tctagttgcc agccatctgt tgtttgcccc |
| | | tcccccgtgc cttccttgac cctggaaggt gccactccca ctgtcctttc |
| | | ctaataaaat gaggaaattg catcgcattg tctgagtagg tgtcattcta |
| | | ttctgggggg tggggtgggg caggacagca agggggagga ttgggaagac |
| | | aatagcaggc atgctgggga tgcggtgggc tctatgggta cccaggtgct |
| | | gaagaattga cccggttcct cctgggccag aaagaagcag gcacatcccc |
| | | ttctctgtga cacaccctgt ccacgcccct ggttcttagt tccagcccca |
| | | ctcataggac actcatagct caggagggct ccgccttcaa tcccacccgc |
| | | taaagtactt ggagcggtct ctccctccct catcagccca ccaaaccaaa |
| | | cctagcctcc aagagtggga agaaattaaa gcaagatagg ctattaagtg |
| | | cagagggaga gaaaatgcct ccaacatgtg aggaagtaat |
| | | gagagaaatc atagaatttt aaggccatga tttaaggcca tcatggcctt |
| | | aatcttccgc ttcctcgctc actgactcgc tgcgctcggt cgttcggctg |
| | | cggcgagcgg tatcagctca ctcaaaggcg gtaatacggt tatccacaga |
| | | atcaggggat aacgcaggaa agaacatgtg agcaaaaggc cagcaaaagg |
| | | ccaggaaccg taaaaaggcc gcgttgctgg cgtttttcca taggctccgc |
| | | cccccctgacg agcatcacaa aaatcgacgc tcaagtcaga ggtggcgaaa |
| | | cccgacagga ctataaagat accaggcgtt tcccccctgga agctccctcg |
| | | tgcgctctcc tgttccgacc ctgccgctta ccggatacct gtccgccttt |
| | | ctcccttcgg gaagcgtggc gctttctcat agctcacgct gtaggtatct |
| | | cagttcggtg taggtcgttc gctccaagct gggctgtgtg cacgaacccc |
| | | ccgttcagcc cgaccgctgc gccttatccg gtaactatcg tcttgagtcc |
| | | aacccggtaa gacacgactt atcgccactg gcagcagcca ctggtaacag |
| | | gattagcaga gcgaggtatg taggcggtgc tacagagttc ttgaagtggt |
| | | ggcctaacta cggctacact agaagaacag tatttggtat ctgcgctctg |
| | | ctgaagccag ttaccttcgg aaaaagagtt ggtagctctt gatccggcaa |
| | | acaaaccacc gctggtagcg gtggtttttt tgtttgcaag cagcagatta |
| | | cgcgcagaaa aaaaggatct caagaagatc ctttgatctt ttctacgggg |
| | | tctgacgctc agtggaacga aaactcacgt taagggattt tggtcatgag |
| | | attatcaaaa aggatcttca cctagatcct tttaaattaa aaatgaagtt |
| | | ttaaatcaat ctaaagtata tatgagtaaa cttggtctga cagttaccaa |
| | | tgcttaatca gtgaggcacc tatctcagcg atctgtctat ttcgttcatc |
| | | catagttgcc tgactcgggg gggggggcg ctgaggtctg cctcgtgaag |
| | | aaggtgttgc tgactcatac caggcctgaa tcgccccatc atccagccag |
| | | aaagtgaggg agccacggtt gatgagagct ttgttgtagg tggaccagtt |
| | | ggtgattttg aacttttgct ttgccacgga acggtctgcg ttgtcgggaa |
| | | gatgcgtgat ctgatccttc aactcagcaa aagttcgatt tattcaacaa |
| | | agccgccgtc ccgtcaagtc agcgtaatgc tctgccagtg ttacaaccaa |
| | | ttaaccaatt ctgattagaa aaactcatcg agcatcaaat gaaactgcaa |
| | | tttattcata tcaggattat caataccata tttttgaaaa agccgtttct |
| | | gtaatgaagg agaaaactca ccgaggcagt tccataggat ggcaagatcc |
| | | tggtatcggt ctgcgattcc gactcgtcca acatcaatac aacctattaa |
| | | tttcccctcg tcaaaaataa ggttatcaag tgagaaatca ccatgagtga |
| | | cgactgaatc cggtgagaat ggcaaaagct tatgcatttc tttccagact |
| | | tgttcaacag gccagccatt acgctcgtca tcaaaatcac tcgcatcaac |
| | | caaaccgtta ttcattcgtg attgcgcctg agcgagacga aatacgcgat |
| | | cgctgttaaa aggacaatta caaacaggaa tcgaatgcaa ccggcgcagg |
| | | aacactgcca gcgcatcaac aatattttca cctgaatcag gatattcttc |
| | | taatacctgg aatgctgttt tcccggggat cgcagtggtg agtaaccatg |

-continued

| SEQ ID NO | Description | Sequence |
|---|---|---|
| | | catcatcagg agtacggata aaatgcttga tggtcggaag aggcataaat<br>tccgtcagcc agtttagtct gaccatctca tctgtaacat cattggcaac<br>gctacctttg ccatgtttca gaaacaactc tggcgcatcg ggcttcccat<br>acaatcgata gattgtcgca cctgattgcc cgacattatc gcgagcccat<br>ttatacccat ataaatcagc atccatgttg gaatttaatc gcggcctcga<br>gcaagacgtt tcccgttgaa tatggctcat aacacccctt gtattactgt<br>ttatgtaagc agacagtttt attgttcatg atgatatatt tttatcttgt<br>gcaatgtaac atcagagatt ttgagacaca acgtggcttt cccccccccc<br>ccattattga agcatttatc agggttattg tctcatgagc ggatacatat<br>ttgaatgtat ttagaaaaat aaacaaatag gggttccgcg cacatttccc<br>cgaaaagtgc cacctgacgt ctaagaaacc attattatca tgacattaac<br>ctataaaaat aggcgtatca cgaggccctt tcgtc |
| 112 | Macaque heavy chain backbone aa sequence | MGWSCIILFLVATATGVHSQVQLVQLHESGPGLVKP<br>SETLSLTCAVSGGSISSSYWSWIRQAPGKGLEWIGYV<br>YGSGRDTNDNPSLKSRVTLSVDTSKNQLSLKLRSVT<br>AADTAVYYCASSGWPPGLDYWGQGVTVTVSSASTK<br>GPSVFPLAPSSRSTSESTAALGCLVKDYFPEPVTVSW<br>NSGSLTSGVHTFPAVLQSSGLYSLSSVVTVPSSSLGT<br>QTYVCNVNHKPSNTKVDKRVEIKTCGGGSKPPTCPP<br>CTSPELLGGPSVFLFPPKPKDTLMISRTPEVTCVVVD<br>VSQEDPDVKFNWYVNGAEVHHAQTKPRETQYNSTY<br>RVVSVLTVTHQDWLNGKEYTCKVSNKALPAPIQKTI<br>SKDKGQPREPQVYTLPPSREELTKNQVSLTCLVKGF<br>YPSDIVVEWESSGQPENTYKTTPPVLDSDGSYFLYSK<br>LTVDKSRWQQGNVFSCSVMHEALHNHYTQKSLSLS<br>PGK |
| 113 | Macaque Kappa chain backbone nucleotide sequence | tcgcgcgttt cggtgatgac ggtgaaaacc tctgacacat gcagctcccg<br>gagacggtca cagcttgtct gtaagcggat gccgggagca gacaagcccg<br>tcagggcgcg tcagcgggtg ttggcgggtg tcggggctgg cttaactatg<br>cggcatcaga gcagattgta ctgagagtgc accatatgcg gtgtgaaata<br>ccgcacagat gcgtaaggag aaaataccgc atcagattgg ctattggcca<br>ttgcatacgt tgtatccata tcataatatg tacatttata ttggctcatg<br>tccaacatta ccgccatgtt gacattgatt attgactagt tattaatagt<br>aatcaattac ggggtcatta gttcatagcc catatatgga gttccgcgtt<br>acataactta cggtaaatgg cccgcctggc tgaccgccca acgacccccg<br>cccattgacg tcaataatga cgtatgttcc catagtaacg ccaataggga<br>ctttccattg acgtcaatgg gtggagtatt tacggtaaac tgcccacttg<br>gcagtacatc aagtgtatca tatgccaagt acgcccccta ttgacgtcaa<br>tgacggtaaa tggcccgcct ggcattatgc ccagtacatg accttatggg<br>actttcctac ttggcagtac atctacgtat tagtcatcgc tattaccatg<br>gtgatgcggt tttggcagta catcaatggg cgtggatagc ggtttgactc<br>acggggattt ccaagtctcc accccattga cgtcaatggg agtttgtttt<br>ggcaccaaaa tcaacgggac tttccaaaat gtcgtaacaa ctccgcccca<br>ttgacgcaaa tgggcggtag gcgtgtacgg tgggaggtct atataagcag<br>agctcgttta gtgaaccgtc agatcgcctg gagacgccat ccacgctgtt<br>ttgacctcca tagaagacac cgggaccgat ccagcctcca tcggctcgca<br>tctctccttc acgcgcccgc cgccctacct gaggccgcca tccacgccgg<br>ttgagtcgcg ttctgccgcc tcccgcctgt ggtgcctcct gaactgcgtc<br>cgccgtctag gtaagtttaa agctcaggtc gagaccgggc ctttgtccgg<br>cgctcccttg gagcctacct agactcagcc ggctctccac gctttgcctg<br>accctgcttg ctcaactcta gttaacggtg gagggcagtg tagtctgagc<br>agtacacgtt gctgccgcgc gcgccaccag acataatagc tgacagacta<br>acagactgtt cctttccatg ggtcttttct gcagtcaccg tcgtcgacac<br>gtgtgatcag atatcgcggc cgctctagac caccatggga tggtcatgta<br>tcatcctttt tctagtagca actgcaaccg gtgtacattc agaaattgtg<br>ttgacacagt ctccaggcac cctgtctttg tctccagggg aaacagccat<br>catctcttgt cggaccagtc agtatggttc cttagcctgg tatcaacaga<br>ggcccggcca ggcccccagg ctcgtcatct attcgggctc tactcgggcc<br>gctggcatcc cagacaggtt cagcggcagt cggtgggggc cagactacaa<br>tctcaccatc agcaacctgg agtcgggaga ttttggtgtt tattattgcc<br>agcagtatga atttttggc caggggacca aggtccaggt<br>cgacattaaa cgtacggtgg ctgcaccatc tgtcttcatc ttcccgccat<br>ctgaggatca ggtgaaatct ggaactgtct ctgttgtgtg cctgctgaat<br>aacttctatc ccagagaggc cagcgtaaag tggaaggtgg atggtgccct<br>caaaacgggt aactcccagg agagtgtcac agagcaggac agcaaggaca<br>acacctacag cctgagcagc accctgacgc tgagcagcac agagtaccag<br>agtcacaaag tctatgcctg cgaagtcacc catcagggcc tgagctcgcc<br>cgtcaccaag agcttcaaca gaggagagtg ttagggatcc agatctgctg<br>tgccttctag ttgccagcca tctgttgttt gcccctcccc cgtgccttcc<br>ttgaccctgg aaggtgccac tcccactgtc ctttcctaat aaaatgagga<br>aattgcatcg cattgtctga gtaggtgtca ttctattctg gggggtgggg<br>tggggcagga cagcaagggg gaggattggg aagacaatag<br>caggcatgct ggggatgcgg tgggctctat gggtacccag gtgctgaaga<br>attgacccgg ttcctcctgg gccagaaaga agcaggcaca tccccttctc |

-continued

| SEQ ID NO | Description | Sequence |
|---|---|---|
| | | tgtgacacac cctgtccacg cccctggttc ttagttccag ccccactcat<br>aggacactca tagctcagga gggctccgcc ttcaatccca cccgctaaag<br>tacatggagc ggtctctccc tccctcatca gcccaccaaa ccaaacctag<br>cctccaagag tgggaagaaa ttaaagcaag ataggctatt aagtgcagag<br>ggagagaaaa tgcctccaac atgtgaggaa gtaatgagag aaatcataga<br>attttaaggc catgatttaa ggccatcatg gccttaatct tccgcttcct<br>cgctcactga ctcgctgcgc tcggtcgttc ggctgcggcg agcggtatca<br>gctcactcaa aggcggtaat acggttatcc acagaatcag gggataacgc<br>aggaaagaac atgtgagcaa aaggccagca aaaggccagg<br>aaccgtaaaa aggccgcgtt gctggcgttt ttccataggc tccgcccccc<br>tgacgagcat cacaaaaatc gacgctcaag tcagaggtgg cgaaacccga<br>caggactata aagataccag gcgtttcccc ctggaagctc cctcgtgcgc<br>tctcctgttc cgaccctgcc gcttaccgga tacctgtccg cctttctccc<br>ttcgggaagc gtggcgcttt ctcatagctc acgctgtagg<br>tatctcagtt cggtgtaggt cgttcgctcc aagctgggct gtgtgcacga<br>accccccgtt cagcccgacc gctgcgcctt atccggtaac tatcgtcttg<br>agtccaaccc ggtaagacac gacttatcgc cactggcagc agccactggt<br>aacaggatta gcagagcgag gtatgtaggc ggtgctacag agttcttgaa<br>gtggtggcct aactacggct acactagaag aacagtattt<br>ggtatctgcg ctctgctgaa gccagttacc ttcggaaaaa gagttggtag<br>ctcttgatcc ggcaaacaaa ccaccgctgg tagcggtggt ttttttgttt<br>gcaagcagca gattacgcgc agaaaaaaag gatctcaaga agatcctttg<br>atcttttcta cggggtctga cgctcagtgg aacgaaaact cacgttaagg<br>gattttggtc atgagattat caaaaaggat cttcacctag atccttttaa<br>attaaaaatg aagttttaaa tcaatctaaa gtatatatga gtaaacttgg<br>tctgacagtt accaatgctt aatcagtgag gcacctatct cagcgatctg<br>tctatttcgt tcatccatag ttgcctgact cggggggggg gggcgctgag<br>gtctgcctcg tgaagaaggt gttgctgact cataccaggc ctgaatcgcc<br>ccatcatcca gccagaaagt gagggagcca cggttgatga gagctttgtt<br>gtaggtggac cagttggtga ttttgaactt ttgctttgcc acggaacggt<br>ctgcgttgtc gggaagatgc gtgatctgat ccttcaactc agcaaaagtt<br>cgatttattc aacaaagccg ccgtcccgtc aagtcagcgt aatgctctgc<br>cagtgttaca accaattaac caattctgat tagaaaaact catcgagcat<br>caaatgaaac tgcaatttat tcatatcagg attatcaata ccatattttt<br>gaaaaagccg tttctgtaat gaaggagaaa actcaccgag gcagttccat<br>aggatggcaa gatcctggta tcggtctgcg attccgactc<br>gtccaacatc aatacaacct attaatttcc cctcgtcaaa aataaggtta<br>tcaagtgaga aatcaccatg agtgacgact gaatccggtg agaatggcaa<br>aagcttatgc atttctttcc agacttgttc aacaggccag ccattacgct<br>cgtcatcaaa atcactcgca tcaaccaaac cgttattcat tcgtgattgc<br>gcctgagcga gacgaaatac gcgatcgctg ttaaaaggac<br>aattacaaac aggaatcgaa tgcaaccggc gcaggaacac tgccagcgca<br>tcaacaatat tttcacctga atcaggatat tcttctaata cctggaatgc<br>tgttttcccg gggatcgcag tggtgagtaa ccatgcatca tcaggagtac<br>ggataaaatg cttgatggtc ggaagaggca taaattccgt cagccagttt<br>agtctgacca tctcatctgt aacatcattg gcaacgctac ctttgccatg<br>tttcagaaac aactctggcg catcgggctt cccatacaat cgatagattg<br>tcgcacctga ttgcccgaca ttatcgcgag cccatttata cccatataaa<br>tcagcatcca tgttggaatt taatcgcggc ctcgagcaag acgtttcccg<br>ttgaatatgg ctcataacac cccttgtatt actgtttatg taagcagaca<br>gttttattgt tcatgatgat atatttttat cttgtgcaat gtaacatcag agattttgag<br>acacaacgtg gctttccccc cccccccatt attgaagcat ttatcagggt<br>tattgtctca tgagcggata catatttgaa tgtatttaga aaaataaaca<br>aataggggtt ccgcgcacat ttccccgaaa agtgccacct gacgtctaag<br>aaaccattat tatcatgaca ttaacctata aaaataggcg tatcacgagg<br>ccctttcgtc |
| 114 | Macaque Kappa chain backbone aa sequence | MGWSCIILFLVATATGVHSEIVLTQSPGTLSLSPGETA<br>IISCRTSQYGSLAWYQQRPGQAPRLVIYSGSTRAAGI<br>PDRFSGSRWGPDYNLTISNLESGDFGVYYCQQYEFF<br>GQGTKVQVDIKRTVAAPSVFIFPPSEDQVKSGTVSVV<br>CLLNNFYPREASVKWKVDGALKTGNSQESVTEQDS<br>KDNTYSLSSTLTLSSTEYQSHKVYACEVTHQGLSSPV<br>TKSFNRGEC |
| 115 | Macaque Light chain backbone aa sequence | MGWSCIILFLVATATGVHSQSALTQPPSVSGSPGQSV<br>TISCTGTSSDVDGYNYVSWYQQHPGKAPKLMIYGVS<br>NRPSGVSDRFSGSKSGNTASLTISGLQAEDEADYYCC<br>SSTTSYTYIFGTGTKVTVLGQPKAAPSVTLFPPSSEEL<br>QANKATLVCLISDFYPGAVEVAWKADGSAVNAGVE<br>TTKPSKQSNNKYAASSYLSLTSDQWKSHKSYSCQVT<br>HEGSTVEKTVAPAECS |
| 116 | Macaque Heavy chain backbone nucleotide sequence-H02 | tcgcgcgttt cggtgatgac ggtgaaaacc tctgacacat gcagctcccg<br>gagacggtca cagcttgtct gtaagcggat gccgggagca gacaagcccg<br>tcagggcgcg tcagcgggtg ttggcgggtg tcggggctgg cttaactatg |

-continued

| SEQ ID NO | Description | Sequence |
|---|---|---|
| | | cggcatcaga gcagattgta ctgagagtgc accatatgcg gtgtgaaata |
| | | ccgcacagat gcgtaaggag aaaataccgc atcagattgg |
| | | ctattggcca ttgcatacgt tgtatccata tcataatatg tacatttata |
| | | ttggctcatg tccaacatta ccgccatgtt gacattgatt attgactagt |
| | | tattaatagt aatcaattac ggggtcatta gttcatagcc catatatgga |
| | | gttccgcgtt acataactta cggtaaatgg cccgcctggc tgaccgccca |
| | | acgacccccg cccattgacg tcaataatga cgtatgttcc |
| | | catagtaacg ccaataggga ctttccattg acgtcaatgg gtggagtatt |
| | | tacggtaaac tgcccacttg gcagtacatc aagtgtatca tatgccaagt |
| | | acgcccccta ttgacgtcaa tgacggtaaa tggcccgcct ggcattatgc |
| | | ccagtacatg accttatggg actttcctac ttggcagtac atctacgtat |
| | | tagtcatcgc tattaccatg gtgatgcggt tttggcagta catcaatggg |
| | | cgtggatagc ggtttgactc acggggattt ccaagtctcc accccattga |
| | | cgtcaatggg agtttgtttt ggcaccaaaa tcaacgggac tttccaaaat |
| | | gtcgtaacaa ctccgcccca ttgacgcaaa tgggcggtag gcgtgtacgg |
| | | tgggaggtct atataagcag agctcgttta gtgaaccgtc agatcgcctg |
| | | gagacgccat ccacgctgtt ttgacctcca tagaagacac cgggaccgat |
| | | ccagcctcca tcggctcgca tctctccttc acgcgcccgc |
| | | cgccctacct gaggccgcca tccacgccgg ttgagtcgcg ttctgccgcc |
| | | tcccgcctgt ggtgcctcct gaactgcgtc cgccgtctag gtaagtttaa |
| | | agctcaggtc gagaccgggc ctttgtccgg cgctcccttg gagcctacct |
| | | agactcagcc ggctctccac gctttgcctg accctgcttg ctcaactcta |
| | | gttaacggtg gagggcagtg tagtctgagc agtactcgtt gctgccgcgc |
| | | gcgccaccag acataatagc tgacagacta acagactgtt cctttccatg |
| | | ggtcttttct gcagtcaccg tcgtcgacac gtgtgatcag atatcgcggc |
| | | cgctctagac caccatggga tggtcatgta tcatcctttt tctagtagca |
| | | actgcaaccg gtgtacattc ccaactgcag ttgcaggagt cgggcccagg |
| | | agtggtgaag ccttcggaga ccctgtccct cacctgcact atctctggtg |
| | | gctccttcag tacttactac tggacctgga ttcgccagcc cccagggaag |
| | | ggactggagt gggttgggta tatcggtaat ggtggtcgta gcctcaacta |
| | | caacccctcc ctcaagagtc gcatcaccct gtcagtagac gcgtccaaga |
| | | accagttctc cctgaaggtg acctctgtga ccgccgcgga cacggccgtc |
| | | tattactgtg ggagagccag gggactccgc ggaaactggt tcgatgtctg |
| | | gggcccggga gtcctggtca ccgtctcctc agctagcacc aagggcccta |
| | | gtgtgtttcc tctggcccct agcagcagaa gcacatctga atctacagcc |
| | | gccctgggct gcctggtgaa agattacttc cccgagcccg tgaccgtgtc |
| | | ttggaatagc ggctctctga ccagcggcgt gcacacattt ccagctgtgc |
| | | tgcagagcag cggcctgtat tctctgagca gcgtggtgac agtgccaagc |
| | | agctctctgg gcacccagac ctacgtgtgc aacgtgaacc acaagcccag |
| | | caacaccaag gtggacaagc gggtggaaat caagacctgt ggcggcggaa |
| | | gcaagcctcc tacctgtcct ccttgtacca gccctgaact gctgggcgga |
| | | cctagcgtgt tcctgttccc cccaaagccc aaggacaccc tgatgatcag |
| | | cagaaccccc gaagtgacct gcgtggtggt ggatgtgtcc caggaagatc |
| | | ccgacgtgaa gttcaattgg tacgtgaacg gcgccgaggt gcaccatgcc |
| | | cagacaaagc ccagagagac acagtacaac agcacctacc gggtggtgtc |
| | | tgtgctgacc gtgacacacc aggactggct gaacggcaaa gagtacacat |
| | | gcaaggtgtc caacaaggcc ctgcctgccc ccatccagaa aaccatcagc |
| | | aaggacaagg gccagcccag agaacctcag gtgtacacac tgcccccccag |
| | | cagagaggaa ctgaccaaga atcaggtgtc cctgacctgt ctggtgaaag |
| | | gcttctaccc cagcgacatc gtggtggaat gggagtctag cggacagccc |
| | | gagaacacct acaagaccac ccctccagtg ctggatagcg acggcagcta |
| | | cttcctgtac agcaagctga ccgtggacaa gagcagatgg cagcagggca |
| | | acgtgttcag ctgctctgtg atgcacgagg ccctgcacaa ccactacacc |
| | | cagaagtctc tgagcctgag ccccggaaag tgatgatgaa cacgtgggat |
| | | ccagatctgc tgtgccttct agttgccagc catctgttgt ttgcccctcc |
| | | cccgtgcctt ccttgaccct ggaaggtgcc actcccactg tcctttccta |
| | | ataaaatgag gaaattgcat cgcattgtct gagtaggtgt cattctattc |
| | | tggggggtgg ggtggggcag gacagcaagg gggaggattg ggaagacaat |
| | | agcaggcatg ctggggatgc ggtgggctct atgggtaccc aggtgctgaa |
| | | gaattgaccc ggttcctcct gggccagaaa gaagcaggca catccccttc |
| | | tctgtgacac accctgtcca cgcccctggt tcttagttcc agccccactc |
| | | ataggacact catagctcag gagggctccg ccttcaatcc cacccgctaa |
| | | agtacttgga gcggtctctc cctccctcat cagcccacca aaccaaacct |
| | | agcctccaag agtgggaaga aattaaagca agataggcta ttaagtgcag |
| | | agggagagaa aatgcctcca acatgtgagg aagtaatgag agaaatcata |
| | | gaattttaag gccatgattt aaggccatca tggccttaat cttccgcttc |
| | | ctcgctcact gactcgctgc gctcggtcgt tcggctgcgg cgagcggtat |
| | | cagctcactc aaaggcggta atacggttat ccacagaatc aggggataac |
| | | gcaggaaaga acatgtgagc aaaaggccag caaaaggcca ggaaccgtaa |
| | | aaaggccgcg ttgctggcgt ttttccatag gctccgcccc cctgacgagc |
| | | atcacaaaaa tcgacgctca agtcagaggt ggcgaaaccc gacaggacta |
| | | taaagatacc aggcgtttcc ccctggaagc tccctcgtgc gctctcctgt |
| | | tccgaccctg ccgcttaccg gatacctgtc cgcctttctc ccttcgggaa |
| | | gcgtggcgct ttctcatagc tcacgctgta ggtatctcag ttcggtgtag |
| | | gtcgttcgct ccaagctggg ctgtgtgcac gaaccccccg ttcagcccga |
| | | ccgctgcgcc ttatccggta actatcgtct tgagtccaac ccggtaagac |

-continued

| SEQ ID NO | Description | Sequence |
| --- | --- | --- |
| | | acgacttatc gccactggca gcagccactg gtaacaggat tagcagagcg aggtatgtag gcggtgctac agagttcttg aagtggtggc ctaactacgg ctacactaga agaacagtat ttggtatctg cgctctgctg aagccagtta ccttcggaaa aagagttggt agctcttgat ccggcaaaca aaccaccgct ggtagcggtg gtttttttgt ttgcaagcag cagattacgc gcagaaaaaa aggatctcaa gaagatcctt tgatcttttc tacggggtct gacgctcagt ggaacgaaaa ctcacgttaa gggattttgg tcatgagatt atcaaaaagg atcttcacct agatcctttt aaattaaaaa tgaagtttta aatcaatcta aagtatatat gagtaaactt ggtctgacag ttaccaatgc ttaatcagtg aggcacctat ctcagcgatc tgtctatttc gttcatccat agttgcctga ctcggggggg gggggcgctg aggtctgcct cgtgaagaag gtgttgctga ctcataccag gcctgaatcg ccccatcatc cagccagaaa gtgagggagc cacggttgat gagagctttg ttgtaggtgg accagttggt gattttgaac ttttgctttg ccacggaacg gtctgcgttg tcgggaagat gcgtgatctg atccttcaac tcagcaaaag ttcgatttat tcaacaaagc cgccgtcccg tcaagtcagc gtaatgctct gccagtgtta caaccaatta accaattctg attagaaaaa ctcatcgagc atcaaatgaa actgcaattt attcatatca ggattatcaa taccatattt ttgaaaaagc cgtttctgta atgaaggaga aaactcaccg aggcagttcc ataggatggc aagatcctgg tatcggtctg cgattccgac tcgtccaaca tcaatacaac ctattaattt cccctcgtca aaaataaggt tatcaagtga gaaatcacca tgagtgacga ctgaatccgg tgagaatggc aaaagcttat gcatttcttt ccagacttgt tcaacaggcc agccattacg ctcgtcatca aaatcactcg catcaaccaa accgttattc attcgtgatt gcgcctgagc gagacgaaat acgcgatcgc tgttaaaagg acaattacaa acaggaatcg aatgcaaccg gcgcaggaac actgccagcg catcaacaat attttcacct gaatcaggat attcttctaa tacctggaat gctgttttcc cggggatcgc agtggtgagt aaccatgcat catcaggagt acggataaaa tgcttgatgg tcggaagagg cataaattcc gtcagccagt ttagtctgac catctcatct gtaacatcat tggcaacgct acctttgcca tgtttcagaa acaactctgg cgcatcgggc ttcccataca atcgatagat tgtcgcacct gattgcccga cattatcgcg agcccattta tacccatata aatcagcatc catgttggaa tttaatcgcg gcctcgagca agacgtttcc cgttgaatat ggctcataac accccttgta ttactgttta tgtaagcaga cagttttatt gttcatgatg atatattttt atcttgtgca atgtaacatc agagattttg agacacaacg tggctttccc cccccccca ttattgaagc atttatcagg gttattgtct catgagcgga tacatatttg aatgtattta gaaaaataaa caaatagggg ttccgcgcac atttccccga aaagtgccac ctgacgtcta agaaaccatt attatcatga cattaaccta taaaaatagg cgtatcacga ggccctttcg tc |
| 117 | Macaque Heavy chain backbone aa sequence-H02 | MGWSCIILFLVATATGVHSQLQLQESGPGVVKPSET LSLTCTISGGSFSTYYWTWIRQPPGKGLEWVGYIGN GGRSLNYNPSLKSRITLSVDASKNQFSLKVTSVTAAD TAVYYCGRARGLRGNWFDVWGPGVLVTVSSASTK GPSVFPLAPSSRSTSESTAALGCLVKDYFPEPVTVSW NSGSLTSGVHTFPAVLQSSGLYSLSSVVTVPSSSLGT QTYVCNVNHKPSNTKVDKRVEIKTCGGGSKPPTCPP CTSPELLGGPSVFLFPPKPKDTLMISRTPEVTCVVVD VSQEDPDVKFNWYVNGAEVHHAQTKPRETQYNSTY RVVSVLTVTHQDWLNGKEYTCKVSNKALPAPIQKTI SKDKGQPREPQVYTLPPSREELTKNQVSLTCLVKGF YPSDIVVEWESSGQPENTYKTTPPVLDSDGSYFLYSK LTVDKSRWQQGNVFSCSVMHEALHNHYTQKSLSLS PGK |
| 118 | Macaque Light chain backbone nucleotide sequence-H02 | tcgcgcgttt cggtgatgac ggtgaaaacc tctgacacat gcagctcccg gagacggtca cagcttgtct gtaagcggat gccgggagca gacaagcccg tcagggcgcg tcagcgggtg ttggcgggtg tcggggctgg cttaactatg cggcatcaga gcagattgta ctgagagtgc accatatgcg gtgtgaaata ccgcacagat gcgtaaggag aaaataccgc atcagattgg ctattggcca ttgcatacgt tgtatccata tcataatatg tacatttata ttggctcatg tccaacatta ccgccatgtt gacattgatt attgactagt tattaatagt aatcaattac ggggtcatta gttcatagcc catatatgga gttccgcgtt acataactta cggtaaatgg cccgcctggc tgaccgccca acgacccccg cccattgacg tcaataatga cgtatgttcc catagtaacg ccaataggga ctttccattg acgtcaatgg gtggagtatt tacggtaaac tgcccacttg gcagtacatc aagtgtatca tatgccaagt acgcccccta ttgacgtcaa tgacggtaaa tggcccgcct ggcattatgc ccagtacatg accttatggg actttcctac ttggcagtac atctacgtat tagtcatcgc tattaccatg gtgatgcggt tttggcagta catcaatggg cgtggatagc ggtttgactc acggggattt ccaagtctcc accccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag agctcgttta gtgaaccgtc agatcgcctg gagacgccat ccacgctgtt ttgacctcca tagaagacac cgggaccgat ccagcctcca tcggctcgca tctctccttc acgcgcccgc cgccctacct gaggccgcca |

-continued

| SEQ ID NO | Description | Sequence |
|---|---|---|
| | | tccacgccgg ttgagtcgcg ttctgccgcc tcccgcctgt ggtgcctcct |
| | | gaactgcgtc cgccgtctag gtaagtttaa agctcaggtc gagaccgggc |
| | | ctttgtccgg cgctcccttg gagcctacct agactcagcc ggctctccac |
| | | gctttgcctg accctgcttg ctcaactcta gttaacggtg gagggcagtg |
| | | tagtctgagc agtacacgtt gctgccgcgc gcgccaccag acataatagc |
| | | tgacagacta acagactgtt cctttccatg ggtcttttct gcagtcaccg |
| | | tcgtcgacac gtgtgatcag atatcgcggc cgctctagac caccatggga |
| | | tggtcatgta tcatcctttt tctagtagca actgcaaccg gtgtacattc |
| | | ccaggctgcc ctgactcagc ctccctctgt gtctgggtct cctggacagt |
| | | cggtcaccat ctcctgcact ggaaccagca gtgacatcgg tggttataac |
| | | tatgtctcct ggtaccaaca acacccaggc aaagccccca aagtcatgat |
| | | ttatgaggtc agtaagcggc cctcaggggt ctctgatcgc ttctctggtt |
| | | ccaaatctgg caacatagcc tccctgacca tctctgggct ccaggctgag |
| | | gacgaggctg attattactg cagctcatat gcaggcagca acactttctt |
| | | attcggagga gggacccggc tgacagtact aggtcagccc aaggctgccc |
| | | cctcggtcac tctcttcccg ccctcctctg aggagcttca agccaacaag |
| | | gccacactag tgtgtctgat cagtgacttc tacccgggag ccgtggaagt |
| | | ggcctggaag gcagatggca gcgctgtcaa cgcgggagtg gagaccacca |
| | | aaccctccaa acagagcaac aacaagtacg cggccagcag ctacctgagc |
| | | ctgacgtccg accagtggaa gtcccacaag agctacagct gccaggtcac |
| | | gcacgaaggg agcaccgtgg agaagacagt ggcccctgca gaatgttcat |
| | | agggatccag atctgctgtg ccttctagtt gccagccatc tgttgtttgc |
| | | ccctcccccg tgccttcctt gaccctggaa ggtgccactc ccactgtcct |
| | | ttcctaataa aatgaggaaa ttgcatcgca ttgtctgagt aggtgtcatt |
| | | ctattctggg gggtggggtg gggcaggaca gcaaggggga |
| | | ggattgggaa gacaatagca ggcatgctgg ggatgcggtg ggctctatgg |
| | | gtacccaggt gctgaagaat tgacccggtt cctcctgggc cagaaagaag |
| | | caggcacatc cccttctctg tgacacaccc tgtccacgcc cctggttctt |
| | | agttccagcc ccactcatag gacactcata gctcaggagg gctccgcctt |
| | | caatcccacc cgctaaagta catggagcgg tctctccctc cctcatcagc |
| | | ccaccaaacc aaacctagcc tccaagagtg ggaagaaatt aaagcaagat |
| | | aggctattaa gtgcagaggg agagaaaatg cctccaacat gtgaggaagt |
| | | aatgagagaa atcatagaat tttaaggcca tgatttaagg ccatcatggc |
| | | cttaatcttc cgcttcctcg ctcactgact cgctgcgctc ggtcgttcgg |
| | | ctgcggcgag cggtatcagc tcactcaaag gcggtaatac ggttatccac |
| | | agaatcaggg gataacgcag gaaagaacat gtgagcaaaa ggccagcaaa |
| | | aggccaggaa ccgtaaaaag gccgcgttgc tggcgttttt ccataggctc |
| | | cgcccccctg acgagcatca caaaaatcga cgctcaagtc agaggtggcg |
| | | aaacccgaca ggactataaa gataccaggc gtttccccct ggaagctccc |
| | | tcgtgcgctc tcctgttccg accctgccgc ttaccggata cctgtccgcc |
| | | tttctccctt cgggaagcgt ggcgctttct catagctcac gctgtaggta |
| | | tctcagttcg gtgtaggtcg ttcgctccaa gctgggctgt gtgcacgaac |
| | | cccccgttca gcccgaccgc tgcgccttat ccggtaacta tcgtcttgag |
| | | tccaacccgg taagacacga cttatcgcca ctggcagcag ccactggtaa |
| | | caggattagc agagcgaggt atgtaggcgg tgctacagag ttcttgaagt |
| | | ggtggcctaa ctacggctac actagaagaa cagtatttgg tatctgcgct |
| | | ctgctgaagc cagttacctt cggaaaaaga gttggtagct cttgatccgg |
| | | caaacaaacc accgctggta gcggtggttt ttttgtttgc aagcagcaga |
| | | ttacgcgcag aaaaaaagga tctcaagaag atcctttgat cttttctacg |
| | | gggtctgacg ctcagtggaa cgaaaactca cgttaaggga ttttggtcat |
| | | gagattatca aaaaggatct tcacctagat ccttttaaat taaaaatgaa |
| | | gttttaaatc aatctaaagt atatatgagt aaacttggtc tgacagttac |
| | | caatgcttaa tcagtgaggc acctatctca gcgatctgtc tatttcgttc |
| | | atccatagtt gcctgactcg gggggggggg gcgctgaggt |
| | | ctgcctcgtg aagaaggtgt tgctgactca taccaggcct gaatcgcccc |
| | | atcatccagc cagaaagtga gggagccacg gttgatgaga gctttgttgt |
| | | aggtggacca gttggtgatt ttgaactttt gctttgccac ggaacggtct |
| | | gcgttgtcgg gaagatgcgt gatctgatcc ttcaactcag caaaagttcg |
| | | atttattcaa caaagccgcc gtcccgtcaa gtcagcgtaa tgctctgcca |
| | | gtgttacaac caattaacca attctgatta gaaaaactca tcgagcatca |
| | | aatgaaactg caatttattc atatcaggat tatcaatacc atatttttga |
| | | aaaagccgtt tctgtaatga aggagaaaac tcaccgaggc agttccatag |
| | | gatggcaaga tcctggtatc ggtctgcgat tccgactcgt ccaacatcaa |
| | | tacaacctat taatttcccc tcgtcaaaaa taaggttatc aagtgagaaa |
| | | tcaccatgag tgacgactga atccggtgag aatggcaaaa |
| | | gcttatgcat ttctttccag acttgttcaa caggccagcc attacgctcg |
| | | tcatcaaaat cactcgcatc aaccaaaccg ttattcattc gtgattgcgc |
| | | ctgagcgaga cgaaatacgc gatcgctgtt aaaaggacaa ttacaaacag |
| | | gaatcgaatg caaccggcgc aggaacactg ccagcgcatc aacaatattt |
| | | tcacctgaat caggatattc ttctaatacc tggaatgctg ttttcccggg |
| | | gatcgcagtg gtgagtaacc atgcatcatc aggagtacgg ataaaatgct |
| | | tgatggtcgg aagaggcata aattccgtca gccagtttag tctgaccatc |
| | | tcatctgtaa catcattggc aacgctacct ttgccatgtt tcagaaacaa |
| | | ctctggcgca tcgggcttcc catacaatcg atagattgtc gcacctgatt |
| | | gcccgacatt atcgcgagcc catttatacc catataaatc agcatccatg |
| | | ttggaattta atcgcggcct cgagcaagac gtttcccgtt gaatatggct |

-continued

| SEQ ID NO | Description | Sequence |
|---|---|---|
| | | cataacaccc cttgtattac tgtttatgta agcagacagt tttattgttc atgatgatat atttttatct tgtgcaatgt aacatcagag attttgagac acaacgtggc tttccccccc cccccattat tgaagcattt atcagggtta ttgtctcatg agcggataca tatttgaatg tatttagaaa aataaacaaa taggggttcc gcgcacattt ccccgaaaag tgccacctga cgtctaagaa accattatta tcatgacatt aacctataaa aataggcgta tcacgaggcc ctttcgtc |
| 119 | Macaque Light chain backbone aa sequence-H02 | MGWSCIILFLVATATGVHSQAALTQPPSVSGSPGQSV TISCTGTSSDIGGYNYVSWYQQHPGKAPKVMIYEVS KRPSGVSDRFSGSKSGNIASLTISGLQAEDEADYYCS SYAGSNTFLFGGGTRLTVLGQPKAAPSVTLFPPSSEE LQANKATLVCLISDFYPGAVEVAWKADGSAVNAGV ETTKPSKQSNNKYAASSYLSLTSDQWKSHKSYSCQV THEGSTVEKTVAPAECS |
| 120 | Humanized H02 heavy chain backbone nucleotide sequence | tcgcgcgttt cggtgatgac ggtgaaaacc tctgacacat gcagctcccg gagacggtca cagcttgtct gtaagcggat gccgggagca gacaagcccg tcagggcgcg tcagcgggtg ttggcgggtg tcggggctgg cttaactatg cggcatcaga gcagattgta ctgagagtgc accatatgcg gtgtgaaata ccgcacagat gcgtaaggag aaaataccgc atcagattgg ctattggcca ttgcatacgt tgtatccata tcataatatg tacatttata ttggctcatg tccaacatta ccgccatgtt gacattgatt attgactagt tattaatagt aatcaattac ggggtcatta gttcatagcc catatatgga gttccgcgtt acataactta cggtaaatgg cccgcctggc tgaccgccca acgacccccg cccattgacg tcaataatga cgtatgttcc catagtaacg ccaataggga ctttccattg acgtcaatgg gtggagtatt tacggtaaac tgcccacttg gcagtacatc aagtgtatca tatgccaagt acgcccccta ttgacgtcaa tgacggtaaa tggcccgcct ggcattatgc ccagtacatg accttatggg actttcctac ttggcagtac atctacgtat tagtcatcgc tattaccatg gtgatgcggt tttggcagta catcaatggg cgtggatagc ggtttgactc acggggattt ccaagtctcc accccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag agctcgttta gtgaaccgtc agatcgcctg gagacgccat ccacgctgtt ttgacctcca tagaagacac cgggaccgat ccagcctcca tcggctcgca tctctccttc acgcgcccgc cgccctacct gaggccgcca tccacgccgg ttgagtcgcg ttctgccgcc tcccgcctgt ggtgcctcct gaactgcgtc cgccgtctag gtaagtttaa agctcaggtc gagaccgggc ctttgtccgg cgctcccttg gagcctacct agactcagcc ggctctccac gctttgcctg accctgcttg ctcaactcta gttaacggtg gagggcagtg tagtctgagc agtactcgtt gctgccgcgc gcgccaccag acataatagc tgacagacta acagactgtt cctttccatg ggtcttttct gcagtcaccg tcgtcgacac gtgtgatcag atatcgcggc cgctctagac caccatggga tggtcatgta tcatcctttt tctagtagca actgcaaccg gtgtacattc ccaactgcag ttgcaggagt cgggcccagg agtggtgaag ccttcggaga ccctgtccct cacctgcact atctctggtg gctccttcag tacttactac tggacctgga ttcgccagcc cccagggaag ggactggagt gggttgggta tatcggtaat ggtggtcgta gcctcaacta caacccctcc ctcaagagtc gcatcaccct gtcagtagac gcgtccaaga accagttctc cctgaaggtg acctctgtga ccgccgcgga cacggccgtc tattactgtg ggagagccag gggactccgc ggaaactggt tcgatgtctg gggcccggga gtcctggtca ccgtctcctc agctagcacc aagggcccat cggtcttccc cctggcaccc tcctccaaga gcacctctgg gggcacagcg gccctgggct gcctggtcaa ggactacttc cccgaaccgg tgacggtgtc gtggaactca ggcgccctga ccagcggcgt gcacaccttc ccggctgtcc tacagtcctc aggactctac tccctcagca gcgtggtgac cgtgccctcc agcagcttgg gcacccagac ctacatctgc aacgtgaatc acaagcccag caacaccaag gtggacaaga aagttgagcc caaatcttgt gacaaaactc acacatgccc accgtgccca gcacctgaac tcctgggggg accgtcagtc ttcctcttcc ccccaaaacc caaggacacc ctcatgatct cccggacccc tgaggtcaca tgcgtggtgg tggacgtgag ccacgaagac cctgaggtca agttcaactg gtacgtggac ggcgtggagg tgcataatgc caagacaaag ccgcgggagg agcagtacaa cagcacgtac cgtgtggtca gcgtcctcac cgtcctgcac caggactggc tgaatggcaa ggagtacaag tgcaaggtct ccaacaaagc cctcccagcc cccatcgaga aaaccatctc caaagccaaa gggcagcccc gagaaccaca ggtgtacacc ctgcccccat cccgggatga gctgaccaag aaccaggtca gcctgacctg cctggtcaaa ggcttctatc ccagcgacat cgccgtggag tgggagagca atgggcagcc ggagaacaac tacaagacca cgcctcccgt gctggactcc gacggctcct tcttcctcta cagcaagctc accgtggaca agagcaggtg gcagcagggg aacgtcttct catgctccgt gatgcatgag gctctgcaca accactacac gcagaagagc ctctccctgt ctccgggtaa atgatgagga tccagatctg ctgtgccttc tagttgccag ccatctgttg tttgcccctc ccccgtgcct tccttgaccc tggaaggtgc cactcccact gtcctttcct aataaaatga ggaaattgca tcgcattgtc tgagtaggtg tcattctatt ctggggggtg gggtggggca ggacagcaag ggggaggatt |

-continued

| SEQ ID NO | Description | Sequence |
|---|---|---|
| | | gggaagacaa tagcaggcat gctggggatg cggtgggctc tatgggtacc<br>caggtgctga agaattgacc cggttcctcc tgggccagaa agaagcaggc<br>acatcccctt ctctgtgaca caccctgtcc acgcccctgg ttcttagttc<br>cagccccact cataggacac tcatagctca ggagggctcc gccttcaatc<br>ccacccgcta aagtacttgg agcggtctct ccctccctca tcagcccacc<br>aaaccaaacc tagcctccaa gagtgggaag aaattaaagc aagataggct<br>attaagtgca gagggagaga aaatgcctcc aacatgtgag gaagtaatga<br>gagaaatcat agaattttaa ggccatgatt taaggccatc atggccttaa<br>tcttccgctt cctcgctcac tgactcgctg cgctcggtcg ttcggctgcg<br>gcgagcggta tcagctcact caaaggcggt aatacggtta tccacagaat<br>caggggataa cgcaggaaag aacatgtgag caaaaggcca gcaaaaggcc<br>aggaaccgta aaaaggccgc gttgctggcg tttttccata ggctccgccc<br>ccctgacgag catcacaaaa atcgacgctc aagtcagagg tggcgaaacc<br>cgacaggact ataaagatac caggcgtttc cccctggaag ctccctcgtg<br>cgctctcctg ttccgaccct gccgcttacc ggatacctgt ccgcctttct<br>cccttcggga agcgtggcgc tttctcatag ctcacgctgt aggtatctca<br>gttcggtgta ggtcgttcgc tccaagctgg gctgtgtgca cgaacccccc<br>gttcagcccg accgctgcgc cttatccggt aactatcgtc ttgagtccaa<br>cccggtaaga cacgacttat cgccactggc agcagccact ggtaacagga<br>ttagcagagc gaggtatgta ggcggtgcta cagagttctt gaagtggtgg<br>cctaactacg gctacactag aagaacagta tttggtatct gcgctctgct<br>gaagccagtt accttcggaa aaagagttgg tagctcttga tccggcaaac<br>aaaccaccgc tggtagcggt ggtttttttg tttgcaagca gcagattacg<br>cgcagaaaaa aaggatctca agaagatcct ttgatctttt ctacggggtc<br>tgacgctcag tggaacgaaa actcacgtta agggattttg gtcatgagat<br>tatcaaaaag gatcttcacc tagatccttt taaattaaaa atgaagtttt<br>aaatcaatct aaagtatata tgagtaaact tggtctgaca gttaccaatg<br>cttaatcagt gaggcaccta tctcagcgat ctgtctattt cgttcatcca<br>tagttgcctg actcgggggg ggggggcgct gaggtctgcc tcgtgaagaa<br>ggtgttgctg actcatacca ggcctgaatc gccccatcat ccagccagaa<br>agtgagggag ccacggttga tgagagcttt gttgtaggtg gaccagttgg<br>tgattttgaa cttttgcttt gccacggaac ggtctgcgtt gtcgggaaga<br>tgcgtgatct gatccttcaa ctcagcaaaa gttcgattta ttcaacaaag<br>ccgccgtccc gtcaagtcag cgtaatgctc tgccagtgtt acaaccaatt<br>aaccaattct gattagaaaa actcatcgag catcaaatga aactgcaatt<br>tattcatatc aggattatca ataccatatt tttgaaaaag ccgtttctgt<br>aatgaaggag aaaactcacc gaggcagttc cataggatgg caagatcctg<br>gtatcggtct gcgattccga ctcgtccaac atcaatacaa cctattaatt<br>tcccctcgtc aaaaataagg ttatcaagtg agaaatcacc atgagtgacg<br>actgaatccg gtgagaatgg caaaagctta tgcatttctt tccagacttg<br>ttcaacaggc cagccattac gctcgtcatc aaaatcactc gcatcaacca<br>aaccgttatt cattcgtgat tgcgcctgag cgagacgaaa tacgcgatcg<br>ctgttaaaag gacaattaca aacaggaatc gaatgcaacc ggcgcaggaa<br>cactgccagc gcatcaacaa tattttcacc tgaatcagga tattcttcta<br>atacctggaa tgctgttttc ccggggatcg cagtggtgag taaccatgca<br>tcatcaggag tacggataaa atgcttgatg gtcggaagag gcataaattc<br>cgtcagccag tttagtctga ccatctcatc tgtaacatca ttggcaacgc<br>tacctttgcc atgtttcaga aacaactctg gcgcatcggg cttcccatac<br>aatcgataga ttgtcgcacc tgattgcccg acattatcgc gagcccattt<br>atacccatat aaatcagcat ccatgttgga atttaatcgc ggcctcgagc<br>aagacgtttc ccgttgaata tggctcataa caccccttgt attactgttt<br>atgtaagcag acagttttat tgttcatgat gatatatttt tatcttgtgc<br>aatgtaacat cagagatttt gagacacaac gtggctttcc cccccccccc<br>attattgaag catttatcag ggttattgtc tcatgagcgg atacatattt<br>gaatgtattt agaaaaataa acaaataggg gttccgcgca catttccccg<br>aaaagtgcca cctgacgtct aagaaaccat tattatcatg acattaacct<br>ataaaaatag gcgtatcacg aggccctttc gtc |
| 121 | Humanized H02 heavy chain backbone aa sequence | MGWSCIILFLVATATGVHSQLQLQESGPGVVKPSET<br>LSLTCTISGGSFSTYYWTWIRQPPGKGLEWVGYIGN<br>GGRSLNYNPSLKSRITLSVDASKNQFSLKVTSVTAAD<br>TAVYYCGRARGLRGNWFDVWGPGVLVTVSSASTK<br>GPSVFPLAPSSKSTSGGTAALGCLVKDYFPEPVTVSW<br>NSGALTSGVHTFPAVLQSSGLYSLSSVVTVPSSSLGT<br>QTYICNVNHKPSNTKVDKKVEPKSCDKTHTCPPCPA<br>PELLGGPSVFLFPPKPKDTLMISRTPEVTCVVVDVSH<br>EDPEVKFNWYVDGVEVHNAKTKPREEQYNSTYRVV<br>SVLTVLHQDWLNGKEYKCKVSNKALPAPIEKTISKA<br>KGQPREPQVYTLPPSRDELTKNQVSLTCLVKGFYPS<br>DIAVEWESNGQPENNYKTTPPVLDSDGSFFLYSKLT<br>VDKSRWQQGNVFSCSVMHEALHNHYTQKSLSLSPG<br>K |
| 122 | Humanized H02 light chain backbone aa sequence | tcgcgcgttt cggtgatgac ggtgaaaacc tctgacacat gcagctcccg<br>gagacggtca cagcttgtct gtaagcggat gccgggagca gacaagcccg<br>tcagggcgcg tcagcgggtg ttggcgggtg tcggggctgg cttaactatg |

-continued

| SEQ ID NO | Description | Sequence |
|---|---|---|
| | | cggcatcaga gcagattgta ctgagagtgc accatatgcg gtgtgaaata |
| | | ccgcacagat gcgtaaggag aaaataccgc atcagattgg ctattggcca |
| | | ttgcatacgt tgtatccata tcataatatg tacatttata ttggctcatg |
| | | tccaacatta ccgccatgtt gacattgatt attgactagt tattaatagt |
| | | aatcaattac ggggtcatta gttcatagcc catatatgga gttccgcgtt |
| | | acataactta cggtaaatgg cccgcctggc tgaccgccca acgacccccg |
| | | cccattgacg tcaataatga cgtatgttcc catagtaacg ccaataggga |
| | | ctttccattg acgtcaatgg gtggagtatt tacggtaaac tgcccacttg |
| | | gcagtacatc aagtgtatca tatgccaagt acgcccccta ttgacgtcaa |
| | | tgacggtaaa tggcccgcct ggcattatgc ccagtacatg accttatggg |
| | | actttcctac ttggcagtac atctacgtat tagtcatcgc tattaccatg |
| | | gtgatgcggt tttggcagta catcaatggg cgtggatagc ggtttgactc |
| | | acggggattt ccaagtctcc accccattga cgtcaatggg agtttgtttt |
| | | ggcaccaaaa tcaacgggac tttccaaaat gtcgtaacaa ctccgcccca |
| | | ttgacgcaaa tgggcggtag gcgtgtacgg tgggaggtct atataagcag |
| | | agctcgttta gtgaaccgtc agatcgcctg gagacgccat ccacgctgtt |
| | | ttgacctcca tagaagacac cgggaccgat ccagcctcca tcggctcgca |
| | | tctctccttc acgcgcccgc cgccctacct gaggccgcca tccacgccgg |
| | | ttgagtcgcg ttctgccgcc tcccgcctgt ggtgcctcct gaactgcgtc |
| | | cgccgtctag gtaagtttaa agctcaggtc gagaccgggc ctttgtccgg |
| | | cgctcccttg gagcctacct agactcagcc ggctctccac gctttgcctg |
| | | accctgcttg ctcaactcta gttaacggtg gagggcagtg tagtctgagc |
| | | agtactcgtt gctgccgcgc gcgccaccag acataatagc tgacagacta |
| | | acagactgtt cctttccatg ggtcttttct gcagtcaccg tcgtcgacac |
| | | gtgtgatcag atatcgcggc cgctctagac caccatggga tggtcatgta |
| | | tcatcctttt tctagtagca actgcaaccg gtgtacattc ccaggctgcc |
| | | ctgactcagc ctccctctgt gtctgggtct cctggacagt cggtcaccat |
| | | ctcctgcact ggaaccagca gtgacatcgg tggttataac tatgtctcct |
| | | ggtaccaaca acacccaggc aaagccccca aagtcatgat ttatgaggtc |
| | | agtaagcggc cctcaggggt ctctgatcgc ttctctggtt ccaaatctgg |
| | | caacatagcc tccctgacca tctctgggct ccaggctgag gacgaggctg |
| | | attattactg cagctcatat gcaggcagca acactttctt attcggagga |
| | | gggacccggc tgacagtCct aggtcagccc aaggctgccc cctcggtcac |
| | | tctgttcccg ccctcctctg aggagcttca agccaacaag gccacactgg |
| | | tgtgtctcat aagtgacttc tacccgggag ccgtgacagt ggcctggaag |
| | | gcagatagca gccccgtcaa ggcgggagtg gagaccacca caccctccaa |
| | | acaaagcaac aacaagtacg cggccagcag ctatctgagc ctgacgcctg |
| | | agcagtggaa gtcccacaga agctacagct gccaggtcac gcatgaaggg |
| | | agcaccgtgg agaagacagt ggcccctaca gaatgttcat gaggatccag |
| | | atctgctgtg ccttctagtt gccagccatc tgttgtttgc ccctcccccg |
| | | tgccttcctt gaccctggaa ggtgccactc ccactgtcct ttcctaataa |
| | | aatgaggaaa ttgcatcgca ttgtctgagt aggtgtcatt ctattctggg |
| | | gggtggggtg gggcaggaca gcaaggggga ggattgggaa gacaatagca |
| | | ggcatgctgg ggatgcggtg ggctctatgg gtacccaggt gctgaagaat |
| | | tgacccggtt cctcctgggc cagaaagaag caggcacatc cccttctctg |
| | | tgacacaccc tgtccacgcc cctggttctt agttccagcc ccactcatag |
| | | gacactcata gctcaggagg gctccgcctt caatcccacc cgctaaagta |
| | | cttggagcgg tctctccctc cctcatcagc ccaccaaacc aaacctagcc |
| | | tccaagagtg ggaagaaatt aaagcaagat aggctattaa gtgcagaggg |
| | | agagaaaatg cctccaacat gtgaggaagt aatgagagaa atcatagaat |
| | | tttaaggcca tgatttaagg ccatcatggc cttaatcttc cgcttcctcg |
| | | ctcactgact cgctgcgctc ggtcgttcgg ctgcggcgag cggtatcagc |
| | | tcactcaaag gcggtaatac ggttatccac agaatcaggg gataacgcag |
| | | gaaagaacat gtgagcaaaa ggccagcaaa aggccaggaa ccgtaaaaag |
| | | gccgcgttgc tggcgttttt ccataggctc cgcccccctg acgagcatca |
| | | caaaaatcga cgctcaagtc agaggtggcg aaacccgaca ggactataaa |
| | | gataccaggc gtttccccct ggaagctccc tcgtgcgctc tcctgttccg |
| | | accctgccgc ttaccggata cctgtccgcc tttctccctt cgggaagcgt |
| | | ggcgctttct catagctcac gctgtaggta tctcagttcg gtgtaggtcg |
| | | ttcgctccaa gctgggctgt gtgcacgaac cccccgttca gcccgaccgc |
| | | tgcgccttat ccggtaacta tcgtcttgag tccaacccgg taagacacga |
| | | cttatcgcca ctggcagcag ccactggtaa caggattagc agagcgaggt |
| | | atgtaggcgg tgctacagag ttcttgaagt ggtggcctaa ctacggctac |
| | | actagaagaa cagtatttgg tatctgcgct ctgctgaagc cagttacctt |
| | | cggaaaaaga gttggtagct cttgatccgg caaacaaacc accgctggta |
| | | gcggtggttt ttttgtttgc aagcagcaga ttacgcgcag aaaaaaagga |
| | | tctcaagaag atcctttgat cttttctacg gggtctgacg ctcagtggaa |
| | | cgaaaactca cgttaaggga ttttggtcat gagattatca aaaaggatct |
| | | tcacctagat ccttttaaat taaaaatgaa gttttaaatc aatctaaagt |
| | | atatatgagt aaacttggtc tgacagttac caatgcttaa tcagtgaggc |
| | | acctatctca gcgatctgtc tatttcgttc atccatagtt gcctgactcg |
| | | gggggggggg gcgctgaggt ctgcctcgtg aagaaggtgt tgctgactca |
| | | taccaggcct gaatcgcccc atcatccagc cagaaagtga gggagccacg |
| | | gttgatgaga gctttgttgt aggtggacca gttggtgatt ttgaactttt |
| | | gctttgccac ggaacggtct gcgttgtcgg gaagatgcgt gatctgatcc |
| | | ttcaactcag caaaagttcg atttattcaa caaagccgcc gtcccgtcaa |

-continued

| SEQ ID NO | Description | Sequence |
|---|---|---|
| | | gtcagcgtaa tgctctgcca gtgttacaac caattaacca attctgatta gaaaaactca tcgagcatca aatgaaactg caatttattc atatcaggat tatcaatacc atatttttga aaaagccgtt tctgtaatga aggagaaaac tcaccgaggc agttccatag gatggcaaga tcctggtatc ggtctgcgat tccgactcgt ccaacatcaa tacaacctat taatttcccc tcgtcaaaaa taaggttatc aagtgagaaa tcaccatgag tgacgactga atccggtgag aatggcaaaa gcttatgcat ttctttccag acttgttcaa caggccagcc attacgctcg tcatcaaaat cactcgcatc aaccaaaccg ttattcattc gtgattgcgc ctgagcgaga cgaaatacgc gatcgctgtt aaaaggacaa ttacaaacag gaatcgaatg caaccggcgc aggaacactg ccagcgcatc aacaatattt tcacctgaat caggatattc ttctaatacc tggaatgctg ttttcccggg gatcgcagtg gtgagtaacc atgcatcatc aggagtacgg ataaaatgct tgatggtcgg aagaggcata aattccgtca gccagtttag tctgaccatc tcatctgtaa catcattggc aacgctacct ttgccatgtt tcagaaacaa ctctggcgca tcgggcttcc catacaatcg atagattgtc gcacctgatt gcccgacatt atcgcgagcc catttatacc catataaatc agcatccatg ttggaattta atcgcggcct cgagcaagac gtttcccgtt gaatatggct cataacaccc cttgtattac tgtttatgta agcagacagt tttattgttc atgatgatat atttttatct tgtgcaatgt aacatcagag atttgagac acaacgtggc tttccccccc cccccattat tgaagcattt atcagggtta ttgtctcatg agcggataca tatttgaatg tatttagaaa aataaacaaa taggggttcc gcgcacattt ccccgaaaag tgccacctga cgtctaagaa accattatta tcatgacatt aacctataaa aataggcgta tcacgaggcc ctttcgtc |
| 123 | Humanized H02 light chain backbone aa sequence | MGWSCIILFLVATATGVHSQAALTQPPSVSGSPGQSV TISCTGTSSDIGGYNYVSWYQQHPGKAPKVMIYEVS KRPSGVSDRFSGSKSGNIASLTISGLQAEDEADYYCS SYAGSNTFLFGGGTRLTVLGQPKAAPSVTLFPPSSEE LQANKATLVCLISDFYPGAVTVAWKADSSPVKAGV ETTTPSKQSNNKYAASSYLSLTPEQWKSHRSYSCQV THEGSTVEKTVAPTECS |
| 124 | EBV gp350 GenBank: AIM62208.1 | MEAALLVCQYTIQSLIHLTGEDPGFFNVEIPEFPFYPTC NVCTADVNVTINFDVGGKKHQLDLDFGQLTPHTKAVYQP RGAFGGSENATNLFLLELLGAGELALTMRSKKLPINVTT GEEQQVSLESVDVYFQDVFGTMWCHHAEMQNPVYLIPET VPYIKWDNCNSTNITAVVRAQGLDVTLPLSLPTSAQDSN FSVKTEMLGNEIDIECIMEDGEISQVLPGDNKFNITCSG YESHVPSGGILTSTSPVATPIPGTGYAYSLRLTPRPVSR FLGNNSILYVFYSGNGPKASGGDYCIQSNIVFSDEIPAS QDMPTNTTDITYVGDNATYSVPMVTSEDANSPNVTVTAF WAWPNNTETDFKCKWTLTSGTPSGCENISGAFASNRTFD ITVSGLGTAPKTLIITRTATNATTTTHKVIFSKAPESTT TSPTSNTTGFAAPNTTTGLPSSTHVPTNLTAPASTGPTV STADVTSPTPAGTTSGASPVTPSPSPRDNGTESKAPDMT SPTSAVTTPTPNATSPTSAVTTPTPNATSPTPAVTTPTP NATSPTLGKTSPTSAVTTPTPNATSPTLGKTSPTSAVTT PTPNATSPTLGKTSPTSAVTTPTPNATSPTVGETSPQAN TTNHTLGGTSSTPVVTSPPKNATSAVTTGQHNITSSSTS SMSLRPSSISETLSPSTSDNSTSHMPLLTSAHPTGGENI TQVTPASTSTHHVSTSSPAPRPGTTSQASGPGNSSTSTK PGEVNVTKGTPPKNATSPQAPSGQKTAVPTVTSTGGKAN STTGGKHTTGHGARTSTEPTTDYGGDSTTPRTRYNATTY LPPSTSSELRPRWTFTSPPVTTAQATVPVPPTSQPRFSN LSMLVLQWASLAVLTLLLLLVMADCAFRRNLSTSHTYTT PPYDDAETYV |
| 125 | gp350 B95-8 amino acids 2-425 Avi | EAALLVCQYTIQSLIHLTGEDPGFFNVEIPEFPFYPTCN VCTADVNVTINFDVGGKKHQLDLDFGQLTPHTKAVYQPR GAFGGSENATNLFLLELLGAGELALTMRSKKLPINVTTG EEQQVSLESVDVYFQDVFGTMWCHHAEMQNPVYLIPETV PYIKWDNCNSTNITAVVRAQGLDVTLPLSLPTSAQDSNF SVKTEMLGNEIDIECIMEDGEISQVLPGDNKFNITCSGY ESHVPSGGILTSTSPVATPIPGTGYAYSLRLTPRPVSRF LGNNSILYVFYSGNGPKASGGDYCIQSNIVFSDEIPASQ DMPTNTTDITYVGDNATYSVPMVTSEDANSPNVTVTAFW AWPNNTETDFKCKWTLTSGTPSGCENISGAFASNRTFDI TVSGLGTAPKTLIITRTATNATTTTHKVIFSKAPGS |
| 126 | NAM encoding SEQ ID NO: 125 | gaagctgccctgctcgtgtgccagtacaccatccagagcctgatccacctgaccg gcgaggaccccggcttcttcaacgtggaaatccccgagttcccctcctaccctacct gcaacgtgtgcaccgccgacgtgaacgtgaccatcaacttcgacgtgggcggca agaagcaccagctggacctggatttcggccagctgaccccctcacaccaaggccgt gtatcagcccagaggcgcctttggcggcagcgagaacgccaccaatctgtttctgc tggaactcctaggcgccggcgagctggccctgaccatgagaagcaagaaactgc |

-continued

| SEQ ID NO | Description | Sequence |
|---|---|---|
| | | ccatcaatgtgaccacaggcgaggaacagcaggtgtccctggaaagcgtgg acg<br>tgtactttcaagacgtgttcggcaccatgtggtgccaccacgccgagatgcagaac<br>cccgtgtacctgatccccgagacagtgccctacatcaagtgggacaactgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagacccgtgtccagattcctg<br>ggcaacaacagcatcctgtacgtgttctacagcggcaacggccccaaggcctctg<br>gcggcgattactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagccccaacgtgaccgt<br>gacagccttttgggcctggcctaacaacaccgagacagacttcaagtgcaagtgg<br>accctgacctccggcacccctagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctctggc |
| 127 | gp350 B95-8 (2-425)<br>Q122N*Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQ**N**VSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGS |
| 128 | NAM encoding SEQ ID<br>NO: 127 | gaagctgccctgctcgtgtgccagtacaccatccagagcctgatccacctgaccg<br>gcgaggaccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgacccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagaacgtgtccctggaaagcgtggacg<br>tgtactttcaagacgtgttcggcaccatgtggtgccaccacgccgagatgcagaac<br>cccgtgtacctgatccccgagacagtgccctacatcaagtgggacaactgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagacccgtgtccagattcctg<br>ggcaacaacagcatcctgtacgtgttctacagcggcaacggccccaaggcctctg<br>gcggcgattactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagccccaacgtgaccgt<br>gacagccttttgggcctggcctaacaacaccgagacagacttcaagtgcaagtgg<br>accctgacctccggcacccctagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 129 | gp350 B95-8 (2-425)<br>D163N*/164bSAvi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKW**NNS**CNSTNITAVVRAQGLDVTLPLSLPTSAQDSN<br>FSVKTEMLGNEIDIECIMEDGEISQVLPGDNKFNITCSG<br>YESHVPSGGILTSTSPVATPIPGTGYAYSLRLTPRPVSR<br>FLGNNSILYVFYSGNGPKASGGDYCIQSNIVFSDEIPAS<br>QDMPTNTTDITYVGDNATYSVPMVTSEDANSPNVTVTAF<br>WAWPNNTETDFKCKWTLTSGTPSGCENISGAFASNRTFD<br>ITVSGLGTAPKTLIITRTATNATTTTHKVIFSKAPGS |
| 130 | NAM encoding SEQ ID<br>NO: 129 | gaagctgccctgctcgtgtgccagtacaccatccagagcctgatccacctgaccg<br>gcgaggaccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgacccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtgg acg<br>tgtactttcaagacgtgttcggcaccatgtggtgccaccacgccgagatgcagaac |

-continued

| SEQ ID NO | Description | Sequence |
|---|---|---|
| | | cccgtgtacctgatccccgagacagtgccctacatcaagtggaacaacagctgca acagcaccaacatcaccgccgtcgtgcgggcccagggactggatgtgacactgc ctctgagcctgcctaccagcgcccaggacagcaacttcagcgtgaaaaccgagat gctgggcaacgagatcgacatcgagtgcatcatggaagatggcgagatcagcca ggtgctgcccggcgacaacaagttcaacatcacatgcagcggctacgagagcca cgtgccatctggcggcatcctgaccagcacaagcccagtggccacacccatccct ggcacaggctacgcctacagcctgagactgacccccagacccgtgtccagattcc tgggcaacaacagcatcctgtacgtgttctacagcggcaacggccccaaggcctc tggcggcgattactgtatccagagcaacatcgtgttcagcgacgagatccccgcca gccaggacatgcccaccaataccaccgacatcacgtacgtgggcgacaatgcca cctacagcgtgccaatggtcacctccgaggacgccaacagccccaacgtgaccg tgacagccttttgggcctggcctaacaacaccgagacagacttcaagtgcaagtgg accctgacctccggcacccctagcggctgcgagaatatcagcggagccttcgcca gcaaccggaccttcgatatcaccgtgtctggcctgggcaccgcccccaagaccct gatcatcaccagaaccgccacaaatgccaccaccacaacccacaaagtgatcttc agcaaggcccccggctct |
| 131 | gp350 B95-8 (2-425) D296R Avi | EAALLVCQYTIQSLIHLTGEDPGFFNVEIPEFPFYPTCN VCTADVNVTINFDVGGKKHQLDLDFGQLTPHTKAVYQPR GAFGGSENATNLFLLELLGAGELALTMRSKKLPINVTTG EEQQVSLESVDVYFQDVFGTMWCHHAEMQNPVYLIPETV PYIKWDNCNSTNITAVVRAQGLDVTLPLSLPTSAQDSNF SVKTEMLGNEIDIECIMEDGEISQVLPGDNKFNITCSGY ESHVPSGGILTSTSPVATPIPGTGYAYSLRLTPRPVSRF LGNNSILYVFYSGNGPKASGG**R**YCIQSNIVFSDEIPASQ DMPTNTTDITYVGDNATYSVPMVTSEDANSPNVTVTAFW AWPNNTETDFKCKWTLTSGTPSGCENISGAFASNRTFDI TVSGLGTAPKTLIITRTATNATTTTHKVIFSKAPGS |
| 132 | NAM encoding SEQ ID NO: 131 | gaagctgccctgctcgtgtgccagtacaccatccagagcctgatccacctgaccg gcgaggaccccggcttcttcaacgtggaaatccccgagttccccttctaccctacct gcaacgtgtgcaccgccgacgtgaacgtgaccatcaacttcgacgtgggcggca agaagcaccagctggacctggatttcggccagctgacccctcacaccaaggccgt gtatcagcccagaggcgcctttggcggcagcgagaacgccaccaatctgtttctgc tggaactcctaggcgccggcgagctggccctgaccatgagaagcaagaaactgc ccatcaatgtgaccacaggcgaggaacagcaggtgtccctggaaagcgtggacg tgtactttcaagacgtgttcggcaccatgtggtgccaccacgccgagatgcagaac cccgtgtacctgatccccgagacagtgccctacatcaagtgggacaactgcaaca gcaccaacatcaccgccgtcgtgcgggcccagggactggatgtgacactgcctct gagcctgcctaccagcgcccaggacagcaacttcagcgtgaaaaccgagatgct gggcaacgagatcgacatcgagtgcatcatggaagatggcgagatcagccaggt gctgcccggcgacaacaagttcaacatcacatgcagcggctacgagagccacgt gccatctggcggcatcctgaccagcacaagcccagtggccacacccatccctgg cacaggctacgcctacagcctgagactgacccccagacccgtgtccagattcctg ggcaacaacagcatcctgtacgtgttctacagcggcaacggccccaaggcctctg gcggccggtactgtatccagagcaacatcgtgttcagcgacgagatccccgccag ccaggacatgcccaccaataccaccgacatcacgtacgtgggcgacaatgccac ctacagcgtgccaatggtcacctccgaggacgccaacagccccaacgtgaccgt gacagccttttgggcctggcctaacaacaccgagacagacttcaagtgcaagtgg accctgacctccggcacccctagcggctgcgagaatatcagcggagccttcgcca gcaaccggaccttcgatatcaccgtgtctggcctgggcaccgcccccaagaccct gatcatcaccagaaccgccacaaatgccaccaccacaacccacaaagtgatcttc agcaaggcccccggctct |
| 133 | gp350 B95-8 (2-425) WDN162-4AAA Avi | EAALLVCQYTIQSLIHLTGEDPGFFNVEIPEFPFYPTCN VCTADVNVTINFDVGGKKHQLDLDFGQLTPHTKAVYQPR GAFGGSENATNLFLLELLGAGELALTMRSKKLPINVTTG EEQQVSLESVDVYFQDVFGTMWCHHAEMQNPVYLIPETV PYIK**AAA**CNSTNITAVVRAQGLDVTLPLSLPTSAQDSNF SVKTEMLGNEIDIECIMEDGEISQVLPGDNKFNITCSGY ESHVPSGGILTSTSPVATPIPGTGYAYSLRLTPRPVSRF LGNNSILYVFYSGNGPKASGGDYCIQSNIVFSDEIPASQ DMPTNTTDITYVGDNATYSVPMVTSEDANSPNVTVTAFW AWPNNTETDFKCKWTLTSGTPSGCENISGAFASNRTFDI TVSGLGTAPKTLIITRTATNATTTTHKVIFSKAPGS |
| 134 | NAM encoding SEQ ID NO: 133 | gaagctgccctgctcgtgtgccagtacaccatccagagcctgatccacctgaccg gcgaggaccccggcttcttcaacgtggaaatccccgagttccccttctaccctacct gcaacgtgtgcaccgccgacgtgaacgtgaccatcaacttcgacgtgggcggca agaagcaccagctggacctggatttcggccagctgacccctcacaccaaggccgt gtatcagcccagaggcgcctttggcggcagcgagaacgccaccaatctgtttctgc tggaactcctaggcgccggcgagctggccctgaccatgagaagcaagaaactgc ccatcaatgtgaccacaggcgaggaacagcaggtgtccctggaaagcgtgg acg tgtactttcaagacgtgttcggcaccatgtggtgccaccacgccgagatgcagaac cccgtgtacctgatccccgagacagtgccctacatcaaggccgccgcctgcaaca gcaccaacatcaccgccgtcgtgcgggcccagggactggatgtgacactgcctct |

-continued

| SEQ ID NO | Description | Sequence |
|---|---|---|
| | | gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagacccgtgtccagattcctg<br>ggcaacaacagcatcctgtacgtgttctacagcggcaacggccccaaggcctctg<br>gcggcgattactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagccccaacgtgaccgt<br>gacagccttttgggcctggcctaacaacaccgagacagacttcaagtgcaagtgg<br>accctgacctccggcacccctagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 135 | gp350 B95-8 (2-425) D296R/1160R Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PY**RK**WDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGS |
| 136 | NAM encoding SEQ ID NO: 135 | gaagctgccctgctcgtgtgccagtacaccatccagagcctgatccacctgaccg<br>gcgaggaccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgacccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtggacg<br>tgtactttcaagacgtgttcggcaccatgtggtgccaccacgccgagatgcagaac<br>cccgtgtacctgatccccgagacagtgccctaccggaagtgggacaactgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagacccgtgtccagattcctg<br>ggcaacaacagcatcctgtacgtgttctacagcggcaacggccccaaggcctctg<br>gcggccggtactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagccccaacgtgaccgt<br>gacagccttttgggcctggcctaacaacaccgagacagacttcaagtgcaagtgg<br>accctgacctccggcacccctagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 137 | gp350 B95-8 (2-425) D296R/P158R Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>**R**YIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGS |
| 138 | NAM encoding SEQ ID NO: 137 | gaagctgccctgctcgtgtgccagtacaccatccagagcctgatccacctgaccg<br>gcgaggaccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgacccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtgg acg<br>tgtactttcaagacgtgttcggcaccatgtggtgccaccacgccgagatgcagaac<br>cccgtgtacctgatccccgagacagtgcggtacatcaagtgggacaactgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt |

-continued

| SEQ ID NO | Description | Sequence |
| --- | --- | --- |
| | | gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagacccgtgtccagattcctg<br>ggcaacaacagcatcctgtacgtgttctacagcggcaacggccccaaggcctctg<br>gcggccggtactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagccccaacgtgaccgt<br>gacagccttttgggcctggcctaacaacaccgagacagacttcaagtgcaagtgg<br>accctgacctccggcacccctagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 139 | gp350 B95-8 (2-425)<br>D296R/P158N*/I160T Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>**N**Y**T**KWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGS |
| 140 | NAM encoding SEQ ID<br>NO: 139 | gaagctgccctgctcgtgtgccagtacaccatccagagcctgatccacctgaccg<br>gcgaggaccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgacccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtggacg<br>tgtactttcaagacgtgttcggcaccatgtggtgccaccacgccgagatgcagaac<br>cccgtgtacctgatccccgagacagtgaactacaccaagtgggacaactgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagacccgtgtccagattcctg<br>ggcaacaacagcatcctgtacgtgttctacagcggcaacggccccaaggcctctg<br>gcggccggtactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagccccaacgtgaccgt<br>gacagccttttgggcctggcctaacaacaccgagacagacttcaagtgcaagtgg<br>accctgacctccggcacccctagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 141 | gp350 B95-8 (2-425)<br>D296R/P158R/I160R Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>**R**Y**R**KWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGS |
| 142 | NAM encoding SEQ ID<br>NO: 141 | gaagctgccctgctcgtgtgccagtacaccatccagagcctgatccacctgaccg<br>gcgaggaccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgacccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtgg acg<br>tgtactttcaagacgtgttcggcaccatgtggtgccaccacgccgagatgcagaac<br>cccgtgtacctgatccccgagacagtgcggtaccggaagtgggacaactgcaac<br>agcaccaacatcaccgccgtcgtgcgggcccagggactggatgtgacactgcct<br>ctgagcctgcctaccagcgcccaggacagcaacttcagcgtgaaaaccgagatg<br>ctgggcaacgagatcgacatcgagtgcatcatggaagatggcgagatcagccag<br>gtgctgcccggcgacaacaagttcaacatcacatgcagcggctacgagagccac<br>gtgccatctggcggcatcctgaccagcacaagcccagtggccacacccatccctg |

-continued

| SEQ ID NO | Description | Sequence |
|---|---|---|
| | | gcacaggctacgcctacagcctgagactgacccccagacccgtgtccagattcct<br>gggcaacaacagcatcctgtacgtgttctacagcggcaacggccccaaggcctct<br>ggcggccggtactgtatccagagcaacatcgtgttcagcgacgagatccccgcca<br>gccaggacatgcccaccaataccaccgacatcacgtacgtgggcgacaatgcca<br>cctacagcgtgccaatggtcacctccgaggacgccaacagccccaacgtgaccg<br>tgacagccttttgggcctggcctaacaacaccgagacagacttcaagtgcaagtgg<br>accctgacctccggcacccctagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 143 | gp350 B95-8 (2-425)<br>Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 144 | NAM encoding SEQ ID<br>NO: 143 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>ccctacatcaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggcgattactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 145 | gp350 B95-8 (2-425) Q122N*<br>Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQ**N**VSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 146 | NAM encoding SEQ ID<br>NO: 145 | gaagctgccctgctcgtgtgccagtacaccatccagagc<br>ctgatccacctgaccggcgaggaccccggcttcttcaac<br>gtggaaatccccgagttccccttctaccctacctgcaac |

-continued

| SEQ ID NO | Description | Sequence |
|---|---|---|
| | | gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagaacgtgtccctggaaagcgtggacgtgtac<br>tttcaagacgtgttcggcaccatgtggtgccaccacgcc<br>gagatgcagaaccccgtgtacctgatccccgagacagtg<br>ccctacatcaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggcgattactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 147 | gp350 B95-8 (2-425)<br>D163N*/164bS Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKW**N**N**S**CNSTNITAVVRAQGLDVTLPLSLPTSAQDSN<br>FSVKTEMLGNEIDIECIMEDGEISQVLPGDNKFNITCSG<br>YESHVPSGGILTSTSPVATPIPGTGYAYSLRLTPRPVSR<br>FLGNNSILYVFYSGNGPKASGGDYCIQSNIVFSDEIPAS<br>QDMPTNTTDITYVGDNATYSVPMVTSEDANSPNVTVTAF<br>WAWPNNTETDFKCKWTLTSGTPSGCENISGAFASNRTFD<br>ITVSGLGTAPKTLIITRTATNATTTTHKVIFSKAPGSGL<br>NDIFEAQKIEWHEHHHHHH |
| 148 | NAM encoding SEQ ID<br>NO: 147 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>ccctacatcaagtggaacaacagctgcaacagcaccaac<br>atcaccgccgtcgtgcgggcccagggactggatgtgaca<br>ctgcctctgagcctgcctaccagcgcccaggacagcaac<br>ttcagcgtgaaaaccgagatgctgggcaacgagatcgac<br>atcgagtgcatcatggaagatggcgagatcagccaggtg<br>ctgcccggcgacaacaagttcaacatcacatgcagcggc<br>tacgagagccacgtgccatctggcggcatcctgaccagc<br>acaagcccagtggccacacccatccctggcacaggctac<br>gcctacagcctgagactgacccccagacccgtgtccaga<br>ttcctgggcaacaacagcatcctgtacgtgttctacagc<br>ggcaacggccccaaggcctctggcggcgattactgtatc<br>cagagcaacatcgtgttcagcgacgagatccccgccagc<br>caggacatgcccaccaataccaccgacatcacgtacgtg<br>ggcgacaatgccacctacagcgtgccaatggtcacctcc<br>gaggacgccaacagccccaacgtgaccgtgacagccttt<br>tgggcctggcctaacaacaccgagacagacttcaagtgc<br>aagtggaccctgacctccggcacccctagcggctgcgag<br>aatatcagcggagccttcgccagcaaccggaccttcgat |

-continued

| SEQ ID NO | Description | Sequence |
|---|---|---|
| | | atcaccgtgtctggcctgggcaccgcccccaagaccctg<br>atcatcaccagaaccgccacaaatgccaccaccacaacc<br>cacaaagtgatcttcagcaaggcccccggctctggcctg<br>aacgacatttttgaggcccagaagattgagtggcatgaa<br>catcaccaccaccaccat |
| 149 | gp350 B95-8 (2-425) D296R Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 150 | NAM encoding SEQ ID NO: 149 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>ccctacatcaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 151 | gp350 B95-8 (2-425) WDN162-4AAA Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIK**AAA**CNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 152 | NAM encoding SEQ ID NO: 151 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc |

-continued

| SEQ ID NO | Description | Sequence |
|---|---|---|
| | | atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>ccctacatcaaggccgccgcctgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggcgattactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacattttttgaggcccagaagattgagtggcatgaacat<br>caccaccaccaccat |
| 153 | gp350 B95-8 (2-425)<br>D296R/I160R Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PY**R**KWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 154 | NAM encoding SEQ ID<br>NO: 153 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>ccctaccggaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacattttttgaggcccagaagattgagtggcatgaacat<br>caccaccaccaccat |

-continued

| SEQ ID NO | Description | Sequence |
|---|---|---|
| 155 | gp350 B95-8 (2-425) D296R/P158R Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>**R**YIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 156 | NAM encoding SEQ ID NO: 155 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>cggtacatcaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 157 | gp350 B95-8 (2-425) D296R/P158N*/I160T Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>**N**Y**T**KWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 158 | NAM encoding SEQ ID NO: 157 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>aactacaccaagtgggacaactgcaacagcaccaacatc |

-continued

| SEQ ID NO | Description | Sequence |
|---|---|---|
| | | accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 159 | gp350 B95-8 (2-425)<br>D296R/P158R/I160R<br>Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>**R**Y**R**KWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG**R**YCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 160 | NAM encoding SEQ ID<br>NO: 159 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>cggtaccggaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 161 | E7 clone Heavy Chain aa<br>sequence | QVQLVQSGADVRKPGASVKVSCKASTYIFTGYYIH<br>WVRQAPGRGLEWLGWIHPNSGGTTYSQMFQGRVT<br>MTRDRSITTSYMELSRLQSDDTAIYYCATLRFVEYSF<br>DSWGQGTLVTVSS |

-continued

| SEQ ID NO | Description | Sequence |
|---|---|---|
| 162 | E7 clone Heavy Chain nucleotide sequence | CAGGTGCAGCTGGTGCAGTCTGGCGCAGACGTGA GGAAGCCAGGAGCCTCCGTGAAGGTGTCTTGTAA GGCCAGCACCTACATCTTCACAGGCTACTATATCC ACTGGGTGAGGCAGGCACCAGGAAGGGGCCTGGA GTGGCTGGGCTGGATTCACCCTAACTCTGGCGGCA CCACATACAGCCAGATGTTTCAGGGCAGAGTGAC CATGACACGGGACAGATCCATCACCACATCTTATA TGGAGCTGAGCCGGCTGCAGTCCGACGATACCGC CATCTACTATTGCGCCACACTGAGATTCGTGGAGT ATTCTTTTGATAGCTGGGGCCAGGGCACCCTGGTG ACAGTGAGCTCC |
| 163 | E7 clone Heavy Chain CDR1 | TYIFTGY |
| 164 | E7 clone Heavy Chain CDR2 | HPNSGG |
| 165 | E7 clone Heavy Chain CDR3 | LRFVEYSFDS |
| 166 | E7 clone Kappa Chain aa sequence | EIVLTQSPGTLSLSPGERATLSCRASQSISSTYLAWYQ QIPGQAPRLLIYGASSRAAGIPDRFSGGSGTDFTLTI SRLEPEDFAVYYCQQYGSSPRSFGQGTKLEIK |
| 167 | E7 clone Kappa Chain nucleotide sequence | GAGATCGTGCTGACCCAGAGCCCAGGCACACTGA GCCTGTCCCCAGGAGAGAGGGCCACCCTGTCCTGT AGAGCCTCTCAGAGCATCAGCTCCACATACCTGGC CTGGTATCAGCAGATCCCAGGACAGGCACCTAGG CTGCTGATCTACGGAGCCTCTAGCAGGGCAGCAG GCATCCCCGACCGCTTCTCCGGCGGAGGCTCTGGC ACCGACTTCACCCTGACAATCTCTCGGCTGGAGCC TGAGGACTTCGCCGTGTACTATTGCCAGCAGTATG GCTCCTCTCCAAGGTCCTTTGGCCAGGGCACAAAG CTGGAGATCAAG |
| 168 | E7 clone Kappa Chain CDR1 | RASQSISSTYLA |
| 169 | E7 clone Kappa Chain CDR2 | GASSRAA |
| 170 | E7 clone Kappa Chain CDR3 | QQYGSSPRS |
| 171 | B8 clone Heavy Chain aa sequence | EVQLLESGGALVQPGGSLRLSCAASGFTFKTYAMSW VRQVPGKGLEWVSAISGSGTASYYADSVKGRFTLSR DNSKNTLYLQLSSLRDEDTGVYYCARRFLDWFGMD VWGLGTTVTVSS |
| 172 | B8 clone Heavy Chain nucleotide sequence | GAGGTGCAGCTGCTGGAGAGCGGCGGCGCCCTGG TGCAGCCAGGAGGCAGCCTGCGGCTGTCCTGTGCC GCCTCTGGCTTCACCTTTAAGACATACGCCATGTC CTGGGTGAGGCAGGTGCCTGGCAAGGGCCTGGAG TGGGTGTCTGCCATCTCCGGCTCTGGCACCGCCTC TTACTATGCCGACAGCGTGAAGGGCAGGTTCACCC TGAGCCGCGATAACTCCAAGAATACACTGTATCTG CAGCTGAGCTCCCTGCGGGACGAGGATACCGGCG TGTACTATTGCGCCCGGAGATTCCTGGACTGGTTT GGCATGGACGTGTGGGGCCTGGGCACCACAGTGA CAGTGTCTAGC |
| 173 | B8 clone Heavy Chain CDR1 | GFTFKTY |
| 174 | B8 clone Heavy Chain CDR2 | SGSGTA |
| 175 | B8 clone Heavy Chain CDR3 | RFLDWFGMDV |
| 176 | B8 clone Kappa Chain aa sequence | DIVMTQSPLSLPVTPGEPASISCLSSQSLLQSNGYNYV DWYLQKPGQSPQLLIYLGSNRASGVPDRFSGSGSGT DFTLKISRVEAEDVGVYYCMVTLHPPTFGQGAKVEI K |
| 177 | B8 clone Kappa Chain nucleotide sequence | GACATCGTGATGACCCAGTCCCCTCTGTCTCTGCC AGTGACACCCGGCGAGCCTGCCTCTATCAGCTGTC TGAGCTCCCAGAGCCTGCTGCAGTCCAACGGCTAC AATTATGTGGATTGGTACCTGCAGAAGCCAGGCC AGTCCCCCCAGCTGCTGATCTATCTGGGCTCTAAC AGGGCCAGCGGCGTGCCCGACAGATTCTCCGGCT CTGGCAGCGGCACCGACTTCACCCTGAAGATCTCT CGGGTGGAGGCAGAGGACGTGGGCGTGTACTATT |

-continued

| SEQ ID NO | Description | Sequence |
|---|---|---|
| | | GCATGGTGACCCTGCACCCACCTACATTCGGCCAG GGAGCCAAGGTGGAGATCAAG |
| 178 | B8 clone Kappa Chain CDR1 | LSSQSLLQSNGYNYVD |
| 179 | B8 clone Kappa Chain CDR2 | LGSNRAS |
| 180 | B8 clone Kappa Chain CDR3 | MVTLHPPT |
| 181 | B3 clone Heavy Chain aa sequence | EGQLVQSGGGLVQPGGSLTLSCEVSGFTFKNYEMN WVRQAPGKGLEWVSYISSGGIAIFHADSVKGRFTVS RDNAKNLLYLQMNSLRVEDTAVYYCARDENNVRR PFDHWGQGTLVTVSS |
| 182 | B3 clone Heavy Chain nucleotide sequence | GAGGGACAGCTGGTGCAGTCCGGCGGAGGCCTGG TGCAGCCAGGAGGCTCCCTGACCCTGTCTTGTGAG GTGAGCGGCTTCACCTTCAAGAACTACGAGATGA ATTGGGTGCGGCAGGCACCTGGCAAGGGCCTGGA GTGGGTGTCTTATATCAGCTCCGGCGGAATCGCAA TCTTCCACGCAGATTCCGTGAAGGGCAGGTTTACC GTGTCTCGCGACAACGCCAAGAATCTGCTGTACCT GCAGATGAACAGCCTGCGGGTGGAGGACACAGCC GTGTACTATTGCGCCAGGGATGAGAACAACGTGC GGCGGCCCTTCGACCACTGGGGACAGGGCACCCT GGTGACAGTGTCTAGC |
| 183 | B3 clone Heavy Chain CDR1 | GFTFKNY |
| 184 | B3 clone Heavy Chain CDR2 | SSGGIA |
| 185 | B3 clone Heavy Chain CDR3 | DENNVRRPFDH |
| 186 | B3 clone Lambda Chain aa sequence | QSVLTQPPSASGSPGQSVTISCTGSSSDVGAYDFVSW FQQYPGQAPKLIIYEVNKRPSGVPARFSGSKSGNTAS LTVSGLQAEDEADYFCFSYGGTTNLRVFGGGTKLT |
| 187 | B3 clone Lambda Chain nucleotide sequence | CAGTCTGTGCTGACCCAGCCACCTAGCGCCTCCGG CTCTCCCGGCCAGAGCGTGACCATCTCCTGTACAG GCAGCTCCTCTGACGTGGGCGCCTACGATTTCGTG AGCTGGTTTCAGCAGTATCCAGGCCAGGCCCCCAA GCTGATCATCTACGAGGTGAACAAGCGGCCTTCCG GCGTGCCAGCCAGATTCAGCGGCTCCAAGTCTGGC AATACCGCCTCTCTGACAGTGAGCGGCCTGCAGGC AGAGGACGAGGCAGATTACTTCTGCTTTTCTTATG GCGGCACCACAAACCTGCGGGTGTTTGGCGGCGG CACCAAGCTGACA |
| 188 | B3 clone Kappa Chain CDR1 | TGSSSDVGAYDFVS |
| 189 | B3 clone Kappa Chain CDR2 | EVNKRPS |
| 190 | B3 clone Kappa Chain CDR3 | FSYGGTTNLRV |
| 191 | C7 clone Heavy Chain aa sequence | EVQLVESGGNLVQPGASLRLSCTASRFNFNKYAMH WVRQTPGKGLEWVSAISWDSTYIDYGNSVKGRFTIS RDNTRNSLYLQMNSLTAEDTALYYCAKCEDYLRLC SAYDIWGHGTMVTVSS |
| 192 | C7 clone Heavy Chain nucleotide sequence | GAGGTGCAGCTGGTGGAGAGCGGCGGAAACCTGG TGCAGCCAGGAGCCTCTCTGAGGCTGAGCTGTACC GCCTCCCGCTTCAACTTTAATAAGTACGCAATGCA CTGGGTGCGGCAGACCCCTGGCAAGGGCCTGGAG TGGGTGTCTGCCATCAGCTGGGACTCCACATACAT CGATTATGGCAACTCCGTGAAGGGCAGGTTCACC ATCTCTCGGGACAACACAAGAAATAGCCTGTATCT GCAGATGAATTCCCTGACCGCCGAGGATACAGCC CTGTACTATTGCGCCAAGTGTGAGGACTACCTGCG GCTGTGCTCTGCCTATGATATCTGGGGCCACGGCA CCATGGTGACAGTGAGCTCC |
| 193 | C7 clone Heavy Chain CDR1 | RFNFNKY |
| 194 | C7 clone Heavy Chain CDR2 | SWDSTY |
| 195 | C7 clone Heavy Chain CDR3 | CEDYLRLCSAYDI |

-continued

| SEQ ID NO | Description | Sequence |
| --- | --- | --- |
| 196 | C7 clone Kappa Chain aa sequence | DIVMTQSPLSLPVTPGESASISCRSSQSLLHSNGKNYL SWYLQKPGQSPQLLIDLGSNRASGVSDRFSGSGSGT DFTLKISRVEADDVGVYYCMQAVQTPITFGQGTRLA IK |
| 197 | C7 clone Kappa Chain nucleotide sequence | GACATCGTGATGACCCAGTCTCCTCTGAGCCTGCC CGTGACACCTGGCGAGTCTGCCAGCATCTCCTGTC GGAGCTCCCAGAGCCTGCTGCACTCCAACGGCAA GAATTACCTGTCTTGGTATCTGCAGAAGCCAGGCC AGAGCCCCCAGCTGCTGATCGATCTGGGCTCCAAC AGGGCCTCCGGCGTGTCTGACAGATTCTCTGGCAG CGGCTCCGGCACCGACTTCACCCTGAAGATCAGCA GGGTGGAGGCCGACGATGTGGGCGTGTACTATTG CATGCAGGCCGTGCAGACCCCAATCACATTCGGCC AGGGAACCCGCCTGGCCATCAAG |
| 198 | C7 clone Kappa Chain CDR1 | RSSQSLLHSNGKNYLS |
| 199 | C7 clone Kappa Chain CDR2 | LGSNRAS |
| 200 | C7 clone Kappa Chain CDR3 | MQAVQTPIT |
| 201 | A9 clone Heavy Chain aa sequence | QVQLVQSGAELKTPGASVKVSCKASGYTFTGYYIH WVRQAPGEGLEWTGWINPNSGATRYGQKFQGRVTL TSDTSSSTVYMEVSNLTSDDSAVYYCARELSYSIRGT GPLGYWGLGTLVTVSS |
| 202 | A9 clone Heavy Chain nucleotide sequence | CAGGTGCAGCTGGTGCAGTCCGGCGCAGAGCTGA AGACCCCAGGAGCCAGCGTGAAGGTGTCCTGTAA GGCCTCTGGCTACACCTTCACAGGCTACTATATCC ACTGGGTGCGGCAGGCACCAGGAGAGGGCCTGGA GTGGACCGGCTGGATCAACCCTAATAGCGGCGCC ACAAGATACGGCCAGAAGTTTCAGGGCCGCGTGA CCCTGACAAGCGACACCAGCTCCTCTACAGTGTAT ATGGAGGTGTCCAACCTGACCTCCGACGATTCTGC CGTGTACTATTGCGCCCGGGAGCTGTCTTACAGCA TCAGAGGAACAGGACCACTGGGATATTGGGGCCT GGGCACCCTGGTGACAGTGAGCTCC |
| 203 | A9 clone Heavy Chain CDR1 | GYTFTGY |
| 204 | A9 clone Heavy Chain CDR2 | NPNSGA |
| 205 | A9 clone Heavy Chain CDR3 | ELSYSIRGTGPLGY |
| 206 | A9 clone Kappa Chain aa sequence | EIVLTQSPGTLSLSPGERATLSCRASQSVASKYLAWY QQKPGQAPRLLIYGASSRATGIPDRFSGSGSGTDFTL TISRLEPEDFAVYYCQYYGSSPLTFGQGTKVEIK |
| 207 | A9 clone Kappa Chain nucleotide sequence | GAGATCGTGCTGACCCAGTCTCCAGGCACACTGTC CCTGTCTCCAGGAGAGAGGGCCACCCTGTCTTGTA GAGCCAGCCAGTCCGTGGCCAGCAAGTACCTGGC CTGGTATCAGCAGAAGCCAGGACAGGCACCTAGG CTGCTGATCTACGGAGCCAGCTCCAGGGCAACCG GCATCCCCGACCGCTTCTCTGGCAGCGGCTCCGGC ACAGACTTCACCCTGACAATCTCCAGGCTGGAGCC TGAGGACTTCGCCGTGTACTATTGCCAGTACTATG GCTCTAGCCCACTGACCTTTGGCCAGGGCACAAAG GTGGAGATCAAG |
| 208 | A9 clone Kappa Chain CDR1 | RASQSVASKYLA |
| 209 | A9 clone Kappa Chain CDR2 | GASSRAT |
| 210 | A9 clone Kappa Chain CDR3 | QYYGSSPLT |
| 211 | A2 clone Heavy Chain aa sequence | EVQLAESGGGVVHPGGSLRLSCTASGFTFSRHSMHW VRQAPGKGLEWVAVISHDGSHKFYVDSVKGRFSISR DNAKNTLYLQMSSLSGADTAVYYCVKDISSRSYGY LAGDSWGQGSLVTVSS |
| 212 | A2 clone Heavy Chain nucleotide sequence | GAGGTGCAGCTGGCCGAGTCTGGCGGAGGAGTGG TGCACCCAGGAGGCTCCCTGAGGCTGTCTTGTACC GCCAGCGGCTTCACATTTTCTAGGCACAGCATGCA CTGGGTGCGCCAGGCACCTGGCAAGGGCCTGGAG TGGGTGGCCGTGATCTCCCACGACGGCTCTCACAA |

-continued

| SEQ ID NO | Description | Sequence |
|---|---|---|
| | | GTTCTACGTGGATTCCGTGAAGGGCCGGTTTAGCA TCTCCAGAGACAACGCCAAGAATACCCTGTATCTG CAGATGAGCTCCCTGTCTGGCGCCGACACAGCCGT GTACTATTGCGTGAAGGATATCTCTAGCAGGAGCT ACGGCTATCTGGCAGGCGATAGCTGGGGACAGGG CTCCCTGGTGACCGTGTCCTCT |
| 213 | A2 clone Heavy Chain CDR1 | GFTFSRH |
| 214 | A2 clone Heavy Chain CDR2 | SHDGSH |
| 215 | A2 clone Heavy Chain CDR3 | DISSRSYGYLAGDS |
| 216 | A2 clone Kappa Chain aa sequence | DIQMTQSPSSLSASVGDIITITCRASQSVVTYLNWYQ QKPGGAPRLLIYTTSKLQSGVPSRFSGSGSGTLFTLTI NGLRPEDFATYYCQQSYGTPPFTFGPGTRVEIN |
| 217 | A2 clone Kappa Chain nucleotide sequence | GATATTCAGATGACTCAGTCCCCAAGCAGCCTGAG CGCCTCCGTGGGCGACATCATCACCATCACATGCA GGGCCTCTCAGAGCGTGGTGACCTACCTGAACTGG TATCAGCAGAAGCCAGGAGGAGCACCTAGGCTGC TGATCTACACCACATCCAAGCTGCAGTCTGGCGTG CCATCCAGATTCTCCGGCTCTGGCAGCGGCACCCT GTTTACCCTGACAATCAATGGCCTGCGGCCCGAGG ATTTCGCCACATACTATTGTCAGCAGAGCTATGGA ACCCCCCCCTTTACTTTTGGACCAGGCACAAGAGT GGAGATTAAC |
| 218 | A2 clone Kappa Chain CDR1 | RASQSVVTYLN |
| 219 | A2 clone Kappa Chain CDR2 | TTSKLQS |
| 220 | A2 clone Kappa Chain CDR3 | QQSYGTPPFT |
| 221 | E1 clone Heavy Chain aa sequence | QVHLQQWGAGLVKPSETLSLTCAVQGGPFSGYYWS WIRQPPGKGLEWIGEINHSGNTHYNPSLKSRVTISVD TSGNYFSLKLTSVTAADAAVYFCARGQQLLRNYYY YSGMDVWGQGTTVTVSS |
| 222 | E1 clone Heavy Chain nucleotide sequence | CAGGTGCACCTGCAGCAGTGGGGAGCAGGCCTGG TGAAGCCATCCGAGACACTGTCTCTGACATGTGCA GTGCAGGGAGGACCCTTCTCTGGCTACTATTGGAG CTGGATCAGGCAGCCACCTGGCAAGGGCCTGGAG TGGATCGGCGAGATCAACCACAGCGGCAATACCC ACTACAACCCCTCTCTGAAGAGCCGGGTGACCATC AGCGTGGACACATCCGGCAATTACTTCTCCCTGAA GCTGACCTCTGTGACAGCCGCCGATGCCGCCGTGT ATTTTTGCGCCCGGGGCCAGCAGCTGCTGAGAAAC TACTATTACTATTCCGGCATGGACGTGTGGGGACA GGGAACCACAGTGACAGTGAGCTCC |
| 223 | E1 clone Heavy Chain CDR1 | GGPFSGY |
| 224 | E1 clone Heavy Chain CDR2 | NHSGN |
| 225 | E1 clone Heavy Chain CDR3 | GQQLLRNYYYYSGMDV |
| 226 | E1 clone Kappa Chain aa sequence | EIVLTQSPGTLSLSPGERATLSCRASQSVTSTYLAWY QQKLGQPPRLLIFGASNRATGIPDRFSGSGSGTDFTLT ITRLEPEDFAVYYCQRYGGSITFGQGTRLEIK |
| 227 | E1 clone Kappa Chain nucleotide sequence | GAGATCGTGCTGACACAGTCCCCAGGCACCCTGA GCCTGTCCCCAGGAGAGCGGGCCACACTGTCCTGT AGAGCCTCTCAGAGCGTGACCTCTACATACCTGGC CTGGTATCAGCAGAAGCTGGGCCAGCCCCCTAGG CTGCTGATCTTCGGCGCCTCTAACAGGGCCACAGG CATCCCTGACCGCTTCTCCGGCTCTGGCAGCGGCA CCGACTTCACCCTGACAATCACCAGACTGGAGCCC GAGGACTTCGCCGTGTACTATTGCCAGCGGTACGG CGGCAGCATCACATTTGGCCAGGGCACCAGACTG GAGATCAAG |
| 228 | E1 clone Kappa Chain CDR1 | RASQSVTSTYLA |
| 229 | E1 clone Kappa Chain CDR2 | GASNRAT |

-continued

| SEQ ID NO | Description | Sequence |
| --- | --- | --- |
| 230 | E1 clone Kappa Chain CDR3 | QRYGGSIT |
| 231 | C10 clone Heavy Chain aa sequence | EVQLVQSGGGVVQPRRSLRLSCAASGFTFSNYGMH WVRQVPGKGLQWVAIIWYDGSNKHYAASVQGRFRI SRDNSKNTVYLQMDGLRAEDTGMYYCVRDATTAT TEGTSQYYFDLWGQGALVTVSS |
| 232 | C10 clone Heavy Chain nucleotide sequence | GAGGTGCAGCTGGTGCAGTCCGGCGGAGGAGTGG TGCAGCCACGGAGATCTCTGAGGCTGAGCTGTGCC GCCTCCGGCTTCACCTTTTCTAACTACGGAATGCA CTGGGTGCGCCAGGTGCCTGGCAAGGGCCTGCAG TGGGTGGCCATCATCTGGTACGACGGCTCCAATAA GCACTATGCCGCCTCTGTGCAGGGCAGGTTCCGCA TCTCTCGGGATAACAGCAAGAATACCGTGTATCTG CAGATGGACGGCCTGCGGGCCGAGGATACAGGCA TGTACTATTGCGTGAGAGACGCCACCACAGCCACC ACAGAGGGCACCAGCCAGTACTATTTTGATCTGTG GGGACAGGGCGCCCTGGTGACAGTGAGCTCC |
| 233 | C10 clone Heavy Chain CDR1 | GFTFSNY |
| 234 | C10 clone Heavy Chain CDR2 | WYDGSN |
| 235 | C10 clone Heavy Chain CDR3 | DATTATTEGTSQYYFDL |
| 236 | C10 clone Kappa Chain aa sequence | DIVMTQSPDSLAVSLGERATINCKSSQTLLYTSNSKN YLAWYQQKVGQPPRLLIYWASTRESGVPDRFSGSGS GTDFTLTISSLLAEDVAVYYCQQYYTTPLTFGGGTK VEVK |
| 237 | C10 clone Kappa Chain nucleotide sequence | GACATCGTGATGACCCAGAGCCCCGATTCCCTGGC CGTGTCTCTGGGAGAGAGGGCAACAATCAACTGT AAGAGCTCCCAGACCCTGCTGTACACATCCAACTC TAAGAATTACCTGGCCTGGTATCAGCAGAAAGTG GGACAGCCACCTAGGCTGCTGATCTATTGGGCCTC TACCAGGGAGAGCGGCGTGCCAGACAGATTCAGC GGCTCCGGCTCTGGCACAGACTTCACCCTGACAAT CTCTAGCCTGCTGGCCGAGGACGTGGCCGTGTACT ATTGCCAGCAGTACTATACCACACCCCTGACCTTC GGCGGCGGCACAAAGGTGGAGGTGAAG |
| 238 | C10 clone Kappa Chain CDR1 | KSSQTLLYTSNSKNYLA |
| 239 | C10 clone Kappa Chain CDR2 | WASTRES |
| 240 | C10 clone Kappa Chain CDR3 | QQYYTTPLT |
| 241 | B12 clone Heavy Chain aa sequence | EVQLVESGGGVVHPGKSLTLSCEASGFTFNDHGIHW VRRAPGKGLEWLALISKDGSKEYSTDSVKGRFTVSR DNSRNTVFLQMKSLTTEDTAIYYCAKDMGQCSSPSC STMDSYFAMDVWGQGTTVIVSS |
| 242 | B12 clone Heavy Chain nucleotide sequence | GAGGTGCAGCTGGTGGAGTCCGGCGGAGGAGTGG TGCACCCTGGCAAGTCTCTGACCCTGAGCTGTGAG GCCAGCGGCTTCACCTTCAACGACCACGGCATCCA CTGGGTGCGGAGAGCACCTGGCAAGGGCCTGGAG TGGCTGGCCCTGATCTCTAAGGACGGCAGCAAGG AGTACAGCACCGATTCCGTGAAGGGCCGGTTCAC AGTGTCCAGGGATAACTCTCGCAATACCGTGTTTC TGCAGATGAAGTCTCTGACCACAGAGGACACAGC CATCTACTATTGCGCCAAGGATATGGGCCAGTGCA GCTCCCCCTCCTGTTCTACCATGGACAGCTATTTC GCAATGGACGTGTGGGGACAGGGAACCACAGTGA TCGTGTCTAGC |
| 243 | B12 clone Heavy Chain CDR1 | GFTFNDH |
| 244 | B12 clone Heavy Chain CDR2 | SKDGSK |
| 245 | B12 clone Heavy Chain CDR3 | DMGQCSSPSCSTMDSYFAMDV |
| 246 | B12 clone Kappa Chain aa sequence | DIVMTQSPLSLPVTPGEPASISCRSSQNLRHNNGYNY LNWYLQKPGQSPQLLIYLGSIRASGVPDRFSGSGSGT DFTLKISRVEAEDVGVYYCMQALQTPPWTFGQGTK VDFK |

-continued

| SEQ ID NO | Description | Sequence |
|---|---|---|
| 247 | B12 clone Kappa Chain nucleotide sequence | GACATCGTGATGACCCAGTCCCCTCTGTCTCTGCC AGTGACACCCGGCGAGCCTGCCTCTATCAGCTGTC GGAGCTCCCAGAACCTGAGACACAACAATGGCTA CAACTATCTGAATTGGTACCTGCAGAAGCCAGGCC AGTCTCCCCAGCTGCTGATCTATCTGGGCAGCATC AGGGCCTCCGGCGTGCCCGACCGCTTCTCCGGCTC TGGCAGCGGCACCGACTTCACCCTGAAGATCAGC CGGGTGGAGGCAGAGGACGTGGGCGTGTACTATT GCATGCAGGCCCTGCAGACCCCCCCTTGGACATTC GGCCAGGGCACCAAGGTGGACTTCAAG |
| 248 | B12 clone Kappa Chain CDR1 | RSSQNLRHNNGYNYLN |
| 249 | B12 clone Kappa Chain CDR2 | LGSIRAS |
| 250 | B12 clone Kappa Chain CDR3 | MQALQTPPWT |
| 251 | G7 clone Heavy Chain aa sequence | QVQLVQSGAEVKKPGASVKVSCKASGYTFTSHYMH WVRQAPGQGLEWMGIISPTGDFTNYAQKFQGRVTL TRDTSTSTDYMEVTSLRSEDTAVYYCARDCSAWAP DYWGQGTLVTVSS |
| 252 | G7 clone Heavy Chain nucleotide sequence | CAGGTGCAGCTGGTGCAGTCCGGCGCAGAGGTGA AGAAGCCAGGAGCCAGCGTGAAGGTGTCCTGTAA GGCCTCTGGCTACACCTTCACATCTCACTATATGC ACTGGGTGCGGCAGGCACCAGGACAGGGCCTGGA GTGGATGGGCATCATCAGCCCTACAGGCGACTTCA CCAACTACGCCCAGAAGTTTCAGGGCCGGGTGAC CCTGACAAGAGACACCTCTACAAGCACCGATTAT ATGGAGGTGACATCCCTGAGGTCTGAGGATACCG CCGTGTACTATTGCGCAAGGGACTGTTCCGCCTGG GCCCCCGATTACTGGGGACAGGGCACACTGGTGA CCGTGAGCTCC |
| 253 | G7 clone Heavy Chain CDR1 | GYTFTSH |
| 254 | G7 clone Heavy Chain CDR2 | SPTGDF |
| 255 | G7 clone Heavy Chain CDR3 | DCSAWAPDY |
| 256 | G7 clone Kappa Chain aa sequence | QSALTRPPSVSRCPGQSITISCSGTSSDVGHDNHVSW YQQHPGRAPKLMVYEVRNRPSGVSDRFSGSKSGNT ASLTISGLQAEDEATYYCCSYTTTHRYIFGGGTKLT |
| 257 | G7 clone Kappa Chain nucleotide sequence | CAGTCTGCCCTGACAAGGCCCCCTTCTGTGAGCCG CTGCCCTGGACAGAGCATCACAATCTCCTGTTCTG GCACCAGCTCCGACGTGGGCCACGATAACCACGT GTCCTGGTACCAGCAGCACCCAGGAAGGGCACCC AAGCTGATGGTGTATGAGGTGCGGAACAGACCAA GCGGCGTGTCCGACAGGTTCAGCGGCTCCAAGTCT GGCAATACAGCCTCTCTGACCATCAGCGGCCTGCA GGCAGAGGATGAGGCAACCTACTATTGCTGTTCTT ACACCACAACCCACCGGTATATCTTTGGCGGCGGC ACAAAGCTGACC |
| 258 | G7 clone Kappa Chain CDR1 | SGTSSDVGHDNHVS |
| 259 | G7 clone Kappa Chain CDR2 | EVRNRPS |
| 260 | G7 clone Kappa Chain CDR3 | CSYTTTHRYI |
| 261 | E11 clone Heavy Chain aa sequence | QVQLLGSGPGLVKPSETLSLTCTVSGASISSPGYYWG FIRQSPGKGLEWIGSMVSGGTTYYNPSLKSRVTISMD MSNNQFSLRLNSVTAADTALYYCARGSRQLVRRATI DYWGQGALFTVSP |
| 262 | E11 clone Heavy Chain nucleotide sequence | CAGGTGCAGCTGCTGGGCAGCGGCCCAGGCCTGG TGAAGCCTTCTGAGACACTGAGCCTGACCTGTACA GTGTCTGGCGCCAGCATCAGCTCCCCAGGCTACTA TTGGGGCTTCATCAGGCAGAGCCCAGGCAAGGGC CTGGAGTGGATCGGCTCCATGGTGTCTGGCGGCAC CACATACTATAACCCTAGCCTGAAGTCCCGGGTGA CAATCTCCATGGACATGTCTAACAATCAGTTCAGC CTGAGGCTGAATTCCGTGACCGCCGCCGATACAGC |

-continued

| SEQ ID NO | Description | Sequence |
|---|---|---|
| | | CCTGTACTATTGCGCAAGGGGCTCCCGCCAGCTGG TGCGGAGAGCAACCATCGACTACTGGGGACAGGG CGCCCTGTTTACAGTGTCTCCC |
| 263 | E11 clone Heavy Chain CDR1 | GASISSPGY |
| 264 | E11 clone Heavy Chain CDR2 | VSGGT |
| 265 | E11 clone Heavy Chain CDR3 | GSRQLVRRATIDY |
| 266 | E11 clone Lambda Chain aa sequence | QSVLTGPPSVSAGPGQQVFISCSGNSSNIGNNYVSWY QQLPGTAPKLLIYDSNKRPSGIPDRFSGSKSGTSATLG ITGLQTGDEADYYCGTWDSSLSAGVFGGGTKLT |
| 267 | E11 clone Lambda Chain nucleotide sequence | CAGTCTGTGCTGACCGGACCACCTTCCGTGTCTGC CGGACCAGGACAGCAGGTGTTCATCAGCTGTTCCG GCAACAGCTCCAATATCGGCAACAATTACGTGTCT TGGTATCAGCAGCTGCCAGGCACAGCCCCCAAGC TGCTGATCTACGACTCTAACAAGCGGCCTAGCGGC ATCCCAGATAGATTCTCTGGCAGCAAGTCCGGCAC CAGCGCCACACTGGGCATCACCGGCCTGCAGACA GGCGACGAGGCAGATTACTATTGCGGAACCTGGG ACTCTAGCCTGTCCGCCGGCGTGTTTGGAGGAGGA ACCAAGCTGACA |
| 268 | E11 clone Lambda Chain CDR1 | SGNSSNIGNNYVS |
| 269 | E11 clone Lambda Chain CDR2 | DSNKRPS |
| 270 | E11 clone Lambda Chain CDR3 | GTWDSSLSAGV |
| 271 | G5 clone Heavy Chain aa sequence | EVQLVESGGGLVKPGESLRLSCAASGFTFSSYSMSW VRQAPGKGLEWVSCITSSGHTYYADSVKGRFAISRD NGKNSLYLQMNNLRAEDTAVYFCAKELGAHSGLFY NGVFDYWGQGNPVTVSS |
| 272 | G5 clone Heavy Chain nucleotide sequence | GAGGTGCAGCTGGTGGAGTCCGGCGGAGGCCTGG TGAAGCCAGGCGAGTCTCTGAGGCTGAGCTGTGC CGCCTCCGGCTTCACCTTTAGCTCCTACAGCATGT CCTGGGTGCGCCAGGCACCTGGCAAGGGCCTGGA GTGGGTGTCCTGCATCACCTCTAGCGGCCACACAT ACTATGCCGACTCTGTGAAGGGCCGGTTCGCCATC AGCCGGGATAACGGCAAGAATAGCCTGTACCTGC AGATGAACAATCTGCGGGCCGAGGACACCGCCGT GTATTTTTGTGCAAAGGAGCTGGGAGCACACTCTG GCCTGTTCTACAACGGCGTGTTTGATTATTGGGGC CAGGGCAATCCCGTGACAGTGTCCTCT |
| 273 | G5 clone Heavy Chain CDR1 | GFTFSSY |
| 274 | G5 clone Heavy Chain CDR2 | TSSGH |
| 275 | G5 clone Heavy Chain CDR3 | ELGAHSGLFYNGVFDY |
| 276 | G5 clone Lambda Chain aa sequence | QSALTQPASVSGSPGQSITISCTGTSSDVGGYNYVSW YQQHPGKAPKLMIYEVSNRPSGVSNRFSGSKGNTAS LTISGLRGEDEADYYCSSYTSSSTLVVFGGGTKLT |
| 277 | G5 clone Lambda Chain nucleotide sequence | CAGTCCGCCCTGACCCAGCCAGCCTCCGTGTCTGG CAGCCCCGGCCAGTCTATCACAATCAGCTGTACCG GCACAAGCTCCGACGTGGGCGGCTACAACTACGT GAGCTGGTACCAGCAGCACCCAGGCAAGGCACCT AAGCTGATGATCTATGAGGTGTCCAACAGGCCAA GCGGCGTGTCCAATAGATTCTCCGGCTCTAAGGGC AATACCGCCTCCCTGACAATCTCTGGCCTGAGGGG AGAGGACGAGGCAGATTACTATTGCTCTAGCTAC ACCTCCTCTAGCACACTGGTGGTGTTTGGCGGCGG CACCAAGCTGACA |
| 278 | G5 clone Lambda Chain CDR1 | TGTSSDVGGYNYVS |

-continued

| SEQ ID NO | Description | Sequence |
|---|---|---|
| 279 | G5 clone Lambda Chain CDR2 | EVSNRPS |
| 280 | G5 clone Lambda Chain CDR3 | SSYTSSSTLVV |
| 281 | H8 clone Heavy Chain aa sequence | QVHLQQWGAGLVKPSETLSLTCAVQGGPFSGYYWS WIRQPPGKGLEWIGEINHSGNTHYNPSLKSRVTISVD TSGNYFSLKLTSVTAADAAVYFCARGQQLLRNYYY YSGMDVWGQGTTVTVSS |
| 282 | H8 clone Heavy Chain nucleotide sequence | CAGGTGCACCTGCAGCAGTGGGGAGCAGGCCTGG TGAAGCCATCCGAGACACTGTCTCTGACATGTGCA GTGCAGGGAGGACCCTTCTCTGGCTACTATTGGAG CTGGATCAGGCAGCCACCTGGCAAGGGCCTGGAG TGGATCGGCGAGATCAACCACAGCGGCAATACCC ACTACAACCCCTCTCTGAAGAGCCGGGTGACCATC AGCGTGGACACATCCGGCAATTACTTCTCCCTGAA GCTGACCTCTGTGACAGCCGCCGATGCCGCCGTGT ATTTTTGCGCCCGGGGCCAGCAGCTGCTGAGAAAC TACTATTACTATTCCGGCATGGACGTGTGGGGACA GGGAACCACAGTGACAGTGAGCTCC |
| 283 | H8 clone Heavy Chain CDR1 | GGPFSGY |
| 284 | H8 clone Heavy Chain CDR2 | NHSGN |
| 285 | H8 clone Heavy Chain CDR3 | GQQLLRNYYYYSGMDV |
| 286 | H8 clone Lambda Chain aa sequence | QSALTQPASVSGSPGQSITISCTETSRDVGDYNYVSW YQQHPGPAPKLIMYEVHKRPSGISNRFSGSKSGTTAS LTISGLQADDEGDYYCSSYTDKNTYVFGSGTQVT |
| 287 | H8 clone Lambda Chain nucleotide sequence | CAGTCTGCCCTGACCCAGCCAGCCTCTGTGAGCGG CTCCCCTGGCCAGTCCATCACAATCTCTTGTACCG AGACATCTCGGGACGTGGGCGATTACAACTATGT GAGCTGGTACCAGCAGCACCCAGGACCTGCACCA AAGCTGATCATGTATGAGGTGCACAAGCGGCCCT CTGGCATCAGCAATAGATTCTCTGGCAGCAAGTCC GGCACCACAGCCAGCCTGACCATCTCCGGCCTGCA GGCAGACGATGAGGGCGACTACTATTGCAGCTCC TACACCGATAAGAACACATACGTGTTCGGCAGCG GCACCCAGGTGACA |
| 288 | H8 clone Lambda Chain CDR1 | TETSRDVGDYNYVS |
| 289 | H8 clone Lambda Chain CDR2 | EVHKRPS |
| 290 | H8 clone Lambda Chain CDR3 | SSYTDKNTYV |
| 291 | gp350 B95-8 (2-425) D296R/I160R Avi-His | EAALLVCQYTIQSLIHLTGEDPGFFNVEIPEFPFYPTC NVCTADVNVTINFDVGGKKHQLDLDFGQLTPHTKA VYQPRGAFGGSENATNLFLLELLGAGELALTMRSKK LPINVTTGEEQQVSLESVDVYFQDVFGTMWCHHAE MQNPVYLIPETVPYIDWDNCNSTNITAVVRAQGLDV TLPLSLPTSAQDSNFSVKTEMLGNEIDIECIMEDGEIS QVLPGDNKFNITCSGYESHVPSGGILTSTSPVATPIPG TGYAYSLRLTPRPVSRFLGNNSILYVFYSGNGPKASG GRYCIQSNIVFSDEIPASQDMPTNTTDITYVGDNATY SVPMVTSEDANSPNVTVTAFWAWPNNTETDFKCKW TLTSGTPSGCENISGAFASNRTFDITVSGLGTAPKTLII TRTATNATTTTHKVIFSKAPGSGLNDIFEAQKIEWHE HHHHHH |
| 292 | NAM encoding SEQ ID NO: 281 | GAAGCTGCCCTGCTCGTGTGCCAGTACACCATCCA GAGCCTGATCCACCTGACCGGCGAGGACCCCGGC TTCTTCAACGTGGAAATCCCCGAGTTCCCCTTCTA CCCTACCTGCAACGTGTGCACCGCCGACGTGAACG TGACCATCAACTTCGACGTGGGCGGCAAGAAGCA CCAGCTGGACCTGGATTTCGGCCAGCTGACCCCTC ACACCAAGGCCGTGTATCAGCCCAGAGGCGCCTTT GGCGGCAGCGAGAACGCCACCAATCTGTTTCTGCT |

-continued

| SEQ ID NO | Description | Sequence |
|---|---|---|
| | | GGAACTCCTAGGCGCCGGCGAGCTGGCCCTGACC<br>ATGAGAAGCAAGAAACTGCCCATCAATGTGACCA<br>CAGGCGAGGAACAGCAGGTGTCCCTGGAAAGCGT<br>GGACGTGTACTTTCAAGACGTGTTCGGCACCATGT<br>GGTGCCACCACGCCGAGATGCAGAACCCCGTGTA<br>CCTGATCCCCGAGACAGTGCCCTACATCGATTGGG<br>ACAACTGCAACAGCACCAACATCACCGCCGTCGT<br>GCGGGCCCAGGGACTGGATGTGACACTGCCTCTG<br>AGCCTGCCTACCAGCGCCCAGGACAGCAACTTCA<br>GCGTGAAAACCGAGATGCTGGGCAACGAGATCGA<br>CATCGAGTGCATCATGGAAGATGGCGAGATCAGC<br>CAGGTGCTGCCCGGCGACAACAAGTTCAACATCA<br>CATGCAGCGGCTACGAGAGCCACGTGCCATCTGG<br>CGGCATCCTGACCAGCACAAGCCCAGTGGCCACA<br>CCCATCCCTGGCACAGGCTACGCCTACAGCCTGAG<br>ACTGACCCCCAGACCCGTGTCCAGATTCCTGGGCA<br>ACAACAGCATCCTGTACGTGTTCTACAGCGGCAAC<br>GGCCCCAAGGCCTCTGGCGGCCGGTACTGTATCCA<br>GAGCAACATCGTGTTCAGCGACGAGATCCCCGCC<br>AGCCAGGACATGCCCACCAATACCACCGACATCA<br>CGTACGTGGGCGACAATGCCACCTACAGCGTGCC<br>AATGGTCACCTCCGAGGACGCCAACAGCCCCAAC<br>GTGACCGTGACAGCCTTTTGGGCCTGGCCTAACAA<br>CACCGAGACAGACTTCAAGTGCAAGTGGACCCTG<br>ACCTCCGGCACCCCTAGCGGCTGCGAGAATATCA<br>GCGGAGCCTTCGCCAGCAACCGGACCTTCGATATC<br>ACCGTGTCTGGCCTGGGCACCGCCCCCAAGACCCT<br>GATCATCACCAGAACCGCCACAAATGCCACCACC<br>ACAACCCACAAAGTGATCTTCAGCAAGGCCCCCG<br>GCTCTGGCCTGAACGACATTTTTGAGGCCCAGAAG<br>ATTGAGTGGCATGAACATCACCACCACCACCAT |
| 293 | Macaque Light chain backbone nucleotide sequence | tcgcgcgttt cggtgatgac ggtgaaaacc tctgacacat gcagctcccg<br>gagacggtca cagcttgtct gtaagcggat gccgggagca gacaagcccg<br>tcagggcgcg tcagcgggtg ttggcgggtg tcggggctgg cttaactatg<br>cggcatcaga gcagattgta ctgagagtgc accatatgcg gtgtgaaata<br>ccgcacagat gcgtaaggag aaaataccgc atcagattgg<br>ctattggcca ttgcatacgt tgtatccata tcataatatg tacatttata<br>ttggctcatg tccaacatta ccgccatgtt gacattgatt attgactagt<br>tattaatagt aatcaattac ggggtcatta gttcatagcc catatatgga<br>gttccgcgtt acataactta cggtaaatgg cccgcctggc tgaccgccca<br>acgacccccg cccattgacg tcaataatga cgtatgttcc<br>catagtaacg ccaataggga ctttccattg acgtcaatgg gtggagtatt<br>tacggtaaac tgcccacttg gcagtacatc aagtgtatca tatgccaagt<br>acgcccccta ttgacgtcaa tgacggtaaa tggcccgcct ggcattatgc<br>ccagtacatg accttatggg actttcctac ttggcagtac atctacgtat<br>tagtcatcgc tattaccatg gtgatgcggt tttggcagta<br>catcaatggg cgtggatagc ggtttgactc acggggattt ccaagtctcc<br>accccattga cgtcaatggg agtttgtttt ggcaccaaaa tcaacgggac<br>tttccaaaat gtcgtaacaa ctccgcccca ttgacgcaaa tgggcggtag<br>gcgtgtacgg tgggaggtct atataagcag agctcgttta gtgaaccgtc<br>agatcgcctg gagacgccat ccacgctgtt ttgacctcca<br>tagaagacac cgggaccgat ccagcctcca tcggctcgca tctctccttc<br>acgcgcccgc cgccctacct gaggccgcca tccacgccgg ttgagtcgcg<br>ttctgccgcc tcccgcctgt ggtgcctcct gaactgcgtc cgccgtctag<br>gtaagtttaa agctcaggtc gagaccgggc ctttgtccgg cgctcccttg<br>gagcctacct agactcagcc ggctctccac gctttgcctg<br>accctgcttg ctcaactcta gttaacggtg gagggcagtg tagtctgagc<br>agtacacgtt gctgccgcgc gcgccaccag acataatagc tgacagacta<br>acagactgtt cctttccatg ggtcttttct gcagtcaccg tcgtcgacac<br>gtgtgatcag atatcgcggc cgctctagac caccatggga tggtcatgta<br>tcatcctttt tctagtagca actgcaaccg gtgtacattc ccagtctgcc<br>ctgactcagc ctccctctgt gtctgggtct cctggacagt cggtcaccat<br>ctcctgcact ggaaccagca gtgacgttga tggttataac tatgtctcct<br>ggtaccaaca acatccaggc aaagccccca aactcatgat ttatggtgtc<br>agcaatcggc cctcaggggt ctctgatcgc ttctctggct ccaagtctgg<br>caacacggcc tccctgacca tctctgggct ccaggctgag gacgaggctg<br>attattactg ttgttcatct acaaccagtt acacttacat cttcggaact<br>gggaccaagg tcacagtact aggtcagccc aaggctgccc cctcggtcac<br>tctcttcccg ccctcctctg aggagcttca agccaacaag gccacactag<br>tgtgtctgat cagtgacttc tacccgggag ccgtggaagt ggcctggaag<br>gcagatggca gcgctgtcaa cgcgggagtg gagaccacca aaccctccaa<br>acagagcaac aacaagtacg cggccagcag ctacctgagc ctgacgtccg<br>accagtggaa gtcccacaag agctacagct gccaggtcac<br>gcacgaaggg agcaccgtgg agaagacagt ggcccctgca gaatgttcat<br>agggatccag atctgctgtg ccttctagtt gccagccatc tgttgtttgc |

-continued

| SEQ ID NO | Description | Sequence |
|---|---|---|
| | | ccctccccg tgccttcctt gaccctggaa ggtgccactc ccactgtcct |
| | | ttcctaataa aatgaggaaa ttgcatcgca ttgtctgagt aggtgtcatt |
| | | ctattctggg gggtggggtg gggcaggaca gcaaggggga |
| | | ggattgggaa gacaatagca ggcatgctgg ggatgcggtg ggctctatgg |
| | | gtacccaggt gctgaagaat tgacccggtt cctcctgggc cagaaagaag |
| | | caggcacatc cccttctctg tgacacaccc tgtccacgcc cctggttctt |
| | | agttccagcc ccactcatag gacactcata gctcaggagg gctccgcctt |
| | | caatcccacc cgctaaagta catggagcgg tctctccctc |
| | | cctcatcagc ccaccaaacc aaacctagcc tccaagagtg ggaagaaatt |
| | | aaagcaagat aggctattaa gtgcagaggg agagaaaatg cctccaacat |
| | | gtgaggaagt aatgagagaa atcatagaat tttaaggcca tgatttaagg |
| | | ccatcatggc cttaatcttc cgcttcctcg ctcactgact cgctgcgctc |
| | | ggtcgttcgg ctgcggcgag cggtatcagc tcactcaaag |
| | | gcggtaatac ggttatccac agaatcaggg gataacgcag gaaagaacat |
| | | gtgagcaaaa ggccagcaaa aggccaggaa ccgtaaaaag gccgcgttgc |
| | | tggcgttttt ccataggctc cgcccccctg acgagcatca caaaaatcga |
| | | cgctcaagtc agaggtggcg aaacccgaca ggactataaa gataccaggc |
| | | gtttccccct ggaagctccc tcgtgcgctc tcctgttccg |
| | | accctgccgc ttaccggata cctgtccgcc tttctccctt cgggaagcgt |
| | | ggcgctttct catagctcac gctgtaggta tctcagttcg gtgtaggtcg |
| | | ttcgctccaa gctgggctgt gtgcacgaac cccccgttca gcccgaccgc |
| | | tgcgccttat ccggtaacta tcgtcttgag tccaacccgg taagacacga |
| | | cttatcgcca ctggcagcag ccactggtaa caggattagc |
| | | agagcgaggt atgtaggcgg tgctacagag ttcttgaagt ggtggcctaa |
| | | ctacggctac actagaagaa cagtatttgg tatctgcgct ctgctgaagc |
| | | cagttacctt cggaaaaaga gttggtagct cttgatccgg caaacaaacc |
| | | accgctggta gcggtggttt ttttgtttgc aagcagcaga ttacgcgcag |
| | | aaaaaaagga tctcaagaag atcctttgat cttttctacg gggtctgacg |
| | | ctcagtggaa cgaaaactca cgttaaggga ttttggtcat gagattatca |
| | | aaaaggatct tcacctagat ccttttaaat taaaaatgaa gttttaaatc |
| | | aatctaaagt atatatgagt aaacttggtc tgacagttac caatgcttaa |
| | | tcagtgaggc acctatctca gcgatctgtc tatttcgttc atccatagtt |
| | | gcctgactcg gggggggggg gcgctgaggt ctgcctcgtg aagaaggtgt |
| | | tgctgactca taccaggcct gaatcgcccc atcatccagc cagaaagtga |
| | | gggagccacg gttgatgaga gctttgttgt aggtggacca gttggtgatt |
| | | ttgaactttt gctttgccac ggaacggtct gcgttgtcgg gaagatgcgt |
| | | gatctgatcc ttcaactcag caaaagttcg atttattcaa caaagccgcc |
| | | gtcccgtcaa gtcagcgtaa tgctctgcca gtgttacaac caattaacca |
| | | attctgatta gaaaaactca tcgagcatca aatgaaactg caatttattc |
| | | atatcaggat tatcaatacc atatttttga aaaagccgtt tctgtaatga |
| | | aggagaaaac tcaccgaggc agttccatag gatggcaaga tcctggtatc |
| | | ggtctgcgat tccgactcgt ccaacatcaa tacaacctat taatttcccc |
| | | tcgtcaaaaa taaggttatc aagtgagaaa tcaccatgag tgacgactga |
| | | atccggtgag aatggcaaaa gcttatgcat ttctttccag acttgttcaa |
| | | caggccagcc attacgctcg tcatcaaaat cactcgcatc aaccaaaccg |
| | | ttattcattc gtgattgcgc ctgagcgaga cgaaatacgc gatcgctgtt |
| | | aaaaggacaa ttacaaacag gaatcgaatg caaccggcgc aggaacactg |
| | | ccagcgcatc aacaatattt tcacctgaat caggatattc ttctaatacc |
| | | tggaatgctg ttttcccggg gatcgcagtg gtgagtaacc atgcatcatc |
| | | aggagtacgg ataaaatgct tgatggtcgg aagaggcata aattccgtca |
| | | gccagtttag tctgaccatc tcatctgtaa catcattggc aacgctacct |
| | | ttgccatgtt tcagaaacaa ctctggcgca tcgggcttcc catacaatcg |
| | | atagattgtc gcacctgatt gcccgacatt atcgcgagcc catttatacc |
| | | catataaatc agcatccatg ttggaattta atcgcggcct cgagcaagac |
| | | gtttcccgtt gaatatggct cataacaccc cttgtattac tgtttatgta |
| | | agcagacagt tttattgttc atgatgatat atttttatct tgtgcaatgt |
| | | aacatcagag attttgagac acaacgtggc tttccccccc cccccattat |
| | | tgaagcattt atcagggtta ttgtctcatg agcggataca tatttgaatg |
| | | tatttagaaa aataaacaaa taggggttcc gcgcacattt ccccgaaaag |
| | | tgccacctga cgtctaagaa accattatta tcatgacatt aacctataaa |
| | | aataggcgta tcacgaggcc ctttcgtc |

bolded/underlined letters indicate amino acids that differ from wild-type.

BRIEF DESCRIPTION OF THE FIGURES

FIG. 3A: Lymphocytes were gated by SSC and FSC. FIG. 3: B cells were gated by CD19 and excluding non-B cell surface markers. FIG. 3C: Surface IgG+ B cells were further gated by IgG and excluding IgM. SSC and FSC denote side- and forward-scatter, respectively. FIGS. 3D-3F: staining profile of IgG+ B cells with various EBV gp350 probes. There were three gp350 variants used to co-stain with anti-CD21 (complement receptor 2, CR2); WT, wild-type gp350 (FIG. 3D); D296R (FIG. 3E); and D296R/I160R (FIG. 3F). All the mutant probes were designed to reduce the CR2-binding property of gp350. WT and D296R gp350 probes bind to virtually all the IgG+ B cells while the D296R/I160R gp350 probe completely knocked down non-specific gp350 staining of B cells.

FIG. 5A shows rhesus macaque immunization schedule with EBV gp350 nanoparticles followed by B cell sorting. FIG. 5B shows animals Cy137 and Cy651 displayed the highest neutralization titers and were selected for B cell sorting. FIGS. 5C-5F show the results of B cell sorting strategy for non-human primate B cells.

FIG. 6A shows gp350-specific B cell sorting. FIG. 6B shows the neutralization analysis of select antibodies (72A1 antibody from ATCC is shown for reference).

FIG. 8A shows that humanized H02, as well as murinized H02, neutralize EBV equivalent to the parental macaque H02. FIG. 8B shows that the neutralizing potency of H02 (human, mouse and macaque) is about 50-fold higher than 72A1 antibody (shown for reference).

FIG. 9A is a schematic of the competition-based FACS assay. FIG. 9B shows flow cytometry plots of gp350-binding to B cells in the presence and absence of control antibodies. FIG. 9C shows flow cytometry plots of rhesus macaque antibodies described in this disclosure (two non-neutralizing antibodies F11 and G12 are shown for reference).

FIG. 10A shows the neutralization potency of select antibodies. FIG. 10B shows the affinity of antibodies to gp350. FIG. 10C shows the CDR H3 isoelectric point of select antibodies, indicating that gp350-specific neutralizing antibodies tend to have a higher isoelectric point than typical antibodies (Ebola GP-eleicted antibodies are shown for reference).

DETAILED DESCRIPTION

I. Definitions

Figure 1:
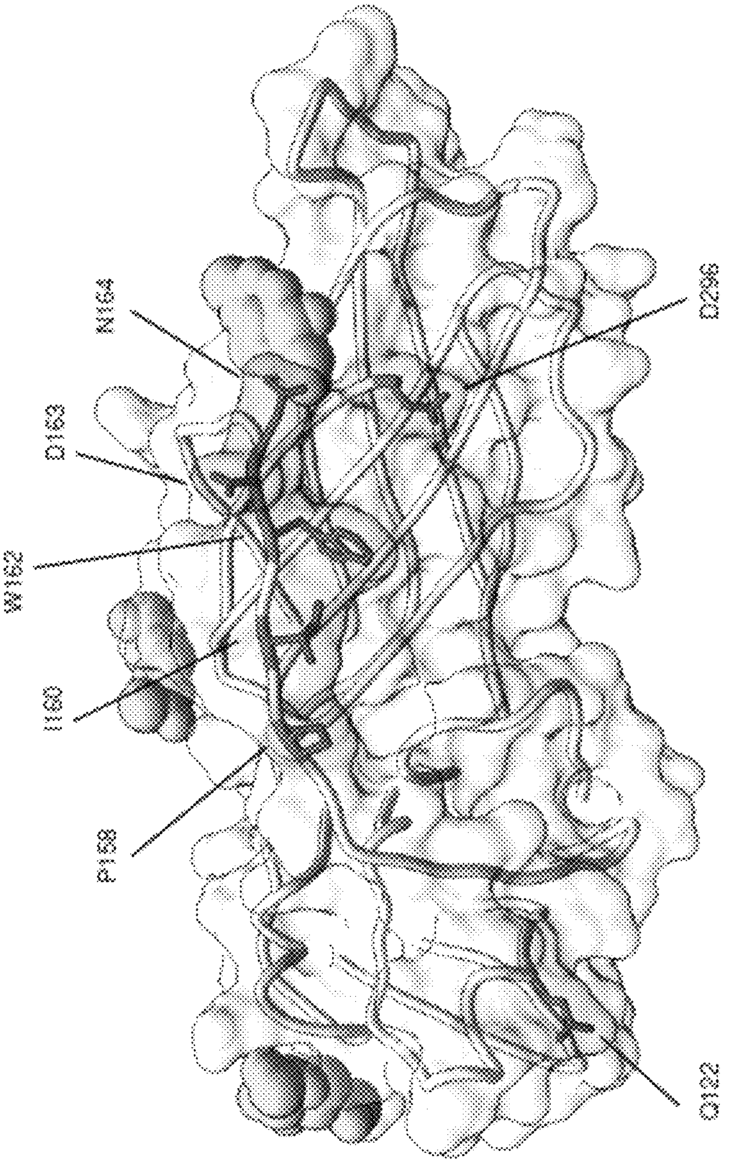
FIG. 1: Design of gp350 probes that knock out CR2-binding property. Selected residues substantially involved in CR2-binding, but less in antibody (H02) recognition, are defined by structures of gp350-CR2 and gp350-H02 Fab complexes. CR2-knock out (KO) mutations are designed by substitution of one or more residues among the selected residues. Experimentally tested mutations include Q122N (glycan addition at 122); D163N/164bS (glycan addition at 163 and one residue insertion between 164 and 165); D296R; W162A/D163A/N164A; D296R/I160R; D296R/P158R; D296R/P158N/I160T (glycan addition at 158); D296R/P158R/I160R.
Figure 2:
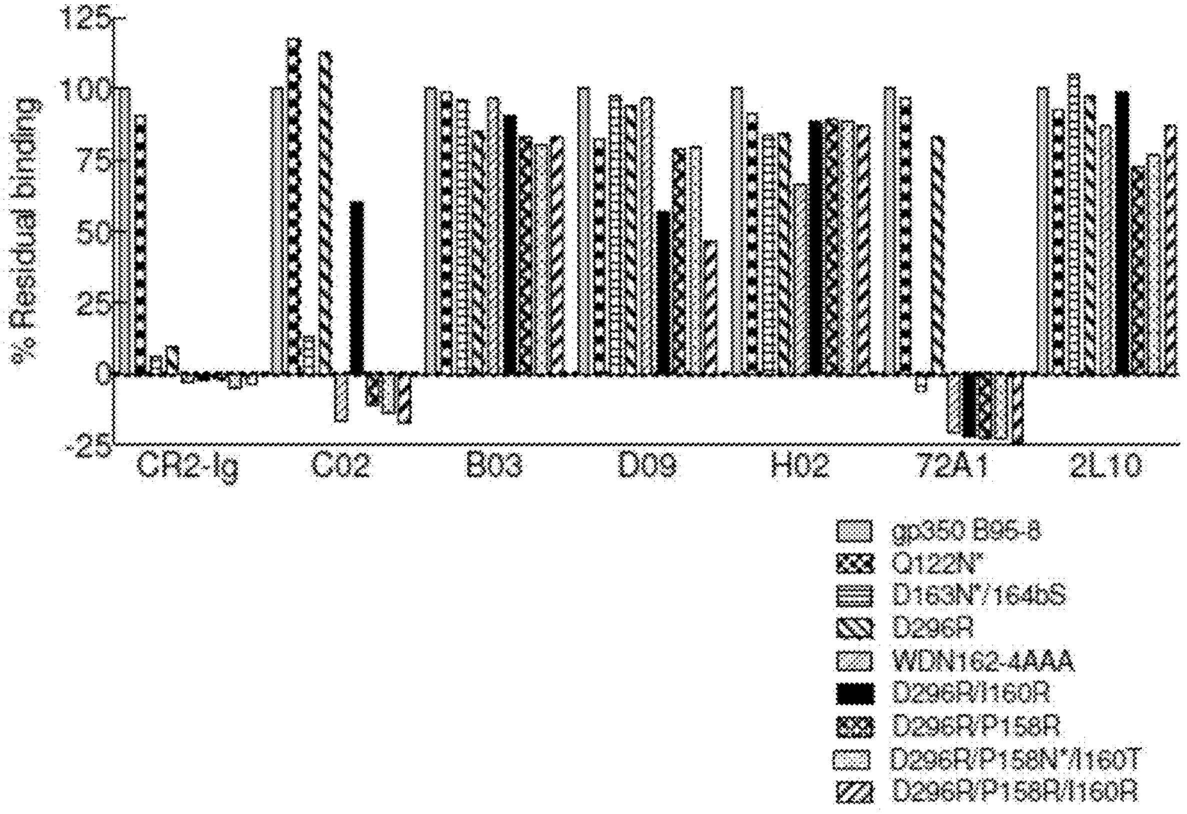
FIG. 2: CR2- and antibody-binding profile of gp350 mutants. Binding of CR2-Ig (chimeric molecule of CR2 SCR1-2 domain and IgG Fc region) and a set of gp350-specific monoclonal antibodies were measured by biolayer interferometry using Octet instrument. CR2-Ig or antibodies were immobilized on biosensors through protein A or anti-mouse Fc antibody (for 2L10) and assessed binding properties of various recombinant gp350 mutants. Graph shows percent binding of each mutant relative to its parental (wild-type) gp350. D296R mutation greatly (but not completely) eliminated CR2-binding while retaining binding of all the monoclonal antibodies. An additional mutation on D296R mutant completely abrogated the CR2-binding property of gp350. Among these variants, D296R/I160R retained binding of most monoclonal antibodies and was therefore chosen for further characterization. 2L10 is a murine non-CR2-binding site targeting antibody, used as a control.
Figure 3A:
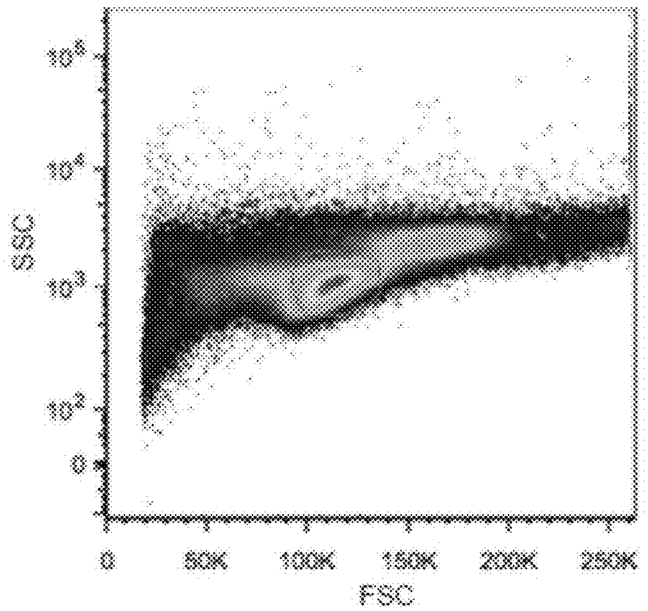
FIGS. 3A-3F: Gating strategy of IgG+ B cell subset in human PBMCs.
Figure 3B:
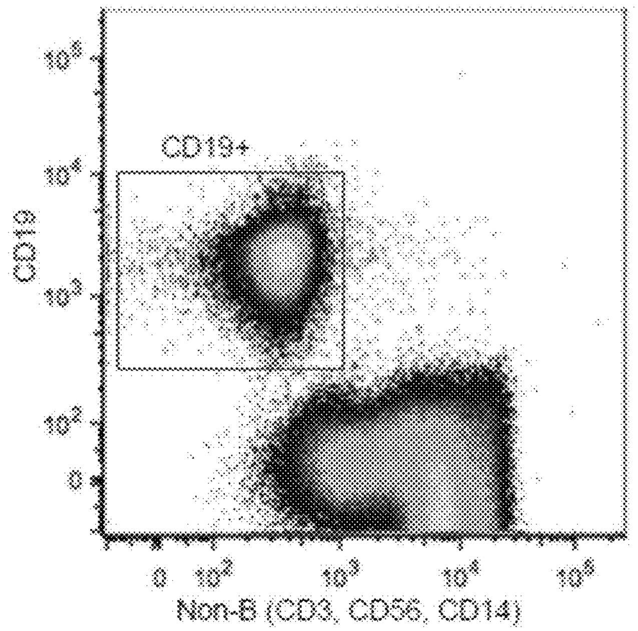
Figure 3C:
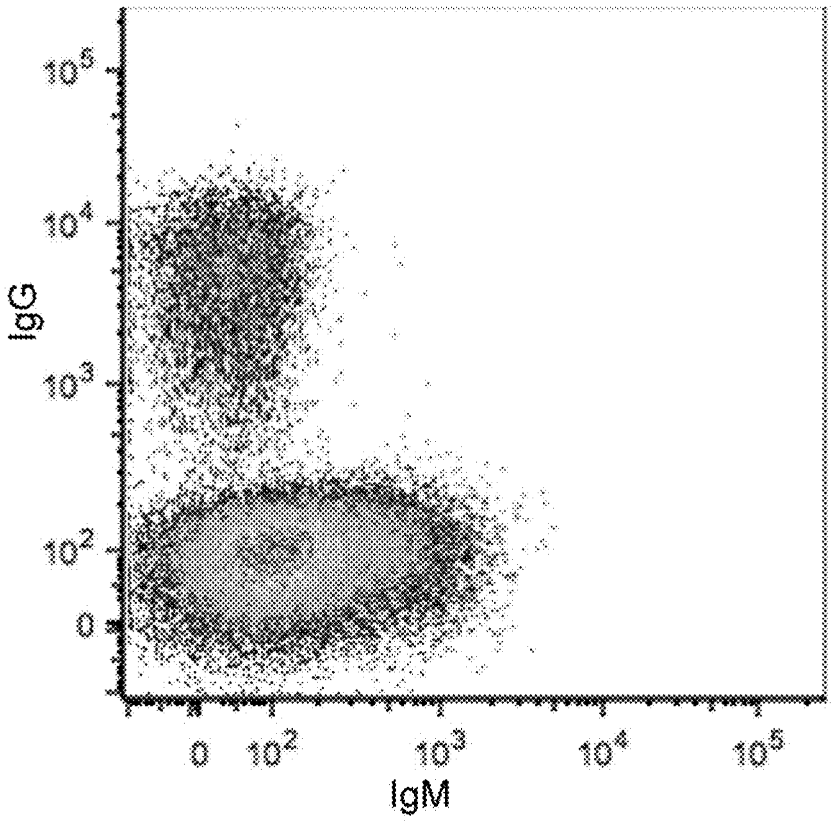
Figure 3D:
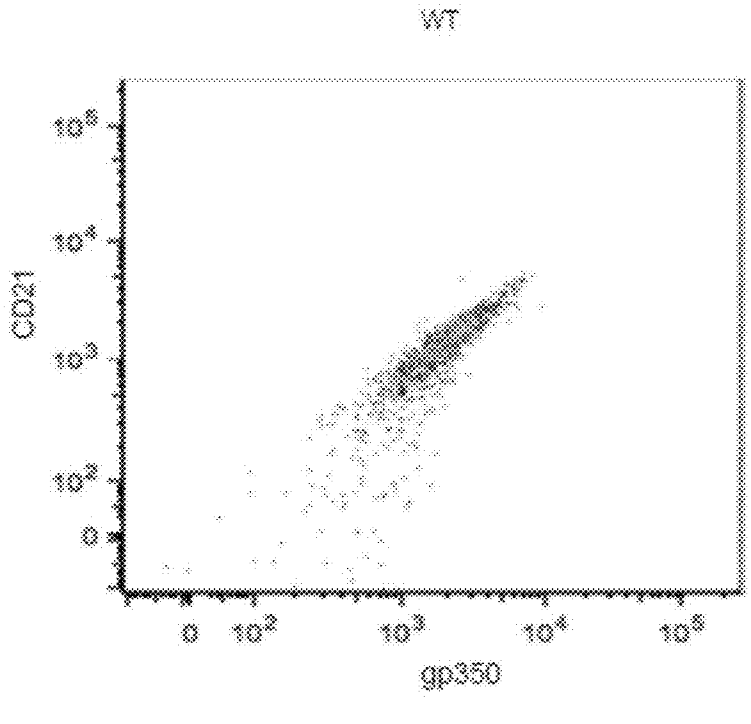
Figure 3E:
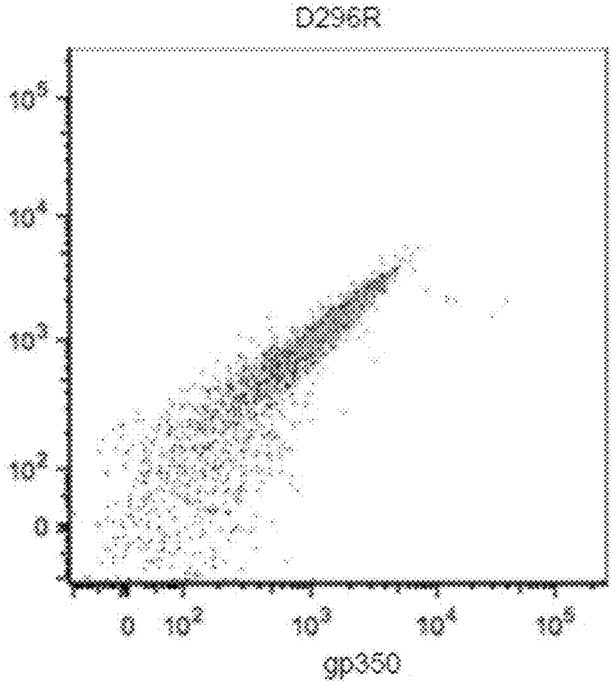
Figure 3F:
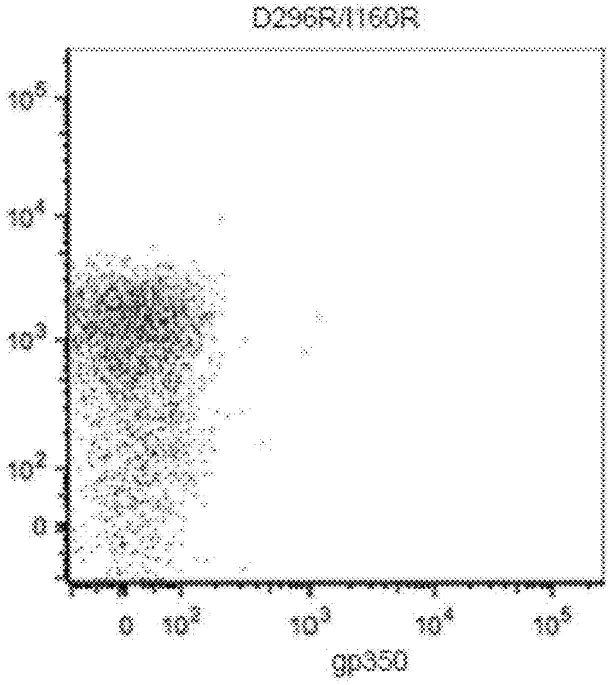
Figure 4A:
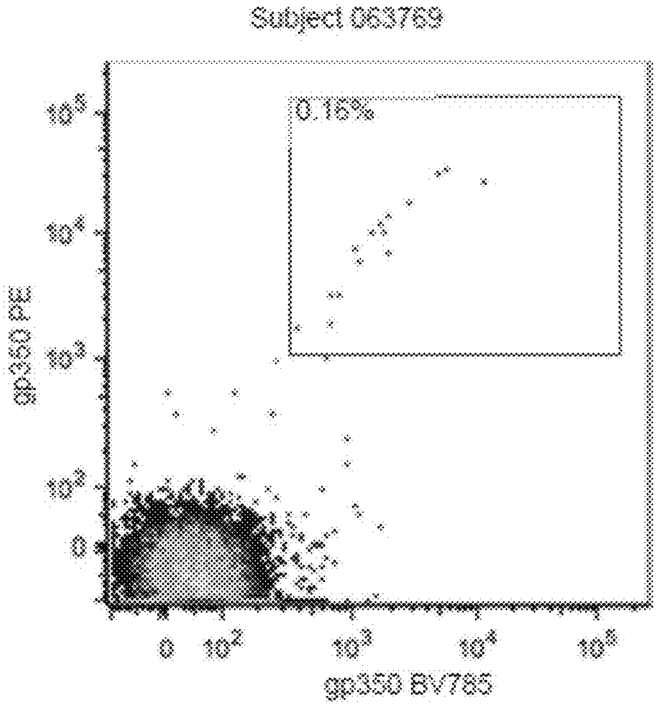
FIGS. 4A and 4B: Identification of EBV gp350-specific IgG+ B cells in individuals who have high serum neutralization titers. Cryopreserved PMBCs were stained with cell lineage differentiation markers as well as gp350 D296R/I160R probe. The gp350 probe were conjugated with two different fluorochromes (PE and BV785) to eliminate false positive events and increase confidence for specificity of stained B cells. Plots shown were IgG+ B cells gated as in previous figures. Rectangles indicate IgG+ B cells stained with gp350 D296R/I160R in two different colors.
Figure 4B:
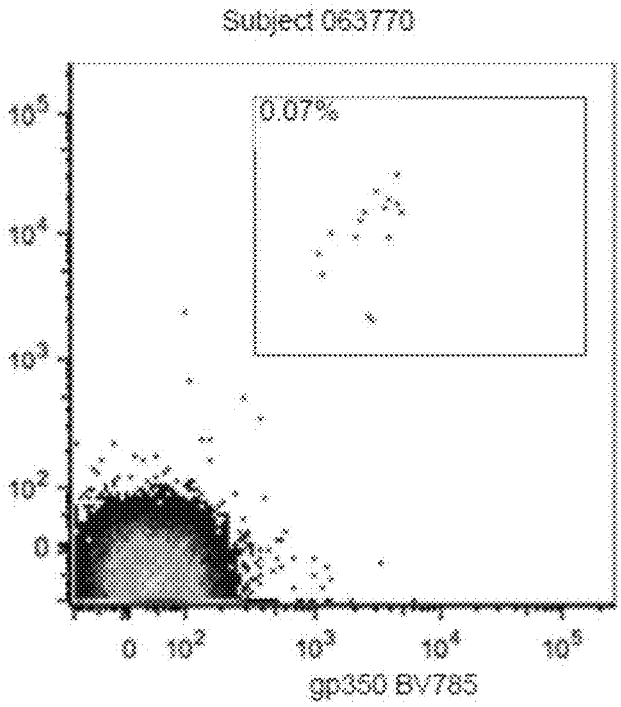
Figure 5A:
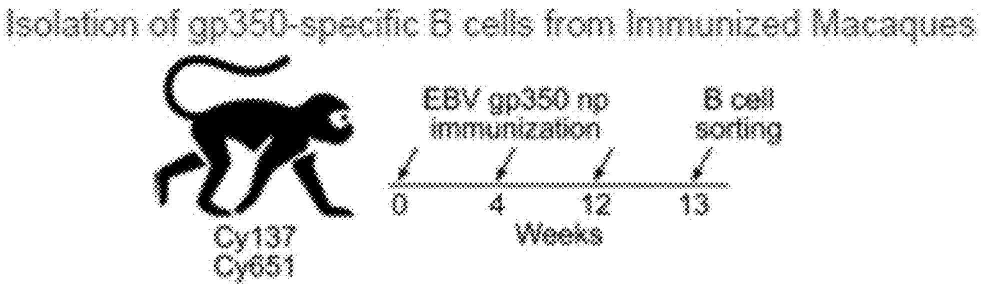
FIGS. 5A-5F: Isolation of gp350-specific B cells from Immunized Macaques.
Figure 5B:
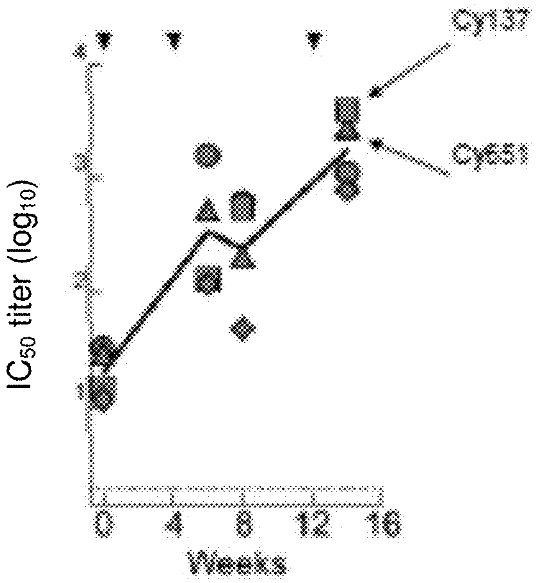
Figure 5C:
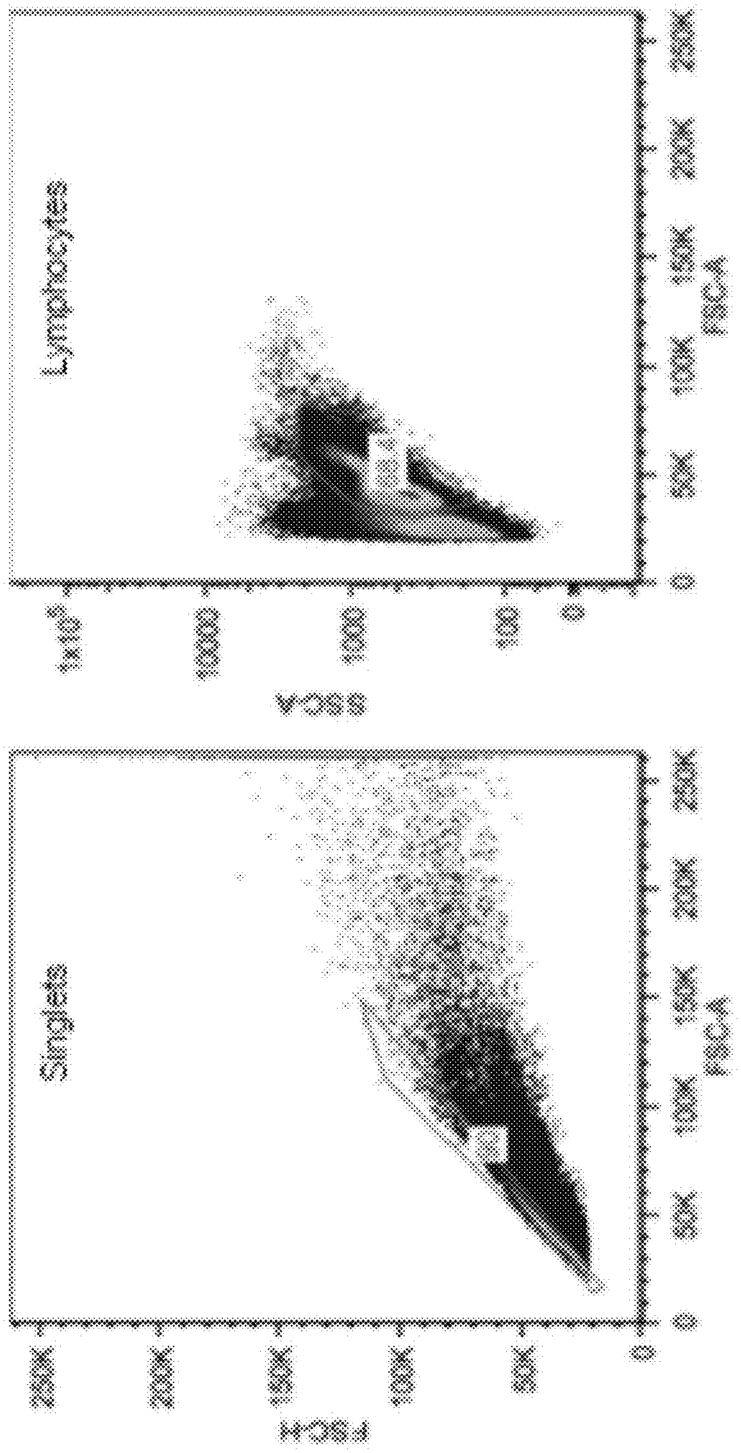
Figure 5D:
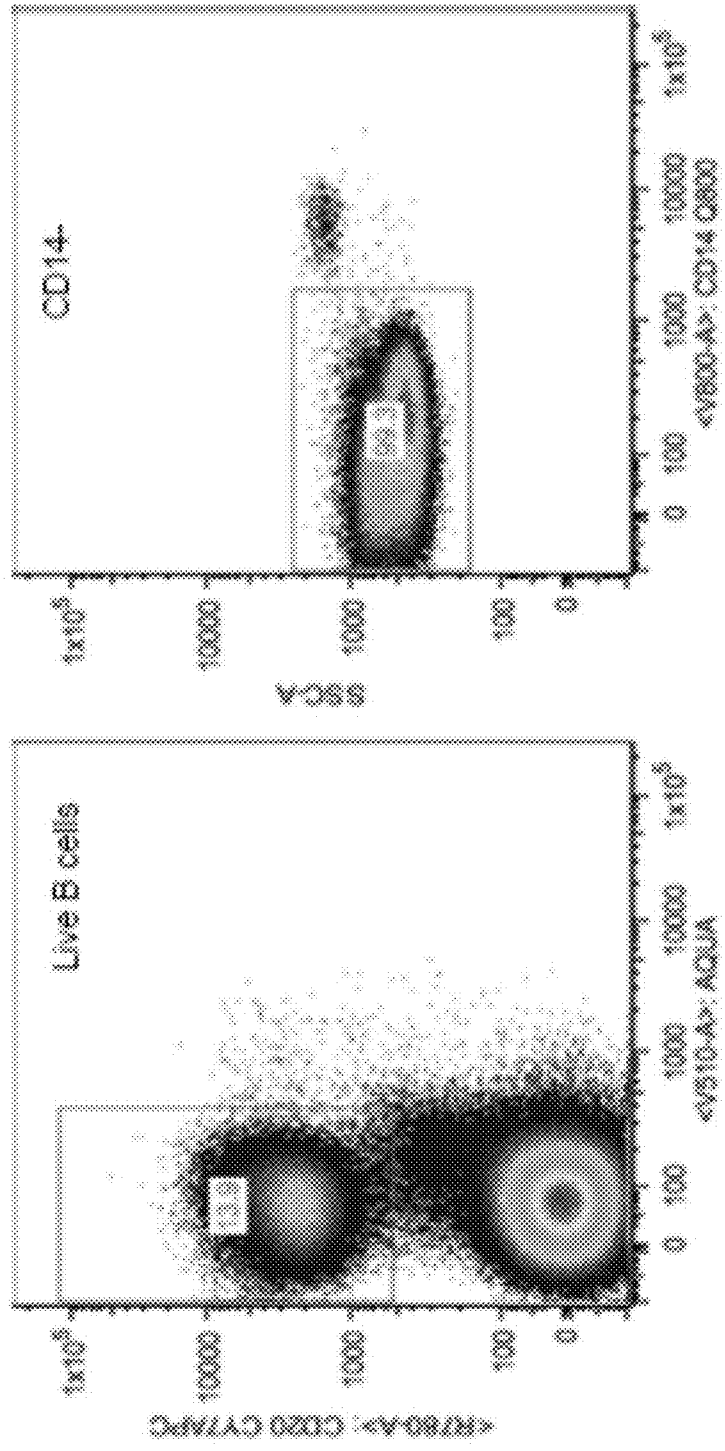
Figure 5E:
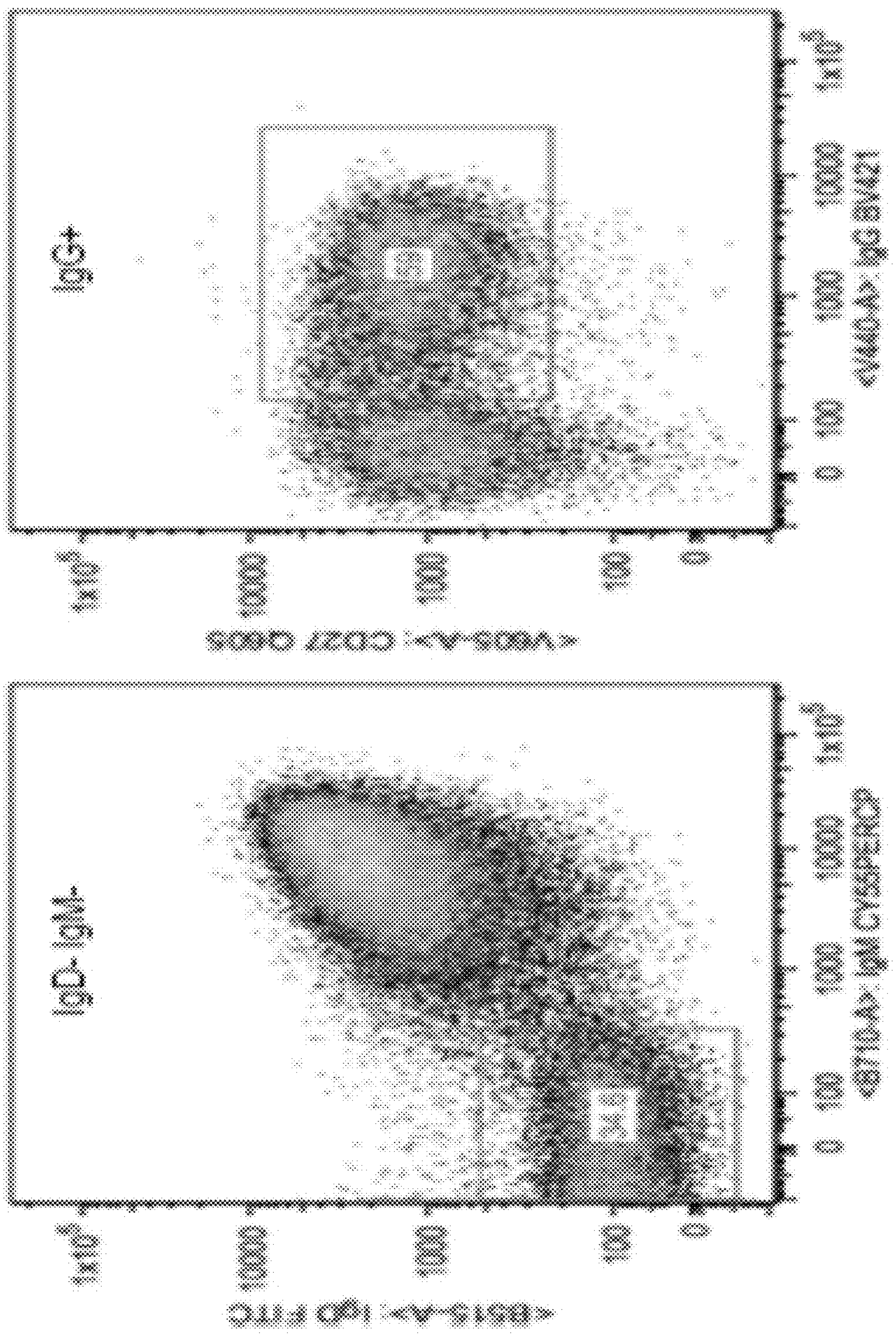
Figure 5F:
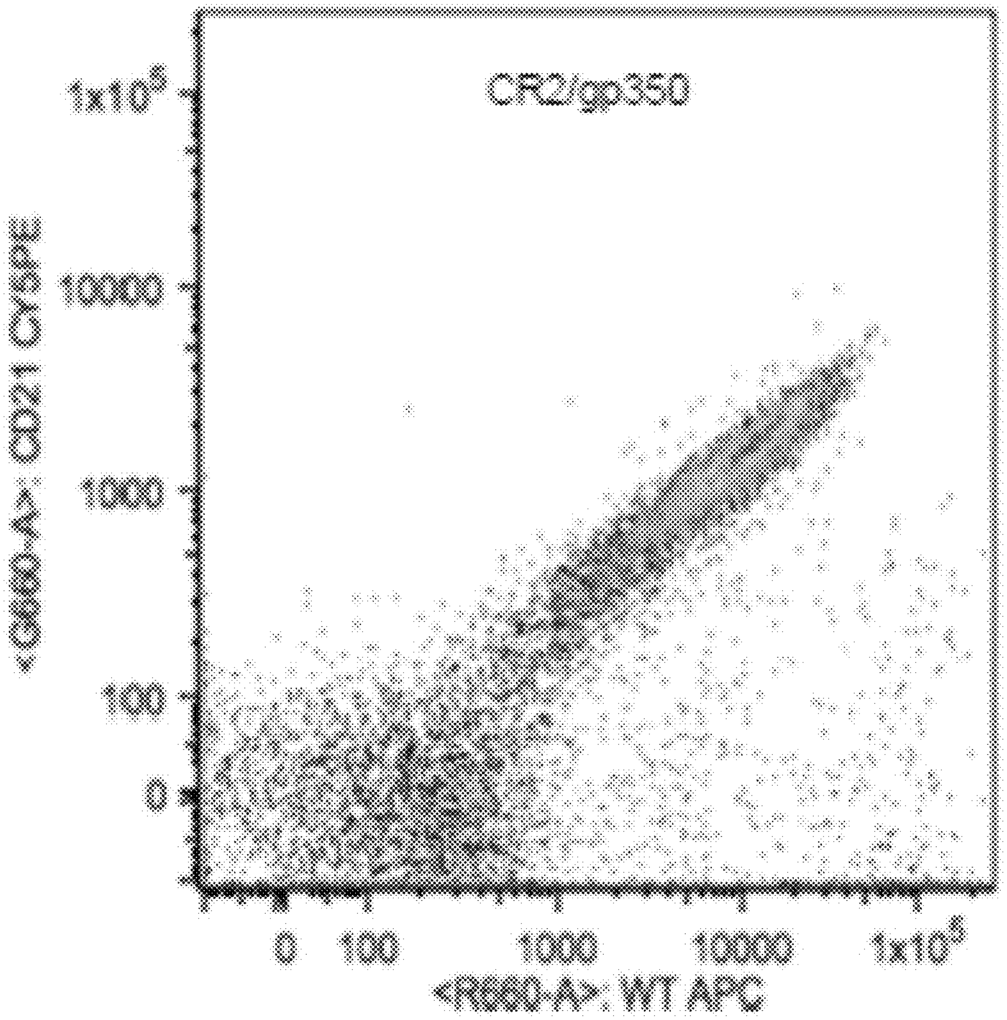
Figure 6A:
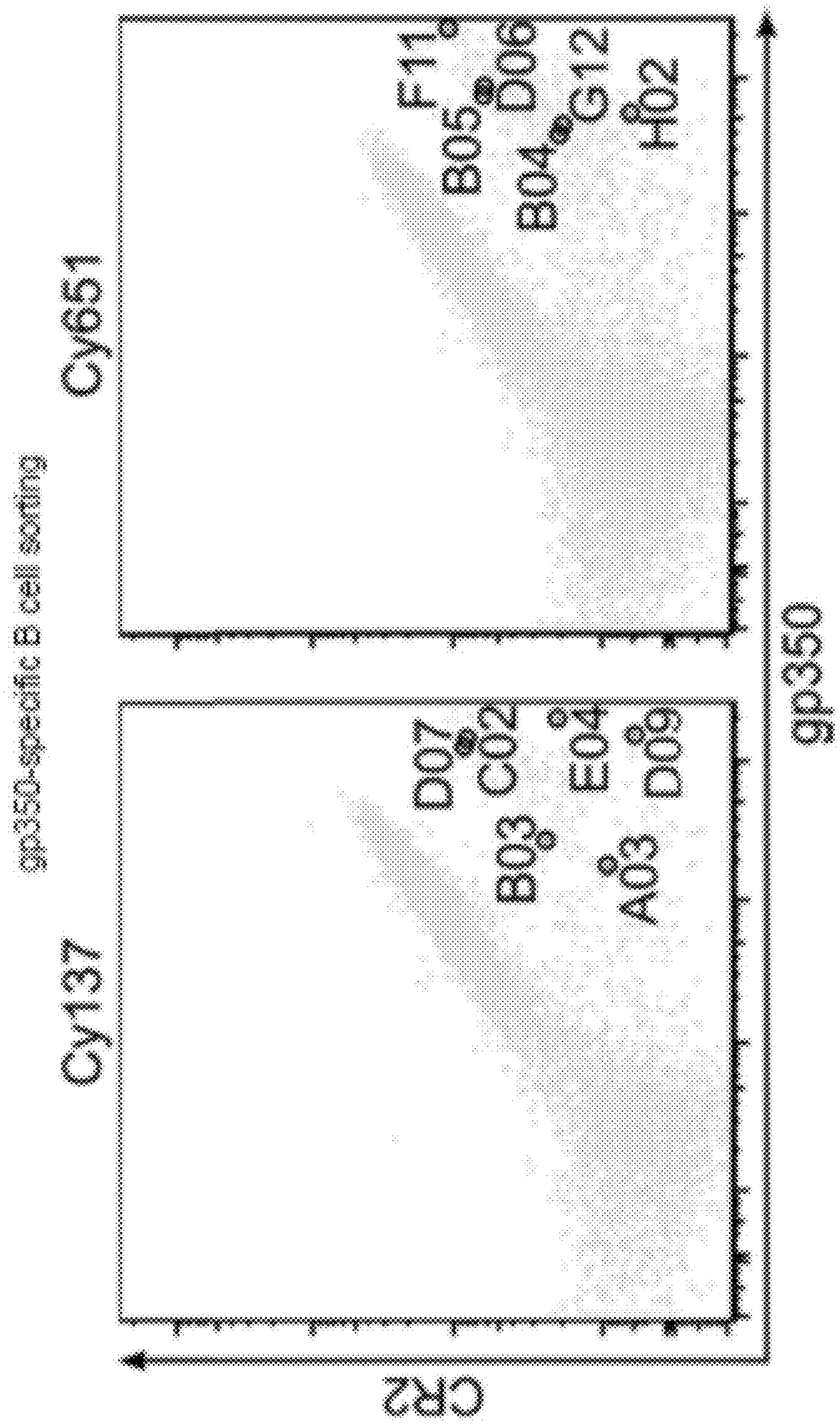
FIGS. 6A and 6B: Identification and analysis of Vaccine-elicited anti-gp350 mAbs.
Figure 6B:
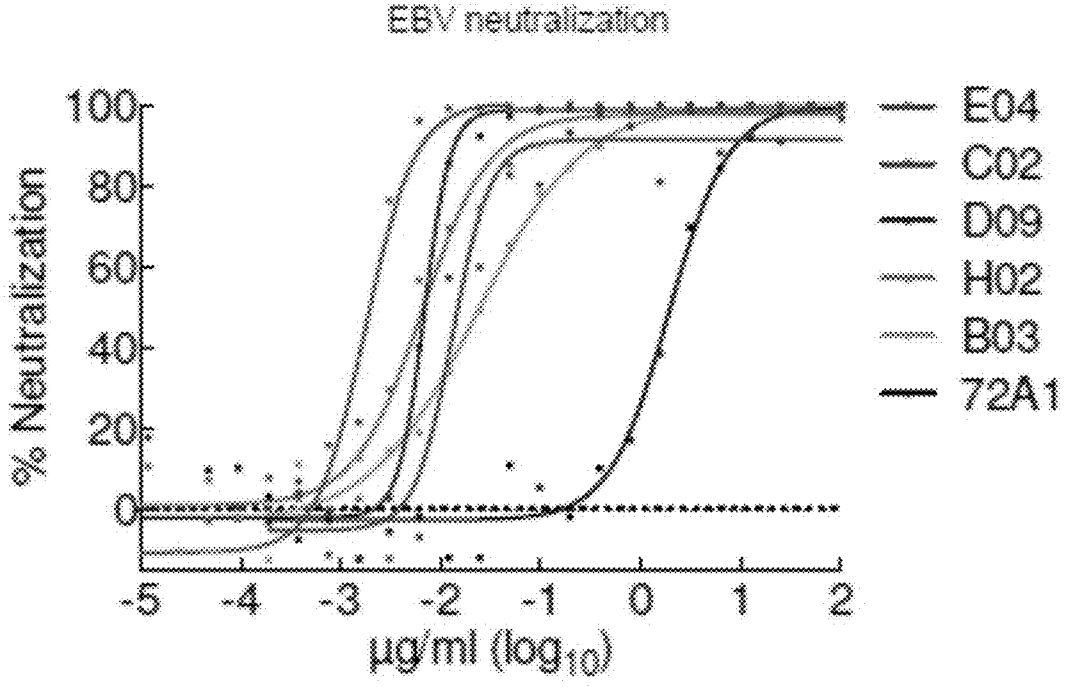
Figure 7:
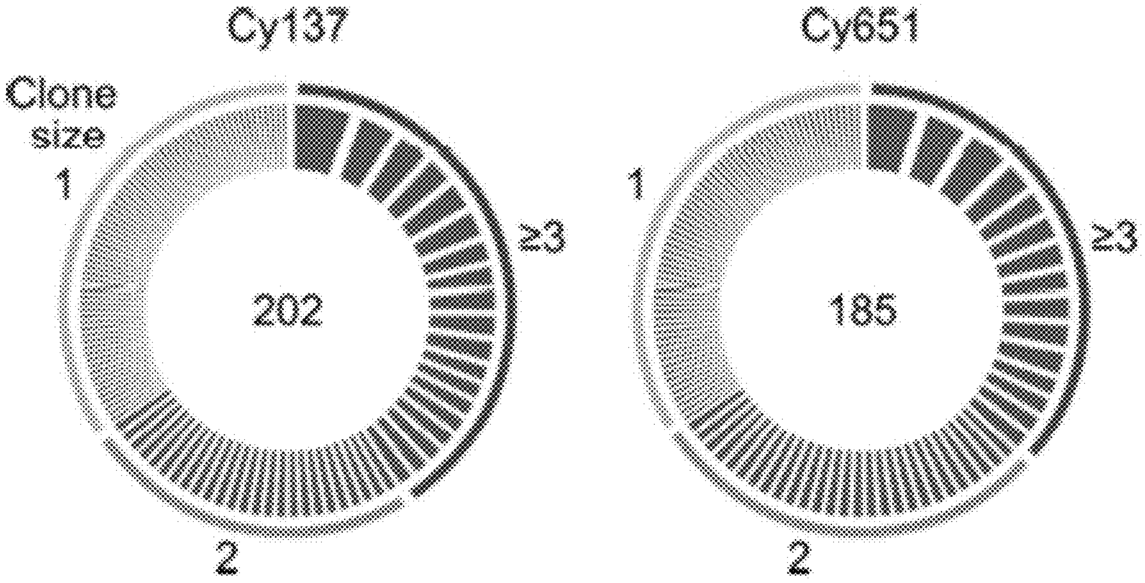
FIG. 7: Clonotype analysis of immunoglobulin heavy chain sequences. Approximately 200 B cells were isolated from each of the two rhesus macaques analyzed. The B cell receptor sequences indicated low clonal expansion in the B cells isolated as judged by the sequence similarity of each B cell receptor.
Figure 8A:
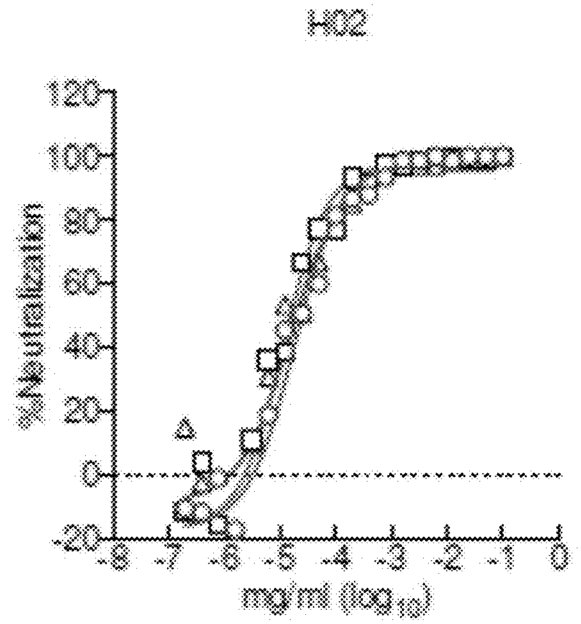
FIGS. 8A and 8B: Neutralization potency of humanized mAb H02.
Figure 8B:
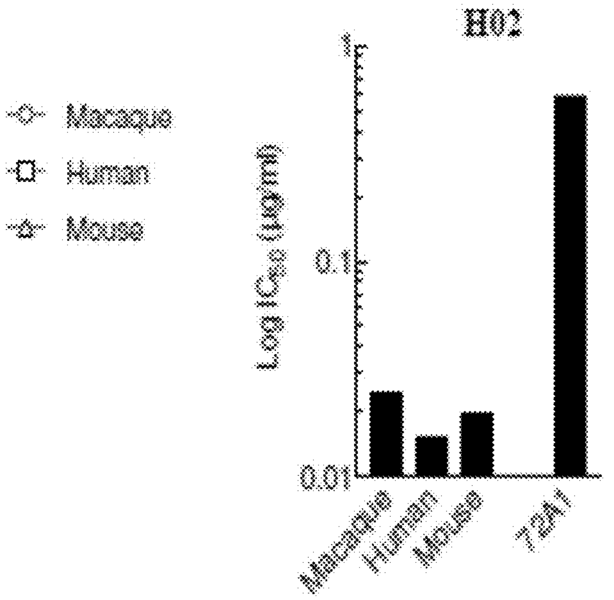
Figure 9A:
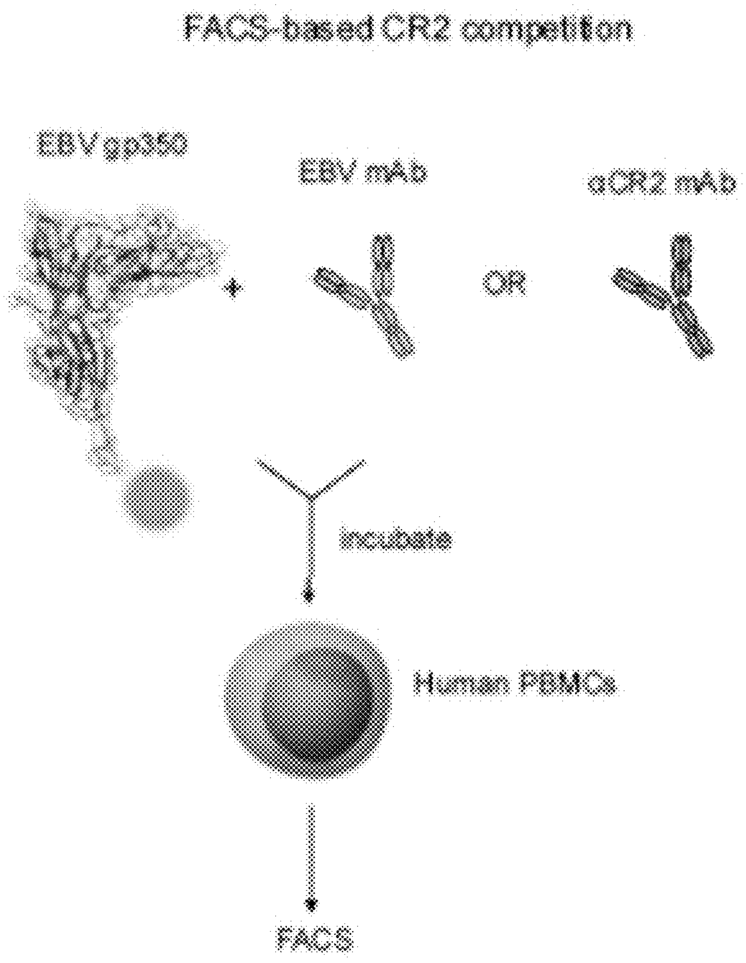
FIGS. 9A-9C: Targeting the receptor (CR2)-binding site of gp350: Flow cytometry based CR2 epitope mapping.
Figure 9B:
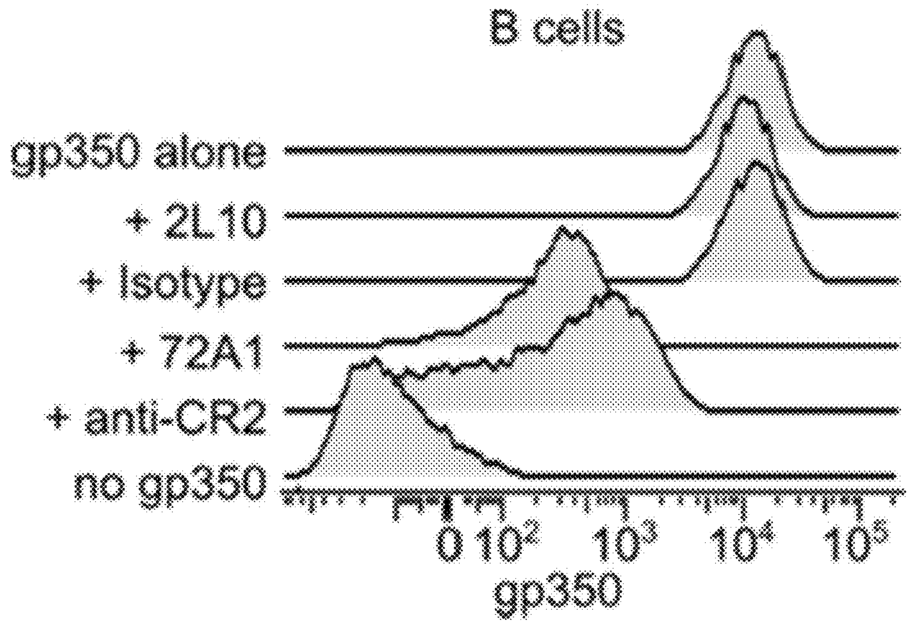
Figure 9C:
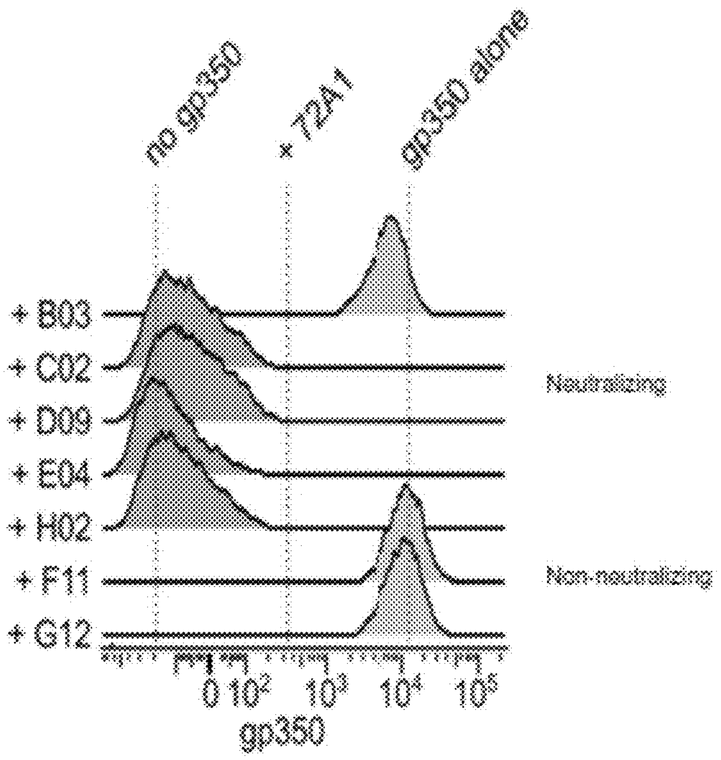
Figure 10C:
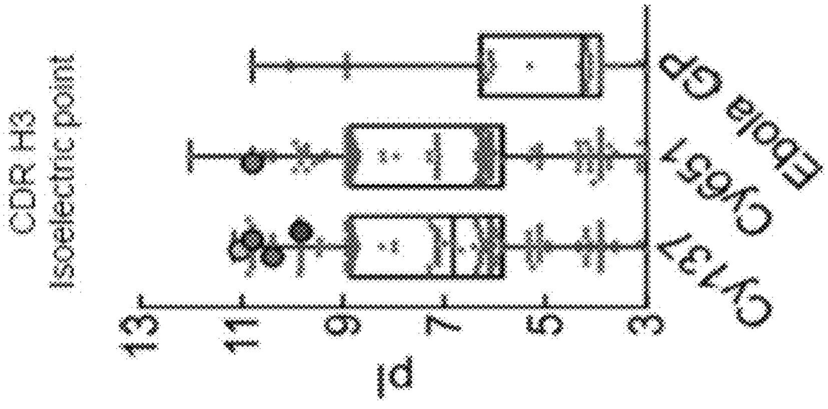
FIGS. 10A-10C: Analysis of Vaccine-elicited Anti-gp350 mAbs: characterization of antibodies.
Figure 10B:
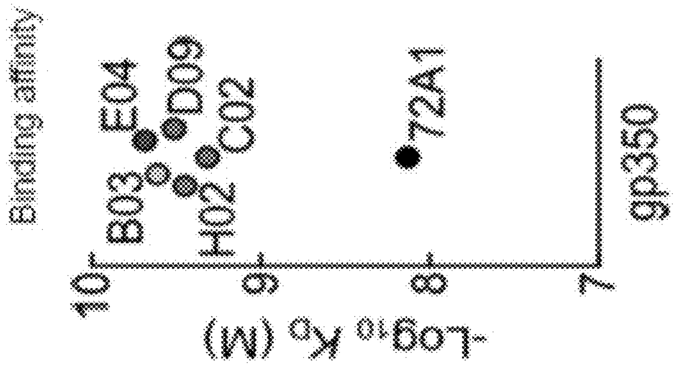
Figure 10A:
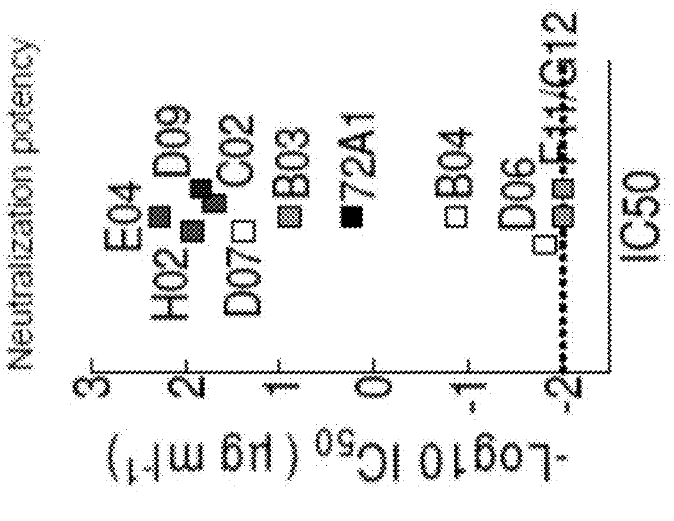
Figure 11:
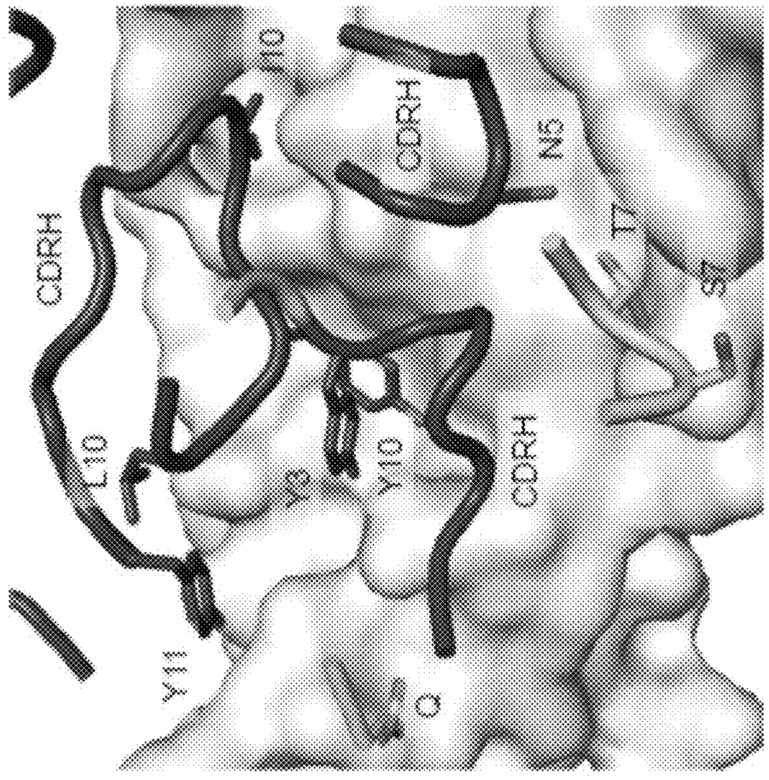
FIG. 11 shows the location of mutations entered into the heavy chain residues of claim A9.
Figure 12:
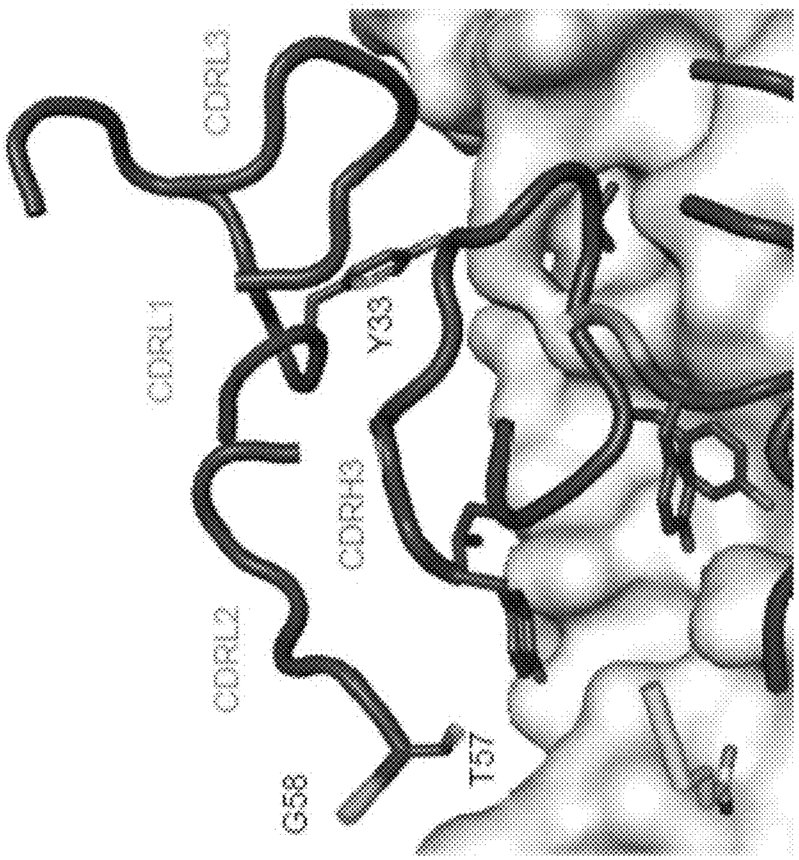
FIG. 12 shows the location of mutations entered into the light chain residues of claim A9.
Figure 13:
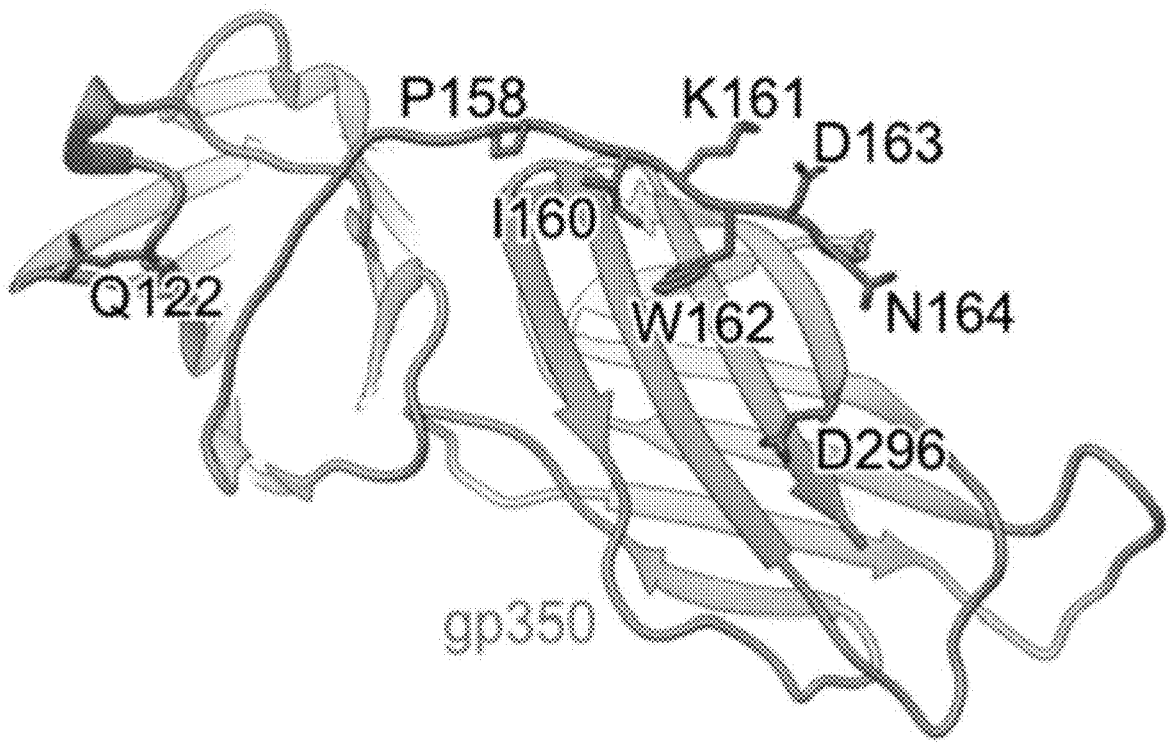
FIG. 13 shows the design of the CR2-binding knockout gp350 probe, including specific residues that were substituted to knock down CR2-binding.
Figure 14:
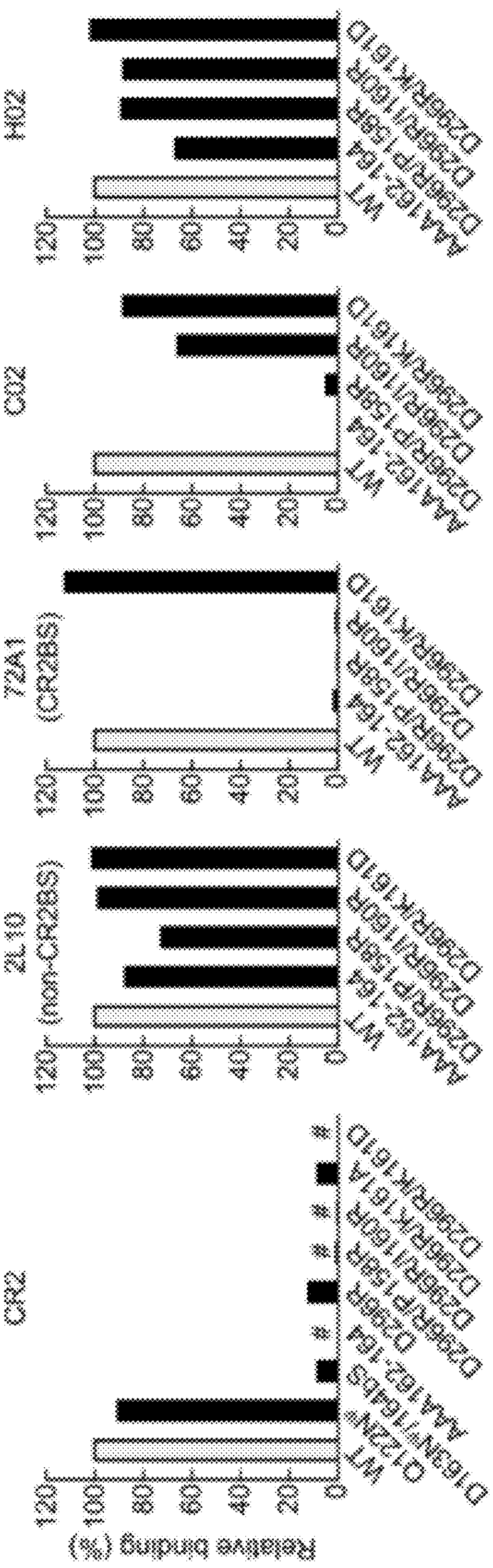
FIG. 14 shows the binding properties of the gp350 mutants. In this figure, # indicates no binding.
Figure 15:
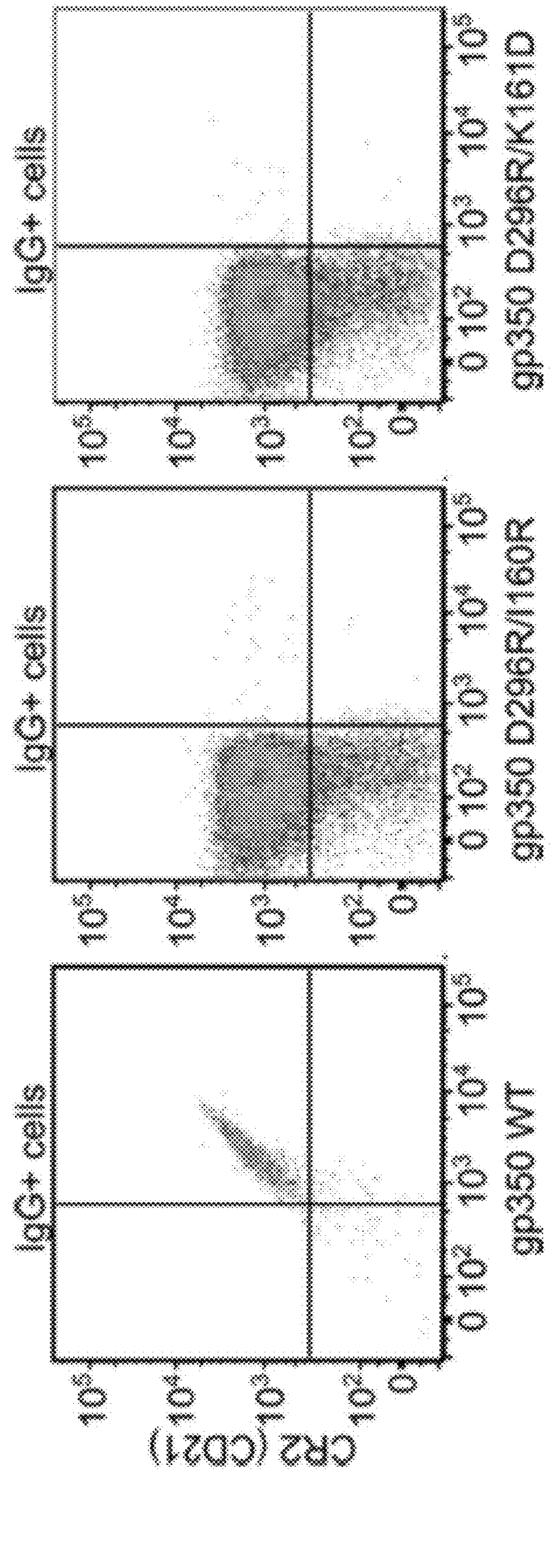
FIG. 15 shows the B cell staining profile of the new CR2-binding knock-out gp350 probe (D296R/K161D).
Figure 16:
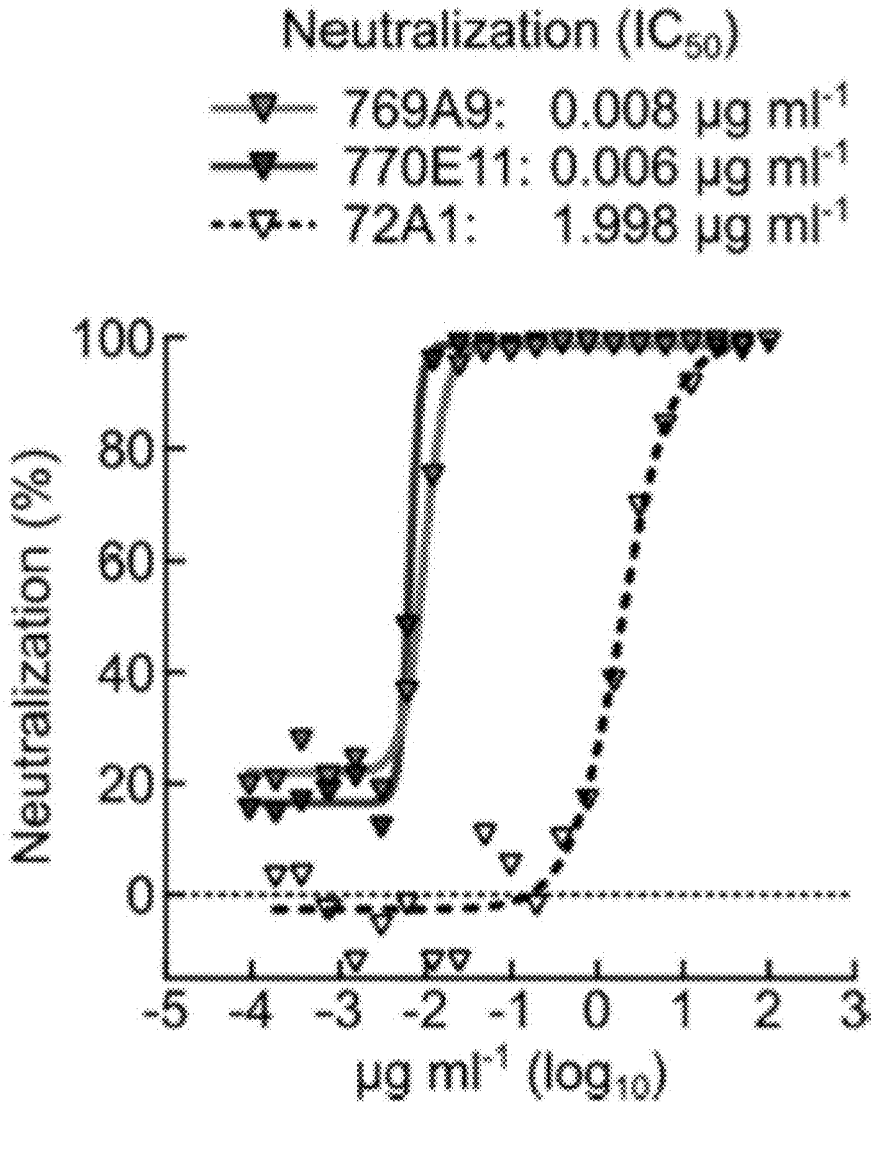
FIG. 16 shows the EBV neutralization potency of the two best human monoclonal antibodies (from clones A9 and E11). In these two clones, mutations were introduced in a structure-guided potency improving mutation analysis. For the mAb of clone A9, the introduced mutations were (referring to Kabat numbering) in the heavy chain were: Q1R, Y32R+Y981, N53F, T701, T70F, L96R, Y98R, Y98W, I100F, I100W, and Y102E; in the light chain were Y32E, G57D, T56Q, and T56E. For the mAb of clone E11, the introduced mutations were (referring to Kabat numbering) in the heavy chain were: V100F, V1001, V100W, V100R, V100Y, Q98R, Q98Y, and Y58R (residues 30-33 and 53-56 were also targeted for mutagenesis); in the light chain, residues 1, 27, 27a, 30, 32, 49, 50, 52, 53, 56, and 93-95 were targeted for mutagenesis.

The terms "EBV gp350 protein" and "gp350" as used herein, refer to various Epstein Barr Virus polypeptides. The EBV gp350 proteins described herein may be isolated from a variety of sources, such as from human tissue types or from another source, or prepared by recombinant or synthetic methods. The term "EBV gp350 protein" refers to each individual gp350 polypeptide disclosed herein. All disclosures in this specification which refer to the "EBV gp350 protein" refer to each of the polypeptides individually as well as jointly. For example, descriptions of the preparation of, purification of, derivation of, formation of antibodies to or against, formation of gp350 binding oligopeptides to or against, administration of, compositions containing, treatment of a disease with, etc., pertain to each polypeptide of the disclosure individually. The term "EBV gp350 protein" also includes variants of the gp350 polypeptides disclosed herein.

A "native sequence EBV gp350 protein" comprises a polypeptide having the same amino acid sequence as the corresponding EBV gp350 protein derived from nature. Such native sequence EBV gp350 proteins can be isolated from nature or can be produced by recombinant or synthetic means. The term "native sequence EBV gp350 protein" specifically encompasses naturally-occurring truncated or secreted forms of the specific EBV gp350 protein (e.g., an extracellular domain sequence), naturally-occurring variant forms (e.g., alternatively spliced forms) and naturally-occurring allelic variants of the polypeptide. The native sequence EBV gp350 proteins disclosed herein may be mature or full-length native sequence polypeptides comprising the full-length amino acids sequences.

"EBV gp350 protein variant" means an EBV gp350 protein, preferably an active EBV gp350 protein, as defined herein having at least about 80% amino acid sequence identity with a full-length native sequence EBV gp350 protein sequence as disclosed herein, an extracellular domain of an EBV gp350 protein, as disclosed herein or any other fragment of a full-length EBV gp350 protein sequence as disclosed herein (such as those encoded by a nucleic acid that represents only a portion of the complete coding sequence for a full-length EBV gp350 protein). Such EBV gp350 protein variants include, for instance, EBV gp350 proteins wherein one or more amino acid residues are added or deleted, at the N- or C-terminus of the full-length native amino acid sequence. Ordinarily, an EBV gp350 protein variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence EBV gp350 protein sequence as disclosed herein, or any other specifically defined fragment of a full-length EBV gp350 protein sequence as disclosed herein. Optionally, gp350 variant polypeptides will have no more than one conservative amino acid substitution as compared to the native EBV gp350 protein sequence, alternatively no more than 2, 3, 4, 5, 6, 7, 8, 9, or 10 conservative amino acid substitution as compared to the native EBV gp350 protein sequence.

"Percent (%) amino acid sequence identity" with respect to the EBV gp350 protein sequences identified herein is defined as the percentage of amino acid residues in a candidate sequence that are identical to the amino acid residues in the specific EBV gp350 protein sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, % amino acid sequence identity values may be generated using the sequence comparison computer program ALIGN-2, wherein the complete source code for the ALIGN-2 program is provided in U.S. Pat. No. 7,160,985, which is incorporated herein by reference. The ALIGN-2 sequence comparison computer program was authored by Genentech, Inc. and the source code thereof has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California or may be compiled from the source code. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as 100 times the fraction X/Y, where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal the % amino acid sequence identity of B to A.

"gp350 variant polynucleotide" or "gp350 variant nucleic acid sequence" means a nucleic acid molecule which encodes an EBV gp350 protein, preferably an active EBV gp350 protein, as defined herein and which has at least about 80% nucleic acid sequence identity with a nucleic acid sequence encoding a full-length native sequence EBV gp350 protein sequence as disclosed herein, an extracellular domain of an EBV gp350 protein, as disclosed herein or any other fragment of a full-length EBV gp350 protein sequence as disclosed herein (such as those encoded by a nucleic acid that represents only a portion of the complete coding sequence for a full-length EBV gp350 protein). Ordinarily, a gp350 variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence EBV gp350 protein sequence, an extracellular domain of an EBV gp350 protein or any other fragment of a full-length EBV gp350 protein sequence. Variants do not encompass the native nucleotide sequence.

Ordinarily, gp350 variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Isolated," when used to describe the various EBV gp350 proteins disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The polypeptide may be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or silver stain. Isolated polypeptide includes polypeptide in situ within recombinant cells, since at least one component of the EBV gp350 protein natural environment will not be present.

Ordinarily, however, isolated polypeptide will be prepared by at least one purification step.

An "isolated" EBV gp350 protein-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature.

The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers (1995).

"Stringent conditions" or "high stringency conditions" as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" used herein refers to a chimeric polypeptide comprising an EBV gp350 protein or anti-gp350 antibody fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of an EBV gp350 protein which retain a biological and/or an immunological activity of native or naturally-occurring gp350, wherein "biological" activity refers to a biological function (either inhibitory or stimulatory) caused by a native or naturally-occurring gp350 other than the ability to induce the production of an antibody against an antigenic epitope possessed by a native or naturally-occurring gp350 and an "immunological" activity refers to the ability to induce the production of an antibody against an antigenic epitope possessed by a native or naturally-occurring gp350.

The term "antagonist" is used in the broadest sense, and includes any molecule that partially or fully blocks, inhibits, or neutralizes a biological activity of a native EBV gp350 protein disclosed herein. In a similar manner, the term "agonist" is used in the broadest sense and includes any molecule that mimics a biological activity of a native EBV gp350 protein disclosed herein. Suitable agonist or antagonist molecules specifically include agonist or antagonist antibodies or antibody fragments, fragments or amino acid sequence variants of native EBV gp350 proteins, peptides, antisense oligonucleotides, small organic molecules, etc. Methods for identifying agonists or antagonists of an EBV gp350 protein may comprise contacting an EBV gp350 protein with a candidate agonist or antagonist molecule and measuring a detectable change in one or more biological activities normally associated with the EBV gp350 protein.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an EBV gp350 protein-expressing viral infection if, after receiving a therapeutic amount of an anti-gp350 antibody or gp350 binding oligopeptide according to the methods of this disclosure, the patient shows observable and/or measurable reduction in or absence of one or more of the following: reduction in the number of infected cells or absence of the infected cells; reduction in the number of infected cells; inhibition (i.e., slow to some extent and preferably stop) of EBV infection including the spread of infection into neurological tissues; inhibition (i.e., slow to some extent and preferably stop) of infection spread; inhibition, to some extent, and/or relief to some extent, of one or more of the symptoms associated with the viral infection; reduced morbidity and mortality, and improvement in quality of life issues. To the extent the anti-gp350 antibody or gp350 binding oligopeptide may prevent growth or infection and/or kill existing infected cells, it may be cytostatic and/or cytotoxic. Reduction of these signs or symptoms may also be felt by the patient. The above parameters for assessing successful treatment and improvement in the EBV-associated diseases and disorders are readily measurable by routine procedures familiar to a medical provider.

"Chronic" administration refers to administration of the agent(s) in a continuous mode as opposed to an acute mode, to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a viral infection refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody or gp350 binding oligopeptide of this disclosure can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate or a lateral flow assay device; in others, it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an EBV gp350 protein, an antibody thereto or a gp350 binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody or gp350 binding oligopeptide, or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, or gp350 binding oligopeptide, or other drug effective to "treat" a disease or disorder in a subject or mammal. In the case of an EBV infection, the therapeutically effective amount of the drug may reduce the number of infected cells; inhibit (i.e., slow to some extent and preferably stop) spread of the infection into other cells, such as lymphatic or neurological cells organs; and/or relieve to some extent one or more of the symptoms associated with the infection. See the definition herein of "treating." To the extent the drug may prevent growth and/or kill existing infected cells, it may be cytostatic, cytotoxic, anti-inflammatory, immunomodulatory, and/or immunosuppressing.

A "growth inhibitory amount" of an anti-gp350 antibody or gp350 binding oligopeptide is an amount capable of inhibiting the growth of a cell, especially virus infected cell, either in vitro or in vivo. A "growth inhibitory amount" of an anti-gp350 antibody or gp350 binding oligopeptide for purposes of inhibiting infected cell growth may be determined empirically and in a routine manner.

A "cytotoxic amount" of an anti-gp350 antibody or gp350 binding is an amount capable of causing the destruction of a cell, especially virus infected cell, either in vitro or in vivo. A "cytotoxic amount" of an anti-gp350 antibody or gp350 binding oligopeptide for purposes of inhibiting cell growth may be determined empirically and in a routine manner.

The term "antibody" is used in the broadest sense and specifically covers, for example, single anti-gp350 monoclonal antibodies (including agonist, antagonist, and neutralizing antibodies), anti-gp350 antibody compositions with polyepitopic specificity, polyclonal antibodies, single chain anti-gp350 antibodies, and fragments of anti-gp350 antibodies (see below) as long as they exhibit the desired biological or immunological activity or specificity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells because at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and c isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and a classes are further divided into subclasses based on relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of an antibody for its antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 3-30, or more typically, 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD (1991)). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, useful monoclonal antibodies of this disclosure may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape, etc.), and human constant region sequences.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide-linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) can recognize and bind antigen, although at a lower affinity than the entire binding site.

"Single-chain Fv" (also abbreviated as "sFv" or "scFv") are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance In general, the humanized antibody will comprise substantially all at least one, and typically two, variable domains, in which all or substantially all the hypervariable loops correspond to those of a non-human immunoglobulin and all or substantially all the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-25 (1986); Riechmann et al., Nature 332:323-329 (1988); and Presta, Curr. Op. Struct. Biol. 2:593-96 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "binds specifically" to a human antigen (i.e., has a binding affinity (Kd) value of no more than about 1×10-7 M, preferably no more than about 1×10-8 and most preferably no more than about 1×10-9 M) but has a binding affinity for a homologue of the antigen from a second non-human mammalian species which is at least about 50-fold, or at least about 500-fold, or at least about 1000-fold, weaker than its binding affinity for the human antigen. The species-dependent antibody can be of any of the various types of antibodies as defined above, but preferably is a humanized or human antibody.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, MD (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same," as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by the values (e.g., Kd values). The difference between the two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of this disclosure. Illustrative embodiments are described in the following.

The "Kd" or "Kd value" according to this disclosure is measured by a radiolabeled antigen binding assay (RIA) performed with the Fab version of an antibody of interest and its antigen as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 mcg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate, 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 microliter/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. The Kd or Kd value may also be measured by using surface plasmon resonance assays using a BIAcore™-2000 or a BIAcore™-3000 (BIAcore, Inc., Piscataway, NJ) at 25° C. with immobilized antigen CMS chips at approx. 10 response units (RU). Briefly, carboxymethylated dextran biosensor chips (CMS, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 mcg/ml (approx. 0.2 uM) before injection at a flow rate of 5 microliter/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol Biol 293:865-881. If the on-rate exceeds $10^6$ M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrometer (Aviv Instruments) or a 8000-series SLM-Aminco spectrophotometer (ThermoSpectronic) with a stir red cuvette.

An "on-rate" or "rate of association" or "association rate" or "kon" according to this disclosure can also be determined with the same surface plasmon resonance technique described above using a BIAcore™-2000 or a BIAcore™-3000 (BIAcore, Inc., Piscataway, NJ) at 25° C. with immobilized antigen CMS chips at approx.10 response units (RU). Briefly, carboxymethylated dextran biosensor chips (CMS, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 mcg/ml (approx.0.2 uM) before injection at a flow rate of 5 microliter/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) was calculated as the ratio koff/kon. See, e.g., Chen, Y., et al., (1999) J. Mol Biol 293:865-81. However, if the on-rate exceeds $10^6$ M-1 S-1 by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the disclosure and the other associated with a reference/comparator antibody) such that one of skill in the art would consider the difference between the two values to be of statistical significance within the context of the biological characteristic measured by the values (e.g., Kd values, HAMA response). The difference between the two values is preferably greater than about 10%, preferably greater than about 20%, preferably greater than about 30%, preferably greater than about 40%, preferably greater than about 50% as a function of the value for the reference/comparator antibody.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is an EBV gp350 polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two, or one of positions 71H, 73H and 78H; for instance, the amino acid residues at those positions may be 71A, 73T and/or 78A. The VL acceptor human framework may be identical in sequence to the VL human immunoglobulin framework sequence or human consensus framework sequence.

Antibodies of this disclosure may be able to compete for binding to the same epitope as is bound by a second antibody. Monoclonal antibodies are considered to share the "same epitope" if each blocks binding of the other by 40% or greater at the same antibody concentration in a standard in vitro antibody competition binding analysis.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. For the VL, the subgroup may be subgroup kappa I as in Kabat et al. For the VH, the subgroup is subgroup III as in Kabat et al.

A "VH subgroup III consensus framework" comprises the consensus sequence obtained from the amino acid sequences in variable heavy subgroup III of Kabat et al.

A "VL subgroup I consensus framework" comprises the consensus sequence obtained from the amino acid sequences in variable light kappa subgroup I of Kabat et al.

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", "HV" or "CDR", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). Several hypervariable region delineations are in use and are encompassed herein. The Kabat Complementarity Determining Regions (CDRs) are based on sequence variability and are the most commonly used. The "contact" hypervariable regions are based on an analysis of the available complex crystal structures. The residues from each of these hypervariable regions are noted below. Unless otherwise denoted, Kabat numbering is employed. Hypervariable region locations are generally: amino acids 24-34 (HVR-L1), amino acids 49-56 (HVR-L2), amino acids 89-97 (HVR-L3), amino acids 26-35A (HVR-H1), amino acids 49-65 (HVR-H2), and amino acids 93-102 (HVR-H3). Hypervariable regions may also comprise "extended hypervariable regions" as follows: amino acids 24-36 (L1), and amino acids 46-56 (L2) in the VL, numbered according to Kabat et al., supra for each of these definitions.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity or binding specificity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-55 (1995); Yelton et al. J. Immunol. 155:1994-2004 (1995); Jackson et al., J. Immunol. 154(7):3310-19 (1995); and Hawkins et al, J. Mol. Biol. 226:889-96 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

A "gp350 binding oligopeptide" is an oligopeptide that binds, preferably specifically, to an EBV gp350 protein. gp350 binding oligopeptides may be chemically synthesized using known oligopeptide synthesis methodology or may be prepared and purified using recombinant technology. gp350 binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides are capable of binding, preferably specifically, to an EBV gp350 protein. gp350 binding oligopeptides of this disclosure preferably comprise or consist of at least one complementarity determining region (CDR) of the antibodies of this disclosure. gp350 binding oligopeptides may be identified without undue experimentation using well known techniques. In this regard, techniques for screening oligopeptide libraries for oligopeptides that are capable of specifically binding to a polypeptide target are known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991)

Proc. Natl. Acad. Sci. USA, 88:8363, and Smith, G. P. (1991) Current Opin. Biotechnol., 2:668).

An antibody, oligopeptide or other organic molecule "which binds" an antigen of interest, e.g. an EBV polypeptide antigen target, is one that binds the antigen with sufficient affinity such that the antibody or oligopeptide is useful as a diagnostic and/or therapeutic agent in targeting a viral particle, or a cell or a tissue expressing the antigen, and does not significantly cross-react with other proteins, such as other herpes virus proteins. The extent of binding of the antibody or oligopeptide to a "non-target" protein will often be less than about 10% of the binding of the antibody or oligopeptide to its target protein as determined by fluorescence activated cell sorting (FACS) analysis or radioimmunoprecipitation (RIA). Regarding the binding of an antibody or oligopeptide to a target molecule, the terms "specific binding" or "specifically binds to" or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or "is specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about 10 M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" may refer to binding where a molecule binds to a particular polypeptide or epitope on a particular polypeptide without substantially binding to any other polypeptide or polypeptide epitope.

An antibody or oligopeptide that "inhibits the growth of infected cells expressing an EBV gp350 protein" or a "growth inhibitory" antibody or oligopeptide is one which results in measurable growth inhibition of infected cells expressing or overexpressing the appropriate EBV gp350 protein. The EBV gp350 protein may be a transmembrane polypeptide expressed on the surface of an infected cell or may be a polypeptide that is produced and secreted by an infected cell. Preferred growth inhibitory anti-gp350 antibodies or oligopeptides inhibit growth of gp350-expressing cells by greater than 20%, preferably from about 20% to about 50%, and even more preferably, by greater than 50% (e.g., from about 50% to about 100%) as compared to the appropriate control, the control typically being cells not treated with the antibody or oligopeptide being tested. Growth inhibition can be measured at an antibody concentration of about 0.1 to 30 mcg/ml or about 0.5 nM to 200 nM in cell culture, where the growth inhibition is determined 1-10 days after exposure of the cells to the antibody. Growth inhibition of cells in vivo can be determined in various ways such as is described in the Examples section below. The antibody is growth inhibitory in vivo if administration of the anti-gp350 antibody at about 1 μg/kg to about 100 mg/kg body weight results in reduction in infected cells or inhibited EBV proliferation within about 1 day to 3 months from the first administration of the antibody, preferably within about 1 to 5 days.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (USA) 95:652-56 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see review M. in Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

An antibody or oligopeptide which "induces cell death" is one which causes a viable cell to become nonviable. The cell is one which expresses an EBV gp350 protein or is infected with EBV. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody or oligopeptide can induce cell death, loss of membrane integrity as evaluated by uptake of propidium iodide (PI), trypan blue (see Moore et al. Cytotechnology 17:1-11 (1995)) or 7AAD can be assessed relative to untreated cells.

A "gp350-expressing cell" is a cell which expresses an endogenous or transfected EBV gp350 protein which may include expression either on the cell surface or in a secreted form.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD, or IgM.

The word "label" when used herein refers to a detectable compound or composition which is conjugated directly or indirectly to an antibody or oligopeptide to generate a "labeled" antibody or oligopeptide. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32 and radioactive isotopes of Lu), chemotherapeutic agents, enzymes and fragments thereof such as nucleolytic enzymes, antibiotics, immune suppressants, and toxins such as small molecule toxins or enzymatically active toxins of bacterial, fungal, plant or animal origin, including fragments and/or variants thereof. An antiviral agent causes destruction of virus-infected cells.

A "growth inhibitory agent" when used herein refers to a compound or composition which inhibits growth of a cell, especially an EBV-infected cell, either in vitro or in vivo. Thus, the growth inhibitory agent may be one which significantly reduces the percentage of EBV-infected cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

II. Compositions and Methods

A. Anti-gp350 Antibodies

This disclosure provides anti-gp350 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous or intraperitoneal injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl2, or R1N═C═NR, where R and R1 are different alkyl groups.

Animals are immunized against the antigen, immunogenic conjugates, or derivatives by combining, e.g., 100 mcg or 5 mcg of the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to fourteen days later, the animals are bled and the serum is assayed for antibody titer Animals are boosted until the titer plateaus. Conjugates also can be made in recombinant cell culture as protein fusions. Also, aggregating agents such as alum are suitably used to enhance the immune response.

2. Monoclonal Antibodies Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, California USA, and SP-2 and derivatives e.g., X63-Ag8-653 cells available from the American Type Culture Collection, Manassas, Virginia, USA. Human myeloma and mouse-human heteromyeloma cell lines also have been described for producing human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs. 130:151-188 (1992).

Monoclonal antibodies or antibody fragments may be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-66 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-gp350 antibodies of this disclosure may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-25 (1986); Riechmann et al., Nature, 332:323-29 (1988); and Presta, Curr. Op. Struct. Biol., 2:593-96 (1992)).

Methods for humanizing non-human antibodies are known in the art. Generally, a humanized antibody has one or more amino acid residues introduced into it from a source which is non-human. These non-human amino acid residues are often referred to as "import" residues, which are typically taken from an "import" variable domain Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is important to reduce antigenicity and HAMA response (human anti-mouse antibody) when the antibody is intended for human therapeutic use. According to the "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a framework region derived from the consensus sequence of all human antibodies of a subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity or specificity for the target antigen(s), is achieved. In general, the hypervariable region residues are directly and most substantially involved in influencing antigen binding.

Various forms of humanized anti-gp350 antibodies are contemplated. For example, the humanized antibody may be an antibody fragment, such as a Fab, which is optionally conjugated with one or more cytotoxic agent(s) to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-58 (1993); Bruggemann et al., Year in Immuno. 7:33 (1993); U.S. Pat. Nos. 5,545,806, 5,569,825, 5,591,669 (all of GenPharm); 5,545,807; and WO 97/17852.

Alternatively, phage display technology (McCafferty et al., Nature 348:552-53 (1990)) can be used to produce human antibodies and antibody fragments in vitro, from immunoglobulin variable (V) domain gene repertoires from unimmunized donors. Using this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-71 (1993). Several sources of V-gene segments can be used for phage display. Clackson et al., Nature, 352:624-28 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-97 (1991), or Griffith et al., EMBO J. 12:725-34 (1993). See, also, U.S. Pat. Nos. 5,565,332 and 5,573,905.

As discussed above, human antibodies may also be generated in vitro in activated B cells (see, for example, U.S. Pat. Nos. 5,567,610 and 5,229,275).

4. Antibody Fragments

In certain circumstances, there are advantages to using antibody fragments, rather than whole antibodies. The smaller size of the fragments allows for rapid clearance, and may lead to improved access to EBV-infected cells or organs in a mammal.

Various techniques have been developed to produce antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-67 (1992)). Using another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques to produce antibody fragments will be apparent to the skilled practitioner. The antibody of choice may also be a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870. Such linear antibody fragments may be monospecific or bispecific.

5. Bispecific Antibodies

Bispecific antibodies have binding specificities for at least two different epitopes. Exemplary bispecific antibodies may bind to two different epitopes of a gp350 protein. Other such antibodies may combine a gp350 binding site with a binding site for another protein. Alternatively, an anti-gp350 arm may be combined with an arm which binds to a triggering molecule on a leukocyte such as a T-cell receptor molecule (e.g. CD3) (see, e.g., Baeuerle, et al., Curr. Opin. Mol. Ther. 11(1):22-30 (2009)), or Fc receptors for IgG (FcγR), such as FcγRI (CD64), FcγRII (CD32) and FcγRIII (CD16), to focus and localize cellular defense mechanisms to the gp350-expressing cell. Bispecific antibodies may also be used to localize cytotoxic agents to EBV-infected cells which express gp350. These antibodies possess a gp350-binding arm and an arm which binds the cytotoxic agent (e.g., saporin, anti-interferon-α, *vinca* alkaloid, ricin A chain, methotrexate or radioactive isotope hapten). Bispecific antibodies can be prepared as full length antibodies or antibody fragments (e.g., F(ab')2 bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. Nos. 5,821,337 and 6,407,213 teach bispecific anti-ErbB2/anti-CD3 antibodies. Additional bispecific antibodies that bind an epitope on the CD3 antigen and a second epitope have been described in U.S. Pat. No. 5,078,998 (anti-CD3/tumor cell antigen); U.S. Pat. No. 5,601,819 (anti-CD3/IL-2R; anti-CD3/CD28; anti-CD3/CD45); U.S. Pat. No. 6,129,914 (anti-CD3/malignant B cell antigen); U.S. Pat. No. 7,112,324 (anti-CD3/CD19); U.S. Pat. No. 6,723,538 (anti-CD3/CCR5); U.S. Pat. No. 7,235,641 (anti-CD3/EpCAM); U.S. Pat. No. 7,262,276 (anti-CD3/ovarian tumor antigen); and U.S. Pat. No. 5,731,168 (anti-CD3/CD4IgG).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-39 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-59 (1991).

Using a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three-polypeptide fragment when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Preferably, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

Using another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine).

This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with several cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med. 175: 217-25 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed could bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., J. Immunol. 148(5):1547-53 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized to produce antibody homodimers. The "diabody" technology described by Hollinger et al., Proc. Natl. Acad. Sci. USA 90:6444-48 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments using single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

6. Heteroconjugate Antibodies

Heteroconjugate antibodies are also within the scope of this disclosure. Heteroconjugate antibodies are composed of two covalently joined antibodies. Such antibodies have been proposed to target immune system cells to unwanted cells (see U.S. Pat. No. 4,676,980), and for treatment of HIV infection (see WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of this disclosure may be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody preferably further comprises at least two (and preferably four) light chain variable domain polypeptides. The multivalent antibody may comprise from about two to about eight light chain variable domain polypeptides. The light chain variable domain polypeptides contemplated here comprise a light chain variable domain and, optionally, further comprise a CL domain 8. Effector Function Engineering It may be desirable to modify the antibody of the disclosure with respect to effector function, e.g., to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-95 (1992) and Shopes, B. J. Immunol. 148:2918-22 (1992). Homodimeric antibodies with enhanced anti-viral activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-30 (1989).

To increase the serum half-life of the antibody, a salvage receptor binding epitope may be incorporated into the antibody (especially an antibody fragment) as described in U.S. Pat. No. 5,739,277. The term “salvage receptor binding epitope” refers to an epitope of the Fc region of an IgG molecule (e.g., IgG1, IgG2, IgG3, or IgG4) that is responsible for increasing the in vivo serum half-life of the IgG molecule.

9. Immunoconjugates

The disclosure also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate). Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

This disclosure further contemplates an immunoconjugate formed between an antibody and a compound with nucleolytic activity (e.g., a ribonuclease or a DNA endonuclease such as a deoxyribonuclease; DNase).

For selective destruction of an EBV-infected cell, the antibody may comprise a radioactive atom. A variety of radioactive isotopes are available to produce radioconjugated anti-gp350 antibodies. Examples include At211, I131, I125, Y90, Re186, Re188, Sm153, Bi212, P32, Pb212 and radioactive isotopes of Lu. When the conjugate is used for diagnosis, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or 1123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. “Monoclonal Antibodies in Immunoscintigraphy” (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a “cleavable linker” facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the disclosure expressly contemplate, but are not limited to, an ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate) which are commercially available from Pierce Biotechnology, Inc., Rockford, IL).

Alternatively, a fusion protein comprising the anti-EBV gp350 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibody may also be conjugated to a “receptor” (such streptavidin) for utilization in pre-targeting of viral infected cells, wherein the antibody-receptor conjugate is administered to the patient, followed by removal of unbound conjugate from the circulation using a clearing agent and then administration of a “ligand” (e.g., avidin) which is conjugated to a cytotoxic agent (e.g., a radionucleotide).

10. Immunoliposomes

The anti-gp350 antibodies disclosed herein may also be formulated as immunoliposomes. A “liposome” is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of this disclosure can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

B. gp350 Binding Oligopeptides gp350 binding oligopeptides of this disclosure are oligopeptides that bind, preferably specifically, to an EBV gp350 protein. gp350 binding oligopeptides may be chemically synthesized using known oligopeptide synthesis methodology or may be prepared and purified using recombinant technology. gp350 binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to an EBV gp350 protein. gp350 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

Bacteriophage (phage) display is one known technique used to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249:386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215:439 (1998); Zhu et al., Cancer Research, 58(15): 3209-14 (1998); Jiang et al., Infection & Immunity, 65(11): 4770-77 (1997); Ren et al., Gene, 195(2):303-11 (1997); Ren, Protein Sci., 5: 1833 (1996); Efimov et al., Virus Genes, 10:173 (1995)) and T7 phage display systems (Smith and Scott, Methods in Enzymology, 217: 228-57 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphlylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Screening for Anti-gp350 Antibodies and gp350 Binding Oligopeptides with the Desired Properties Techniques for generating antibodies or oligopeptides that bind to EBV gp350 proteins have been described above. One may further select antibodies or oligopeptides with certain biological characteristics, as desired.

The growth inhibitory effects of an anti-gp350 antibody of this disclosure may be assessed by methods known in the art, e.g., using cells which express an EBV gp350 protein either endogenously or following transfection with the gp350 gene. For example, appropriate EBV infected cells may be treated with an anti-gp350 monoclonal antibody or oligopeptide of this disclosure at various concentrations for a few days (e.g., 2-7) and stained with crystal violet or MTT or analyzed by some other colorimetric assay.

Another method of measuring proliferation would be by comparing 3H-thymidine uptake by the cells treated in the presence or absence an anti-gp350 antibody, or gp350 binding oligopeptide of the disclosure. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of infected cells in vivo can be determined in various ways known in the art. Preferably, the anti-gp350 antibody, or gp350 binding oligopeptide will inhibit cell proliferation of an EBV infected cell in vitro or in vivo by about 25-100% compared to the untreated infected cell, more preferably, by about 30-100%, and even more preferably by about 50-100% or 70-100%. Growth inhibition can be measured at an antibody concentration of about 0.5 to 30 μg/ml or about 0.5 nM to 200 nM in cell culture, where the growth inhibition is determined 1-10 days after exposure of the cells to the antibody. The antibody is growth inhibitory in vivo if administration of the anti-gp350 antibody at about 1 μg/kg to about 100 mg/kg body weight results in reduction in cell growth or proliferation within about 5 days to 3 months from the first administration of the antibody, preferably within about 5 to 30 days.

To select for an anti-gp350 antibody, gp350 binding oligopeptide which induces cell death, loss of membrane integrity as indicated by, e.g., propidium iodide (PI), trypan blue or 7AAD uptake may be assessed relative to control. A PI uptake assay can be performed in the absence of complement and immune effector cells. EBV gp350 protein-expressing cells are incubated with medium alone or medium containing the appropriate anti-gp350 antibody (e.g., at about 10 μg/ml), gp350 binding oligopeptide. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those anti-gp350 antibodies, or gp350 binding oligopeptides that induce statistically significant levels of cell death as determined by PI uptake may be selected as cell death-inducing anti-gp350 antibodies or gp350 binding oligopeptides.

To screen for antibodies or oligopeptides which bind to an epitope on an EBV gp350 protein bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody or oligopeptide binds the same site or epitope as a known anti-gp350 antibody. Alternatively or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of an EBV gp350 protein can be used in competition assays with the test antibodies or with a test antibody and an antibody with a characterized or known epitope.

D. Anti-Gp350 Antibody and EBV Gp350 Binding Oligopeptide Variants

In addition to the anti-gp350 antibodies described herein, it is contemplated that anti-gp350 antibody variants can be prepared. Anti-gp350 antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-gp350 antibody, such as changing the number or position of glycosylation sites or altering the membrane anchoring characteristics.

Variations in the anti-gp350 antibodies described herein can be made, for example, using any of the techniques and guidelines for conservative and non-conservative mutations set forth, for instance, in U.S. Pat. No. 5,364,934. Variations may be a substitution, deletion, or insertion of one or more codons encoding the antibody or polypeptide that results in a change in the amino acid sequence as compared with the native sequence antibody or polypeptide. Optionally, the variation is by substitution of at least one amino acid with any other amino acid in one or more of the domains of the anti-gp350 antibody. Guidance in determining which amino acid residue may be inserted, substituted or deleted without adversely affecting the desired activity may be found by comparing the sequence of the anti-gp350 antibody with that of homologous known protein molecules and minimizing the number of amino acid sequence changes made in regions of high homology Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions, or substitutions of amino acids in the sequence and testing the resulting variants for activity exhibited by the full-length or mature native sequence.

Anti-gp350 antibody fragments are provided herein. Such fragments may be truncated at the N-terminus or C-terminus, or may lack internal residues, for example, when compared with a full length native antibody. Certain fragments lack amino acid residues that are not essential for a desired biological activity of the anti-gp350 antibody.

Anti-gp350 antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-gp350 antibody fragments share at least one biological and/or immunological activity with the native anti-gp350 antibodies disclosed herein.

Conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the anti-gp350 antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the anti-gp350 antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-85 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Any cysteine residue not involved in maintaining the proper conformation of the anti-gp350 antibody also may be substituted, generally with serine, to improve the oxidative stability of the molecule and prevent aberrant crosslinking Conversely, cysteine bond(s) may be added to the anti-gp350 antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. To identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and EBV gp350 protein. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-gp350 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-gp350 antibody.

E. Modifications of Anti-gp350 Antibodies

Covalent modifications of anti-gp350 antibodies and EBV gp350 proteins are included within the scope of this disclosure. One type of covalent modification includes reacting targeted amino acid residues of an anti-gp350 antibody with an organic derivatizing agent that can react with selected side chains or the N- or C-terminal residues of the anti-gp350 antibody. Derivatization with bifunctional agents is useful, for instance, for crosslinking anti-gp350 antibody to a water-insoluble support matrix or surface for use in purifying anti-gp350 antibodies, or detection of gp350 protein in biological samples, or EBV diagnostic assays. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the anti-gp350 antibody included within the scope of this disclosure comprises altering the native glycosylation pattern of the antibody or polypeptide. "Altering the native glycosylation pattern" is intended for purposes herein to mean deleting one or more carbohydrate moieties found in native sequence anti-gp350 antibody (either by removing the underlying glycosylation site or by deleting the glycosylation by chemical and/or enzymatic means), and/or adding one or more glycosylation sites that are not present in the native sequence anti-gp350 antibody. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl galactosamine, galactose, or xylose to a hydroxyamino acid, most commonly serine or threonine, although 5-hydroxyproline or 5-hydroxylysine may also be used.

Addition of glycosylation sites to the anti-gp350 antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-gp350 antibody (for O-linked glycosylation sites). The anti-gp350 antibody amino acid sequence may optionally be altered through changes at the DNA level, particularly by mutating the DNA encoding the anti-gp350 antibody at preselected bases such that codons are generated that will translate into the desired amino acids.

Another means of increasing the number of carbohydrate moieties on the anti-gp350 antibody is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the anti-gp350 antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved using a variety of endo- and exo-glycosidases as described by Thotakura et al., Meth. Enzymol., 138:350 (1987).

Another type of covalent modification of anti-gp350 antibody comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-gp350 antibody of this disclosure may also be modified in a way to form chimeric molecules comprising an anti-gp350 antibody fused to another, heterologous polypeptide or amino acid sequence.

Such a chimeric molecule may comprise a fusion of the anti-gp350 antibody with a tag polypeptide which provides an epitope to which an anti-tag antibody can selectively bind. The epitope tag is generally placed at the amino- or carboxyl-terminus of the anti-gp350 antibody. The presence of such epitope-tagged forms of the anti-gp350 antibody can be detected using an antibody against the tag polypeptide. Also, provision of the epitope tag enables the anti-gp350 antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-16 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-10 (1988)); the KT3 epitope peptide (Martin et al., Science, 255:192-194 (1992)); an α-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

Alternatively, the chimeric molecule may comprise a fusion of the anti-gp350 antibody with an immunoglobulin or a region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-gp350 antibody in place of at least one variable region within an Ig molecule. Preferably, the immunoglobulin fusion includes the hinge, CH2 and CH3, or the hinge, CH1, CH2 and CH3 regions of an IgG1 molecule. For the production of immunoglobulin fusions, see also U.S. Pat. No. 5,428,130.

F. Preparation of Anti-Gp350 Antibodies and EBV Gp350 Binding Oligopeptides

The description below relates primarily to production of anti-gp350 antibodies and EBV gp350 binding oligopeptides by culturing cells transformed or transfected with a vector containing anti-gp350 antibody-, or EBV gp350 binding oligopeptide-encoding nucleic acid. It is, of course, contemplated that alternative methods, which are well known in the art, may be employed to prepare anti-gp350 antibodies and EBV gp350 binding oligopeptides. For instance, the appropriate amino acid sequence, or portions thereof, may be produced by direct peptide synthesis using solid-phase techniques (e.g., Stewart et al., Solid-Phase Peptide Synthesis, W.H. Freeman Co., San Francisco, CA (1969); Merrifield, J. Am. Chem. Soc., 85:2149-54 (1963)). In vitro protein synthesis may be performed using manual techniques or by automation. Automated synthesis may be accomplished, for instance, using an Applied Biosystems Peptide Synthesizer (Foster City, CA) using manufacturer's instructions. Various portions of the anti-gp350 antibody may be chemically synthesized separately and combined using chemical or enzymatic methods to produce the desired anti-gp350 antibody.

1. Isolation of DNA Encoding Anti-gp350 Antibody

DNA encoding anti-gp350 antibody may be obtained from a cDNA library prepared from tissue believed to possess the anti-gp350 antibody mRNA and to express it at a detectable level. Accordingly, human anti-gp350 antibody DNA can be conveniently obtained from a cDNA library prepared from human tissue. The anti-gp350 antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding anti-gp350 antibody is to use PCR methodology [Sambrook et al., supra; Dieffenbach et al., PCR Primer: A Laboratory Manual (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 32P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acids having protein coding sequences may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-gp350 antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, CaCl2, CaPO4, liposome-mediated, and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kanr; *E. coli* W3110 strain 37D6, which has the complete genotype tonA ptr3 phoA E15 (argF-lac)169 degP ompT rbs7 ilvG kanr; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in EBV or EBV-infected cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed, e.g., in CHO cells.

In addition to prokaryotes, eukaryotic microbes such as filamentous fungi or yeast are suitable cloning or expression hosts for anti-gp350 antibody-encoding vectors. *Saccharomyces cerevisiae* is a commonly used lower eukaryotic host microorganism. Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/Technology, 9:968-975 (1991)) such as, e.g., *K. lactis* (MW98-8C, CBS683, CBS4574; Louvencourt et al., J. Bacteriol., 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265-278 [1988]); *Candida; Trichoderma* reesia (EP 244,234); *Neurospora crassa* (Case et al., Proc. Natl. Acad. Sci. USA, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and *A. niger* (Kelly and Hynes, EMBO J., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated anti-gp350 antibody are derived from multicellular organisms. Examples of invertebrate cells include insect cells such as *Drosophila* S2 and *Spodoptera* Sf9, as well as plant cells, such as cell cultures of cotton, corn, potato, soybean, *petunia*, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to this disclosure, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-gp350 antibody production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-gp350 antibody may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The anti-gp350 monoclonal antibodies may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-gp350 antibody-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion, the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-gp350 antibody-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trpl gene present in the yeast plasmid YRp7 [Stinchcomb et al., Nature, 282:39 (1979); Kingsman et al., Gene, 7:141 (1979); Tschemper et al., Gene, 10:157 (1980)]. The trpl gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the anti-gp350 antibody-encoding nucleic acid sequence to direct mRNA synthesis. Promoters recognized by a variety of potential host cells are well known. Promoters suitable for use with prokaryotic hosts include the β-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980)), and hybrid promoters such as the tac promoter (deBoer et al., Proc. Natl. Acad. Sci. USA, 80:21-25 (1983)). Promoters for use in bacterial systems also will contain a Shine-Dalgarno sequence operably linked to the DNA encoding anti-gp350 antibody.

Examples of suitable promoting sequences for use with yeast hosts include the promoters for 3-phosphoglycerate kinase (Hitzeman et al., J. Biol. Chem., 255:2073 (1980)) or other glycolytic enzymes (Hess et al., J. Adv. Enzyme Reg., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-gp350 antibody transcription from vectors in mammalian host cells is controlled, for example, by promoters obtained from the genomes of viruses such as polyoma virus, fowlpox virus (UK 2,211,504), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-gp350 antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-gp350 antibody coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-gp350 antibody.

Still other methods, vectors, and host cells suitable for adaptation to the synthesis of anti-gp350 antibody in recombinant vertebrate cell culture are described in Gething et al., Nature, 293:620-25 (1981); Mantei et al., Nature, 281:40-46 (1979); EP 117,060; and EP 117,058.

4. Culturing the Host Cells

The host cells used to produce the anti-gp350 antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem.102:255 (1980), U.S. Pat. Nos. 4,767,704; 4,657,866; 4,927,762; 4,560,655; or 5,122,469; WO 90/03430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence EBV gp350 protein or against a synthetic peptide based on the DNA sequences provided herein or against exogenous sequence fused to gp350 DNA and encoding a specific antibody epitope.

6. Purification of Anti-Gp350 Antibodies and Gp350 Binding Oligopeptides

Forms of anti-gp350 antibody may be recovered from culture medium or from host cell lysates. If membrane-bound, it can be released from the membrane using a suitable detergent solution (e.g. Triton-X 100) or by enzymatic cleavage. Cells employed in expression of anti-gp350 antibody can be disrupted by various physical or chemical means, such as freeze-thaw cycling, sonication, mechanical disruption, or cell lysing agents.

It may be desired to purify anti-gp350 antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-gp350 antibody and EBV gp350 protein. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the anti-gp350 antibody produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABXTMresin (J. T. Baker, Phillipsburg, NJ) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

G. Pharmaceutical Formulations

Therapeutic formulations of the anti-gp350 antibodies or gp350 binding oligopeptides of this disclosure are prepared for storage by mixing the antibody, polypeptide, or oligopeptide having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the indication being treated, preferably those with complementary activities that do not adversely affect each other. For example, in addition to an anti-gp350 antibody or gp350 binding oligopeptide, it may be desirable to include in the one formulation, an additional antibody, e.g., a second anti-gp350 antibody which binds a different epitope on the EBV gp350 protein. Alternatively, or additionally, the composition may further comprise a cytokine, an anti-inflammatory agent, or an interferon. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

H. Diagnosis and Treatment with Anti-gp350 Antibodies or gp350 Binding Oligopeptides gp350 expression may be evaluated using an in vivo diagnostic assay, e.g., by administering a molecule (such as an anti-gp350 antibody or gp350 binding oligopeptide) which binds the molecule to be detected and is tagged with a detectable label (e.g., a radioactive isotope or a fluorescent label) and externally scanning the patient for localization of the label.

As described above, the anti-gp350 antibodies or oligopeptides of this disclosure have various non-therapeutic applications. The anti-gp350 antibodies or oligopeptides of this disclosure are useful for diagnosis and staging of EBV infections. The antibodies or oligopeptides are also useful for purification or immunoprecipitation of EBV gp350 protein from cells, for detection and quantitation of EBV gp350 protein in vitro, e.g., in an ELISA or a Western blot, to kill and eliminate gp350-expressing cells from a population of mixed cells as a step in the purification of other cells.

Currently, EBV infection prevention and treatment involves preventing transmission of the virus, vaccination, or administration of interferons. Anti-gp350 antibody or oligopeptide therapy (such as by passive immunotherapy) may be especially desirable in elderly patients or immunocompromised patients or pregnant patients who may not tolerate the side effects of vaccination or vaccine components or interferons, or who cannot mount an immunological response.

A conjugate comprising an anti-gp350 antibody or oligopeptide conjugated with a cytotoxic agent may be administered to the patient. Preferably, the immunoconjugate bound to the anti-gp350 antibody is internalized by the cell, resulting in increased therapeutic efficacy of the immunoconjugate in killing the infected cell to which it binds. Preferably, the cytotoxic agent targets or interferes with the nucleic acid in the infected cell. The anti-gp350 antibodies or oligopeptides or conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody or oligopeptide is preferred.

Other therapeutic regimens may be combined with the administration of the anti-gp350 antibody or oligopeptide. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-gp350 antibody or antibodies or oligopeptides with administration of an antibody directed against another EBV antigen.

The therapeutic treatment methods of this disclosure may include the combined administration of an anti-gp350 antibody (or antibodies) or oligopeptides and an interferon.

For the prevention or treatment of EBV infection or EBV-associated disease, the dosage and mode of administration of these antibodies and therapeutic proteins will be chosen by the medical provider according to known criteria. The appropriate dosage of antibody or oligopeptide will depend on the type of disease to be treated, as defined above, the severity and course of the disease, whether the antibody or oligopeptide is administered for preventive or therapeutic purposes, previous therapy, the patient's clinical history and response to the antibody or oligopeptide and the discretion of the medical provider. The antibody or oligopeptide is suitably administered to the patient at one time or over a series of treatments. Preferably, the antibody or oligopeptide is administered by intravenous infusion or by subcutaneous injections. Depending on the type and severity of the disease, about 1 mcg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-gp350 antibody. However, other dosage regimens may be useful. A typical daily dosage might range from about 1 mcg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to medical providers of skill in the art.

Aside from administration of the anti-gp350 antibody to a patient, this disclosure contemplates administration of the antibody by gene therapy. Such administration of nucleic acid encoding the antibody is encompassed by the expression "administering a therapeutically effective amount of an antibody." See, for example, WO96/07321 concerning the use of gene therapy to generate intracellular antibodies.

There are two major approaches to getting the nucleic acid (optionally contained in a vector) into the patient's cells; in vivo and ex vivo. For in vivo delivery, the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

The anti-gp350 antibodies of the disclosure can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail above, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, to minimize side effects or therapeutic complications, certain other Fc regions may be used.

These antibodies may include an antibody that competes for binding or binds substantially to, the same epitope as the antibodies of the disclosure. Antibodies having the biological characteristics of the present anti-gp350 antibodies of this disclosure are also contemplated, specifically including the in vivo targeting, and infection inhibiting or preventing, or cytotoxic characteristics.

The present anti-gp350 antibodies or oligopeptides are useful for treating an EBV infection or alleviating one or more symptoms of the infection in a mammal. The antibody or oligopeptide can bind to at least a portion of an infected cell that express EBV gp350 protein in the mammal Preferably, the antibody or oligopeptide is effective to destroy or kill gp350-expressing cells or inhibit the growth of such cells, in vitro or in vivo, upon binding to EBV gp350 protein on the cell. Such an antibody includes a naked anti-gp350 antibody (not conjugated to any agent). Naked antibodies that have cytotoxic or cell growth inhibition properties can be further harnessed with a cytotoxic agent to render them even more potent in EBV or EBV-infected cell destruction. Cytotoxic properties can be conferred to an anti-gp350 antibody by, e.g., conjugating the antibody with a cytotoxic agent, to form an immunoconjugate as described herein. The cytotoxic agent or a growth inhibitory agent is preferably a small molecule.

This disclosure also provides a composition comprising an anti-gp350 antibody or oligopeptide of the disclosure, and a carrier. For the purposes of treating EBV infection, compositions can be administered to the patient in need of such treatment, wherein the composition can comprise one or more anti-gp350 antibodies present as an immunoconjugate or as the naked antibody. The compositions may comprise these antibodies or oligopeptides in combination with other therapeutic agents. The formulation may be a therapeutic formulation comprising a pharmaceutically acceptable carrier.

This disclosure also provides isolated nucleic acids encoding the anti-gp350 antibodies. Nucleic acids encoding both the H and L chains and especially the hypervariable region residues, chains which encode the native sequence antibody as well as variants, modifications and humanized versions of the antibody, are encompassed.

The disclosure also provides methods useful for treating an EBV infection or alleviating one or more symptoms of the infection in a mammal, comprising administering a therapeutically effective amount of an anti-gp350 antibody or oligopeptide of this disclosure to the mammal. The antibody or oligopeptide therapeutic compositions can be administered short term (acutely) or chronically, or intermittently as directed by a medical professional. Also provided are methods of inhibiting the growth of, and killing an EBV gp350 protein-expressing cell.

This disclosure also provides methods useful for treating or preventing post-transplant lymphoproliferative disorder (PTLD) in a mammal. In these methods, the antibodies or fragments thereof, are particularly effective for PTLD in EBV-seronegative persons (i.e., not previously infected with EBV) and given within a few days of solid organ or bone marrow transplant. In these methods, multiple doses of the antibodies, or functional fragments thereof, may be given over time (for example, in persons undergoing solid organ transplants, these proteins may be given within 72 hours of transplant and additional doses may be given at 1, 4, 6, 8, 12, and 16 weeks after transplant). Virtually all transplant recipients are screened for EBV and CMV serology prior to transplant. The antibodies, or functional fragments thereof, may also be administered to EBV-seropositive persons, but the rate of PTLD is lower is EBV seropositive persons than seronegative persons. In these methods, the antibodies, or functional fragments thereof, and an EBV vaccine may be co-administered. In these co-administration methods, the antibodies, or functional fragments thereof, and the vaccine(s) may be administered on the same day at different sites, as is done for combined treatment with vaccine and immunoglobulin for rabies, hepatitis B, or tetanus exposure. In these methods, a single dose of the antibodies, or functional fragments thereof, would likely be given because the recipient would be expected to produce antibody in response to the vaccine.

J. Articles of Manufacture and Kits

This disclosure also provides assay devices, kits, and articles of manufacture comprising at least one anti-gp350 antibody or oligopeptide of this disclosure, optionally linked to a label, such as a fluorescent or radiolabel. The articles of manufacture may contain materials useful for the detection, diagnosis, or treatment of EBV infection. A preferred device is a lateral flow assay device which provides for point-of-care detection and/or diagnosis of an EBV infection. The article of manufacture comprises a container and a label or package insert on or associated with the container. Suitable containers include, for example, bottles, vials, syringes, etc. The containers may be formed from a variety of materials such as glass or plastic. The container holds a composition which is effective for detecting or treating the EBV infection and may have a sterile access port (for example the container may be an intravenous solution bag or a vial having a stopper pierceable by a hypodermic injection needle). At least one active agent in the composition is an anti-gp350 antibody or oligopeptide of this disclosure. The label or package insert indicates that the composition is used for detecting or treating EBV infection. The label or package insert may further comprise instructions for using the antibody or oligopeptide composition, e.g., in the testing or treating of the infected patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for EBV-infected cell killing assays, for purification, or immunoprecipitation of EBV gp350 protein from cells. For isolation and purification of EBV gp350 protein, the kit can contain an anti-gp350 antibodies or oligopeptides coupled to beads (e.g., sepharose beads). Kits can be provided which contain the antibodies or oligopeptides for detection and quantitation of EBV gp350 protein in vitro, e.g., in an ELISA or a Western blot. As with the article of manufacture, the kit comprises a container and a label or package insert on or associated with the container. The container holds a composition comprising at least one anti-gp350 antibody or oligopeptide of the disclosure. Additional containers may be included that contain, e.g., diluents and buffers, control antibodies. The label or package insert may provide a description of the composition as well as instructions for the intended in vitro or diagnostic use.

The anti-gp350 antibody or oligopeptide of this disclosure may also be provided as part of an assay device. Such assay devices include lateral flow assay devices. A common type of disposable lateral flow assay device includes a zone or area for receiving the liquid sample, a conjugate zone, and a reaction zone. These assay devices are commonly known as lateral flow test strips. They employ a porous material, e.g., nitrocellulose, defining a path for fluid flow capable of supporting capillary flow. Examples include those described in U.S. Pat. Nos. 5,559,041, 5,714,389, 5,120,643, and 6,228,660 all of which are incorporated herein by reference in their entireties. The anti-gp350 antibody or oligopeptide of this disclosure may also be used in a lateral flow assay device in conjunction with other antibodies to detect multiple EBV proteins or other herpesvirus proteins using a single biological sample from a subject or patient being tested on one portable, point-of-care device.

Another type of assay device is a non-porous assay device having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

K. Anti-gp350 Antibody Probes and B-cell Probes

Anti-gp350 antibody and anti-gp350 B-cell probes of this disclosure are polypeptides that bind, preferably specifically, to an anti-gp350 antibody, or a B-cell expressing an anti-gp350 B cell receptor (BCR) (anti-gp350 B cell). Accordingly, the three-dimensional structure of such a probe resembles the three-dimensional structure of at least a portion of the EBV gp350 protein. The three-dimensional structure of an anti-gp350 antibody probe, or an anti-gp350 B-cell probe, of this disclosure may resemble the three-dimensional structure of the CR2-binding region of an EBV gp350 protein. An anti-gp350 antibody probe, or an anti-gp350 B-cell probe, of this disclosure may comprise an amino acid sequence from the CR2-binding region of an EBV gp350 protein. An anti-gp350 antibody probe, or an anti-gp350 B-cell probe, of this disclosure may comprise at least 10, at least 20, at least 30, at least 40, at east 50, at least 75, at least 100, at least 150, at least 200, at least 250, or at least 350 contiguous amino acids from the amino acid sequence forming the CR2-binding region of an EBV gp350 protein, wherein the probe has the ability to bind an anti-gp350 antibody, or a B-cell expressing an anti-gp350 BCR, and wherein the binding of the B-cell is through the BCR. An anti-gp350 antibody probe, or anti-gp350 B-cell probe, of this disclosure may comprise an amino acid sequence at least 90%, at least 95%, at least 97% or at least 99% identical to the amino acid sequence of the CR2-binding region of EBV gp350, wherein the probe can bind an anti-gp350 antibody, or a B-cell expressing an anti-gp350 BCR, and wherein the binding of the B-cell is through the BCR.

Anti-gp350 antibody probes, and anti-gp350 B-cell probes, of this disclosure can be any size sufficient to bind to an anti-gp350 antibody or an anti-gp350 B-cell. An anti-gp350 antibody probe, or an anti-gp350 B-cell probe, of this disclosure may comprise at least 10, at least 20, at least 30, at least 40, at east 50, at least 75, at least 100, at least 150, at least 200, at least 250, at last 300, at least 350, at least 400, or at least 450 amino acids in length. An anti-gp350 antibody probe, or an anti-gp350 B-cell probe, of this disclosure may comprise at least 10, at least 20, at least 30, at least 40, at east 50, at least 75, at least 100, at least 150, at least 200, at least 250, at last 300, at east 350, at least 400, or at least 450 contiguous amino acids from the amino acid sequence forming the CR2-binding region of and EBV gp350 protein, wherein the probe has the ability to bind an anti-gp350 antibody, or a B-cell expressing an anti-gp350 BCR, and wherein the binding of the B-cell is through the BCR.

Using an anti-gp350 antibody probe, or anti-gp350 B-cell probe, of this disclosure having a sequence identical to that of EBV gp35, to isolate gp350-specific B-cells might be problematic, because most B-cells, including memory B-cells, constitutively express CR2 on their surface. Consequently, probes having a three-dimensional structure, and/or a sequence, identical to the three-dimensional structure, and/or sequence, of the CR2-binding region of EBV gp350 will bind to almost all B-cells. Thus, anti-gp350 antibody probes, and anti-gp350 B-cell probes, of this disclosure may lack the ability to bind CR2. Such anti-gp350 antibody probes, and anti-gp350 B-cell probes, can be constructed, for example, by using the sequence of the CR2-binding region of an EBV gp350 protein to construct the probe, and then altering the sequence so that it no longer binds CR2. Thus, anti-gp350 antibody probes, or an anti-gp350 B-cell probes, of this disclosure may comprise a variant sequence of an EBV gp350 CR2 binding region. An anti-gp350 antibody probe, or anti-gp350 B-cell probe, of this disclosure comprises the sequence of an EBV gp350 CR2 binding region, wherein the sequence has been altered to reduce, or eliminate, binding of the probe to CR2. Such alterations include, but are not limited to, substitutions, insertions, and deletions of amino acid residues. Such probes preferentially bind to an anti-gp350 antibody, or an anti-gp350 BCR, but do not bind CR2. An anti-gp350 antibody probe, or anti-gp350 B-cell probe, of this disclosure may comprise an amino acid sequence at least 80% identical, at last 85% identical, at least 90% identical, at least 95% identical, at least 97% identical, or at least 99% identical to an EBV gp350 CR2 binding region, wherein the probe binds to an anti-gp350 antibody, or an anti-gp350 BCR, and wherein the probe does not bind CR2. An anti-gp350 antibody probe, or anti-gp350 B-cell probe, of this disclosure may comprise an amino acid sequence at least 80% identical, at last 85% identical, at least 90% identical, at least 95% identical, at least 97% identical, or at least 99% identical to SEQ ID NO:124, wherein the probe binds to an anti-gp350 antibody, or an anti-gp350 BCR, and wherein the probe, does not bind CR2.

An anti-gp350 antibody probe, or an anti-gp350 B-cell probe, of the disclosure, that binds to an anti-gp350 antibody or an anti-gp350 B cell expressing an anti-gp350 BCR, but that does not bind CR2, can be designed using methods known to those skilled in the art. For example, nucleic acid molecules encoding the CR2-binding region of an EBV gp350 protein can be randomly mutated, the mutated molecules inserted into expression vectors, the vectors introduced into cells capable of expressing them, and the cells cultured such that the encoded, mutated probes are expressed on the cells surface. The cells could then be screened to identify antibodies, B-cells, that bind to the expressed probes. Following identification of such antibodies, and/or B-cells, the identified antibodies, and/or B-cells, can then be tested for their ability to bind CR2. In an alternative method, the three-dimensional model of a complex between EBV gp350 and an anti-gp350 antibody is determined, and the amino acid residues involved in binding of the two molecules determined. A second molecule of a complex between gp350 and CR2 could also be produced, and the amino acid residues involved in formation of this complex determined. Using these models, a person skilled in the art could then chose specific locations within the gp350 protein that could be altered. For example, amino acid residues involved in pairing ofgp350 and CR2, but which are not involved in pairing of gp350 and an anti-gp350 antibody, could be chosen for alteration. Once a variant sequence has been designed, nucleic acid molecules encoding the variant proteins can be synthesized, or produced from wild-type sequences using mutagenesis techniques E.g., PCR), and the encoded proteins expressed and tested for activity.

Using methodology such as that described above, the present inventors have identified amino acid residues involved in binding of EBV gp350 to CR2 and to an anti-gp350 antibody. In particular, the inventors have determined that at least residues Q122, P158, 1160, K161, W162, D163, N164, and D296 of the EBV gp350 protein (amino acid number 1 is the first residue of the protein represented by SEQ ID NO:124) are involved in binding of the protein with CR2. Thus, an anti-gp350 antibody probe, or an anti-gp350 B-cell probe, of this disclosure may comprise an amino acid sequence from the CR2-binding region an EBV gp350 protein, wherein at least one amino acid corresponding to amino acid Q122, P158, I160, K161, W162, D163, N164, or D296, of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein at least one amino acid corresponding to amino acid Q122, P158, I160, K161, W162, D163, N164, or D296, of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. When an amino acid residue is substituted, it is preferred that that the substituting amino acid residue have binding properties (e.g., ionic charge, hydrophobicity, etc.) different from the amino acid residue being replaced.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 Cr2-binding region, wherein the amino acid corresponding to amino acid Q122 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, and aspartate, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been substituted with asparagine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid P158 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid P158 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid P158 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, and aspartate, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid I160 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid I160 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid I160 of SEQ ID NO:124 has been substituted with an amino acid residue selected from the group consisting of serine, threonine, cysteine, proline, asparagine, glutamine, tyrosine, phenylalanine, tryptophan, glutamate, aspartate, arginine, glutamine, histidine and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid I160 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid W162 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been substituted with an amino acid residue selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been substituted with alanine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D163 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been substituted with asparagine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid N164 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid N164 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid N164 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, serine, and aspartate, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid N164 of SEQ ID NO:124 has been substituted with a serine residue, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein one or more amino acids has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein one or more amino acids has been inserted between the amino acid corresponding to amino acid N164 of SEQ ID NO:124 and the amino acid corresponding to C165 of SEQ ID NO:124, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein one or more amino acids selected from the group consisting of serine, threonine, cysteine, proline, asparagine, and glutamine, has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein a serine residue has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D163 of SEQ ID NO:124 has been deleted, or has been substituted with one or more amino acid residues, wherein one or more amino acids has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been deleted, or has been substituted with one or more amino acid residues, wherein one or more amino acids has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein one or more amino acids selected from the group consisting of serine, threonine, cysteine, proline, asparagine, and glutamine, has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been substituted with asparagine, wherein a serine residue has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 Cr2-binding region, wherein the amino acids corresponding to amino acids W162-N164 of SEQ ID NO:124 have been deleted, or have been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acids corresponding to amino acids W162-N164 of SEQ ID NO:124 have been deleted, or have been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acids corresponding to amino acids W162-N164 of SEQ ID NO:124 have been deleted, or have been substituted with an amino acid residue selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acids corresponding to amino acids W162-N164 of SEQ ID NO:124 have each been substituted with an alanine residue, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has substituted with one or more amino acid residues, wherein the amino acid corresponding to amino acid I160 of SEQ ID NO:124 has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with one or more amino acid residues, wherein the amino acid corresponding to amino acid I160 of SEQ ID NO:124 has substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the amino acid corresponding to amino acid I160 of SEQ ID NO:124 has been substituted with an amino acid residue selected from the group consisting of serine, threonine, cysteine, proline, asparagine, glutamine, tyrosine, phenylalanine, tryptophan, glutamate, aspartate, arginine, glutamine, histidine and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the amino acid corresponding to amino acid I160 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has substituted with one or more amino acid residues, wherein the amino acid corresponding to amino acid P158 of SEQ ID NO:124 has been substituted with one or more amino acid residues, wherein the amino acid corresponding to amino acid I160 of SEQ ID NO:124 has substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has substituted with one or more amino acid residues, wherein the amino acid corresponding to amino acid P158 of SEQ ID NO:124 has been substituted with one or more amino acid residues, wherein the amino acid corresponding to amino acid I160 of SEQ ID NO:124 has substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the amino acid corresponding to amino acid P158 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, and aspartate, wherein the amino acid corresponding to amino acid I160 of SEQ ID NO:124 has been substituted with an amino acid residue selected from the group consisting of serine, threonine, cysteine, proline, asparagine, glutamine, tyrosine, phenylalanine, tryptophan, glutamate, aspartate, arginine, glutamine, histidine and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the amino acid corresponding to amino acid P158 of SEQ ID NO:124 has been substituted with asparagine, wherein the amino acid corresponding to amino acid I160 of SEQ ID NO:124 has been substituted with threonine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the amino acid corresponding to amino acid P158 of SEQ ID NO:124 has been substituted with arginine, wherein the amino acid corresponding to amino acid I160 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid K161 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid K161 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid K161 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, serine, and aspartate, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:127 or SEQ ID NO:145, wherein the amino acid corresponding to amino acid Q122 of SEQ ID NO:124 is asparagine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:127 or SEQ ID NO:145.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:129 or SEQ ID NO:147, wherein the amino acid corresponding to amino acid D163 of SEQ ID NO:124 is asparagine, and wherein a serine residue has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:129 or SEQ ID NO:147.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:131 or SEQ ID NO:149, wherein the amino acid corresponding to amino acid D296 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:131 or SEQ ID NO:149.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:133 or SEQ ID NO:151, wherein the amino acids corresponding to amino acids W162-N164 of SEQ ID NO:124 have each been substituted with an alanine residue, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:133 or SEQ ID NO:151.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:135 or SEQ ID NO:153, wherein the amino acid corresponding to amino acid D296 of SEQ ID NO:124 is arginine, wherein the amino acid corresponding to amino acid I160 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:135 or SEQ ID NO:153.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:137 or SEQ ID NO:155, wherein the amino acid corresponding to amino acid D296 of SEQ ID NO:124 is arginine, wherein the amino acid corresponding to amino acid P158 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:137 or SEQ ID NO:155.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:139 or SEQ ID NO:157, wherein the amino acid corresponding to amino acid D296 of SEQ ID NO:124 is arginine, wherein the amino acid corresponding to amino acid P158 of SEQ ID NO:124 is asparagine, wherein the amino acid corresponding to amino acid I160 of SEQ ID NO:124 is threonine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:139 or SEQ ID NO:157.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:141 or SEQ ID NO:159, wherein the amino acid corresponding to amino acid D296 of SEQ ID NO:124 is arginine, wherein the amino acid corresponding to amino acid P158 of SEQ ID NO:124 is arginine, wherein the amino acid corresponding to amino acid I160 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:141 or SEQ ID NO:159.

Thus, this disclosure includes a nucleic acid molecule encoding an anti-gp350 antibody probe, or an anti-gp350 B-cell probe, disclosed herein. Such nucleic acid molecule includes DNA, RNA, mixtures thereof, and modified forms thereof. This disclosure also includes nucleic acid vectors, such as, for example, plasmids, expression vectors, viral vectors, etc., as well as cells comprising such nucleic acid vectors. Methods of producing nucleic acid molecules and nucleic acid vectors of the invention have been described herein.

Anti-gp350 antibody and anti-gp350 B-cell probes of this disclosure can be produced chemically (e.g., oligopeptide synthesis methodology), or they can be produced using recombinant technology. For example, an anti-gp350 antibody probe, or anti-gp350 B-cell probe can be deigned, by producing a nucleic acid molecule encoding the probe, and the nucleic acid molecule introduced into a cell where it can be expressed.

This disclosure includes methods of identifying anti-gp350 antibodies, comprising contacting a test solution containing antibodies with an anti-gp350 antibody probe, or an anti-gp350 B-cell probe, of the disclosure, and isolating an antibody that specifically binds to the anti-gp350 antibody probe, or the anti-gp350 B-cell probe, thereby identifying an anti-gp350 antibody. The anti-gp350 antibody probe may be joined to an affinity tag such as, for example, a His tag, an epitope tag or a labeled tag (e.g., fluorescent label). The anti-gp350 antibody probe, or the anti-gp350 B-cell, may be immobilized on a surface.

This disclosure also includes methods of identifying an anti-gp350 B-cell (i.e., a B-cell expressing an anti-gp350 B-cell receptor), comprising contacting a test solution containing B-cells with an anti-gp350 antibody probe, or an anti-gp350 B-cell probe, of the disclosure, and isolating a B-cell that specifically binds to the anti-gp350 antibody probe, or the anti-gp350 B-cell probe, thereby identifying a B-cell expressing an anti-gp350 B-cell receptor. The anti-gp350 antibody probe, or the anti-gp350 B-cell probe, may be joined to an affinity tag such as, for example, a His tag, an epitope tag or a labeled tag (e.g., fluorescent label). The anti-gp350 antibody probe, or the anti-gp350 B-cell probe, may be immobilized on a surface.

All patent and literature references cited in the present specification are hereby incorporated by reference in their entirety.

The foregoing disclosure is sufficient to enable one skilled in the art to practice the invention. The present invention is not to be limited in scope by the constructs described, because the described embodiments are intended as illustrations of certain aspects of the invention and any constructs that are functionally equivalent are within the scope of this invention.

EXAMPLE

The inventors isolated and characterized a set of human monoclonal antibodies from two blood bank donors who have extraordinally high serum neutralizing antibody titers to EBV. Using the receptor-binding null gp350 probes described in this invention they successfully identified gp350-specific B cells in peripheral blood mononuclear cells without having issues with non-targeting memory B cells that ubiquitously express CR2 (i.e. gp350 receptor) on their surface. Of those monoclonal antibodies, antibodies named A9 and E11 derived from 2 independent donors possessed the highest neutralization activity against EBV, and hence, they were structurally characterized. Structures of antigen-binding fragment (Fab) of A9 and E11 were solved to resolution of 2.4 and 1.8 Å, respectively. Additionally, the structure of Fab A9 in complex with gp350 receptor-binding domain was solved to 3.5 Å. Based on the structural information they designed a set of mutations on both antibodies A9 and E11 that potentially improve affinity and therefore, enhance neutralization potency.

These highly potent neutralizing monoclonal antibodies are useful in prophylaxis to prevent EBV infection in EBV-naïve transplantation receipients who reveive organs/bone marrow from EBV-positive donors. These EBV-naïve transplantation receipients are at high risk for developong lymphoproliferative disease caused by EBV. Also, patients with certain genetic disorders (e.g. XLP1) are at high risk of developing fatal mononucleosis after primary infection with the virus. Currently, there are no such countermeasures that specifically target EBV.

These antibodies are also useful as therapeutics to treat infectious mononucleosis or to prevent reactivation of virus in persistently EBV infected individuals.

The invention claimed is:

1. A protein comprising:

a polypeptide sequence at least 85% identical to the amino acid sequence of the complement receptor 2 (CR2)-binding region of Epstein-Barr virus (EBV) gp350 set forth as amino acid residues 2-425 of SEQ ID NO: 124, wherein the amino acid residue corresponding to amino acid D296 of SEQ ID NO: 124 is substituted with arginine, wherein the protein can bind an anti-gp350 antibody, or a B-cell expressing an anti-gp350 B-cell receptor (BCR), wherein binding of the B-cell is through the BCR, and wherein binding of the protein to CR2 is substantially reduced compared binding of wild-type gp350 to CR2.

2. The protein of claim 1, wherein the polypeptide sequence is at least 90% identical to amino acid residues 2-425 of SEQ ID NO: 124, wherein the amino acid residue corresponding to amino acid D296 of SEQ ID NO: 124 is substituted with arginine.

3. The protein of claim 1, wherein the amino acid corresponding to amino acid Q122 of SEQ ID NO: 124 is substituted with asparagine, methionine, leucine, isoleucine, glycine, alanine, valine, phenylalanine, tyrosine, tryptophan, lysine, arginine, histidine, glutamate, or aspartate.

4. The protein of claim 1, wherein the amino acid corresponding to amino acid P158 of SEQ ID NO: 124 is substituted with arginine, methionine, leucine, isoleucine, glycine, alanine, valine, phenylalanine, tyrosine, tryptophan, lysine, histidine, glutamate, or aspartate.

5. The protein of claim 1, wherein the amino acid corresponding to amino acid I160 of SEQ ID NO: 124 is substituted with arginine, serine, threonine, cysteine, proline, asparagine, glutamine, tyrosine, phenylalanine, tryptophan, glutamate, aspartate, glutamine, histidine, or lysine.

6. The protein of claim 1, wherein the amino acid corresponding to amino acid W162 of SEQ ID NO: 124 is substituted with alanine, serine, threonine, cysteine, proline, asparagine, glutamine, aspartate, glutamate, asparagine, arginine, glutamate, histidine, glycine, valine, leucine, methionine, isoleucine, or lysine.

7. The protein of claim 1, wherein the amino acid corresponding to amino acid D163 of SEQ ID NO: 124 is substituted with asparagine, tyrosine, phenylalanine, tryptophan, serine, threonine, cysteine, proline, glutamine, lysine, arginine, histidine, glycine, alanine, valine, leucine, methionine, or isoleucine.

8. The protein of claim 1, wherein the amino acid corresponding to amino acid N164 of SEQ ID NO: 124 is substituted with serine, methionine, leucine, isoleucine, glycine, alanine, valine, phenylalanine, tyrosine, tryptophan, lysine, arginine, histidine, glutamate, or aspartate.

9. The protein of claim 1, wherein the amino acid corresponding to amino acid K161 of SEQ ID NO: 124 is substituted with methionine, leucine, isoleucine, glycine, alanine, valine, phenylalanine, tyrosine, tryptophan, lysine, arginine, histidine, glutamate, serine, or aspartate.

10. The protein of claim 1, wherein the amino acid corresponding to amino acid P158 of SEQ ID NO: 124 is substituted with arginine; and the amino acid corresponding to amino acid I160 of SEQ ID NO:124 is substituted with arginine.

11. The protein of claim 1, wherein a serine, threonine, cysteine, proline, asparagine, or glutamine residue is inserted between the amino acid corresponding to amino acid N164 of SEQ ID NO: 124 and the amino acid corresponding to C165 of SEQ ID NO: 124.

12. The protein of claim 1, wherein the amino acids corresponding to amino acids W162-N164 of SEQ ID NO: 124 are each substituted with an alanine residue.

13. The protein of claim 1, wherein the protein comprises an amino acid sequence selected from the group consisting of SEQ ID NO: 131, SEQ ID NO: 135, SEQ ID NO: 137, SEQ ID NO: 139, SEQ ID NO: 141, SEQ ID NO: 149, SEQ ID NO: 153, SEQ ID NO: 155, SEQ ID NO: 157 and SEQ ID NO: 159.

14. A nucleic acid molecule encoding the protein of claim 13.

15. A nucleic acid molecule encoding the protein of claim 1.

16. A method for identifying an anti-gp350 antibody, or an anti-gp350 B cell, comprising: contacting the protein of claim 1 with a solution comprising antibodies or B cells; and isolating antibodies or B cells that specifically bind to the protein.

17. The protein of claim 1, wherein the polypeptide sequence consists of amino acid residues 2-425 of SEQ ID NO: 124, wherein the amino acid residue corresponding to amino acid D296 of SEQ ID NO: 124 is substituted with arginine.

18. A nucleic acid molecule encoding the protein of claim 17.

19. The protein of claim 1, wherein the polypeptide sequence consists of amino acid residues 2-425 of SEQ ID NO: 124, wherein amino acid residue corresponding to amino acid D296 of SEQ ID NO: 124 is substituted with arginine and the amino acid corresponding to amino acid I160 of SEQ ID NO: 124 is substituted with arginine.

20. A nucleic acid molecule encoding the protein of claim 19.

* * * * *

SEQUENCE LISTING

```
<160> NUMBER OF SEQ ID NOS: 293

<210> SEQ ID NO 1
<211> LENGTH: 121
<212> TYPE: PRT
<213> ORGANISM: Homo sapiens

<400> SEQUENCE: 1

Gln Val Gln Leu Gln Glu Ser Gly Pro Gly Leu Val Lys Pro Ala Glu
1               5                   10                  15

Thr Leu Ser Leu Thr Cys Thr Val Ser Gly Gly Ser Phe Ser Ser Tyr
            20                  25                  30

Trp Trp Gly Trp Ile Arg Gln Ser Pro Gly Lys Gly Leu Glu Trp Ile
        35                  40                  45

Gly His Ile Ser Ser Gly Gly Asn Asn Tyr Leu Asn Pro Ser Leu Lys
    50                  55                  60

Ser Arg Val Thr Leu Ser Leu Asp Thr Ser Lys Asn Gln Phe Ser Leu
65                  70                  75                  80
```

Lys Leu Asn Ser Val Thr Ala Ala Asp Ser Ala Val Tyr Tyr Cys Ala
85 90 95

Arg Ala Pro Arg Ile Val Val Arg Gly Arg Tyr Phe Asp Gln Trp Gly
100 105 110

Gln Gly Val Leu Val Thr Val Ser Ser
115 120

<210> SEQ ID NO 2
<211> LENGTH: 363
<212> TYPE: DNA
<213> ORGANISM: Homo sapiens

<400> SEQUENCE: 2
caggtgcagc tgcaggagtc gggcccagga ctggtgaagc ctgcggagac cctgtccctc 60
acctgcactg tctctggtgg ctctttcagc agttactggt ggggctggat ccgtcagtcc 120
ccagggaagg gactggagtg gattgggcat atcagtagtg gtggaaacaa ctaccttaat 180
ccgtccctca agagtcgagt caccctgtca ctagacacgt ccaagaacca gttctccctg 240
aagctgaact ctgtgaccgc cgcggactcg gccgtgtatt actgtgccag agcccccccgt 300 attgttgtta gaggccgata ctttgaccaa tggggccagg gagtcctggt caccgtctcc 360
tca 363

<210> SEQ ID NO 3
<211> LENGTH: 8
<212> TYPE: PRT
<213> ORGANISM: Homo sapiens

<400> SEQUENCE: 3

Gly Gly Ser Phe Ser Ser Tyr Trp
1 5

<210> SEQ ID NO 4
<211> LENGTH: 7
<212> TYPE: PRT
<213> ORGANISM: Homo sapiens

<400> SEQUENCE: 4

Ile Ser Ser Gly Gly Asn Asn
1 5

<210> SEQ ID NO 5
<211> LENGTH: 16
<212> TYPE: PRT
<213> ORGANISM: Homo sapiens

<400> SEQUENCE: 5

Ala Pro Ala Pro Arg Ile Val Val Arg Gly Arg Tyr Phe Asp Gln Trp
1 5 10 15

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1 5 10 15

Asp Thr Val Thr Ile Thr Cys Arg Ala Ser Gln Gly Ile Asn Ile Tyr
20 25 30

-continued

```
Leu Asn Trp Phe Gln Gln Arg Pro Gly Lys Ala Pro Lys Leu Leu Ile
        35                  40                  45

Tyr Ala Ala Thr Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Cys Glu Ser Tyr Pro Leu
                85                  90                  95

Thr Phe Gly Gly Gly Thr Lys Val Glu Ile Lys
            100                 105


<210> SEQ ID NO 7
<211> LENGTH: 321
<212> TYPE: DNA
<213> ORGANISM: Homo sapiens

<400> SEQUENCE: 7

gacatccaga tgacccagtc tccatcctcc ctgtctgcat ctgtaggaga cactgtcacc      60

atcacttgcc gggcaagtca gggtatcaat atctacctga attggtttca gcagagacca     120

gggaaagccc ctaaactcct gatctatgct gcgaccactt tacaaagtgg ggtcccatca     180

agattcagcg gcagtggatc tgggacagat ttcactctca ccatcagcag cctgcagcct     240

gaagatttcg caacttatta ctgtctacag tgtgaaagtt atccgctcac tttcggcgga     300

gggaccaagg tggagatcaa a                                               321


<210> SEQ ID NO 8
<211> LENGTH: 6
<212> TYPE: PRT
<213> ORGANISM: Homo sapiens

<400> SEQUENCE: 8

Gln Gly Ile Asn Ile Tyr
1               5


<210> SEQ ID NO 9
<211> LENGTH: 3
<212> TYPE: PRT
<213> ORGANISM: Homo sapiens

<400> SEQUENCE: 9

Ala Ala Thr
1


<210> SEQ ID NO 10
<211> LENGTH: 9
<212> TYPE: PRT
<213> ORGANISM: Homo sapiens

<400> SEQUENCE: 10

Leu Gln Cys Glu Ser Tyr Pro Leu Thr
1               5


<210> SEQ ID NO 11
<211> LENGTH: 123
<212> TYPE: PRT
<213> ORGANISM: Homo sapiens

<400> SEQUENCE: 11

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Gly Ala
            20                  25                  30

Tyr Tyr Tyr Trp Ser Trp Ile Arg Gln Pro Pro Gly Lys Gly Leu Asp
        35                  40                  45

Trp Ile Gly Tyr Ile Tyr Gly Ser Phe Gly Ser Ala Tyr Tyr Asn Pro
    50                  55                  60

Ser Leu Lys Ser Arg Ala Thr Ile Ser Lys Asp Thr Pro Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Gly Arg Arg Leu Gly Tyr Ser Asn Trp Phe Asp Val
            100                 105                 110

Trp Gly Pro Gly Val Leu Val Thr Val Ser Ser
        115                 120


<210> SEQ ID NO 12
<211> LENGTH: 369
<212> TYPE: DNA
<213> ORGANISM: Homo sapiens

<400> SEQUENCE: 12

caggtgcaac tgcaggagtc gggcccagga ctggtgaagc cttcggagac cctgtccctc      60

acctgcactg tctctggtgg ctccatcagc ggtgcttact actactggag ctggattcga     120

cagcccccgg ggaagggact ggactggatt ggatatatct atggaagttt tgggagtgcc     180

tactacaacc cctccctcaa gagtcgagcc accatttcaa aagacacgcc caagaaccag     240

ttctccctga aactgagctc tgtgaccgcc gcggacacgg ccgtgtatta ctgtgcgaga     300

ggaaggcgac taggctattc gaactggttc gatgtctggg gcccgggagt cctggtcacc     360

gtctcctca                                                             369


<210> SEQ ID NO 13
<211> LENGTH: 10
<212> TYPE: PRT
<213> ORGANISM: Homo sapiens

<400> SEQUENCE: 13

Gly Gly Ser Ile Ser Gly Ala Tyr Tyr Tyr
1               5                   10


<210> SEQ ID NO 14
<211> LENGTH: 8
<212> TYPE: PRT
<213> ORGANISM: Homo sapiens

<400> SEQUENCE: 14

Ile Tyr Gly Ser Phe Gly Ser Ala
1               5


<210> SEQ ID NO 15
<211> LENGTH: 15
<212> TYPE: PRT
<213> ORGANISM: Homo sapiens

<400> SEQUENCE: 15

Ala Arg Gly Arg Arg Leu Gly Tyr Ser Asn Trp Phe Asp Val Trp
1               5                   10                  15


<210> SEQ ID NO 16
<211> LENGTH: 107
```

<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1 5 10 15

Asp Lys Val Thr Ile Thr Cys Arg Thr Ser Gln Asp Val Ser Ser Tyr
20 25 30

Leu Ala Trp Tyr Gln Gln Lys Pro Gly Lys Ala Pro Gln Leu Leu Ile
35 40 45

Tyr Ala Ala Ser Ser Leu Gln Ser Gly Val Pro Ser Arg Phe Thr Gly
50 55 60

Ser Gly Ser Gly Ala Glu Phe Thr Leu Thr Ile Ser Ser Leu Gln Pro
65 70 75 80

Glu Asp Phe Ala Ser Tyr Tyr Cys Gln Gln Tyr Lys Asn Leu Pro Leu
85 90 95

Thr Phe Gly Gly Gly Thr Lys Val Glu Ile Lys
100 105

<210> SEQ ID NO 17
<211> LENGTH: 321
<212> TYPE: DNA
<213> ORGANISM: Homo sapiens

<400> SEQUENCE: 17
gacatccaga tgacccagtc tccatcttcc ctgtctgcat ctgtaggaga caaagtcacc 60
atcacttgtc ggacaagtca ggacgttagc agttatttag cctggtatca gcagaaacca 120
gggaaagccc ctcagctcct gatctatgct gcatccagtt tgcaaagtgg ggtcccatca 180
aggttcaccg gcagtggatc tggggcagaa ttcactctca ccatcagcag ccttcagcct 240
gaagattttg catcatatta ctgtcaacag tataaaaatc tcccgctcac tttcggcgga 300
gggaccaaag tggagatcaa a 321

<210> SEQ ID NO 18
<211> LENGTH: 6
<212> TYPE: PRT
<213> ORGANISM: Homo sapiens

<400> SEQUENCE: 18

Gln Asp Val Ser Ser Tyr
1 5

<210> SEQ ID NO 19
<211> LENGTH: 3
<212> TYPE: PRT
<213> ORGANISM: Homo sapiens

<400> SEQUENCE: 19

Ala Ala Ser
1

<210> SEQ ID NO 20
<211> LENGTH: 9
<212> TYPE: PRT
<213> ORGANISM: Homo sapiens

<400> SEQUENCE: 20

Gln Gln Tyr Lys Asn Leu Pro Leu Thr
1 5

<210> SEQ ID NO 21
<211> LENGTH: 129
<212> TYPE: PRT
<213> ORGANISM: Homo sapiens

<400> SEQUENCE: 21

```
Gln Val Gln Leu Gln Glu Ser Gly Pro Gly Leu Val Lys Pro Ser Glu
1               5                   10                  15

Thr Leu Ser Leu Thr Cys Asp Val Ser Gly Gly Ser Phe Ser Gly Asp
            20                  25                  30

Phe Tyr Trp Ser Trp Ile Arg Gln Pro Pro Gly Lys Gly Leu Asp Trp
        35                  40                  45

Ile Gly Asn Ile His Gly Ser Ser Ala Gly Thr Lys Tyr Lys Pro Ser
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Gly Pro Leu Ser Arg Ile Val Ala Gly Phe Gly Arg Gly
            100                 105                 110

Ile Asn Trp Phe Asp Val Trp Gly Pro Gly Val Leu Val Thr Val Ser
        115                 120                 125

Ser
```

<210> SEQ ID NO 22
<211> LENGTH: 387
<212> TYPE: DNA
<213> ORGANISM: Homo sapiens

<400> SEQUENCE: 22

```
caggtgcagc tgcaggagtc gggcccagga ctggtgaagc cttcggagac cctgtccctc      60

acctgcgatg tctctggtgg ctccttcagc ggtgatttct actggagctg gatccgccag     120

cccccaggga agggactgga ctggattggg aatatccatg gcagcagtgc gggcaccaaa     180

tacaagccct ccctcaagag tcgagtcacc atttcaaaag acacgtccaa gaaccagttc     240

tccctgaaac tgagctctgt gaccgccgcg gacacggccg tctattactg tacgagaggc     300

ccccttagta ggatagtagc tggttttggg agggggatta actggttcga tgtctggggc     360

ccgggagtcc tggtcaccgt ctcctca                                         387
```

<210> SEQ ID NO 23
<211> LENGTH: 9
<212> TYPE: PRT
<213> ORGANISM: Homo sapiens

<400> SEQUENCE: 23

```
Gly Gly Ser Phe Ser Gly Asp Phe Tyr
1               5
```

<210> SEQ ID NO 24
<211> LENGTH: 8
<212> TYPE: PRT
<213> ORGANISM: Homo sapiens

<400> SEQUENCE: 24

```
Ile His Gly Ser Ser Ala Gly Thr
1               5
```

<210> SEQ ID NO 25
<211> LENGTH: 22
<212> TYPE: PRT
<213> ORGANISM: Homo sapiens

<400> SEQUENCE: 25

```
Thr Arg Gly Pro Leu Ser Arg Ile Val Ala Gly Phe Gly Arg Gly Ile
1               5                   10                  15

Asn Trp Phe Asp Val Trp
            20
```

<210> SEQ ID NO 26
<211> LENGTH: 116
<212> TYPE: PRT
<213> ORGANISM: Homo sapiens

<400> SEQUENCE: 26

```
Gln Pro Val Leu Thr Gln Pro Thr Ser Leu Ser Ala Ser Pro Gly Ala
1               5                   10                  15

Ser Val Arg Leu Ser Cys Thr Leu Ser Ser Gly Ile Asn Val Gly Ser
            20                  25                  30

Tyr Ser Ile Phe Trp Tyr Gln Gln Lys Pro Gly Ser Pro Pro Arg Tyr
        35                  40                  45

Leu Leu Phe Tyr Phe Ser Asp Ser Ser Lys His Gln Gly Ser Gly Val
    50                  55                  60

Pro Ser Arg Phe Ser Gly Ser Lys Asp Thr Ser Ala Asn Ala Gly Leu
65                  70                  75                  80

Leu Leu Ile Ser Gly Leu Gln Ser Glu Asp Glu Ala Asp Tyr Tyr Cys
                85                  90                  95

Ala Ile Trp His Ser Ser Ala Ser Val Leu Phe Gly Gly Gly Thr Arg
            100                 105                 110

Leu Thr Val Leu
        115
```

<210> SEQ ID NO 27
<211> LENGTH: 348
<212> TYPE: DNA
<213> ORGANISM: Homo sapiens

<400> SEQUENCE: 27

```
cagcctgtgc tgacccagcc aacctccctc tcagcatctc cgggagcatc agtcagactc      60

agctgcacct tgagcagtgg catcaatgtt ggtagttaca gcatattctg gtaccagcag     120

aagccaggga gtcctccccg gtaccttctg ttctatttct cagactcaag taagcaccag     180

ggctctggag tccccagccg tttctctgga tccaaggata cttcagccaa tgcagggctt     240

ttactgatct ctgggctcca gtctgaagat gaggctgact attactgtgc catatggcac     300

agcagcgctt ctgtgttatt cggaggaggg acccggctga cagtacta                  348
```

<210> SEQ ID NO 28
<211> LENGTH: 14
<212> TYPE: PRT
<213> ORGANISM: Homo sapiens

<400> SEQUENCE: 28

```
Thr Leu Ser Ser Gly Ile Asn Val Gly Ser Tyr Ser Ile Phe
1               5                   10
```

<210> SEQ ID NO 29
<211> LENGTH: 7

<212> TYPE: PRT
<213> ORGANISM: Homo sapiens

<400> SEQUENCE: 29

Tyr Phe Ser Asp Ser Ser Lys
1               5

<210> SEQ ID NO 30
<211> LENGTH: 10
<212> TYPE: PRT
<213> ORGANISM: Homo sapiens

<400> SEQUENCE: 30

Ala Ile Trp His Ser Ser Ala Ser Val Leu
1               5                   10

<210> SEQ ID NO 31
<211> LENGTH: 120
<212> TYPE: PRT
<213> ORGANISM: Homo sapiens

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Gly Tyr
            20                  25                  30

Tyr Trp Ser Trp Ile Arg Gln Pro Pro Gly Lys Gly Pro Glu Trp Ile
        35                  40                  45

Gly Phe Ile Asp Gly Asn Thr Val Gly Thr Asn Tyr Asn Pro Ser Leu
    50                  55                  60

Lys Ser Arg Val Thr Leu Ser Lys Asp Thr Ser Lys Asn Gln Phe Ser
65                  70                  75                  80

Leu Lys Val Ser Ser Val Thr Ala Ala Asp Thr Ala Val Tyr Tyr Cys
                85                  90                  95

Ala Arg Lys Pro Leu Arg Arg Tyr Phe Trp Phe Asp Val Trp Gly Pro
            100                 105                 110

Gly Val Leu Val Thr Val Ser Ser
        115                 120

<210> SEQ ID NO 32
<211> LENGTH: 360
<212> TYPE: DNA
<213> ORGANISM: Homo sapiens

<400> SEQUENCE: 32
cagctgcagc tgcaggagtc gggcccagga ctggtgaagc cttcggagac cctgtccctc 60
acctgcgctg tctctggtgg ctccatcagc ggttactact ggagttggat tcgccagccc 120
ccagggaagg gaccggagtg gattgggttt attgatggta atactgtggg caccaactac 180
aacccctccc tcaagagtcg agtcaccctt tcaaaagaca cgtccaagaa tcagttctcc 240
ctgaaggtga gttctgtgac cgccgcggac acggccgtgt attactgtgc gaggaagccg 300
ctacgccgtt atttctggtt cgatgtctgg ggcccgggag tcctggtcac cgtctcctca 360

<210> SEQ ID NO 33
<211> LENGTH: 8
<212> TYPE: PRT
<213> ORGANISM: Homo sapiens

<400> SEQUENCE: 33

Gly Gly Ser Ile Ser Gly Tyr Tyr
1               5

<210> SEQ ID NO 34
<211> LENGTH: 8
<212> TYPE: PRT
<213> ORGANISM: Homo sapiens

<400> SEQUENCE: 34

Ile Asp Gly Asn Thr Val Gly Thr
1               5

<210> SEQ ID NO 35
<211> LENGTH: 14
<212> TYPE: PRT
<213> ORGANISM: Homo sapiens

<400> SEQUENCE: 35

Ala Arg Lys Pro Leu Arg Arg Tyr Phe Trp Phe Asp Val Trp
1               5                   10

<210> SEQ ID NO 36
<211> LENGTH: 111
<212> TYPE: PRT
<213> ORGANISM: Homo sapiens

<400> SEQUENCE: 36

Gln Ser Val Leu Thr Gln Pro Pro Ser Val Ser Gly Asp Pro Gly Gln
1               5                   10                  15

Arg Val Thr Ile Ser Cys Thr Gly Ser Ser Ser Asn Ile Gly Ala Gly
            20                  25                  30

Tyr Tyr Val Tyr Trp Tyr Gln Gln Phe Pro Gly Thr Ala Pro Lys Leu
        35                  40                  45

Leu Ile Tyr Gln Asp Asn Lys Arg Pro Ser Gly Val Ser Asp Arg Phe
    50                  55                  60

Ser Gly Ser Lys Ser Gly Thr Ser Ala Ser Leu Thr Ile Thr Gly Leu
65                  70                  75                  80

Gln Pro Gly Asp Glu Ala Asp Tyr Tyr Cys Ser Ala Trp Asp Ser Ser
                85                  90                  95

Leu Ser Ala Val Met Phe Gly Arg Gly Thr Arg Leu Thr Val Leu
            100                 105                 110

<210> SEQ ID NO 37
<211> LENGTH: 333
<212> TYPE: DNA
<213> ORGANISM: Homo sapiens

<400> SEQUENCE: 37
cagtctgtgc tgacgcagcc gccctcagtg tctggggacc ccgggcagag ggtcaccatc      60
tcgtgcactg ggagcagctc caacatcggg gcgggttatt atgtatactg gtaccagcag     120
ttcccaggaa cggcccccaa actcctcatc tatcaagata ataagcgacc ctcaggggtt     180
tctgaccgat tctctggctc caagtctggt acctcagcct ccctgaccat cactgggctc     240
cagcctgggg atgaggctga ttattactgc tcagcatggg atagcagcct gagtgctgtt     300
atgttcggaa gaggcaccag gctgacagta cta                                  333

<210> SEQ ID NO 38

<211> LENGTH: 9
<212> TYPE: PRT
<213> ORGANISM: Homo sapiens

<400> SEQUENCE: 38

```
Ser Ser Asn Ile Gly Ala Gly Tyr Tyr
1               5
```

<210> SEQ ID NO 39
<211> LENGTH: 3
<212> TYPE: PRT
<213> ORGANISM: Homo sapiens

<400> SEQUENCE: 39

```
Gln Asp Asn
1
```

<210> SEQ ID NO 40
<211> LENGTH: 11
<212> TYPE: PRT
<213> ORGANISM: Homo sapiens

<400> SEQUENCE: 40

```
Ser Ala Trp Asp Ser Ser Leu Ser Ala Val Met
1               5                   10
```

<210> SEQ ID NO 41
<211> LENGTH: 120
<212> TYPE: PRT
<213> ORGANISM: Homo sapiens

<400> SEQUENCE: 41

```
Gln Leu Gln Leu Gln Glu Ser Gly Pro Gly Val Val Lys Pro Ser Glu
1               5                   10                  15

Thr Leu Ser Leu Thr Cys Thr Ile Ser Gly Gly Ser Phe Ser Thr Tyr
            20                  25                  30

Tyr Trp Thr Trp Ile Arg Gln Pro Pro Gly Lys Gly Leu Glu Trp Val
        35                  40                  45

Gly Tyr Ile Gly Asn Gly Gly Arg Ser Leu Asn Tyr Asn Pro Ser Leu
    50                  55                  60

Lys Ser Arg Ile Thr Leu Ser Val Asp Ala Ser Lys Asn Gln Phe Ser
65                  70                  75                  80

Leu Lys Val Thr Ser Val Thr Ala Ala Asp Thr Ala Val Tyr Tyr Cys
                85                  90                  95

Gly Arg Ala Arg Gly Leu Arg Gly Asn Trp Phe Asp Val Trp Gly Pro
            100                 105                 110

Gly Val Leu Val Thr Val Ser Ser
        115                 120
```

<210> SEQ ID NO 42
<211> LENGTH: 360
<212> TYPE: DNA
<213> ORGANISM: Homo sapiens

<400> SEQUENCE: 42

```
caactgcagt tgcaggagtc gggcccagga gtggtgaagc cttcggagac cctgtccctc      60

acctgcacta tctctggtgg ctccttcagt acttactact ggacctggat tcgccagccc     120

ccagggaagg gactggagtg ggttgggtat atcggtaatg gtggtcgtag cctcaactac     180

aacccctccc tcaagagtcg catcaccctg tcagtagacg cgtccaagaa ccagttctcc     240
```

ctgaaggtga cctctgtgac cgccgcggac acggccgtct attactgtgg gagagccagg 300
ggactccgcg gaaactggtt cgatgtctgg ggcccgggag tcctggtcac cgtctcctca 360

<210> SEQ ID NO 43
<211> LENGTH: 8
<212> TYPE: PRT
<213> ORGANISM: Homo sapiens

<400> SEQUENCE: 43

Gly Gly Ser Phe Ser Thr Tyr Tyr
1 5

<210> SEQ ID NO 44
<211> LENGTH: 8
<212> TYPE: PRT
<213> ORGANISM: Homo sapiens

<400> SEQUENCE: 44

Ile Gly Asn Gly Gly Arg Ser Leu
1 5

<210> SEQ ID NO 45
<211> LENGTH: 14
<212> TYPE: PRT
<213> ORGANISM: Homo sapiens

<400> SEQUENCE: 45

Gly Arg Ala Arg Gly Leu Arg Gly Asn Trp Phe Asp Val Trp
1 5 10

<210> SEQ ID NO 46
<211> LENGTH: 110
<212> TYPE: PRT
<213> ORGANISM: Homo sapiens

<400> SEQUENCE: 46

Gln Ala Ala Leu Thr Gln Pro Pro Ser Val Ser Gly Ser Pro Gly Gln
1 5 10 15

Ser Val Thr Ile Ser Cys Thr Gly Thr Ser Ser Asp Ile Gly Gly Tyr
20 25 30

Asn Tyr Val Ser Trp Tyr Gln Gln His Pro Gly Lys Ala Pro Lys Val
35 40 45

Met Ile Tyr Glu Val Ser Lys Arg Pro Ser Gly Val Ser Asp Arg Phe
50 55 60

Ser Gly Ser Lys Ser Gly Asn Ile Ala Ser Leu Thr Ile Ser Gly Leu
65 70 75 80

Gln Ala Glu Asp Glu Ala Asp Tyr Tyr Cys Ser Ser Tyr Ala Gly Ser
85 90 95

Asn Thr Phe Leu Phe Gly Gly Gly Thr Arg Leu Thr Val Leu
100 105 110

<210> SEQ ID NO 47
<211> LENGTH: 330
<212> TYPE: DNA
<213> ORGANISM: Homo sapiens

<400> SEQUENCE: 47
caggctgccc tgactcagcc tccctctgtg tctgggtctc ctggacagtc ggtcaccatc 60
tcctgcactg gaaccagcag tgacatcggt ggttataact atgtctcctg gtaccaacaa 120
cacccaggca aagcccccaa agtcatgatt tatgaggtca gtaagcggcc ctcaggggtc 180
tctgatcgct tctctggttc caaatctggc aacatagcct ccctgaccat ctctgggctc 240
caggctgagg acgaggctga ttattactgc agctcatatg caggcagcaa cactttctta 300
ttcggaggag ggacccggct gacagtacta 330

<210> SEQ ID NO 48
<211> LENGTH: 9
<212> TYPE: PRT
<213> ORGANISM: Homo sapiens

<400> SEQUENCE: 48

Ser Ser Asp Ile Gly Gly Tyr Asn Tyr
1               5

<210> SEQ ID NO 49
<211> LENGTH: 3
<212> TYPE: PRT
<213> ORGANISM: Homo sapiens

<400> SEQUENCE: 49

Glu Val Ser
1

<210> SEQ ID NO 50
<211> LENGTH: 10
<212> TYPE: PRT
<213> ORGANISM: Homo sapiens

<400> SEQUENCE: 50

Ser Ser Tyr Ala Gly Ser Asn Thr Phe Leu
1               5                   10

<210> SEQ ID NO 51
<211> LENGTH: 123
<212> TYPE: PRT
<213> ORGANISM: Homo sapiens

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Asn
            20                  25                  30

Tyr Trp Ser Trp Ile Arg Gln Pro Pro Gly Lys Gly Leu Glu Trp Ile
        35                  40                  45

Gly Arg Ile Tyr Gly Ser Gly Gly Ser Thr Asp Tyr Asn Pro Ser Leu
    50                  55                  60

Lys Ser Arg Val Thr Ile Ser Thr Asp Thr Ser Lys Asn Gln Phe Ser
65                  70                  75                  80

Leu Lys Val Ser Ser Val Thr Ala Ala Asp Thr Ala Val Tyr Tyr Cys
                85                  90                  95

Ala Arg Val Arg Ile Gln Trp Val Gln Leu Arg Gly Trp Phe Asp Val
            100                 105                 110

Trp Gly Pro Gly Val Leu Val Thr Val Ser Ser
        115                 120

<210> SEQ ID NO 52
<211> LENGTH: 369
<212> TYPE: DNA
<213> ORGANISM: Homo sapiens

<400> SEQUENCE: 52
caggtgcagc tgcaggagtc gggcccagga ctggtgaagc cttcggagac cctgtccctc 60
acctgcgctg tctctggtgg ctccatcagc agtaactact ggagctggat ccgccagccc 120
ccagggaagg gactggagtg gattggacgt atctatggta gtggtgggag caccgactac 180
aacccctccc tcaagagtcg agtcaccatt tcaacagaca cgtccaagaa ccagttctcc 240
ctgaaggtga gctctgtgac cgccgcggac acggccgtgt attactgtgc gagagtgcgg 300
atacagtggg tacagttgcg aggctggttc gatgtctggg gcccgggagt cctggtcacc 360
gtctcctca 369

<210> SEQ ID NO 53
<211> LENGTH: 10
<212> TYPE: PRT
<213> ORGANISM: Homo sapiens

<400> SEQUENCE: 53

Gly Gly Ser Ile Ser Ser Asn Tyr Trp Ser
1 5 10

<210> SEQ ID NO 54
<211> LENGTH: 8
<212> TYPE: PRT
<213> ORGANISM: Homo sapiens

<400> SEQUENCE: 54

Ile Tyr Gly Ser Gly Gly Ser Thr
1 5

<210> SEQ ID NO 55
<211> LENGTH: 17
<212> TYPE: PRT
<213> ORGANISM: Homo sapiens

<400> SEQUENCE: 55

Ala Arg Val Arg Ile Gln Trp Val Gln Leu Arg Gly Trp Phe Asp Val
1 5 10 15

Trp

<210> SEQ ID NO 56
<211> LENGTH: 107
<212> TYPE: PRT
<213> ORGANISM: Homo sapiens

<400> SEQUENCE: 56

Tyr Ile Gln Met Thr Gln Ser Pro Ser Ser Leu Ser Ala Ser Val Gly
1 5 10 15

Asp Thr Val Thr Phe Thr Gly Pro Ala Ser Gln Ser Phe Ser Ser Ser
20 25 30

Leu Ala Trp Tyr Gln Gln Lys Pro Gly Lys Ala Pro Asn Leu Leu Ile
35 40 45

Tyr Ser Ala Ser Ser Leu Gln Cys Gly Val Arg Ser Arg Phe Ser Gly
50 55 60

Ser Lys Ser Gly Thr Asp Phe Thr Leu Thr Ile Ser Ser Leu Gln Pro
65 70 75 80

```
Glu Asp Ile Ala Ser Tyr Tyr Cys Gln Gln Tyr Tyr Ser Tyr Pro Phe
                85                  90                  95

Thr Phe Gly Pro Gly Thr Lys Leu Asp Ile Lys
            100                 105


<210> SEQ ID NO 57
<211> LENGTH: 321
<212> TYPE: DNA
<213> ORGANISM: Homo sapiens

<400> SEQUENCE: 57

tacatacaga tgacgcagtc tccatcctcc ctgtctgcat ctgtaggaga cacagtcacc      60

ttcactggcc ccgcaagtca gagctttagt agtagtttag cctggtatca gcagaaacca     120

gggaaagccc ctaacctcct gatctatagt gcatccagtt tgcaatgtgg ggttcgttcg     180

aggttcagtg gcagtaagtc tgggacagat ttcactctca ccatcagcag cctgcagcct     240

gaagatattg ctagttatta ctgtcaacag tattacagtt atccattcac tttcggcccc     300

gggaccaaac tggatatcaa a                                               321


<210> SEQ ID NO 58
<211> LENGTH: 6
<212> TYPE: PRT
<213> ORGANISM: Homo sapiens

<400> SEQUENCE: 58

Gln Ser Phe Ser Ser Ser
1               5


<210> SEQ ID NO 59
<211> LENGTH: 3
<212> TYPE: PRT
<213> ORGANISM: Homo sapiens

<400> SEQUENCE: 59

Ser Ala Ser
1


<210> SEQ ID NO 60
<211> LENGTH: 9
<212> TYPE: PRT
<213> ORGANISM: Homo sapiens

<400> SEQUENCE: 60

Gln Gln Tyr Tyr Ser Tyr Pro Phe Thr
1               5


<210> SEQ ID NO 61
<211> LENGTH: 119
<212> TYPE: PRT
<213> ORGANISM: Homo sapiens

<400> SEQUENCE: 61

Gln Val Gln Leu Gln Glu Ser Gly Pro Gly Leu Val Arg Pro Ser Glu
1               5                   10                  15

Thr Leu Ser Leu Thr Cys Ala Val Ser Gly Gly Ser Ile Ser Ser Asn
            20                  25                  30

Tyr Trp Ser Trp Ile Arg Gln Pro Pro Gly Lys Gly Leu Glu Trp Ile
        35                  40                  45

Gly Tyr Ile Ser Gly Ser Thr Gly Ser Thr Tyr Gln Asn Pro Ser Leu
    50                  55                  60
```

-continued

```
Lys Ser Arg Val Thr Val Ser Lys Asp Thr Ser Lys Asn Gln Phe Ser
65                  70                  75                  80

Leu Lys Leu Asn Ser Val Thr Ala Ala Asp Thr Ala Val Tyr Tyr Cys
                85                  90                  95

Ala Arg Ser Gly Arg Arg Gly Ser Ser Leu Asp Leu Trp Gly Arg Gly
            100                 105                 110

Val Leu Val Thr Val Ser Ser
        115


<210> SEQ ID NO 62
<211> LENGTH: 357
<212> TYPE: DNA
<213> ORGANISM: Homo sapiens

<400> SEQUENCE: 62

caggtgcagc tgcaggagtc gggcccagga ctggtgaggc cttcggagac cctatccctc      60

acctgcgctg tctctggtgg ctccatcagc agtaactact ggagctggat tcgccagccc     120

ccagggaagg ggctggagtg gattgggtat atctctggta gtactgggag cacctaccag     180

aacccctccc tcaagagtcg agtcaccgtt tcaaaagaca cgtctaagaa ccagttctcc     240

ctgaagctga attctgtgac cgccgcggac acggccgtgt attactgtgc gagaagtggg     300

agaagaggca gctcattgga tttgtggggc cggggagttc tggtcaccgt ctcctca        357


<210> SEQ ID NO 63
<211> LENGTH: 8
<212> TYPE: PRT
<213> ORGANISM: Homo sapiens

<400> SEQUENCE: 63

Gly Gly Ser Ile Ser Ser Asn Tyr
1               5


<210> SEQ ID NO 64
<211> LENGTH: 8
<212> TYPE: PRT
<213> ORGANISM: Homo sapiens

<400> SEQUENCE: 64

Ile Ser Gly Ser Thr Gly Ser Thr
1               5


<210> SEQ ID NO 65
<211> LENGTH: 13
<212> TYPE: PRT
<213> ORGANISM: Homo sapiens

<400> SEQUENCE: 65

Ala Arg Ser Gly Arg Arg Gly Ser Ser Leu Asp Leu Trp
1               5                   10


<210> SEQ ID NO 66
<211> LENGTH: 111
<212> TYPE: PRT
<213> ORGANISM: Homo sapiens

<400> SEQUENCE: 66

Gln Ser Val Leu Thr Gln Pro Pro Ser Val Ser Gly Asp Pro Gly Gln
1               5                   10                  15

Arg Val Thr Ile Ser Cys Thr Gly Ser Ser Ser Asn Ile Gly Ala Gly
            20                  25                  30
```

```
Tyr Tyr Val Tyr Trp Tyr Gln Gln Phe Pro Gly Thr Ala Pro Lys Leu
        35                  40                  45

Leu Ile Tyr Gln Asp Asn Lys Arg Pro Ser Gly Val Ser Asp Arg Phe
    50                  55                  60

Ser Gly Ser Lys Ser Gly Thr Ser Ala Ser Leu Thr Ile Thr Gly Leu
65                  70                  75                  80

Gln Pro Gly Asp Glu Ala Asp Tyr Tyr Cys Ser Ala Trp Asp Ser Ser
                85                  90                  95

Leu Ser Ala Val Phe Phe Gly Gly Gly Thr Arg Leu Thr Val Leu
            100                 105                 110


<210> SEQ ID NO 67
<211> LENGTH: 333
<212> TYPE: DNA
<213> ORGANISM: Homo sapiens

<400> SEQUENCE: 67

cagtctgtgc tgacgcagcc gccctcagtg tctggggacc ccgggcagag ggtcaccatc      60

tcgtgcactg ggagcagctc caacatcggg gcgggttatt atgtatactg gtaccagcag     120

ttcccaggaa cggcccccaa actcctcatc tatcaagata ataagcgacc ctcaggggtt     180

tctgaccgat tctctggctc caagtctggt acctcagcct ccctgaccat cactgggctc     240

cagcctgggg atgaggctga ttattactgc tcagcatggg atagcagcct gagtgctgtg     300

ttcttcggag gagggacccg gctgacagta cta                                  333


<210> SEQ ID NO 68
<211> LENGTH: 9
<212> TYPE: PRT
<213> ORGANISM: Homo sapiens

<400> SEQUENCE: 68

Ser Ser Asn Ile Gly Ala Gly Tyr Tyr
1               5


<210> SEQ ID NO 69
<211> LENGTH: 3
<212> TYPE: PRT
<213> ORGANISM: Homo sapiens

<400> SEQUENCE: 69

Gln Asp Asn
1


<210> SEQ ID NO 70
<211> LENGTH: 11
<212> TYPE: PRT
<213> ORGANISM: Homo sapiens

<400> SEQUENCE: 70

Ser Ala Trp Asp Ser Ser Leu Ser Ala Val Phe
1               5                   10


<210> SEQ ID NO 71
<211> LENGTH: 121
<212> TYPE: PRT
<213> ORGANISM: Homo sapiens

<400> SEQUENCE: 71

Gln Leu Gln Glu Ser Gly Pro Gly Leu Val Lys Pro Ser Glu Thr Leu
1               5                   10                  15
```

```
Ser Leu Thr Cys Thr Val Ser Gly Gly Ser Ile Ser Asp Thr Tyr Arg
            20                  25                  30

Trp Ser Trp Ile Arg Gln Ser Pro Gly Lys Gly Leu Glu Trp Ile Ala
        35                  40                  45

Tyr Ile Tyr Gly Thr Thr Thr Ser Thr Asn Tyr Asn Pro Ser Leu Lys
    50                  55                  60

Ser Arg Leu Thr Ile Ser Lys Asp Thr Ser Lys Asn Gln Phe Ser Leu
65                  70                  75                  80

Asn Leu Arg Ser Val Thr Ala Ala Asp Thr Ala Val Tyr Tyr Cys Ala
                85                  90                  95

Arg Gly Asp Ser Gly Gly Arg Ser Ala His Val Phe His Phe Trp Gly
            100                 105                 110

Gln Gly Leu Arg Val Thr Val Ser Ser
        115                 120
```

<210> SEQ ID NO 72
<211> LENGTH: 363
<212> TYPE: DNA
<213> ORGANISM: Homo sapiens

<400> SEQUENCE: 72

```
cagctgcagg agtcgggccc aggactggtg aagccttcgg agaccctgtc cctcacctgc     60

actgtctctg gtggctccat cagcgatact taccggtgga gctggattcg ccagtcccca    120

gggaagggac tggagtggat tgcctacatc tatggtacta ctacgagcac caactacaac    180

ccctccctca agagtcgact caccatttca aaagacacgt ccaagaacca gttctccttg    240

aacctgaggt ctgtgaccgc cgcggacacg gccgtgtatt actgtgcgag aggggatagc    300

ggtggccggt cagcgcatgt tttcatttc tggggccaag ggctcagggt caccgtctct     360

tca                                                                  363
```

<210> SEQ ID NO 73
<211> LENGTH: 9
<212> TYPE: PRT
<213> ORGANISM: Homo sapiens

<400> SEQUENCE: 73

```
Gly Gly Ser Ile Ser Asp Thr Tyr Arg
1               5
```

<210> SEQ ID NO 74
<211> LENGTH: 8
<212> TYPE: PRT
<213> ORGANISM: Homo sapiens

<400> SEQUENCE: 74

```
Ile Tyr Gly Thr Thr Thr Ser Thr
1               5
```

<210> SEQ ID NO 75
<211> LENGTH: 16
<212> TYPE: PRT
<213> ORGANISM: Homo sapiens

<400> SEQUENCE: 75

```
Ala Arg Gly Asp Ser Gly Gly Arg Ser Ala His Val Phe His Phe Trp
1               5                   10                  15
```

<210> SEQ ID NO 76

<211> LENGTH: 111
<212> TYPE: PRT
<213> ORGANISM: Homo sapiens

<400> SEQUENCE: 76

```
Gln Ser Val Leu Thr Gln Pro Pro Ser Val Phe Gly Asp Pro Gly Gln
1               5                   10                  15

Arg Ile Thr Ile Ser Cys Thr Gly Ser Ser Ser Asn Ile Gly Ala Gly
            20                  25                  30

Tyr Tyr Val Tyr Trp Tyr Gln Gln Phe Pro Gly Thr Ala Pro Lys Leu
        35                  40                  45

Leu Ile Tyr Gln Asp Asn Lys Arg Pro Ser Gly Val Ser Asp Arg Phe
    50                  55                  60

Ser Gly Ser Lys Ser Gly Ser Ser Ala Ser Leu Thr Ile Thr Gly Leu
65                  70                  75                  80

Gln Pro Gly Asp Glu Ala Asp Tyr Tyr Cys Ser Ala Trp Asp Ser Ser
                85                  90                  95

Leu Ser Val Arg Val Phe Gly Gly Gly Thr Arg Leu Thr Val Leu
            100                 105                 110
```

<210> SEQ ID NO 77
<211> LENGTH: 333
<212> TYPE: DNA
<213> ORGANISM: Homo sapiens

<400> SEQUENCE: 77

```
cagagtgttc tgacgcagcc gccctcagtg tttggggacc ccgggcagag gatcaccatc     60

tcgtgcactg ggagcagctc caacatcggg gcgggttatt atgtatactg gtaccagcag    120

ttcccaggaa cggcccccaa actcctcatc tatcaagata ataagcgacc ctcaggggtt    180

tctgaccgat tttctggctc caagtctggt tcctcagcct ccctgaccat cactgggctc    240

cagcctgggg atgaggctga ttattactgc tcagcatggg atagcagcct gagtgtacgg    300

gttttcggag gagggacccg gctgacagta cta                                 333
```

<210> SEQ ID NO 78
<211> LENGTH: 9
<212> TYPE: PRT
<213> ORGANISM: Homo sapiens

<400> SEQUENCE: 78

```
Ser Ser Asn Ile Gly Ala Gly Tyr Tyr
1               5
```

<210> SEQ ID NO 79
<211> LENGTH: 3
<212> TYPE: PRT
<213> ORGANISM: Homo sapiens

<400> SEQUENCE: 79

```
Gln Asp Asn
1
```

<210> SEQ ID NO 80
<211> LENGTH: 11
<212> TYPE: PRT
<213> ORGANISM: Homo sapiens

<400> SEQUENCE: 80

```
Ser Ala Trp Asp Ser Ser Leu Ser Val Arg Val
1               5                   10
```

<210> SEQ ID NO 81
<211> LENGTH: 122
<212> TYPE: PRT
<213> ORGANISM: Homo sapiens

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ser Phe Ile Thr Asn Thr Gly Lys Thr Thr Tyr Tyr Ala Asp Ser Val
    50                  55                  60

Arg Gly Arg Phe Thr Ile Ser Arg Asp Asn Ala Lys Lys Ser Val Ser
65                  70                  75                  80

Leu Gln Met Ser Ser Leu Arg Ala Glu Asp Thr Ala Val Tyr Tyr Cys
                85                  90                  95

Thr Arg Gly Arg Gly Arg His Gly Trp Ser Ser Gly Val Phe Asp Phe
            100                 105                 110

Trp Gly Gln Gly Leu Arg Val Thr Val Ser
        115                 120
```

<210> SEQ ID NO 82
<211> LENGTH: 368
<212> TYPE: DNA
<213> ORGANISM: Homo sapiens

<400> SEQUENCE: 82

```
gaggtgcaac tggtggagtc tggaggaggc ttggtccagc ctggagggtc cctgagactc      60

tcctgtgcag cctctggatt caccttcagt agttacggca tgaactgggt ccgccaggct     120

ccgggaaagg ggctggagtg ggtctcattc attactaaca ctggtaaaac cacatactac     180

gctgactctg tgaggggccg attcaccatc tccagagaca acgccaagaa gtcggtgtct     240

ctacaaatga gtagcctgag agccgaggac acggccgtct attactgtac taggggaaga     300

ggtagacacg gctggtccag tggtgttttt gatttctggg gccaaggtct cagggtcacc     360

gtctcttc                                                              368
```

<210> SEQ ID NO 83
<211> LENGTH: 8
<212> TYPE: PRT
<213> ORGANISM: Homo sapiens

<400> SEQUENCE: 83

```
Gly Phe Thr Phe Ser Ser Tyr Gly
1               5
```

<210> SEQ ID NO 84
<211> LENGTH: 8
<212> TYPE: PRT
<213> ORGANISM: Homo sapiens

<400> SEQUENCE: 84

```
Ile Thr Asn Thr Gly Lys Thr Thr
1               5
```

<210> SEQ ID NO 85

<211> LENGTH: 16
<212> TYPE: PRT
<213> ORGANISM: Homo sapiens

<400> SEQUENCE: 85

Thr Gly Arg Gly Arg His Gly Trp Ser Ser Gly Val Phe Asp Phe Trp
1               5                   10                  15

<210> SEQ ID NO 86
<211> LENGTH: 111
<212> TYPE: PRT
<213> ORGANISM: Homo sapiens

<400> SEQUENCE: 86

Gln Ser Val Leu Thr Gln Pro Pro Ser Val Phe Gly Asp Pro Gly Gln
1               5                   10                  15

Arg Ile Thr Ile Ser Cys Thr Gly Ser Ser Ser Asn Ile Gly Ala Gly
            20                  25                  30

Tyr Tyr Val Tyr Trp Tyr Gln Gln Phe Pro Gly Thr Ala Pro Lys Leu
        35                  40                  45

Leu Ile Tyr Gln Asp Asn Lys Arg Pro Ser Gly Val Ser Asp Arg Phe
    50                  55                  60

Ser Gly Ser Lys Phe Gly Ser Ser Ala Ser Leu Thr Ile Thr Gly Val
65                  70                  75                  80

Gln Arg Gly Asp Glu Gly Asp Tyr Tyr Cys Ser Ala Trp Asp Ser Ser
                85                  90                  95

Leu Ser Val Arg Val Leu Gly Gly Gly Thr Arg Leu Thr Val Leu
            100                 105                 110

<210> SEQ ID NO 87
<211> LENGTH: 333
<212> TYPE: DNA
<213> ORGANISM: Homo sapiens

<400> SEQUENCE: 87
cagtctgttc tgacgcagcc gccctcagtg ttcggggacc ccgggcagag gatcaccatt      60
tcgtgcactg ggagcagctc caacatcggg gcgggttatt atgtatactg gtaccagcag     120
ttcccaggaa cggcccccaa actcctcatc tatcaagata ataagcgacc ctcaggggtt     180
tctgaccgat tctctggctc caagtttggt tcctcagcct ccctgaccat cactggggtc     240
cagcgtgggg atgagggtga ttattactgc tcagcatggg atagcagcct gagtgtacgg     300
gttttgggag gagggacccg gctgacagta cta                                  333

<210> SEQ ID NO 88
<211> LENGTH: 9
<212> TYPE: PRT
<213> ORGANISM: Homo sapiens

<400> SEQUENCE: 88

Ser Ser Asn Ile Gly Ala Gly Tyr Tyr
1               5

<210> SEQ ID NO 89
<211> LENGTH: 3
<212> TYPE: PRT
<213> ORGANISM: Homo sapiens

<400> SEQUENCE: 89

Gln Asp Asn
1

<210> SEQ ID NO 90
<211> LENGTH: 11
<212> TYPE: PRT
<213> ORGANISM: Homo sapiens

<400> SEQUENCE: 90

```
Ser Ala Trp Asp Ser Ser Leu Ser Val Arg Val
1               5                   10
```

<210> SEQ ID NO 91
<211> LENGTH: 121
<212> TYPE: PRT
<213> ORGANISM: Homo sapiens

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp Arg
            20                  25                  30

Tyr Ile Asp Trp Val Arg Gln Ala Pro Gly Lys Gly Leu Glu Trp Val
        35                  40                  45

Ser Thr Ile Ser Thr Gly Ser Gly Asp Thr Ala Leu Tyr Ser Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg His Ser Gly Thr Phe Tyr Thr His Phe Asp Tyr Trp Gly
            100                 105                 110

Gln Gly Val Leu Val Thr Val Ser Ser
        115                 120
```

<210> SEQ ID NO 92
<211> LENGTH: 363
<212> TYPE: DNA
<213> ORGANISM: Homo sapiens

<400> SEQUENCE: 92

```
gaagtgcagt tggtggagtc tgggggaggc ttggtacagc cggggggtc cctgagactc      60

tcctgtgtag cctctggatt caccttcagt gaccgctaca tagactgggt ccgccaggct    120

ccagggaagg gcctggagtg ggtctcaact attagcactg gtagtggtga taccgcattg    180

tactcagact ctgtcaaggg ccgattcacc atctccagag acaacgccaa gaacacactg    240

tatctgcaaa tgaacagcct gagagccgaa gacacggctg tctattactg tgcgagacat    300

agtggtactt tttacaccca ctttgactac tggggccagg gagtcctggt caccgtctcc    360

tca                                                                  363
```

<210> SEQ ID NO 93
<211> LENGTH: 8
<212> TYPE: PRT
<213> ORGANISM: Homo sapiens

<400> SEQUENCE: 93

```
Gly Phe Thr Phe Ser Asp Arg Tyr
1               5
```

<210> SEQ ID NO 94

<211> LENGTH: 9
<212> TYPE: PRT
<213> ORGANISM: Homo sapiens

<400> SEQUENCE: 94

Ile Ser Thr Gly Ser Gly Asp Thr Ala
1               5

<210> SEQ ID NO 95
<211> LENGTH: 14
<212> TYPE: PRT
<213> ORGANISM: Homo sapiens

<400> SEQUENCE: 95

Ala Arg His Ser Gly Thr Phe Tyr Thr His Phe Asp Tyr Trp
1               5                   10

<210> SEQ ID NO 96
<211> LENGTH: 107
<212> TYPE: PRT
<213> ORGANISM: Homo sapiens

<400> SEQUENCE: 96

Asp Ile Gln Met Thr Gln Ser Pro Ser Ser Leu Ser Ala Ser Val Gly
1               5                   10                  15

Asp Thr Val Thr Phe Thr Cys Arg Ala Ser Arg Ser Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Ser Ser Arg Pro Pro
                85                  90                  95

Thr Phe Gly Gln Gly Thr Lys Val Glu Ile Arg
            100                 105

<210> SEQ ID NO 97
<211> LENGTH: 321
<212> TYPE: DNA
<213> ORGANISM: Homo sapiens

<400> SEQUENCE: 97
gacatccaga tgacccagtc tccatcctcc ctgtctgcat ctgtaggaga cacagtcacc 60
ttcacctgcc gggcgagtcg gagtattagc agctggttag cctggtatca gcagaaacca 120
gggagagccc ctaaagtcct gatctataag gcgtccagtt tgcaaagtgg ggttccttca 180
aggttcagcg gcagtggatc tgggacagac ttcactctca ccatcagcag cctacagtct 240
gaagattttg caacatatta ttgtcaacag tatagtagtc gccctccgac gttcggccaa 300
gggaccaagg tggaaatcag a 321

<210> SEQ ID NO 98
<211> LENGTH: 6
<212> TYPE: PRT
<213> ORGANISM: Homo sapiens

<400> SEQUENCE: 98

Arg Ser Ile Ser Ser Trp
1               5

<210> SEQ ID NO 99
<211> LENGTH: 3
<212> TYPE: PRT
<213> ORGANISM: Homo sapiens

<400> SEQUENCE: 99

Lys Ala Ser
1

<210> SEQ ID NO 100
<211> LENGTH: 9
<212> TYPE: PRT
<213> ORGANISM: Homo sapiens

<400> SEQUENCE: 100

Gln Gln Tyr Ser Ser Arg Pro Pro Thr
1               5

<210> SEQ ID NO 101
<211> LENGTH: 119
<212> TYPE: PRT
<213> ORGANISM: Homo sapiens

<400> SEQUENCE: 101

```
Gln Val Gln Leu Gln Glu Ser Gly Pro Gly Leu Leu Lys Pro Ser Glu
1               5                   10                  15

Thr Leu Ser Leu Thr Cys Ala Val Ser Gly Gly Ser Phe Ser Ser Phe
            20                  25                  30

Trp Trp Ser Trp Leu Arg Gln Pro Pro Glu Lys Gly Leu Glu Trp Ile
        35                  40                  45

Gly Glu Ile Asn Gly Asp Ser Gly Ser Thr Asn Tyr Asn Pro Ser Leu
    50                  55                  60

Lys Ser Arg Val Thr Ile Ser Lys Asp Ala Ser Lys Asn Gln Phe Ser
65                  70                  75                  80

Leu Lys Leu Thr Ser Val Thr Ala Ala Asp Thr Ala Val Phe Tyr Cys
                85                  90                  95

Ala Arg Val Arg Arg Ile Leu Arg Ser Leu Asp Val Trp Gly Arg Gly
            100                 105                 110

Val Leu Val Thr Val Ser Ser
        115
```

<210> SEQ ID NO 102
<211> LENGTH: 357
<212> TYPE: DNA
<213> ORGANISM: Homo sapiens

<400> SEQUENCE: 102

```
caggtgcagc tgcaggagtc gggcccagga ctgctgaagc cttcggagac cctgtccctc     60

acctgcgctg tctctggtgg ctccttcagt agtttctggt ggagctggct ccgccagccc    120

ccagaaaagg gactggagtg gattggggag atcaatggtg atagtgggag caccaactac    180

aacccctccc tcaagagtcg agtcaccatt tcaaaagacg cgtccaagaa ccagttctcc    240

ctgaaactga cctctgtgac cgccgcggac acggccgttt tttactgtgc gagagttcgg    300

cgaattctga ggtcattgga tgtctggggc cggggagttc tggtcaccgt ctcctca       357
```

<210> SEQ ID NO 103
<211> LENGTH: 8
<212> TYPE: PRT

<213> ORGANISM: Homo sapiens

<400> SEQUENCE: 103

Gly Gly Ser Phe Ser Ser Phe Trp
1 5

<210> SEQ ID NO 104
<211> LENGTH: 8
<212> TYPE: PRT
<213> ORGANISM: Homo sapiens

<400> SEQUENCE: 104

Ile Asn Gly Asp Ser Gly Ser Thr
1 5

<210> SEQ ID NO 105
<211> LENGTH: 13
<212> TYPE: PRT
<213> ORGANISM: Homo sapiens

<400> SEQUENCE: 105

Ala Arg Val Arg Arg Ile Leu Arg Ser Leu Asp Val Trp
1 5 10

<210> SEQ ID NO 106
<211> LENGTH: 107
<212> TYPE: PRT
<213> ORGANISM: Homo sapiens

<400> SEQUENCE: 106

Asp Ile Gln Met Thr Gln Ser Pro Phe Ser Leu Phe Ala Phe Val Gly
1 5 10 15

Asp Arg Val Thr Ile Thr Cys Gln Ala Ser Gln Gly Ile Ser His Leu
20 25 30

Leu Ala Trp Tyr Gln Gln Lys Pro Gly Lys Ala Pro Lys Leu Leu Ile
35 40 45

Tyr Ser Ala Ser Thr Leu Gln Ser Gly Val Pro Ser Arg Phe Ser Gly
50 55 60

Ser Gly Phe Gly Thr Glu Phe Thr Leu Thr Ile Ser Ser Leu Gln Pro
65 70 75 80

Glu Asp Phe Ala Thr Tyr Tyr Cys Gln Gln His Asn Ser Tyr Pro Arg
85 90 95

Thr Phe Gly Gln Gly Thr Lys Val Glu Ile Lys
100 105

<210> SEQ ID NO 107
<211> LENGTH: 321
<212> TYPE: DNA
<213> ORGANISM: Homo sapiens

<400> SEQUENCE: 107
gacatccaga tgacccagtc tcctttttcc ttgtttgcat ttgtaggaga cagagtcacc 60
atcacttgcc aagccagtca gggtattagc cacttgttag cttggtatca gcagaaacca 120
gggaaagccc ctaagctcct tatttattct gcatccactt tgcaaagtgg ggtcccatca 180
aggttcagcg gcagtggatt tgggacggaa ttcactctca ccatcagcag cctgcagcct 240
gaagattttg caacttatta ctgtcaacag cataatagtt accctcggac gttcggccaa 300
gggaccaagg tggaaatcaa a 321

<210> SEQ ID NO 108
<211> LENGTH: 6
<212> TYPE: PRT
<213> ORGANISM: Homo sapiens

<400> SEQUENCE: 108

Gln Gly Ile Ser His Leu
1               5

<210> SEQ ID NO 109
<211> LENGTH: 3
<212> TYPE: PRT
<213> ORGANISM: Homo sapiens

<400> SEQUENCE: 109

Ser Ala Ser
1

<210> SEQ ID NO 110
<211> LENGTH: 9
<212> TYPE: PRT
<213> ORGANISM: Homo sapiens

<400> SEQUENCE: 110

Gln Gln His Asn Ser Tyr Pro Arg Thr
1               5

<210> SEQ ID NO 111
<211> LENGTH: 5845
<212> TYPE: DNA
<213> ORGANISM: Homo sapiens

<400> SEQUENCE: 111
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200

```
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
ccaggtgcag ctggtgcagc tgcacgagtc gggcccagga ctggtgaagc cttcggagac   1500
cctgtccctc acctgcgctg tctctggtgg ctctatcagc agtagctact ggagctggat   1560
ccgccaggcc ccagggaagg gactggagtg gattgggtat gtctatggta gtggtcgtga   1620
caccaacgac aacccctccc tcaagagtcg agtcaccctg tcagtagaca cgtccaagaa   1680
ccagctctcc ctgaagctga gatctgtgac cgccgcggac acggccgtgt attactgtgc   1740
gagcagcggc tggcctcctg ggttggacta ctggggccag ggagtcacgg tcaccgtctc   1800
ctcagctagc accaagggcc ctagtgtgtt tcctctggcc cctagcagca gaagcacatc   1860
tgaatctaca gccgccctgg gctgcctggt gaaagattac ttccccgagc ccgtgaccgt   1920
gtcttggaat agcggctctc tgaccagcgg cgtgcacaca tttccagctg tgctgcagag   1980
cagcggcctg tattctctga gcagcgtggt gacagtgcca agcagctctc tgggcaccca   2040
gacctacgtg tgcaacgtga accacaagcc cagcaacacc aaggtggaca agcgggtgga   2100
aatcaagacc tgtggcggcg gaagcaagcc tcctacctgt cctccttgta ccagccctga   2160
actgctgggc ggacctagcg tgttcctgtt ccccccaaag cccaaggaca ccctgatgat   2220
cagcagaacc cccgaagtga cctgcgtggt ggtggatgtg tcccaggaag atcccgacgt   2280
gaagttcaat tggtacgtga acggcgccga ggtgcaccat gcccagacaa agcccagaga   2340
gacacagtac aacagcacct accgggtggt gtctgtgctg accgtgacac accaggactg   2400
gctgaacggc aaagagtaca catgcaaggt gtccaacaag gccctgcctg cccccatcca   2460
gaaaaccatc agcaaggaca agggccagcc cagagaacct caggtgtaca cactgccccc   2520
cagcagagag gaactgacca agaatcaggt gtccctgacc tgtctggtga aaggcttcta   2580
ccccagcgac atcgtggtgg aatgggagtc tagcggacag cccgagaaca cctacaagac   2640
cacccctcca gtgctggata gcgacggcag ctacttcctg tacagcaagc tgaccgtgga   2700
caagagcaga tggcagcagg gcaacgtgtt cagctgctct gtgatgcacg aggccctgca   2760
caaccactac acccagaagt ctctgagcct gagccccgga aagtgatgat gaacacgtgg   2820
gatccagatc tgctgtgcct tctagttgcc agccatctgt tgtttgcccc tcccccgtgc   2880
cttccttgac cctggaaggt gccactccca ctgtcctttc ctaataaaat gaggaaattg   2940
catcgcattg tctgagtagg tgtcattcta ttctgggggg tggggtgggg caggacagca   3000
agggggagga ttgggaagac aatagcaggc atgctgggga tgcggtgggc tctatgggta   3060
cccaggtgct gaagaattga cccggttcct cctgggccag aaagaagcag gcacatcccc   3120
ttctctgtga cacaccctgt ccacgcccct ggttcttagt tccagcccca ctcataggac   3180
actcatagct caggagggct ccgccttcaa tcccacccgc taaagtactt ggagcggtct   3240
ctccctccct catcagccca ccaaaccaaa cctagcctcc aagagtggga agaaattaaa   3300
gcaagatagg ctattaagtg cagagggaga gaaaatgcct ccaacatgtg aggaagtaat   3360
gagagaaatc atagaatttt aaggccatga tttaaggcca tcatggcctt aatcttccgc   3420
ttcctcgctc actgactcgc tgcgctcggt cgttcggctg cggcgagcgg tatcagctca   3480
ctcaaaggcg gtaatacggt tatccacaga atcaggggat aacgcaggaa agaacatgtg   3540
```

-continued

```
agcaaaaggc cagcaaaagg ccaggaaccg taaaaaggcc gcgttgctgg cgtttttcca   3600
taggctccgc ccccctgacg agcatcacaa aaatcgacgc tcaagtcaga ggtggcgaaa   3660
cccgacagga ctataaagat accaggcgtt tccccctgga agctccctcg tgcgctctcc   3720
tgttccgacc ctgccgctta ccggatacct gtccgccttt ctcccttcgg gaagcgtggc   3780
gctttctcat agctcacgct gtaggtatct cagttcggtg taggtcgttc gctccaagct   3840
gggctgtgtg cacgaacccc ccgttcagcc cgaccgctgc gccttatccg gtaactatcg   3900
tcttgagtcc aacccggtaa gacacgactt atcgccactg gcagcagcca ctggtaacag   3960
gattagcaga gcgaggtatg taggcggtgc tacagagttc ttgaagtggt ggcctaacta   4020
cggctacact agaagaacag tatttggtat ctgcgctctg ctgaagccag ttaccttcgg   4080
aaaaagagtt ggtagctctt gatccggcaa acaaaccacc gctggtagcg gtggtttttt   4140
tgtttgcaag cagcagatta cgcgcagaaa aaaaggatct caagaagatc ctttgatctt   4200
ttctacgggg tctgacgctc agtggaacga aaactcacgt taagggattt tggtcatgag   4260
attatcaaaa aggatcttca cctagatcct tttaaattaa aaatgaagtt ttaaatcaat   4320
ctaaagtata tatgagtaaa cttggtctga cagttaccaa tgcttaatca gtgaggcacc   4380
tatctcagcg atctgtctat ttcgttcatc catagttgcc tgactcgggg gggggggcg   4440
ctgaggtctg cctcgtgaag aaggtgttgc tgactcatac caggcctgaa tcgccccatc   4500
atccagccag aaagtgaggg agccacggtt gatgagagct ttgttgtagg tggaccagtt   4560
ggtgattttg aacttttgct ttgccacgga acggtctgcg ttgtcgggaa gatgcgtgat   4620
ctgatccttc aactcagcaa aagttcgatt tattcaacaa agccgccgtc ccgtcaagtc   4680
agcgtaatgc tctgccagtg ttacaaccaa ttaaccaatt ctgattagaa aaactcatcg   4740
agcatcaaat gaaactgcaa tttattcata tcaggattat caataccata tttttgaaaa   4800
agccgtttct gtaatgaagg agaaaactca ccgaggcagt tccataggat ggcaagatcc   4860
tggtatcggt ctgcgattcc gactcgtcca acatcaatac aacctattaa tttcccctcg   4920
tcaaaaataa ggttatcaag tgagaaatca ccatgagtga cgactgaatc cggtgagaat   4980
ggcaaaagct tatgcatttc tttccagact tgttcaacag gccagccatt acgctcgtca   5040
tcaaaatcac tcgcatcaac caaaccgtta ttcattcgtg attgcgcctg agcgagacga   5100
aatacgcgat cgctgttaaa aggacaatta caaacaggaa tcgaatgcaa ccggcgcagg   5160
aacactgcca gcgcatcaac aatattttca cctgaatcag gatattcttc taatacctgg   5220
aatgctgttt tcccggggat cgcagtggtg agtaaccatg catcatcagg agtacggata   5280
aaatgcttga tggtcggaag aggcataaat tccgtcagcc agtttagtct gaccatctca   5340
tctgtaacat cattggcaac gctacctttg ccatgtttca gaaacaactc tggcgcatcg   5400
ggcttcccat acaatcgata gattgtcgca cctgattgcc cgacattatc gcgagcccat   5460
ttatacccat ataaatcagc atccatgttg gaatttaatc gcggcctcga gcaagacgtt   5520
tcccgttgaa tatggctcat aacacccctt gtattactgt ttatgtaagc agacagtttt   5580
attgttcatg atgatatatt tttatcttgt gcaatgtaac atcagagatt ttgagacaca   5640
acgtggcttt cccccccccc ccattattga agcatttatc agggttattg tctcatgagc   5700
ggatacatat ttgaatgtat ttagaaaaat aaacaaatag gggttccgcg cacatttccc   5760
cgaaaagtgc cacctgacgt ctaagaaacc attattatca tgacattaac ctataaaaat   5820
aggcgtatca cgaggccctt tcgtc                                          5845
```

<210> SEQ ID NO 112
<211> LENGTH: 473
<212> TYPE: PRT
<213> ORGANISM: Homo sapiens

<400> SEQUENCE: 112

Met Gly Trp Ser Cys Ile Ile Leu Phe Leu Val Ala Thr Ala Thr Gly
1 5 10 15

Val His Ser Gln Val Gln Leu Val Gln Leu His Glu Ser Gly Pro Gly
20 25 30

Leu Val Lys Pro Ser Glu Thr Leu Ser Leu Thr Cys Ala Val Ser Gly
35 40 45

Gly Ser Ile Ser Ser Ser Tyr Trp Ser Trp Ile Arg Gln Ala Pro Gly
50 55 60

Lys Gly Leu Glu Trp Ile Gly Tyr Val Tyr Gly Ser Gly Arg Asp Thr
65 70 75 80

Asn Asp Asn Pro Ser Leu Lys Ser Arg Val Thr Leu Ser Val Asp Thr
85 90 95

Ser Lys Asn Gln Leu Ser Leu Lys Leu Arg Ser Val Thr Ala Ala Asp
100 105 110

Thr Ala Val Tyr Tyr Cys Ala Ser Ser Gly Trp Pro Pro Gly Leu Asp
115 120 125

Tyr Trp Gly Gln Gly Val Thr Val Thr Val Ser Ser Ala Ser Thr Lys
130 135 140

Gly Pro Ser Val Phe Pro Leu Ala Pro Ser Ser Arg Ser Thr Ser Glu
145 150 155 160

Ser Thr Ala Ala Leu Gly Cys Leu Val Lys Asp Tyr Phe Pro Glu Pro
165 170 175

Val Thr Val Ser Trp Asn Ser Gly Ser Leu Thr Ser Gly Val His Thr
180 185 190

Phe Pro Ala Val Leu Gln Ser Ser Gly Leu Tyr Ser Leu Ser Ser Val
195 200 205

Val Thr Val Pro Ser Ser Ser Leu Gly Thr Gln Thr Tyr Val Cys Asn
210 215 220

Val Asn His Lys Pro Ser Asn Thr Lys Val Asp Lys Arg Val Glu Ile
225 230 235 240

Lys Thr Cys Gly Gly Gly Ser Lys Pro Pro Thr Cys Pro Pro Cys Thr
245 250 255

Ser Pro Glu Leu Leu Gly Gly Pro Ser Val Phe Leu Phe Pro Pro Lys
260 265 270

Pro Lys Asp Thr Leu Met Ile Ser Arg Thr Pro Glu Val Thr Cys Val
275 280 285

Val Val Asp Val Ser Gln Glu Asp Pro Asp Val Lys Phe Asn Trp Tyr
290 295 300

Val Asn Gly Ala Glu Val His His Ala Gln Thr Lys Pro Arg Glu Thr
305 310 315 320

Gln Tyr Asn Ser Thr Tyr Arg Val Val Ser Val Leu Thr Val Thr His
325 330 335

Gln Asp Trp Leu Asn Gly Lys Glu Tyr Thr Cys Lys Val Ser Asn Lys
340 345 350

Ala Leu Pro Ala Pro Ile Gln Lys Thr Ile Ser Lys Asp Lys Gly Gln
355 360 365

Pro Arg Glu Pro Gln Val Tyr Thr Leu Pro Pro Ser Arg Glu Glu Leu
370 375 380

-continued

```
Thr Lys Asn Gln Val Ser Leu Thr Cys Leu Val Lys Gly Phe Tyr Pro
385                 390                 395                 400

Ser Asp Ile Val Val Glu Trp Glu Ser Ser Gly Gln Pro Glu Asn Thr
                405                 410                 415

Tyr Lys Thr Thr Pro Pro Val Leu Asp Ser Asp Gly Ser Tyr Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

```
<210> SEQ ID NO 113
<211> LENGTH: 5100
<212> TYPE: DNA
<213> ORGANISM: Homo sapiens

<400> SEQUENCE: 113

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctcca tcggctcgca tctctccttc acgcgcccgc   1020

cgccctacct gaggccgcca tccacgccgg ttgagtcgcg ttctgccgcc tcccgcctgt   1080

ggtgcctcct gaactgcgtc cgccgtctag gtaagtttaa agctcaggtc gagaccgggc   1140

ctttgtccgg cgctcccttg gagcctacct agactcagcc ggctctccac gctttgcctg   1200

accctgcttg ctcaactcta gttaacggtg gagggcagtg tagtctgagc agtacacgtt   1260

gctgccgcgc gcgccaccag acataatagc tgacagacta acagactgtt cctttccatg   1320

ggtcttttct gcagtcaccg tcgtcgacac gtgtgatcag atatcgcggc cgctctagac   1380

caccatggga tggtcatgta tcatcctttt tctagtagca actgcaaccg gtgtacattc   1440

agaaattgtg ttgacacagt ctccaggcac cctgtctttg tctccagggg aaacagccat   1500

catctcttgt cggaccagtc agtatggttc cttagcctgg tatcaacaga ggcccggcca   1560

ggcccccagg ctcgtcatct attcgggctc tactcgggcc gctggcatcc cagacaggtt   1620
```

cagcggcagt cggtgggggc cagactacaa tctcaccatc agcaacctgg agtcgggaga 1680
ttttggtgtt tattattgcc agcagtatga attttttggc caggggacca aggtccaggt 1740
cgacattaaa cgtacggtgg ctgcaccatc tgtcttcatc ttcccgccat ctgaggatca 1800
ggtgaaatct ggaactgtct ctgttgtgtg cctgctgaat aacttctatc ccagagaggc 1860
cagcgtaaag tggaaggtgg atggtgccct caaaacgggt aactcccagg agagtgtcac 1920
agagcaggac agcaaggaca acacctacag cctgagcagc accctgacgc tgagcagcac 1980
agagtaccag agtcacaaag tctatgcctg cgaagtcacc catcagggcc tgagctcgcc 2040
cgtcaccaag agcttcaaca gaggagagtg ttagggatcc agatctgctg tgccttctag 2100
ttgccagcca tctgttgttt gcccctcccc cgtgccttcc ttgaccctgg aaggtgccac 2160
tcccactgtc ctttcctaat aaaatgagga aattgcatcg cattgtctga gtaggtgtca 2220
ttctattctg gggggtgggg tggggcagga cagcaagggg gaggattggg aagacaatag 2280
caggcatgct ggggatgcgg tgggctctat gggtacccag gtgctgaaga attgacccgg 2340
ttcctcctgg gccagaaaga agcaggcaca tccccttctc tgtgacacac cctgtccacg 2400
cccctggttc ttagttccag ccccactcat aggacactca tagctcagga gggctccgcc 2460
ttcaatccca cccgctaaag tacatggagc ggtctctccc tccctcatca gcccaccaaa 2520
ccaaacctag cctccaagag tgggaagaaa ttaaagcaag ataggctatt aagtgcagag 2580
ggagagaaaa tgcctccaac atgtgaggaa gtaatgagag aaatcataga attttaaggc 2640
catgatttaa ggccatcatg gccttaatct tccgcttcct cgctcactga ctcgctgcgc 2700
tcggtcgttc ggctgcggcg agcggtatca gctcactcaa aggcggtaat acggttatcc 2760
acagaatcag gggataacgc aggaaagaac atgtgagcaa aaggccagca aaaggccagg 2820
aaccgtaaaa aggccgcgtt gctggcgttt ttccataggc tccgcccccc tgacgagcat 2880
cacaaaaatc gacgctcaag tcagaggtgg cgaaacccga caggactata aagataccag 2940
gcgtttcccc ctggaagctc cctcgtgcgc tctcctgttc cgaccctgcc gcttaccgga 3000
tacctgtccg cctttctccc ttcgggaagc gtggcgcttt ctcatagctc acgctgtagg 3060
tatctcagtt cggtgtaggt cgttcgctcc aagctgggct gtgtgcacga accccccgtt 3120
cagcccgacc gctgcgcctt atccggtaac tatcgtcttg agtccaaccc ggtaagacac 3180
gacttatcgc cactggcagc agccactggt aacaggatta gcagagcgag gtatgtaggc 3240
ggtgctacag agttcttgaa gtggtggcct aactacggct acactagaag aacagtattt 3300
ggtatctgcg ctctgctgaa gccagttacc ttcggaaaaa gagttggtag ctcttgatcc 3360
ggcaaacaaa ccaccgctgg tagcggtggt ttttttgttt gcaagcagca gattacgcgc 3420
agaaaaaaag gatctcaaga agatcctttg atcttttcta cggggtctga cgctcagtgg 3480
aacgaaaact cacgttaagg gattttggtc atgagattat caaaaaggat cttcacctag 3540
atccttttaa attaaaaatg aagttttaaa tcaatctaaa gtatatatga gtaaacttgg 3600
tctgacagtt accaatgctt aatcagtgag gcacctatct cagcgatctg tctatttcgt 3660
tcatccatag ttgcctgact cggggggggg gggcgctgag gtctgcctcg tgaagaaggt 3720
gttgctgact cataccaggc ctgaatcgcc ccatcatcca gccagaaagt gagggagcca 3780
cggttgatga gagctttgtt gtaggtggac cagttggtga ttttgaactt ttgctttgcc 3840
acggaacggt ctgcgttgtc gggaagatgc gtgatctgat ccttcaactc agcaaaagtt 3900
cgatttattc aacaaagccg ccgtcccgtc aagtcagcgt aatgctctgc cagtgttaca 3960

-continued

```
accaattaac caattctgat tagaaaaact catcgagcat caaatgaaac tgcaatttat   4020

tcatatcagg attatcaata ccatattttt gaaaaagccg tttctgtaat gaaggagaaa   4080

actcaccgag gcagttccat aggatggcaa gatcctggta tcggtctgcg attccgactc   4140

gtccaacatc aatacaacct attaatttcc cctcgtcaaa aataaggtta tcaagtgaga   4200

aatcaccatg agtgacgact gaatccggtg agaatggcaa aagcttatgc atttctttcc   4260

agacttgttc aacaggccag ccattacgct cgtcatcaaa atcactcgca tcaaccaaac   4320

cgttattcat tcgtgattgc gcctgagcga gacgaaatac gcgatcgctg ttaaaaggac   4380

aattacaaac aggaatcgaa tgcaaccggc gcaggaacac tgccagcgca tcaacaatat   4440

tttcacctga atcaggatat tcttctaata cctggaatgc tgttttcccg gggatcgcag   4500

tggtgagtaa ccatgcatca tcaggagtac ggataaaatg cttgatggtc ggaagaggca   4560

taaattccgt cagccagttt agtctgacca tctcatctgt aacatcattg gcaacgctac   4620

ctttgccatg tttcagaaac aactctggcg catcgggctt cccatacaat cgatagattg   4680

tcgcacctga ttgcccgaca ttatcgcgag cccatttata cccatataaa tcagcatcca   4740

tgttggaatt taatcgcggc ctcgagcaag acgtttcccg ttgaatatgg ctcataacac   4800

cccttgtatt actgtttatg taagcagaca gttttattgt tcatgatgat atatttttat   4860

cttgtgcaat gtaacatcag agattttgag acacaacgtg gctttccccc cccccccatt   4920

attgaagcat ttatcagggt tattgtctca tgagcggata catatttgaa tgtatttaga   4980

aaaataaaca aataggggtt ccgcgcacat ttccccgaaa agtgccacct gacgtctaag   5040

aaaccattat tatcatgaca ttaacctata aaaataggcg tatcacgagg ccctttcgtc   5100
```

<210> SEQ ID NO 114
<211> LENGTH: 229
<212> TYPE: PRT
<213> ORGANISM: Homo sapiens

<400> SEQUENCE: 114

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
            20                  25                  30

Ser Pro Gly Glu Thr Ala Ile Ile Ser Cys Arg Thr Ser Gln Tyr Gly
        35                  40                  45

Ser Leu Ala Trp Tyr Gln Gln Arg Pro Gly Gln Ala Pro Arg Leu Val
    50                  55                  60

Ile Tyr Ser Gly Ser Thr Arg Ala Ala Gly Ile Pro Asp Arg Phe Ser
65                  70                  75                  80

Gly Ser Arg Trp Gly Pro Asp Tyr Asn Leu Thr Ile Ser Asn Leu Glu
                85                  90                  95

Ser Gly Asp Phe Gly Val Tyr Tyr Cys Gln Gln Tyr Glu Phe Phe Gly
            100                 105                 110

Gln Gly Thr Lys Val Gln Val Asp Ile Lys Arg Thr Val Ala Ala Pro
        115                 120                 125

Ser Val Phe Ile Phe Pro Pro Ser Glu Asp Gln Val Lys Ser Gly Thr
    130                 135                 140

Val Ser Val Val Cys Leu Leu Asn Asn Phe Tyr Pro Arg Glu Ala Ser
145                 150                 155                 160

Val Lys Trp Lys Val Asp Gly Ala Leu Lys Thr Gly Asn Ser Gln Glu
                165                 170                 175
```

```
Ser Val Thr Glu Gln Asp Ser Lys Asp Asn Thr Tyr Ser Leu Ser Ser
            180                 185                 190

Thr Leu Thr Leu Ser Ser Thr Glu Tyr Gln Ser His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225


<210> SEQ ID NO 115
<211> LENGTH: 235
<212> TYPE: PRT
<213> ORGANISM: Homo sapiens

<400> SEQUENCE: 115

Met Gly Trp Ser Cys Ile Ile Leu Phe Leu Val Ala Thr Ala Thr Gly
1               5                   10                  15

Val His Ser Gln Ser Ala Leu Thr Gln Pro Pro Ser Val Ser Gly Ser
            20                  25                  30

Pro Gly Gln Ser Val Thr Ile Ser Cys Thr Gly Thr Ser Ser Asp Val
        35                  40                  45

Asp Gly Tyr Asn Tyr Val Ser Trp Tyr Gln Gln His Pro Gly Lys Ala
    50                  55                  60

Pro Lys Leu Met Ile Tyr Gly Val Ser Asn Arg Pro Ser Gly Val Ser
65                  70                  75                  80

Asp Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Cys Ser Ser
            100                 105                 110

Thr Thr Ser Tyr Thr Tyr Ile Phe Gly Thr Gly Thr Lys Val Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Glu Val Ala Trp Lys Ala Asp Gly Ser
                165                 170                 175

Ala Val Asn Ala Gly Val Glu Thr Thr Lys Pro Ser Lys Gln Ser Asn
            180                 185                 190

Asn Lys Tyr Ala Ala Ser Ser Tyr Leu Ser Leu Thr Ser Asp Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Ala Glu Cys Ser
225                 230                 235


<210> SEQ ID NO 116
<211> LENGTH: 5842
<212> TYPE: DNA
<213> ORGANISM: Homo sapiens

<400> SEQUENCE: 116

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180
```

-continued

```
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
ccaactgcag ttgcaggagt cgggcccagg agtggtgaag ccttcggaga ccctgtccct   1500
cacctgcact atctctggtg gctccttcag tacttactac tggacctgga ttcgccagcc   1560
cccagggaag ggactggagt gggttgggta tatcggtaat ggtggtcgta gcctcaacta   1620
caacccctcc ctcaagagtc gcatcaccct gtcagtagac gcgtccaaga accagttctc   1680
cctgaaggtg acctctgtga ccgccgcgga cacggccgtc tattactgtg ggagagccag   1740
gggactccgc ggaaactggt tcgatgtctg gggcccggga gtcctggtca ccgtctcctc   1800
agctagcacc aagggcccta gtgtgtttcc tctggcccct agcagcagaa gcacatctga   1860
atctacagcc gccctgggct gcctggtgaa agattacttc cccgagcccg tgaccgtgtc   1920
ttggaatagc ggctctctga ccagcggcgt gcacacattt ccagctgtgc tgcagagcag   1980
cggcctgtat tctctgagca gcgtggtgac agtgccaagc agctctctgg gcacccagac   2040
ctacgtgtgc aacgtgaacc acaagcccag caacaccaag gtggacaagc gggtggaaat   2100
caagacctgt ggcggcggaa gcaagcctcc tacctgtcct ccttgtacca gccctgaact   2160
gctgggcgga cctagcgtgt tcctgttccc cccaaagccc aaggacaccc tgatgatcag   2220
cagaaccccc gaagtgacct gcgtggtggt ggatgtgtcc caggaagatc ccgacgtgaa   2280
gttcaattgg tacgtgaacg gcgccgaggt gcaccatgcc cagacaaagc ccagagagac   2340
acagtacaac agcacctacc gggtggtgtc tgtgctgacc gtgacacacc aggactggct   2400
gaacggcaaa gagtacacat gcaaggtgtc caacaaggcc ctgcctgccc ccatccagaa   2460
aaccatcagc aaggacaagg gccagcccag agaacctcag gtgtacacac tgccccccag   2520
cagagaggaa ctgaccaaga atcaggtgtc cctgacctgt ctggtgaaag gcttctaccc   2580
```

```
cagcgacatc gtggtggaat gggagtctag cggacagccc gagaacacct acaagaccac   2640
ccctccagtg ctggatagcg acggcagcta cttcctgtac agcaagctga ccgtggacaa   2700
gagcagatgg cagcagggca acgtgttcag ctgctctgtg atgcacgagg ccctgcacaa   2760
ccactacacc cagaagtctc tgagcctgag ccccggaaag tgatgatgaa cacgtgggat   2820
ccagatctgc tgtgccttct agttgccagc catctgttgt ttgcccctcc cccgtgcctt   2880
ccttgaccct ggaaggtgcc actcccactg tcctttccta ataaaatgag gaaattgcat   2940
cgcattgtct gagtaggtgt cattctattc tggggggtgg ggtggggcag gacagcaagg   3000
gggaggattg ggaagacaat agcaggcatg ctggggatgc ggtgggctct atgggtaccc   3060
aggtgctgaa gaattgaccc ggttcctcct gggccagaaa gaagcaggca catccccttc   3120
tctgtgacac accctgtcca cgcccctggt tcttagttcc agccccactc ataggacact   3180
catagctcag gagggctccg ccttcaatcc cacccgctaa agtacttgga gcggtctctc   3240
cctccctcat cagcccacca aaccaaacct agcctccaag agtgggaaga aattaaagca   3300
agataggcta ttaagtgcag agggagagaa aatgcctcca acatgtgagg aagtaatgag   3360
agaaatcata gaattttaag gccatgattt aaggccatca tggccttaat cttccgcttc   3420
ctcgctcact gactcgctgc gctcggtcgt tcggctgcgg cgagcggtat cagctcactc   3480
aaaggcggta atacggttat ccacagaatc aggggataac gcaggaaaga acatgtgagc   3540
aaaaggccag caaaaggcca ggaaccgtaa aaaggccgcg ttgctggcgt ttttccatag   3600
gctccgcccc cctgacgagc atcacaaaaa tcgacgctca agtcagaggt ggcgaaaccc   3660
gacaggacta taaagatacc aggcgtttcc ccctggaagc tccctcgtgc gctctcctgt   3720
tccgaccctg ccgcttaccg gatacctgtc cgcctttctc ccttcgggaa gcgtggcgct   3780
ttctcatagc tcacgctgta ggtatctcag ttcggtgtag gtcgttcgct ccaagctggg   3840
ctgtgtgcac gaaccccccg ttcagcccga ccgctgcgcc ttatccggta actatcgtct   3900
tgagtccaac ccggtaagac acgacttatc gccactggca gcagccactg gtaacaggat   3960
tagcagagcg aggtatgtag gcggtgctac agagttcttg aagtggtggc ctaactacgg   4020
ctacactaga agaacagtat ttggtatctg cgctctgctg aagccagtta ccttcggaaa   4080
aagagttggt agctcttgat ccggcaaaca aaccaccgct ggtagcggtg gtttttttgt   4140
ttgcaagcag cagattacgc gcagaaaaaa aggatctcaa gaagatcctt tgatcttttc   4200
tacggggtct gacgctcagt ggaacgaaaa ctcacgttaa gggattttgg tcatgagatt   4260
atcaaaaagg atcttcacct agatcctttt aaattaaaaa tgaagtttta aatcaatcta   4320
aagtatatat gagtaaactt ggtctgacag ttaccaatgc ttaatcagtg aggcacctat   4380
ctcagcgatc tgtctatttc gttcatccat agttgcctga ctcggggggg gggggcgctg   4440
aggtctgcct cgtgaagaag gtgttgctga ctcataccag gcctgaatcg ccccatcatc   4500
cagccagaaa gtgagggagc cacggttgat gagagctttg ttgtaggtgg accagttggt   4560
gattttgaac ttttgctttg ccacggaacg gtctgcgttg tcgggaagat gcgtgatctg   4620
atccttcaac tcagcaaaag ttcgatttat tcaacaaagc cgccgtcccg tcaagtcagc   4680
gtaatgctct gccagtgtta caaccaatta accaattctg attagaaaaa ctcatcgagc   4740
atcaaatgaa actgcaattt attcatatca ggattatcaa taccatattt ttgaaaaagc   4800
cgtttctgta atgaaggaga aaactcaccg aggcagttcc ataggatggc aagatcctgg   4860
tatcggtctg cgattccgac tcgtccaaca tcaatacaac ctattaattt cccctcgtca   4920
```

-continued

```
aaaataaggt tatcaagtga gaaatcacca tgagtgacga ctgaatccgg tgagaatggc   4980

aaaagcttat gcatttcttt ccagacttgt tcaacaggcc agccattacg ctcgtcatca   5040

aaatcactcg catcaaccaa accgttattc attcgtgatt gcgcctgagc gagacgaaat   5100

acgcgatcgc tgttaaaagg acaattacaa acaggaatcg aatgcaaccg gcgcaggaac   5160

actgccagcg catcaacaat attttcacct gaatcaggat attcttctaa tacctggaat   5220

gctgttttcc cggggatcgc agtggtgagt aaccatgcat catcaggagt acggataaaa   5280

tgcttgatgg tcggaagagg cataaattcc gtcagccagt ttagtctgac catctcatct   5340

gtaacatcat tggcaacgct acctttgcca tgtttcagaa acaactctgg cgcatcgggc   5400

ttcccataca atcgatagat tgtcgcacct gattgcccga cattatcgcg agcccattta   5460

tacccatata aatcagcatc catgttggaa tttaatcgcg gcctcgagca agacgtttcc   5520

cgttgaatat ggctcataac accccttgta ttactgttta tgtaagcaga cagttttatt   5580

gttcatgatg atatattttt atcttgtgca atgtaacatc agagattttg agacacaacg   5640

tggctttccc ccccccccca ttattgaagc atttatcagg gttattgtct catgagcgga   5700

tacatatttg aatgtattta gaaaaataaa caaatagggg ttccgcgcac atttccccga   5760

aaagtgccac ctgacgtcta agaaaccatt attatcatga cattaaccta taaaaatagg   5820

cgtatcacga ggccctttcg tc                                            5842
```

<210> SEQ ID NO 117
<211> LENGTH: 472
<212> TYPE: PRT
<213> ORGANISM: Homo sapiens

<400> SEQUENCE: 117

```
Met Gly Trp Ser Cys Ile Ile Leu Phe Leu Val Ala Thr Ala Thr Gly
1               5                   10                  15

Val His Ser Gln Leu Gln Leu Gln Glu Ser Gly Pro Gly Val Val Lys
            20                  25                  30

Pro Ser Glu Thr Leu Ser Leu Thr Cys Thr Ile Ser Gly Gly Ser Phe
        35                  40                  45

Ser Thr Tyr Tyr Trp Thr Trp Ile Arg Gln Pro Pro Gly Lys Gly Leu
    50                  55                  60

Glu Trp Val Gly Tyr Ile Gly Asn Gly Gly Arg Ser Leu Asn Tyr Asn
65                  70                  75                  80

Pro Ser Leu Lys Ser Arg Ile Thr Leu Ser Val Asp Ala Ser Lys Asn
                85                  90                  95

Gln Phe Ser Leu Lys Val Thr Ser Val Thr Ala Ala Asp Thr Ala Val
            100                 105                 110

Tyr Tyr Cys Gly Arg Ala Arg Gly Leu Arg Gly Asn Trp Phe Asp Val
        115                 120                 125

Trp Gly Pro Gly Val Leu Val Thr Val Ser Ser Ala Ser Thr Lys Gly
    130                 135                 140

Pro Ser Val Phe Pro Leu Ala Pro Ser Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ser Leu Thr Ser Gly Val His Thr Phe
            180                 185                 190

Pro Ala Val Leu Gln Ser Ser Gly Leu Tyr Ser Leu Ser Ser Val Val
        195                 200                 205
```

-continued

```
Thr Val Pro Ser Ser Ser Leu Gly Thr Gln Thr Tyr Val Cys Asn Val
    210                 215                 220

Asn His Lys Pro Ser Asn Thr Lys Val Asp Lys Arg Val Glu Ile Lys
225                 230                 235                 240

Thr Cys Gly Gly Gly Ser Lys Pro Pro Thr Cys Pro Pro Cys Thr Ser
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Asp Val Lys Phe Asn Trp Tyr Val
    290                 295                 300

Asn Gly Ala Glu Val His His Ala Gln Thr Lys Pro Arg Glu Thr Gln
305                 310                 315                 320

Tyr Asn Ser Thr Tyr Arg Val Val Ser Val Leu Thr Val Thr His Gln
                325                 330                 335

Asp Trp Leu Asn Gly Lys Glu Tyr Thr Cys Lys Val Ser Asn Lys Ala
            340                 345                 350

Leu Pro Ala Pro Ile Gln Lys Thr Ile Ser Lys Asp Lys Gly Gln Pro
        355                 360                 365

Arg Glu Pro Gln Val Tyr Thr Leu Pro Pro Ser Arg Glu Glu Leu Thr
    370                 375                 380

Lys Asn Gln Val Ser Leu Thr Cys Leu Val Lys Gly Phe Tyr Pro Ser
385                 390                 395                 400

Asp Ile Val Val Glu Trp Glu Ser Ser Gly Gln Pro Glu Asn Thr Tyr
                405                 410                 415

Lys Thr Thr Pro Pro Val Leu Asp Ser Asp Gly Ser Tyr Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

<210> SEQ ID NO 118
<211> LENGTH: 5118
<212> TYPE: DNA
<213> ORGANISM: Homo sapiens

<400> SEQUENCE: 118

```
tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accatatgcg gtgtgaaata ccgcacagat gcgtaaggag aaaataccgc atcagattgg     240

ctattggcca ttgcatacgt tgtatccata tcataatatg tacatttata ttggctcatg     300

tccaacatta ccgccatgtt gacattgatt attgactagt tattaatagt aatcaattac     360

ggggtcatta gttcatagcc catatatgga gttccgcgtt acataactta cggtaaatgg     420

cccgcctggc tgaccgccca acgacccccg cccattgacg tcaataatga cgtatgttcc     480

catagtaacg ccaataggga ctttccattg acgtcaatgg gtggagtatt tacggtaaac     540

tgcccacttg gcagtacatc aagtgtatca tatgccaagt acgcccccta ttgacgtcaa     600
```

-continued

```
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtacacgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
ccaggctgcc ctgactcagc ctccctctgt gtctgggtct cctggacagt cggtcaccat   1500
ctcctgcact ggaaccagca gtgacatcgg tggttataac tatgtctcct ggtaccaaca   1560
acacccaggc aaagccccca aagtcatgat ttatgaggtc agtaagcggc cctcaggggt   1620
ctctgatcgc ttctctggtt ccaaatctgg caacatagcc tccctgacca tctctgggct   1680
ccaggctgag gacgaggctg attattactg cagctcatat gcaggcagca acactttctt   1740
attcggagga gggacccggc tgacagtact aggtcagccc aaggctgccc cctcggtcac   1800
tctcttcccg ccctcctctg aggagcttca agccaacaag gccacactag tgtgtctgat   1860
cagtgacttc tacccgggag ccgtggaagt ggcctggaag gcagatggca gcgctgtcaa   1920
cgcgggagtg gagaccacca aaccctccaa acagagcaac aacaagtacg cggccagcag   1980
ctacctgagc ctgacgtccg accagtggaa gtcccacaag agctacagct gccaggtcac   2040
gcacgaaggg agcaccgtgg agaagacagt ggcccctgca gaatgttcat agggatccag   2100
atctgctgtg ccttctagtt gccagccatc tgttgtttgc ccctcccccg tgccttcctt   2160
gaccctggaa ggtgccactc ccactgtcct ttcctaataa aatgaggaaa ttgcatcgca   2220
ttgtctgagt aggtgtcatt ctattctggg gggtggggtg gggcaggaca gcaaggggga   2280
ggattgggaa gacaatagca ggcatgctgg ggatgcggtg ggctctatgg gtacccaggt   2340
gctgaagaat tgacccggtt cctcctgggc cagaaagaag caggcacatc cccttctctg   2400
tgacacaccc tgtccacgcc cctggttctt agttccagcc ccactcatag gacactcata   2460
gctcaggagg gctccgcctt caatcccacc cgctaaagta catggagcgg tctctccctc   2520
cctcatcagc ccaccaaacc aaacctagcc tccaagagtg ggaagaaatt aaagcaagat   2580
aggctattaa gtgcagaggg agagaaaatg cctccaacat gtgaggaagt aatgagagaa   2640
atcatagaat tttaaggcca tgatttaagg ccatcatggc cttaatcttc cgcttcctcg   2700
ctcactgact cgctgcgctc ggtcgttcgg ctgcggcgag cggtatcagc tcactcaaag   2760
gcggtaatac ggttatccac agaatcaggg gataacgcag gaaagaacat gtgagcaaaa   2820
ggccagcaaa aggccaggaa ccgtaaaaag gccgcgttgc tggcgttttt ccataggctc   2880
cgcccccctg acgagcatca caaaaatcga cgctcaagtc agaggtggcg aaacccgaca   2940
ggactataaa gataccaggc gtttccccct ggaagctccc tcgtgcgctc tcctgttccg   3000
```

-continued

```
accctgccgc ttaccggata cctgtccgcc tttctccctt cgggaagcgt ggcgctttct   3060
catagctcac gctgtaggta tctcagttcg gtgtaggtcg ttcgctccaa gctgggctgt   3120
gtgcacgaac cccccgttca gcccgaccgc tgcgccttat ccggtaacta tcgtcttgag   3180
tccaacccgg taagacacga cttatcgcca ctggcagcag ccactggtaa caggattagc   3240
agagcgaggt atgtaggcgg tgctacagag ttcttgaagt ggtggcctaa ctacggctac   3300
actagaagaa cagtatttgg tatctgcgct ctgctgaagc cagttacctt cggaaaaaga   3360
gttggtagct cttgatccgg caaacaaacc accgctggta gcggtggttt ttttgtttgc   3420
aagcagcaga ttacgcgcag aaaaaaagga tctcaagaag atcctttgat cttttctacg   3480
gggtctgacg ctcagtggaa cgaaaactca cgttaaggga ttttggtcat gagattatca   3540
aaaaggatct tcacctagat ccttttaaat taaaaatgaa gttttaaatc aatctaaagt   3600
atatatgagt aaacttggtc tgacagttac caatgcttaa tcagtgaggc acctatctca   3660
gcgatctgtc tatttcgttc atccatagtt gcctgactcg gggggggggg gcgctgaggt   3720
ctgcctcgtg aagaaggtgt tgctgactca taccaggcct gaatcgcccc atcatccagc   3780
cagaaagtga gggagccacg gttgatgaga gctttgttgt aggtggacca gttggtgatt   3840
ttgaactttt gctttgccac ggaacggtct gcgttgtcgg gaagatgcgt gatctgatcc   3900
ttcaactcag caaaagttcg atttattcaa caaagccgcc gtcccgtcaa gtcagcgtaa   3960
tgctctgcca gtgttacaac caattaacca attctgatta gaaaaactca tcgagcatca   4020
aatgaaactg caatttattc atatcaggat tatcaatacc atatttttga aaaagccgtt   4080
tctgtaatga aggagaaaac tcaccgaggc agttccatag gatggcaaga tcctggtatc   4140
ggtctgcgat tccgactcgt ccaacatcaa tacaacctat taatttcccc tcgtcaaaaa   4200
taaggttatc aagtgagaaa tcaccatgag tgacgactga atccggtgag aatggcaaaa   4260
gcttatgcat ttctttccag acttgttcaa caggccagcc attacgctcg tcatcaaaat   4320
cactcgcatc aaccaaaccg ttattcattc gtgattgcgc ctgagcgaga cgaaatacgc   4380
gatcgctgtt aaaaggacaa ttacaaacag gaatcgaatg caaccggcgc aggaacactg   4440
ccagcgcatc aacaatattt tcacctgaat caggatattc ttctaatacc tggaatgctg   4500
ttttcccggg gatcgcagtg gtgagtaacc atgcatcatc aggagtacgg ataaaatgct   4560
tgatggtcgg aagaggcata aattccgtca gccagtttag tctgaccatc tcatctgtaa   4620
catcattggc aacgctacct ttgccatgtt tcagaaacaa ctctggcgca tcgggcttcc   4680
catacaatcg atagattgtc gcacctgatt gcccgacatt atcgcgagcc catttatacc   4740
catataaatc agcatccatg ttggaattta atcgcggcct cgagcaagac gtttcccgtt   4800
gaatatggct cataacaccc cttgtattac tgtttatgta agcagacagt tttattgttc   4860
atgatgatat atttttatct tgtgcaatgt aacatcagag attttgagac acaacgtggc   4920
tttccccccc cccccattat tgaagcattt atcagggtta ttgtctcatg agcggataca   4980
tatttgaatg tatttagaaa aataaacaaa taggggttcc gcgcacattt ccccgaaaag   5040
tgccacctga cgtctaagaa accattatta tcatgacatt aacctataaa aataggcgta   5100
tcacgaggcc ctttcgtc                                                 5118
```

<210> SEQ ID NO 119
<211> LENGTH: 235
<212> TYPE: PRT
<213> ORGANISM: Homo sapiens -continued

<400> SEQUENCE: 119

```
Met Gly Trp Ser Cys Ile Ile Leu Phe Leu Val Ala Thr Ala Thr Gly
1               5                   10                  15

Val His Ser Gln Ala Ala Leu Thr Gln Pro Pro Ser Val Ser Gly Ser
            20                  25                  30

Pro Gly Gln Ser Val Thr Ile Ser Cys Thr Gly Thr Ser Ser Asp Ile
        35                  40                  45

Gly Gly Tyr Asn Tyr Val Ser Trp Tyr Gln Gln His Pro Gly Lys Ala
    50                  55                  60

Pro Lys Val Met Ile Tyr Glu Val Ser Lys Arg Pro Ser Gly Val Ser
65                  70                  75                  80

Asp Arg Phe Ser Gly Ser Lys Ser Gly Asn Ile Ala Ser Leu Thr Ile
                85                  90                  95

Ser Gly Leu Gln Ala Glu Asp Glu Ala Asp Tyr Tyr Cys Ser Ser Tyr
            100                 105                 110

Ala Gly Ser Asn Thr Phe Leu Phe Gly Gly Gly Thr Arg Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Glu Val Ala Trp Lys Ala Asp Gly Ser
                165                 170                 175

Ala Val Asn Ala Gly Val Glu Thr Thr Lys Pro Ser Lys Gln Ser Asn
            180                 185                 190

Asn Lys Tyr Ala Ala Ser Ser Tyr Leu Ser Leu Thr Ser Asp Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Ala Glu Cys Ser
225                 230                 235
```

<210> SEQ ID NO 120
<211> LENGTH: 5823
<212> TYPE: DNA
<213> ORGANISM: Homo sapiens

<400> SEQUENCE: 120

```
tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accatatgcg gtgtgaaata ccgcacagat gcgtaaggag aaaataccgc atcagattgg     240

ctattggcca ttgcatacgt tgtatccata tcataatatg tacatttata ttggctcatg     300

tccaacatta ccgccatgtt gacattgatt attgactagt tattaatagt aatcaattac     360

ggggtcatta gttcatagcc catatatgga gttccgcgtt acataactta cggtaaatgg     420

cccgcctggc tgaccgccca acgacccccg cccattgacg tcaataatga cgtatgttcc     480

catagtaacg ccaataggga ctttccattg acgtcaatgg gtggagtatt tacggtaaac     540

tgcccacttg gcagtacatc aagtgtatca tatgccaagt acgcccccta ttgacgtcaa     600

tgacggtaaa tggcccgcct ggcattatgc ccagtacatg accttatggg actttcctac     660

ttggcagtac atctacgtat tagtcatcgc tattaccatg gtgatgcggt tttggcagta     720
```

-continued

```
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
ccaactgcag ttgcaggagt cgggcccagg agtggtgaag ccttcggaga ccctgtccct   1500
cacctgcact atctctggtg gctccttcag tacttactac tggacctgga ttcgccagcc   1560
cccagggaag ggactggagt gggttgggta tatcggtaat ggtggtcgta gcctcaacta   1620
caacccctcc ctcaagagtc gcatcaccct gtcagtagac gcgtccaaga accagttctc   1680
cctgaaggtg acctctgtga ccgccgcgga cacggccgtc tattactgtg ggagagccag   1740
gggactccgc ggaaactggt tcgatgtctg gggcccggga gtcctggtca ccgtctcctc   1800
agctagcacc aagggcccat cggtcttccc cctggcaccc tcctccaaga gcacctctgg   1860
gggcacagcg gccctgggct gcctggtcaa ggactacttc cccgaaccgg tgacggtgtc   1920
gtggaactca ggcgccctga ccagcggcgt gcacaccttc ccggctgtcc tacagtcctc   1980
aggactctac tccctcagca gcgtggtgac cgtgccctcc agcagcttgg gcacccagac   2040
ctacatctgc aacgtgaatc acaagcccag caacaccaag gtggacaaga aagttgagcc   2100
caaatcttgt gacaaaactc acacatgccc accgtgccca gcacctgaac tcctgggggg   2160
accgtcagtc ttcctcttcc ccccaaaacc caaggacacc ctcatgatct cccggacccc   2220
tgaggtcaca tgcgtggtgg tggacgtgag ccacgaagac cctgaggtca agttcaactg   2280
gtacgtggac ggcgtggagg tgcataatgc caagacaaag ccgcgggagg agcagtacaa   2340
cagcacgtac cgtgtggtca gcgtcctcac cgtcctgcac caggactggc tgaatggcaa   2400
ggagtacaag tgcaaggtct ccaacaaagc cctcccagcc cccatcgaga aaaccatctc   2460
caaagccaaa gggcagcccc gagaaccaca ggtgtacacc ctgcccccat cccgggatga   2520
gctgaccaag aaccaggtca gcctgacctg cctggtcaaa ggcttctatc ccagcgacat   2580
cgccgtggag tgggagagca atgggcagcc ggagaacaac tacaagacca cgcctcccgt   2640
gctggactcc gacggctcct tcttcctcta cagcaagctc accgtggaca agagcaggtg   2700
gcagcagggg aacgtcttct catgctccgt gatgcatgag gctctgcaca accactacac   2760
gcagaagagc ctctccctgt ctccgggtaa atgatgagga tccagatctg ctgtgccttc   2820
tagttgccag ccatctgttg tttgcccctc ccccgtgcct tccttgaccc tggaaggtgc   2880
cactcccact gtcctttcct aataaaatga ggaaattgca tcgcattgtc tgagtaggtg   2940
tcattctatt ctggggggtg gggtggggca ggacagcaag ggggaggatt gggaagacaa   3000
tagcaggcat gctggggatg cggtgggctc tatgggtacc caggtgctga agaattgacc   3060
cggttcctcc tgggccagaa agaagcaggc acatcccctt ctctgtgaca caccctgtcc   3120
```

```
acgcccctgg ttcttagttc cagccccact cataggacac tcatagctca ggagggctcc   3180
gccttcaatc ccacccgcta aagtacttgg agcggtctct ccctccctca tcagcccacc   3240
aaaccaaacc tagcctccaa gagtgggaag aaattaaagc aagataggct attaagtgca   3300
gagggagaga aaatgcctcc aacatgtgag gaagtaatga gagaaatcat agaattttaa   3360
ggccatgatt taaggccatc atggccttaa tcttccgctt cctcgctcac tgactcgctg   3420
cgctcggtcg ttcggctgcg gcgagcggta tcagctcact caaaggcggt aatacggtta   3480
tccacagaat caggggataa cgcaggaaag aacatgtgag caaaaggcca gcaaaaggcc   3540
aggaaccgta aaaaggccgc gttgctggcg tttttccata ggctccgccc ccctgacgag   3600
catcacaaaa atcgacgctc aagtcagagg tggcgaaacc cgacaggact ataaagatac   3660
caggcgtttc cccctggaag ctccctcgtg cgctctcctg ttccgaccct gccgcttacc   3720
ggatacctgt ccgcctttct cccttcggga agcgtggcgc tttctcatag ctcacgctgt   3780
aggtatctca gttcggtgta ggtcgttcgc tccaagctgg gctgtgtgca cgaacccccc   3840
gttcagcccg accgctgcgc cttatccggt aactatcgtc ttgagtccaa cccggtaaga   3900
cacgacttat cgccactggc agcagccact ggtaacagga ttagcagagc gaggtatgta   3960
ggcggtgcta cagagttctt gaagtggtgg cctaactacg gctacactag aagaacagta   4020
tttggtatct gcgctctgct gaagccagtt accttcggaa aaagagttgg tagctcttga   4080
tccggcaaac aaaccaccgc tggtagcggt ggtttttttg tttgcaagca gcagattacg   4140
cgcagaaaaa aaggatctca agaagatcct ttgatctttt ctacggggtc tgacgctcag   4200
tggaacgaaa actcacgtta agggattttg gtcatgagat tatcaaaaag gatcttcacc   4260
tagatccttt taaattaaaa atgaagtttt aaatcaatct aaagtatata tgagtaaact   4320
tggtctgaca gttaccaatg cttaatcagt gaggcaccta tctcagcgat ctgtctattt   4380
cgttcatcca tagttgcctg actcgggggg ggggggcgct gaggtctgcc tcgtgaagaa   4440
ggtgttgctg actcatacca ggcctgaatc gccccatcat ccagccagaa agtgagggag   4500
ccacggttga tgagagcttt gttgtaggtg gaccagttgg tgattttgaa cttttgcttt   4560
gccacggaac ggtctgcgtt gtcgggaaga tgcgtgatct gatccttcaa ctcagcaaaa   4620
gttcgattta ttcaacaaag ccgccgtccc gtcaagtcag cgtaatgctc tgccagtgtt   4680
acaaccaatt aaccaattct gattagaaaa actcatcgag catcaaatga aactgcaatt   4740
tattcatatc aggattatca ataccatatt tttgaaaaag ccgtttctgt aatgaaggag   4800
aaaactcacc gaggcagttc cataggatgg caagatcctg gtatcggtct gcgattccga   4860
ctcgtccaac atcaatacaa cctattaatt tcccctcgtc aaaaataagg ttatcaagtg   4920
agaaatcacc atgagtgacg actgaatccg gtgagaatgg caaaagctta tgcatttctt   4980
tccagacttg ttcaacaggc cagccattac gctcgtcatc aaaatcactc gcatcaacca   5040
aaccgttatt cattcgtgat tgcgcctgag cgagacgaaa tacgcgatcg ctgttaaaag   5100
gacaattaca aacaggaatc gaatgcaacc ggcgcaggaa cactgccagc gcatcaacaa   5160
tattttcacc tgaatcagga tattcttcta atacctggaa tgctgttttc ccggggatcg   5220
cagtggtgag taaccatgca tcatcaggag tacggataaa atgcttgatg gtcggaagag   5280
gcataaattc cgtcagccag tttagtctga ccatctcatc tgtaacatca ttggcaacgc   5340
tacctttgcc atgtttcaga aacaactctg gcgcatcggg cttcccatac aatcgataga   5400
ttgtcgcacc tgattgcccg acattatcgc gagcccattt atacccatat aaatcagcat   5460
```

-continued

```
ccatgttgga atttaatcgc ggcctcgagc aagacgtttc ccgttgaata tggctcataa   5520

caccccttgt attactgttt atgtaagcag acagttttat tgttcatgat gatatatttt   5580

tatcttgtgc aatgtaacat cagagatttt gagacacaac gtggctttcc cccccccccc   5640

attattgaag catttatcag ggttattgtc tcatgagcgg atacatattt gaatgtattt   5700

agaaaaataa acaaataggg gttccgcgca catttccccg aaaagtgcca cctgacgtct   5760

aagaaaccat tattatcatg acattaacct ataaaaatag gcgtatcacg aggccctttc   5820

gtc                                                                 5823
```

<210> SEQ ID NO 121
<211> LENGTH: 469
<212> TYPE: PRT
<213> ORGANISM: Homo sapiens

<400> SEQUENCE: 121

```
Met Gly Trp Ser Cys Ile Ile Leu Phe Leu Val Ala Thr Ala Thr Gly
1               5                   10                  15

Val His Ser Gln Leu Gln Leu Gln Glu Ser Gly Pro Gly Val Val Lys
            20                  25                  30

Pro Ser Glu Thr Leu Ser Leu Thr Cys Thr Ile Ser Gly Gly Ser Phe
        35                  40                  45

Ser Thr Tyr Tyr Trp Thr Trp Ile Arg Gln Pro Pro Gly Lys Gly Leu
    50                  55                  60

Glu Trp Val Gly Tyr Ile Gly Asn Gly Gly Arg Ser Leu Asn Tyr Asn
65                  70                  75                  80

Pro Ser Leu Lys Ser Arg Ile Thr Leu Ser Val Asp Ala Ser Lys Asn
                85                  90                  95

Gln Phe Ser Leu Lys Val Thr Ser Val Thr Ala Ala Asp Thr Ala Val
            100                 105                 110

Tyr Tyr Cys Gly Arg Ala Arg Gly Leu Arg Gly Asn Trp Phe Asp Val
        115                 120                 125

Trp Gly Pro Gly Val Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300
```

-continued

```
Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

<210> SEQ ID NO 122
<211> LENGTH: 5118
<212> TYPE: DNA
<213> ORGANISM: Homo sapiens

<400> SEQUENCE: 122

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctcca tcggctcgca tctctccttc acgcgcccgc   1020

cgccctacct gaggccgcca tccacgccgg ttgagtcgcg ttctgccgcc tcccgcctgt   1080

ggtgcctcct gaactgcgtc cgccgtctag gtaagtttaa agctcaggtc gagaccgggc   1140
```

-continued

```
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
ccaggctgcc ctgactcagc ctccctctgt gtctgggtct cctggacagt cggtcaccat   1500
ctcctgcact ggaaccagca gtgacatcgg tggttataac tatgtctcct ggtaccaaca   1560
acacccaggc aaagccccca aagtcatgat ttatgaggtc agtaagcggc cctcaggggt   1620
ctctgatcgc ttctctggtt ccaaatctgg caacatagcc tccctgacca tctctgggct   1680
ccaggctgag gacgaggctg attattactg cagctcatat gcaggcagca acactttctt   1740
attcggagga gggacccggc tgacagtcct aggtcagccc aaggctgccc cctcggtcac   1800
tctgttcccg ccctcctctg aggagcttca agccaacaag gccacactgg tgtgtctcat   1860
aagtgacttc tacccgggag ccgtgacagt ggcctggaag gcagatagca gccccgtcaa   1920
ggcgggagtg gagaccacca caccctccaa acaaagcaac aacaagtacg cggccagcag   1980
ctatctgagc ctgacgcctg agcagtggaa gtcccacaga agctacagct gccaggtcac   2040
gcatgaaggg agcaccgtgg agaagacagt ggcccctaca gaatgttcat gaggatccag   2100
atctgctgtg ccttctagtt gccagccatc tgttgtttgc ccctcccccg tgccttcctt   2160
gaccctggaa ggtgccactc ccactgtcct ttcctaataa aatgaggaaa ttgcatcgca   2220
ttgtctgagt aggtgtcatt ctattctggg gggtggggtg gggcaggaca gcaaggggga   2280
ggattgggaa gacaatagca ggcatgctgg ggatgcggtg ggctctatgg gtacccaggt   2340
gctgaagaat tgacccggtt cctcctgggc cagaaagaag caggcacatc cccttctctg   2400
tgacacaccc tgtccacgcc cctggttctt agttccagcc ccactcatag gacactcata   2460
gctcaggagg gctccgcctt caatcccacc cgctaaagta cttggagcgg tctctccctc   2520
cctcatcagc ccaccaaacc aaacctagcc tccaagagtg ggaagaaatt aaagcaagat   2580
aggctattaa gtgcagaggg agagaaaatg cctccaacat gtgaggaagt aatgagagaa   2640
atcatagaat tttaaggcca tgatttaagg ccatcatggc cttaatcttc cgcttcctcg   2700
ctcactgact cgctgcgctc ggtcgttcgg ctgcggcgag cggtatcagc tcactcaaag   2760
gcggtaatac ggttatccac agaatcaggg gataacgcag gaaagaacat gtgagcaaaa   2820
ggccagcaaa aggccaggaa ccgtaaaaag gccgcgttgc tggcgttttt ccataggctc   2880
cgcccccctg acgagcatca caaaaatcga cgctcaagtc agaggtggcg aaacccgaca   2940
ggactataaa gataccaggc gtttccccct ggaagctccc tcgtgcgctc tcctgttccg   3000
accctgccgc ttaccggata cctgtccgcc tttctccctt cgggaagcgt ggcgctttct   3060
catagctcac gctgtaggta tctcagttcg gtgtaggtcg ttcgctccaa gctgggctgt   3120
gtgcacgaac cccccgttca gcccgaccgc tgcgccttat ccggtaacta tcgtcttgag   3180
tccaacccgg taagacacga cttatcgcca ctggcagcag ccactggtaa caggattagc   3240
agagcgaggt atgtaggcgg tgctacagag ttcttgaagt ggtggcctaa ctacggctac   3300
actagaagaa cagtatttgg tatctgcgct ctgctgaagc cagttacctt cggaaaaaga   3360
gttggtagct cttgatccgg caaacaaacc accgctggta gcggtggttt ttttgtttgc   3420
aagcagcaga ttacgcgcag aaaaaaagga tctcaagaag atcctttgat cttttctacg   3480
gggtctgacg ctcagtggaa cgaaaactca cgttaaggga ttttggtcat gagattatca   3540
```

```
aaaaggatct tcacctagat ccttttaaat taaaaatgaa gttttaaatc aatctaaagt   3600
atatatgagt aaacttggtc tgacagttac caatgcttaa tcagtgaggc acctatctca   3660
gcgatctgtc tatttcgttc atccatagtt gcctgactcg gggggggggg gcgctgaggt   3720
ctgcctcgtg aagaaggtgt tgctgactca taccaggcct gaatcgcccc atcatccagc   3780
cagaaagtga gggagccacg gttgatgaga gctttgttgt aggtggacca gttggtgatt   3840
ttgaactttt gctttgccac ggaacggtct gcgttgtcgg gaagatgcgt gatctgatcc   3900
ttcaactcag caaaagttcg atttattcaa caaagccgcc gtcccgtcaa gtcagcgtaa   3960
tgctctgcca gtgttacaac caattaacca attctgatta gaaaaactca tcgagcatca   4020
aatgaaactg caatttattc atatcaggat tatcaatacc atatttttga aaaagccgtt   4080
tctgtaatga aggagaaaac tcaccgaggc agttccatag gatggcaaga tcctggtatc   4140
ggtctgcgat tccgactcgt ccaacatcaa tacaacctat taatttcccc tcgtcaaaaa   4200
taaggttatc aagtgagaaa tcaccatgag tgacgactga atccggtgag aatggcaaaa   4260
gcttatgcat ttctttccag acttgttcaa caggccagcc attacgctcg tcatcaaaat   4320
cactcgcatc aaccaaaccg ttattcattc gtgattgcgc ctgagcgaga cgaaatacgc   4380
gatcgctgtt aaaaggacaa ttacaaacag gaatcgaatg caaccggcgc aggaacactg   4440
ccagcgcatc aacaatattt tcacctgaat caggatattc ttctaatacc tggaatgctg   4500
ttttcccggg gatcgcagtg gtgagtaacc atgcatcatc aggagtacgg ataaaatgct   4560
tgatggtcgg aagaggcata aattccgtca gccagtttag tctgaccatc tcatctgtaa   4620
catcattggc aacgctacct ttgccatgtt tcagaaacaa ctctggcgca tcgggcttcc   4680
catacaatcg atagattgtc gcacctgatt gcccgacatt atcgcgagcc catttatacc   4740
catataaatc agcatccatg ttggaattta atcgcggcct cgagcaagac gtttcccgtt   4800
gaatatggct cataacaccc cttgtattac tgtttatgta agcagacagt tttattgttc   4860
atgatgatat atttttatct tgtgcaatgt aacatcagag attttgagac acaacgtggc   4920
tttccccccc cccccattat tgaagcattt atcagggtta ttgtctcatg agcggataca   4980
tatttgaatg tatttagaaa aataaacaaa taggggttcc gcgcacattt ccccgaaaag   5040
tgccacctga cgtctaagaa accattatta tcatgacatt aacctataaa aataggcgta   5100
tcacgaggcc ctttcgtc                                                 5118
```

<210> SEQ ID NO 123
<211> LENGTH: 235
<212> TYPE: PRT
<213> ORGANISM: Homo sapiens

<400> SEQUENCE: 123

```
Met Gly Trp Ser Cys Ile Ile Leu Phe Leu Val Ala Thr Ala Thr Gly
1               5                   10                  15

Val His Ser Gln Ala Ala Leu Thr Gln Pro Pro Ser Val Ser Gly Ser
            20                  25                  30

Pro Gly Gln Ser Val Thr Ile Ser Cys Thr Gly Thr Ser Ser Asp Ile
        35                  40                  45

Gly Gly Tyr Asn Tyr Val Ser Trp Tyr Gln Gln His Pro Gly Lys Ala
    50                  55                  60

Pro Lys Val Met Ile Tyr Glu Val Ser Lys Arg Pro Ser Gly Val Ser
65                  70                  75                  80
```

```
Asp Arg Phe Ser Gly Ser Lys Ser Gly Asn Ile Ala Ser Leu Thr Ile
                85                  90                  95

Ser Gly Leu Gln Ala Glu Asp Glu Ala Asp Tyr Tyr Cys Ser Ser Tyr
            100                 105                 110

Ala Gly Ser Asn Thr Phe Leu Phe Gly Gly Gly Thr Arg Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235


<210> SEQ ID NO 124
<211> LENGTH: 907
<212> TYPE: PRT
<213> ORGANISM: Homo sapiens

<400> SEQUENCE: 124

Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205
```

```
Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Ser Asn Thr Thr Gly Phe Ala Ala Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Arg Asp
                485                 490                 495

Asn Gly Thr Glu Ser Lys Ala Pro Asp Met Thr Ser Pro Thr Ser Ala
            500                 505                 510

Val Thr Thr Pro Thr Pro Asn Ala Thr Ser Pro Thr Ser Ala Val Thr
        515                 520                 525

Thr Pro Thr Pro Asn Ala Thr Ser Pro Thr Pro Ala Val Thr Thr Pro
    530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
                565                 570                 575

Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
        595                 600                 605

Pro Asn Ala Thr Ser Pro Thr Val Gly Glu Thr Ser Pro Gln Ala Asn
    610                 615                 620
```

-continued

Thr Thr Asn His Thr Leu Gly Gly Thr Ser Ser Thr Pro Val Val Thr
625 630 635 640

Ser Pro Pro Lys Asn Ala Thr Ser Ala Val Thr Thr Gly Gln His Asn
645 650 655

Ile Thr Ser Ser Ser Thr Ser Ser Met Ser Leu Arg Pro Ser Ser Ile
660 665 670

Ser Glu Thr Leu Ser Pro Ser Thr Ser Asp Asn Ser Thr Ser His Met
675 680 685

Pro Leu Leu Thr Ser Ala His Pro Thr Gly Gly Glu Asn Ile Thr Gln
690 695 700

Val Thr Pro Ala Ser Thr Ser Thr His His Val Ser Thr Ser Ser Pro
705 710 715 720

Ala Pro Arg Pro Gly Thr Thr Ser Gln Ala Ser Gly Pro Gly Asn Ser
725 730 735

Ser Thr Ser Thr Lys Pro Gly Glu Val Asn Val Thr Lys Gly Thr Pro
740 745 750

Pro Lys Asn Ala Thr Ser Pro Gln Ala Pro Ser Gly Gln Lys Thr Ala
755 760 765

Val Pro Thr Val Thr Ser Thr Gly Gly Lys Ala Asn Ser Thr Thr Gly
770 775 780

Gly Lys His Thr Thr Gly His Gly Ala Arg Thr Ser Thr Glu Pro Thr
785 790 795 800

Thr Asp Tyr Gly Gly Asp Ser Thr Thr Pro Arg Thr Arg Tyr Asn Ala
805 810 815

Thr Thr Tyr Leu Pro Pro Ser Thr Ser Ser Glu Leu Arg Pro Arg Trp
820 825 830

Thr Phe Thr Ser Pro Pro Val Thr Thr Ala Gln Ala Thr Val Pro Val
835 840 845

Pro Pro Thr Ser Gln Pro Arg Phe Ser Asn Leu Ser Met Leu Val Leu
850 855 860

Gln Trp Ala Ser Leu Ala Val Leu Thr Leu Leu Leu Leu Leu Val Met
865 870 875 880

Ala Asp Cys Ala Phe Arg Arg Asn Leu Ser Thr Ser His Thr Tyr Thr
885 890 895

Thr Pro Pro Tyr Asp Asp Ala Glu Thr Tyr Val
900 905

<210> SEQ ID NO 125
<211> LENGTH: 426
<212> TYPE: PRT
<213> ORGANISM: Homo sapiens

<400> SEQUENCE: 125

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

Gly Gln Leu Thr Pro His Thr Lys Ala Val Tyr Gln Pro Arg Gly Ala
65 70 75 80

Phe Gly Gly Ser Glu Asn Ala Thr Asn Leu Phe Leu Leu Glu Leu Leu
85 90 95

-continued

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser
            420                 425

<210> SEQ ID NO 126
<211> LENGTH: 1281
<212> TYPE: DNA
<213> ORGANISM: Homo sapiens

<400> SEQUENCE: 126
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240

```
tttggcggca gcgagaacgc caccaatctg tttctgctgg aactcctagg cgccggcgag    300

ctggccctga ccatgagaag caagaaactg cccatcaatg tgaccacagg cgaggaacag    360

caggtgtccc tggaaagcgt ggacgtgtac tttcaagacg tgttcggcac catgtggtgc    420

caccacgccg agatgcagaa ccccgtgtac ctgatccccg agacagtgcc ctacatcaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gcgattactg tatccagagc    900

aacatcgtgt tcagcgacga gatccccgcc agccaggaca tgcccaccaa taccaccgac    960

atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc accccctagcg gctgcgagaa tatcagcgga  1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctctgg c                                             1281
```

<210> SEQ ID NO 127
<211> LENGTH: 426
<212> TYPE: PRT
<213> ORGANISM: Homo sapiens

<400> SEQUENCE: 127

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Asn Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175
```

```
Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser
            420                 425
```

<210> SEQ ID NO 128
<211> LENGTH: 1278
<212> TYPE: DNA
<213> ORGANISM: Homo sapiens

<400> SEQUENCE: 128

```
gaagctgccc tgctcgtgtg ccagtacacc atccagagcc tgatccacct gaccggcgag     60

gaccccggct tcttcaacgt ggaaatcccc gagttcccct tctaccctac ctgcaacgtg    120

tgcaccgccg acgtgaacgt gaccatcaac ttcgacgtgg gcggcaagaa gcaccagctg    180

gacctggatt tcggccagct gacccctcac accaaggccg tgtatcagcc cagaggcgcc    240

tttggcggca gcgagaacgc caccaatctg tttctgctgg aactcctagg cgccggcgag    300

ctggccctga ccatgagaag caagaaactg cccatcaatg tgaccacagg cgaggaacag    360

aacgtgtccc tggaaagcgt ggacgtgtac tttcaagacg tgttcggcac catgtggtgc    420

caccacgccg agatgcagaa ccccgtgtac ctgatccccg agacagtgcc ctacatcaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660
```

-continued

```
ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gcgattactg tatccagagc    900

aacatcgtgt tcagcgacga gatccccgcc agccaggaca tgcccaccaa taccaccgac    960

atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc acccctagcg gctgcgagaa tatcagcgga   1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctct                                                 1278


<210> SEQ ID NO 129
<211> LENGTH: 427
<212> TYPE: PRT
<213> ORGANISM: Homo sapiens

<400> SEQUENCE: 129

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asn Asn Ser Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255
```

-continued

```
Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Gly Ser
            420                 425
```

<210> SEQ ID NO 130
<211> LENGTH: 1281
<212> TYPE: DNA
<213> ORGANISM: Homo sapiens

<400> SEQUENCE: 130

```
gaagctgccc tgctcgtgtg ccagtacacc atccagagcc tgatccacct gaccggcgag      60

gacccccggct tcttcaacgt ggaaatcccc gagttcccct tctaccctac ctgcaacgtg    120

tgcaccgccg acgtgaacgt gaccatcaac ttcgacgtgg gcggcaagaa gcaccagctg     180

gacctggatt tcggccagct gacccctcac accaaggccg tgtatcagcc cagaggcgcc     240

tttggcggca gcgagaacgc caccaatctg tttctgctgg aactcctagg cgccggcgag     300

ctggccctga ccatgagaag caagaaactg cccatcaatg tgaccacagg cgaggaacag     360

caggtgtccc tggaaagcgt ggacgtgtac tttcaagacg tgttcggcac catgtggtgc     420

caccacgccg agatgcagaa ccccgtgtac ctgatccccg agacagtgcc ctacatcaag     480

tggaacaaca gctgcaacag caccaacatc accgccgtcg tgcgggccca gggactggat     540

gtgacactgc ctctgagcct gcctaccagc gcccaggaca gcaacttcag cgtgaaaacc     600

gagatgctgg gcaacgagat cgacatcgag tgcatcatgg aagatggcga gatcagccag     660

gtgctgcccg gcgacaacaa gttcaacatc acatgcagcg gctacgagag ccacgtgcca     720

tctggcggca tcctgaccag cacaagccca gtggccacac ccatccctgg cacaggctac     780

gcctacagcc tgagactgac ccccagaccc gtgtccagat tcctgggcaa caacagcatc     840

ctgtacgtgt tctacagcgg caacggcccc aaggcctctg gcggcgatta ctgtatccag     900

agcaacatcg tgttcagcga cgagatcccc gccagccagg acatgcccac caataccacc     960

gacatcacgt acgtgggcga caatgccacc tacagcgtgc caatggtcac ctccgaggac    1020

gccaacagcc ccaacgtgac cgtgacagcc ttttgggcct ggcctaacaa caccgagaca    1080

gacttcaagt gcaagtggac cctgacctcc ggcacccccta gcggctgcga gaatatcagc   1140
```

```
ggagccttcg ccagcaaccg gaccttcgat atcaccgtgt ctggcctggg caccgccccc   1200

aagaccctga tcatcaccag aaccgccaca aatgccacca ccacaaccca caaagtgatc   1260

ttcagcaagg cccccggctc t                                             1281


<210> SEQ ID NO 131
<211> LENGTH: 426
<212> TYPE: PRT
<213> ORGANISM: Homo sapiens

<400> SEQUENCE: 131

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335
```

-continued

Ser Glu Asp Ala Asn Ser Pro Asn Val Thr Val Thr Ala Phe Trp Ala
340 345 350

Trp Pro Asn Asn Thr Glu Thr Asp Phe Lys Cys Lys Trp Thr Leu Thr
355 360 365

Ser Gly Thr Pro Ser Gly Cys Glu Asn Ile Ser Gly Ala Phe Ala Ser
370 375 380

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His
405 410 415

Lys Val Ile Phe Ser Lys Ala Pro Gly Ser
420 425

<210> SEQ ID NO 132
<211> LENGTH: 1278
<212> TYPE: DNA
<213> ORGANISM: Homo sapiens

<400> SEQUENCE: 132
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240
tttggcggca gcgagaacgc caccaatctg tttctgctgg aactcctagg cgccggcgag 300
ctggccctga ccatgagaag caagaaactg cccatcaatg tgaccacagg cgaggaacag 360
caggtgtccc tggaaagcgt ggacgtgtac tttcaagacg tgttcggcac catgtggtgc 420
caccacgccg agatgcagaa ccccgtgtac ctgatccccg agacagtgcc ctacatcaag 480
tgggacaact gcaacagcac caacatcacc gccgtcgtgc gggcccaggg actggatgtg 540
acactgcctc tgagcctgcc taccagcgcc caggacagca acttcagcgt gaaaaccgag 600
atgctgggca acgagatcga catcgagtgc atcatggaag atggcgagat cagccaggtg 660
ctgcccggcg acaacaagtt caacatcaca tgcagcggct acgagagcca cgtgccatct 720
ggcggcatcc tgaccagcac aagcccagtg gccacaccca tccctggcac aggctacgcc 780
tacagcctga gactgacccc cagacccgtg tccagattcc tgggcaacaa cagcatcctg 840
tacgtgttct acagcggcaa cggccccaag gcctctggcg gccggtactg tatccagagc 900
aacatcgtgt tcagcgacga gatccccgcc agccaggaca tgcccaccaa taccaccgac 960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc accccctagcg gctgcgagaa tatcagcgga 1140
gccttcgcca gcaaccggac cttcgatatc accgtgtctg gcctgggcac cgcccccaag 1200
accctgatca tcaccagaac cgccacaaat gccaccacca caacccacaa agtgatcttc 1260
agcaaggccc ccggctct 1278

<210> SEQ ID NO 133
<211> LENGTH: 426
<212> TYPE: PRT
<213> ORGANISM: Homo sapiens -continued

<400> SEQUENCE: 133

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

Gly Gln Leu Thr Pro His Thr Lys Ala Val Tyr Gln Pro Arg Gly Ala
65 70 75 80

Phe Gly Gly Ser Glu Asn Ala Thr Asn Leu Phe Leu Leu Glu Leu Leu
85 90 95

Gly Ala Gly Glu Leu Ala Leu Thr Met Arg Ser Lys Lys Leu Pro Ile
100 105 110

Asn Val Thr Thr Gly Glu Glu Gln Gln Val Ser Leu Glu Ser Val Asp
115 120 125

Val Tyr Phe Gln Asp Val Phe Gly Thr Met Trp Cys His His Ala Glu
130 135 140

Met Gln Asn Pro Val Tyr Leu Ile Pro Glu Thr Val Pro Tyr Ile Lys
145 150 155 160

Ala Ala Ala Cys Asn Ser Thr Asn Ile Thr Ala Val Val Arg Ala Gln
165 170 175

Gly Leu Asp Val Thr Leu Pro Leu Ser Leu Pro Thr Ser Ala Gln Asp
180 185 190

Ser Asn Phe Ser Val Lys Thr Glu Met Leu Gly Asn Glu Ile Asp Ile
195 200 205

Glu Cys Ile Met Glu Asp Gly Glu Ile Ser Gln Val Leu Pro Gly Asp
210 215 220

Asn Lys Phe Asn Ile Thr Cys Ser Gly Tyr Glu Ser His Val Pro Ser
225 230 235 240

Gly Gly Ile Leu Thr Ser Thr Ser Pro Val Ala Thr Pro Ile Pro Gly
245 250 255

Thr Gly Tyr Ala Tyr Ser Leu Arg Leu Thr Pro Arg Pro Val Ser Arg
260 265 270

Phe Leu Gly Asn Asn Ser Ile Leu Tyr Val Phe Tyr Ser Gly Asn Gly
275 280 285

Pro Lys Ala Ser Gly Gly Asp Tyr Cys Ile Gln Ser Asn Ile Val Phe
290 295 300

Ser Asp Glu Ile Pro Ala Ser Gln Asp Met Pro Thr Asn Thr Thr Asp
305 310 315 320

Ile Thr Tyr Val Gly Asp Asn Ala Thr Tyr Ser Val Pro Met Val Thr
325 330 335

Ser Glu Asp Ala Asn Ser Pro Asn Val Thr Val Thr Ala Phe Trp Ala
340 345 350

Trp Pro Asn Asn Thr Glu Thr Asp Phe Lys Cys Lys Trp Thr Leu Thr
355 360 365

Ser Gly Thr Pro Ser Gly Cys Glu Asn Ile Ser Gly Ala Phe Ala Ser
370 375 380

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His
405 410 415

Lys Val Ile Phe Ser Lys Ala Pro Gly Ser
420 425

<210> SEQ ID NO 134
<211> LENGTH: 1278
<212> TYPE: DNA
<213> ORGANISM: Homo sapiens

<400> SEQUENCE: 134
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240
tttggcggca gcgagaacgc caccaatctg tttctgctgg aactcctagg cgccggcgag 300
ctggccctga ccatgagaag caagaaactg cccatcaatg tgaccacagg cgaggaacag 360
caggtgtccc tggaaagcgt ggacgtgtac tttcaagacg tgttcggcac catgtggtgc 420
caccacgccg agatgcagaa ccccgtgtac ctgatccccg agacagtgcc ctacatcaag 480
gccgccgcct gcaacagcac caacatcacc gccgtcgtgc gggcccaggg actggatgtg 540
acactgcctc tgagcctgcc taccagcgcc caggacagca acttcagcgt gaaaaccgag 600
atgctgggca acgagatcga catcgagtgc atcatggaag atggcgagat cagccaggtg 660
ctgcccggcg acaacaagtt caacatcaca tgcagcggct acgagagcca cgtgccatct 720
ggcggcatcc tgaccagcac aagcccagtg gccacaccca tccctggcac aggctacgcc 780
tacagcctga gactgacccc cagacccgtg tccagattcc tgggcaacaa cagcatcctg 840
tacgtgttct acagcggcaa cggccccaag gcctctggcg gcgattactg tatccagagc 900
aacatcgtgt tcagcgacga gatccccgcc agccaggaca tgcccaccaa taccaccgac 960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc accccctagcg gctgcgagaa tatcagcgga 1140
gccttcgcca gcaaccggac cttcgatatc accgtgtctg gcctgggcac cgcccccaag 1200
accctgatca tcaccagaac cgccacaaat gccaccacca caacccacaa agtgatcttc 1260
agcaaggccc ccggctct 1278

<210> SEQ ID NO 135
<211> LENGTH: 426
<212> TYPE: PRT
<213> ORGANISM: Homo sapiens

<400> SEQUENCE: 135

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

```
Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Arg Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser
            420                 425
```

<210> SEQ ID NO 136
<211> LENGTH: 1278
<212> TYPE: DNA
<213> ORGANISM: Homo sapiens

<400> SEQUENCE: 136
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240
tttggcggca gcgagaacgc caccaatctg tttctgctgg aactcctagg cgccggcgag 300
ctggccctga ccatgagaag caagaaactg cccatcaatg tgaccacagg cgaggaacag 360
caggtgtccc tggaaagcgt ggacgtgtac tttcaagacg tgttcggcac catgtggtgc 420
caccacgccg agatgcagaa ccccgtgtac ctgatccccg agacagtgcc ctaccggaag 480
tgggacaact gcaacagcac caacatcacc gccgtcgtgc gggcccaggg actggatgtg 540
acactgcctc tgagcctgcc taccagcgcc caggacagca acttcagcgt gaaaaccgag 600
atgctgggca acgagatcga catcgagtgc atcatggaag atggcgagat cagccaggtg 660
ctgcccggcg acaacaagtt caacatcaca tgcagcggct acgagagcca cgtgccatct 720
ggcggcatcc tgaccagcac aagcccagtg gccacaccca tccctggcac aggctacgcc 780
tacagcctga gactgacccc cagacccgtg tccagattcc tgggcaacaa cagcatcctg 840
tacgtgttct acagcggcaa cggccccaag gcctctggcg gccggtactg tatccagagc 900
aacatcgtgt tcagcgacga gatccccgcc agccaggaca tgcccaccaa taccaccgac 960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc acccctagcg gctgcgagaa tatcagcgga 1140
gccttcgcca gcaaccggac cttcgatatc accgtgtctg gcctgggcac cgcccccaag 1200
accctgatca tcaccagaac cgccacaaat gccaccacca caacccacaa agtgatcttc 1260
agcaaggccc ccggctct 1278

<210> SEQ ID NO 137
<211> LENGTH: 426
<212> TYPE: PRT
<213> ORGANISM: Homo sapiens

<400> SEQUENCE: 137

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

-continued

```
Val Tyr Phe Gln Asp Val Phe Gly Thr Met Trp Cys His His Ala Glu
    130                 135                 140

Met Gln Asn Pro Val Tyr Leu Ile Pro Glu Thr Val Arg Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser
            420                 425
```

<210> SEQ ID NO 138
<211> LENGTH: 1278
<212> TYPE: DNA
<213> ORGANISM: Homo sapiens

<400> SEQUENCE: 138

```
gaagctgccc tgctcgtgtg ccagtacacc atccagagcc tgatccacct gaccggcgag      60

gaccccggct tcttcaacgt ggaaatcccc gagttcccct tctaccctac ctgcaacgtg     120

tgcaccgccg acgtgaacgt gaccatcaac ttcgacgtgg gcggcaagaa gcaccagctg     180

gacctggatt tcggccagct gacccctcac accaaggccg tgtatcagcc cagaggcgcc     240

tttggcggca gcgagaacgc caccaatctg tttctgctgg aactcctagg cgccggcgag     300

ctggccctga ccatgagaag caagaaactg cccatcaatg tgaccacagg cgaggaacag     360

caggtgtccc tggaaagcgt ggacgtgtac tttcaagacg tgttcggcac catgtggtgc     420
```

-continued

```
caccacgccg agatgcagaa ccccgtgtac ctgatccccg agacagtgcg gtacatcaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gccggtactg tatccagagc    900

aacatcgtgt tcagcgacga gatccccgcc agccaggaca tgcccaccaa taccaccgac    960

atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc acccctagcg gctgcgagaa tatcagcgga   1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctct                                                 1278
```

<210> SEQ ID NO 139
<211> LENGTH: 426
<212> TYPE: PRT
<213> ORGANISM: Homo sapiens

<400> SEQUENCE: 139

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Asn Tyr Thr Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220
```

-continued

```
Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser
            420                 425
```

<210> SEQ ID NO 140
<211> LENGTH: 1278
<212> TYPE: DNA
<213> ORGANISM: Homo sapiens

<400> SEQUENCE: 140

```
gaagctgccc tgctcgtgtg ccagtacacc atccagagcc tgatccacct gaccggcgag     60

gaccccggct tcttcaacgt ggaaatcccc gagttcccct tctaccctac ctgcaacgtg    120

tgcaccgccg acgtgaacgt gaccatcaac ttcgacgtgg gcggcaagaa gcaccagctg    180

gacctggatt tcggccagct gacccctcac accaaggccg tgtatcagcc cagaggcgcc    240

tttggcggca gcgagaacgc caccaatctg tttctgctgg aactcctagg cgccggcgag    300

ctggccctga ccatgagaag caagaaactg cccatcaatg tgaccacagg cgaggaacag    360

caggtgtccc tggaaagcgt ggacgtgtac tttcaagacg tgttcggcac catgtggtgc    420

caccacgccg agatgcagaa ccccgtgtac ctgatccccg agacagtgaa ctacaccaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gccggtactg tatccagagc    900

aacatcgtgt tcagcgacga gatccccgcc agccaggaca tgcccaccaa taccaccgac    960
```

```
atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc acccctagcg gctgcgagaa tatcagcgga   1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctct                                                 1278
```

```
<210> SEQ ID NO 141
<211> LENGTH: 426
<212> TYPE: PRT
<213> ORGANISM: Homo sapiens

<400> SEQUENCE: 141

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Arg Tyr Arg Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300
```

```
Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser
            420                 425


<210> SEQ ID NO 142
<211> LENGTH: 1278
<212> TYPE: DNA
<213> ORGANISM: Homo sapiens

<400> SEQUENCE: 142

gaagctgccc tgctcgtgtg ccagtacacc atccagagcc tgatccacct gaccggcgag      60

gaccccggct tcttcaacgt ggaaatcccc gagttcccct tctaccctac ctgcaacgtg     120

tgcaccgccg acgtgaacgt gaccatcaac ttcgacgtgg gcggcaagaa gcaccagctg     180

gacctggatt tcggccagct gacccctcac accaaggccg tgtatcagcc cagaggcgcc     240

tttggcggca gcgagaacgc caccaatctg tttctgctgg aactcctagg cgccggcgag     300

ctggccctga ccatgagaag caagaaactg cccatcaatg tgaccacagg cgaggaacag     360

caggtgtccc tggaaagcgt ggacgtgtac tttcaagacg tgttcggcac catgtggtgc     420

caccacgccg agatgcagaa ccccgtgtac ctgatccccg agacagtgcg gtaccggaag     480

tgggacaact gcaacagcac caacatcacc gccgtcgtgc gggcccaggg actggatgtg     540

acactgcctc tgagcctgcc taccagcgcc caggacagca acttcagcgt gaaaaccgag     600

atgctgggca acgagatcga catcgagtgc atcatggaag atggcgagat cagccaggtg     660

ctgcccggcg acaacaagtt caacatcaca tgcagcggct acgagagcca cgtgccatct     720

ggcggcatcc tgaccagcac aagcccagtg gccacaccca tccctggcac aggctacgcc     780

tacagcctga gactgacccc cagacccgtg tccagattcc tgggcaacaa cagcatcctg     840

tacgtgttct acagcggcaa cggccccaag gcctctggcg gccggtactg tatccagagc     900

aacatcgtgt tcagcgacga gatccccgcc agccaggaca tgcccaccaa taccaccgac     960

atcacgtacg tgggcgacaa tgccacctac agcgtgccaa tggtcacctc cgaggacgcc    1020

aacagcccca acgtgaccgt gacagccttt tgggcctggc ctaacaacac cgagacagac    1080

ttcaagtgca agtggaccct gacctccggc acccctagcg gctgcgagaa tatcagcgga    1140

gccttcgcca gcaaccggac cttcgatatc accgtgtctg gcctgggcac cgcccccaag    1200

accctgatca tcaccagaac cgccacaaat gccaccacca caacccacaa agtgatcttc    1260

agcaaggccc ccggctct                                                  1278


<210> SEQ ID NO 143
```

<211> LENGTH: 447
<212> TYPE: PRT
<213> ORGANISM: Homo sapiens

<400> SEQUENCE: 143

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380
```

```
Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser Gly Leu Asn Asp Ile Phe
            420                 425                 430

Glu Ala Gln Lys Ile Glu Trp His Glu His His His His His His
        435                 440                 445
```

<210> SEQ ID NO 144
<211> LENGTH: 1341
<212> TYPE: DNA
<213> ORGANISM: Homo sapiens

<400> SEQUENCE: 144

```
gaagctgccc tgctcgtgtg ccagtacacc atccagagcc tgatccacct gaccggcgag     60

gaccccggct tcttcaacgt ggaaatcccc gagttcccct tctaccctac ctgcaacgtg    120

tgcaccgccg acgtgaacgt gaccatcaac ttcgacgtgg gcggcaagaa gcaccagctg    180

gacctggatt tcggccagct gacccctcac accaaggccg tgtatcagcc cagaggcgcc    240

tttggcggca gcgagaacgc caccaatctg tttctgctgg aactcctagg cgccggcgag    300

ctggccctga ccatgagaag caagaaactg cccatcaatg tgaccacagg cgaggaacag    360

caggtgtccc tggaaagcgt ggacgtgtac tttcaagacg tgttcggcac catgtggtgc    420

caccacgccg agatgcagaa ccccgtgtac ctgatccccg agacagtgcc ctacatcaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gcgattactg tatccagagc    900

aacatcgtgt tcagcgacga gatccccgcc agccaggaca tgcccaccaa taccaccgac    960

atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc accccctagcg gctgcgagaa tatcagcgga  1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctctgg cctgaacgac atttttgagg cccagaagat tgagtggcat   1320

gaacatcacc accaccacca t                                              1341
```

<210> SEQ ID NO 145
<211> LENGTH: 447
<212> TYPE: PRT
<213> ORGANISM: Homo sapiens

<400> SEQUENCE: 145

```
Glu Ala Ala Leu Leu Val Cys Gln Tyr Thr Ile Gln Ser Leu Ile His
1               5                   10                  15
```

-continued

```
Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Asn Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser Gly Leu Asn Asp Ile Phe
            420                 425                 430
```

```
Glu Ala Gln Lys Ile Glu Trp His Glu His His His His His His
        435                 440                 445


<210> SEQ ID NO 146
<211> LENGTH: 1341
<212> TYPE: DNA
<213> ORGANISM: Homo sapiens

<400> SEQUENCE: 146

gaagctgccc tgctcgtgtg ccagtacacc atccagagcc tgatccacct gaccggcgag      60

gaccccggct tcttcaacgt ggaaatcccc gagttcccct tctaccctac ctgcaacgtg     120

tgcaccgccg acgtgaacgt gaccatcaac ttcgacgtgg gcggcaagaa gcaccagctg     180

gacctggatt tcggccagct gacccctcac accaaggccg tgtatcagcc cagaggcgcc     240

tttggcggca gcgagaacgc caccaatctg tttctgctgg aactcctagg cgccggcgag     300

ctggccctga ccatgagaag caagaaactg cccatcaatg tgaccacagg cgaggaacag     360

aacgtgtccc tggaaagcgt ggacgtgtac tttcaagacg tgttcggcac catgtggtgc     420

caccacgccg agatgcagaa ccccgtgtac ctgatccccg agacagtgcc ctacatcaag     480

tgggacaact gcaacagcac caacatcacc gccgtcgtgc gggcccaggg actggatgtg     540

acactgcctc tgagcctgcc taccagcgcc caggacagca acttcagcgt gaaaaccgag     600

atgctgggca acgagatcga catcgagtgc atcatggaag atggcgagat cagccaggtg     660

ctgcccggcg acaacaagtt caacatcaca tgcagcggct acgagagcca cgtgccatct     720

ggcggcatcc tgaccagcac aagcccagtg gccacaccca tccctggcac aggctacgcc     780

tacagcctga gactgacccc cagacccgtg tccagattcc tgggcaacaa cagcatcctg     840

tacgtgttct acagcggcaa cggccccaag gcctctggcg gcgattactg tatccagagc     900

aacatcgtgt tcagcgacga gatccccgcc agccaggaca tgcccaccaa taccaccgac     960

atcacgtacg tgggcgacaa tgccacctac agcgtgccaa tggtcacctc cgaggacgcc    1020

aacagcccca acgtgaccgt gacagccttt tgggcctggc ctaacaacac cgagacagac    1080

ttcaagtgca agtggaccct gacctccggc accccctagcg gctgcgagaa tatcagcgga    1140

gccttcgcca gcaaccggac cttcgatatc accgtgtctg gcctgggcac cgcccccaag    1200

accctgatca tcaccagaac cgccacaaat gccaccacca caacccacaa agtgatcttc    1260

agcaaggccc ccggctctgg cctgaacgac atttttgagg cccagaagat tgagtggcat    1320

gaacatcacc accaccacca t                                               1341


<210> SEQ ID NO 147
<211> LENGTH: 448
<212> TYPE: PRT
<213> ORGANISM: Homo sapiens

<400> SEQUENCE: 147

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80
```

```
Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asn Asn Ser Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Gly Ser Gly Leu Asn Asp Ile
            420                 425                 430

Phe Glu Ala Gln Lys Ile Glu Trp His Glu His His His His His His
        435                 440                 445
```

<210> SEQ ID NO 148
<211> LENGTH: 1344
<212> TYPE: DNA
<213> ORGANISM: Homo sapiens

<400> SEQUENCE: 148
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240
tttggcggca gcgagaacgc caccaatctg tttctgctgg aactcctagg cgccggcgag 300
ctggccctga ccatgagaag caagaaactg cccatcaatg tgaccacagg cgaggaacag 360
caggtgtccc tggaaagcgt ggacgtgtac tttcaagacg tgttcggcac catgtggtgc 420
caccacgccg agatgcagaa ccccgtgtac ctgatccccg agacagtgcc ctacatcaag 480
tggaacaaca gctgcaacag caccaacatc accgccgtcg tgcgggccca gggactggat 540
gtgacactgc ctctgagcct gcctaccagc gcccaggaca gcaacttcag cgtgaaaacc 600
gagatgctgg gcaacgagat cgacatcgag tgcatcatgg aagatggcga gatcagccag 660
gtgctgcccg gcgacaacaa gttcaacatc acatgcagcg gctacgagag ccacgtgcca 720
tctggcggca tcctgaccag cacaagccca gtggccacac ccatccctgg cacaggctac 780
gcctacagcc tgagactgac ccccagaccc gtgtccagat tcctgggcaa caacagcatc 840
ctgtacgtgt tctacagcgg caacggcccc aaggcctctg gcggcgatta ctgtatccag 900
agcaacatcg tgttcagcga cgagatcccc gccagccagg acatgcccac caataccacc 960
gacatcacgt acgtgggcga caatgccacc tacagcgtgc caatggtcac ctccgaggac 1020
gccaacagcc ccaacgtgac cgtgacagcc ttttgggcct ggcctaacaa caccgagaca 1080
gacttcaagt gcaagtggac cctgacctcc ggcaccccta gcggctgcga gaatatcagc 1140
ggagccttcg ccagcaaccg gaccttcgat atcaccgtgt ctggcctggg caccgccccc 1200
aagaccctga tcatcaccag aaccgccaca aatgccacca ccacaaccca caaagtgatc 1260
ttcagcaagg cccccggctc tggcctgaac gacatttttg aggcccagaa gattgagtgg 1320
catgaacatc accaccacca ccat 1344

<210> SEQ ID NO 149
<211> LENGTH: 447
<212> TYPE: PRT
<213> ORGANISM: Homo sapiens

<400> SEQUENCE: 149

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

```
Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser Gly Leu Asn Asp Ile Phe
            420                 425                 430

Glu Ala Gln Lys Ile Glu Trp His Glu His His His His His His
        435                 440                 445
```

<210> SEQ ID NO 150
<211> LENGTH: 1341
<212> TYPE: DNA
<213> ORGANISM: Homo sapiens

<400> SEQUENCE: 150

```
gaagctgccc tgctcgtgtg ccagtacacc atccagagcc tgatccacct gaccggcgag      60

gaccccggct tcttcaacgt ggaaatcccc gagttcccct tctaccctac ctgcaacgtg     120

tgcaccgccg acgtgaacgt gaccatcaac ttcgacgtgg gcggcaagaa gcaccagctg     180

gacctggatt tcggccagct gacccctcac accaaggccg tgtatcagcc cagaggcgcc     240
```

```
tttggcggca gcgagaacgc caccaatctg tttctgctgg aactcctagg cgccggcgag    300

ctggccctga ccatgagaag caagaaactg cccatcaatg tgaccacagg cgaggaacag    360

caggtgtccc tggaaagcgt ggacgtgtac tttcaagacg tgttcggcac catgtggtgc    420

caccacgccg agatgcagaa ccccgtgtac ctgatccccg agacagtgcc ctacatcaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gccggtactg tatccagagc    900

aacatcgtgt tcagcgacga gatccccgcc agccaggaca tgcccaccaa taccaccgac    960

atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc accccctagcg gctgcgagaa tatcagcgga   1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctctgg cctgaacgac atttttgagg cccagaagat tgagtggcat   1320

gaacatcacc accaccacca t                                             1341
```

<210> SEQ ID NO 151
<211> LENGTH: 447
<212> TYPE: PRT
<213> ORGANISM: Homo sapiens

<400> SEQUENCE: 151

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Ala Ala Ala Cys Asn Ser Thr Asn Ile Thr Ala Val Val Arg Ala Gln
                165                 170                 175
```

Gly Leu Asp Val Thr Leu Pro Leu Ser Leu Pro Thr Ser Ala Gln Asp
180 185 190

Ser Asn Phe Ser Val Lys Thr Glu Met Leu Gly Asn Glu Ile Asp Ile
195 200 205

Glu Cys Ile Met Glu Asp Gly Glu Ile Ser Gln Val Leu Pro Gly Asp
210 215 220

Asn Lys Phe Asn Ile Thr Cys Ser Gly Tyr Glu Ser His Val Pro Ser
225 230 235 240

Gly Gly Ile Leu Thr Ser Thr Ser Pro Val Ala Thr Pro Ile Pro Gly
245 250 255

Thr Gly Tyr Ala Tyr Ser Leu Arg Leu Thr Pro Arg Pro Val Ser Arg
260 265 270

Phe Leu Gly Asn Asn Ser Ile Leu Tyr Val Phe Tyr Ser Gly Asn Gly
275 280 285

Pro Lys Ala Ser Gly Gly Asp Tyr Cys Ile Gln Ser Asn Ile Val Phe
290 295 300

Ser Asp Glu Ile Pro Ala Ser Gln Asp Met Pro Thr Asn Thr Thr Asp
305 310 315 320

Ile Thr Tyr Val Gly Asp Asn Ala Thr Tyr Ser Val Pro Met Val Thr
325 330 335

Ser Glu Asp Ala Asn Ser Pro Asn Val Thr Val Thr Ala Phe Trp Ala
340 345 350

Trp Pro Asn Asn Thr Glu Thr Asp Phe Lys Cys Lys Trp Thr Leu Thr
355 360 365

Ser Gly Thr Pro Ser Gly Cys Glu Asn Ile Ser Gly Ala Phe Ala Ser
370 375 380

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His
405 410 415

Lys Val Ile Phe Ser Lys Ala Pro Gly Ser Gly Leu Asn Asp Ile Phe
420 425 430

Glu Ala Gln Lys Ile Glu Trp His Glu His His His His His His
435 440 445

<210> SEQ ID NO 152
<211> LENGTH: 1341
<212> TYPE: DNA
<213> ORGANISM: Homo sapiens

<400> SEQUENCE: 152
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240
tttggcggca gcgagaacgc caccaatctg tttctgctgg aactcctagg cgccggcgag 300
ctggccctga ccatgagaag caagaaactg cccatcaatg tgaccacagg cgaggaacag 360
caggtgtccc tggaaagcgt ggacgtgtac tttcaagacg tgttcggcac catgtggtgc 420
caccacgccg agatgcagaa ccccgtgtac ctgatccccg agacagtgcc ctacatcaag 480
gccgccgcct gcaacagcac caacatcacc gccgtcgtgc gggcccaggg actggatgtg 540
acactgcctc tgagcctgcc taccagcgcc caggacagca acttcagcgt gaaaaccgag 600

```
atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gcgattactg tatccagagc    900

aacatcgtgt tcagcgacga gatccccgcc agccaggaca tgcccaccaa taccaccgac    960

atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc acccctagcg gctgcgagaa tatcagcgga   1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctctgg cctgaacgac atttttgagg cccagaagat tgagtggcat   1320

gaacatcacc accaccacca t                                              1341


<210> SEQ ID NO 153
<211> LENGTH: 447
<212> TYPE: PRT
<213> ORGANISM: Homo sapiens

<400> SEQUENCE: 153

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Arg Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240
```

```
Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser Gly Leu Asn Asp Ile Phe
            420                 425                 430

Glu Ala Gln Lys Ile Glu Trp His Glu His His His His His His
        435                 440                 445
```

<210> SEQ ID NO 154
<211> LENGTH: 1341
<212> TYPE: DNA
<213> ORGANISM: Homo sapiens

<400> SEQUENCE: 154

```
gaagctgccc tgctcgtgtg ccagtacacc atccagagcc tgatccacct gaccggcgag     60

gaccccggct tcttcaacgt ggaaatcccc gagttcccct tctaccctac ctgcaacgtg    120

tgcaccgccg acgtgaacgt gaccatcaac ttcgacgtgg gcggcaagaa gcaccagctg    180

gacctggatt tcggccagct gacccctcac accaaggccg tgtatcagcc cagaggcgcc    240

tttggcggca gcgagaacgc caccaatctg tttctgctgg aactcctagg cgccggcgag    300

ctggccctga ccatgagaag caagaaactg cccatcaatg tgaccacagg cgaggaacag    360

caggtgtccc tggaaagcgt ggacgtgtac tttcaagacg tgttcggcac catgtggtgc    420

caccacgccg agatgcagaa ccccgtgtac ctgatccccg agacagtgcc ctaccggaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gccggtactg tatccagagc    900

aacatcgtgt tcagcgacga gatccccgcc agccaggaca tgcccaccaa taccaccgac    960
```

atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc acccctagcg gctgcgagaa tatcagcgga 1140
gccttcgcca gcaaccggac cttcgatatc accgtgtctg gcctgggcac cgcccccaag 1200
accctgatca tcaccagaac cgccacaaat gccaccacca caacccacaa agtgatcttc 1260
agcaaggccc ccggctctgg cctgaacgac atttttgagg cccagaagat tgagtggcat 1320
gaacatcacc accaccacca t 1341

<210> SEQ ID NO 155
<211> LENGTH: 447
<212> TYPE: PRT
<213> ORGANISM: Homo sapiens

<400> SEQUENCE: 155

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Arg Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

```
Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Gly Ser Gly Leu Asn Asp Ile Phe
            420                 425                 430

Glu Ala Gln Lys Ile Glu Trp His Glu His His His His His His
        435                 440                 445
```

<210> SEQ ID NO 156
<211> LENGTH: 1341
<212> TYPE: DNA
<213> ORGANISM: Homo sapiens

<400> SEQUENCE: 156

```
gaagctgccc tgctcgtgtg ccagtacacc atccagagcc tgatccacct gaccggcgag      60

gaccccggct tcttcaacgt ggaaatcccc gagttcccct tctaccctac ctgcaacgtg     120

tgcaccgccg acgtgaacgt gaccatcaac ttcgacgtgg gcggcaagaa gcaccagctg     180

gacctggatt tcggccagct gacccctcac accaaggccg tgtatcagcc cagaggcgcc     240

tttggcggca gcgagaacgc caccaatctg tttctgctgg aactcctagg cgccggcgag     300

ctggccctga ccatgagaag caagaaactg cccatcaatg tgaccacagg cgaggaacag     360

caggtgtccc tggaaagcgt ggacgtgtac tttcaagacg tgttcggcac catgtggtgc     420

caccacgccg agatgcagaa ccccgtgtac ctgatccccg agacagtgcg gtacatcaag     480

tgggacaact gcaacagcac caacatcacc gccgtcgtgc gggcccaggg actggatgtg     540

acactgcctc tgagcctgcc taccagcgcc caggacagca acttcagcgt gaaaaccgag     600

atgctgggca acgagatcga catcgagtgc atcatggaag atggcgagat cagccaggtg     660

ctgcccggcg acaacaagtt caacatcaca tgcagcggct acgagagcca cgtgccatct     720

ggcggcatcc tgaccagcac aagcccagtg gccacaccca tccctggcac aggctacgcc     780

tacagcctga gactgacccc cagacccgtg tccagattcc tgggcaacaa cagcatcctg     840

tacgtgttct acagcggcaa cggccccaag gcctctggcg gccggtactg tatccagagc     900

aacatcgtgt tcagcgacga gatccccgcc agccaggaca tgcccaccaa taccaccgac     960

atcacgtacg tgggcgacaa tgccacctac agcgtgccaa tggtcacctc cgaggacgcc    1020

aacagcccca acgtgaccgt gacagccttt tgggcctggc ctaacaacac cgagacagac    1080

ttcaagtgca agtggaccct gacctccggc accccctagcg gctgcgagaa tatcagcgga   1140

gccttcgcca gcaaccggac cttcgatatc accgtgtctg gcctgggcac cgcccccaag    1200
```

accctgatca tcaccagaac cgccacaaat gccaccacca caacccacaa agtgatcttc 1260
agcaaggccc ccggctctgg cctgaacgac atttttgagg cccagaagat tgagtggcat 1320
gaacatcacc accaccacca t 1341

<210> SEQ ID NO 157
<211> LENGTH: 447
<212> TYPE: PRT
<213> ORGANISM: Homo sapiens

<400> SEQUENCE: 157

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

Gly Gln Leu Thr Pro His Thr Lys Ala Val Tyr Gln Pro Arg Gly Ala
65 70 75 80

Phe Gly Gly Ser Glu Asn Ala Thr Asn Leu Phe Leu Leu Glu Leu Leu
85 90 95

Gly Ala Gly Glu Leu Ala Leu Thr Met Arg Ser Lys Lys Leu Pro Ile
100 105 110

Asn Val Thr Thr Gly Glu Glu Gln Gln Val Ser Leu Glu Ser Val Asp
115 120 125

Val Tyr Phe Gln Asp Val Phe Gly Thr Met Trp Cys His His Ala Glu
130 135 140

Met Gln Asn Pro Val Tyr Leu Ile Pro Glu Thr Val Asn Tyr Thr Lys
145 150 155 160

Trp Asp Asn Cys Asn Ser Thr Asn Ile Thr Ala Val Val Arg Ala Gln
165 170 175

Gly Leu Asp Val Thr Leu Pro Leu Ser Leu Pro Thr Ser Ala Gln Asp
180 185 190

Ser Asn Phe Ser Val Lys Thr Glu Met Leu Gly Asn Glu Ile Asp Ile
195 200 205

Glu Cys Ile Met Glu Asp Gly Glu Ile Ser Gln Val Leu Pro Gly Asp
210 215 220

Asn Lys Phe Asn Ile Thr Cys Ser Gly Tyr Glu Ser His Val Pro Ser
225 230 235 240

Gly Gly Ile Leu Thr Ser Thr Ser Pro Val Ala Thr Pro Ile Pro Gly
245 250 255

Thr Gly Tyr Ala Tyr Ser Leu Arg Leu Thr Pro Arg Pro Val Ser Arg
260 265 270

Phe Leu Gly Asn Asn Ser Ile Leu Tyr Val Phe Tyr Ser Gly Asn Gly
275 280 285

Pro Lys Ala Ser Gly Gly Arg Tyr Cys Ile Gln Ser Asn Ile Val Phe
290 295 300

Ser Asp Glu Ile Pro Ala Ser Gln Asp Met Pro Thr Asn Thr Thr Asp
305 310 315 320

Ile Thr Tyr Val Gly Asp Asn Ala Thr Tyr Ser Val Pro Met Val Thr
325 330 335

-continued

Ser Glu Asp Ala Asn Ser Pro Asn Val Thr Val Thr Ala Phe Trp Ala
340 345 350

Trp Pro Asn Asn Thr Glu Thr Asp Phe Lys Cys Lys Trp Thr Leu Thr
355 360 365

Ser Gly Thr Pro Ser Gly Cys Glu Asn Ile Ser Gly Ala Phe Ala Ser
370 375 380

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His
405 410 415

Lys Val Ile Phe Ser Lys Ala Pro Gly Ser Gly Leu Asn Asp Ile Phe
420 425 430

Glu Ala Gln Lys Ile Glu Trp His Glu His His His His His His
435 440 445

<210> SEQ ID NO 158
<211> LENGTH: 1341
<212> TYPE: DNA
<213> ORGANISM: Homo sapiens

<400> SEQUENCE: 158
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240
tttggcggca gcgagaacgc caccaatctg tttctgctgg aactcctagg cgccggcgag 300
ctggccctga ccatgagaag caagaaactg cccatcaatg tgaccacagg cgaggaacag 360
caggtgtccc tggaaagcgt ggacgtgtac tttcaagacg tgttcggcac catgtggtgc 420
caccacgccg agatgcagaa ccccgtgtac ctgatccccg agacagtgaa ctacaccaag 480
tgggacaact gcaacagcac caacatcacc gccgtcgtgc gggcccaggg actggatgtg 540
acactgcctc tgagcctgcc taccagcgcc caggacagca acttcagcgt gaaaaccgag 600
atgctgggca acgagatcga catcgagtgc atcatggaag atggcgagat cagccaggtg 660
ctgcccggcg acaacaagtt caacatcaca tgcagcggct acgagagcca cgtgccatct 720
ggcggcatcc tgaccagcac aagcccagtg gccacaccca tccctggcac aggctacgcc 780
tacagcctga gactgacccc cagacccgtg tccagattcc tgggcaacaa cagcatcctg 840
tacgtgttct acagcggcaa cggccccaag gcctctggcg gccggtactg tatccagagc 900
aacatcgtgt tcagcgacga gatccccgcc agccaggaca tgcccaccaa taccaccgac 960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc accccctagcg gctgcgagaa tatcagcgga 1140
gccttcgcca gcaaccggac cttcgatatc accgtgtctg gcctgggcac cgccccccaag 1200 accctgatca tcaccagaac cgccacaaat gccaccacca caacccacaa agtgatcttc 1260
agcaaggccc ccggctctgg cctgaacgac atttttgagg cccagaagat tgagtggcat 1320
gaacatcacc accaccacca t 1341

<210> SEQ ID NO 159
<211> LENGTH: 447

<212> TYPE: PRT
<213> ORGANISM: Homo sapiens

<400> SEQUENCE: 159

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Arg Tyr Arg Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400
```

```
Thr Leu Ile Ile Thr Arg Thr Ala Thr Asn Ala Thr Thr Thr Thr His
                405                 410                 415

Lys Val Ile Phe Ser Lys Ala Pro Gly Ser Gly Leu Asn Asp Ile Phe
            420                 425                 430

Glu Ala Gln Lys Ile Glu Trp His Glu His His His His His His
        435                 440                 445


<210> SEQ ID NO 160
<211> LENGTH: 1341
<212> TYPE: DNA
<213> ORGANISM: Homo sapiens

<400> SEQUENCE: 160

gaagctgccc tgctcgtgtg ccagtacacc atccagagcc tgatccacct gaccggcgag     60

gaccccggct tcttcaacgt ggaaatcccc gagttcccct tctaccctac ctgcaacgtg    120

tgcaccgccg acgtgaacgt gaccatcaac ttcgacgtgg gcggcaagaa gcaccagctg    180

gacctggatt tcggccagct gacccctcac accaaggccg tgtatcagcc cagaggcgcc    240

tttggcggca gcgagaacgc caccaatctg tttctgctgg aactcctagg cgccggcgag    300

ctggccctga ccatgagaag caagaaactg cccatcaatg tgaccacagg cgaggaacag    360

caggtgtccc tggaaagcgt ggacgtgtac tttcaagacg tgttcggcac catgtggtgc    420

caccacgccg agatgcagaa ccccgtgtac ctgatccccg agacagtgcg gtaccggaag    480

tgggacaact gcaacagcac caacatcacc gccgtcgtgc gggcccaggg actggatgtg    540

acactgcctc tgagcctgcc taccagcgcc caggacagca acttcagcgt gaaaaccgag    600

atgctgggca acgagatcga catcgagtgc atcatggaag atggcgagat cagccaggtg    660

ctgcccggcg acaacaagtt caacatcaca tgcagcggct acgagagcca cgtgccatct    720

ggcggcatcc tgaccagcac aagcccagtg gccacaccca tccctggcac aggctacgcc    780

tacagcctga gactgacccc cagacccgtg tccagattcc tgggcaacaa cagcatcctg    840

tacgtgttct acagcggcaa cggccccaag gcctctggcg gccggtactg tatccagagc    900

aacatcgtgt tcagcgacga gatccccgcc agccaggaca tgcccaccaa taccaccgac    960

atcacgtacg tgggcgacaa tgccacctac agcgtgccaa tggtcacctc cgaggacgcc   1020

aacagcccca acgtgaccgt gacagccttt tgggcctggc ctaacaacac cgagacagac   1080

ttcaagtgca agtggaccct gacctccggc acccctagcg gctgcgagaa tatcagcgga   1140

gccttcgcca gcaaccggac cttcgatatc accgtgtctg gcctgggcac cgcccccaag   1200

accctgatca tcaccagaac cgccacaaat gccaccacca caacccacaa agtgatcttc   1260

agcaaggccc ccggctctgg cctgaacgac atttttgagg cccagaagat tgagtggcat   1320

gaacatcacc accaccacca t                                              1341


<210> SEQ ID NO 161
<211> LENGTH: 119
<212> TYPE: PRT
<213> ORGANISM: Homo sapiens

<400> SEQUENCE: 161

Gln Val Gln Leu Val Gln Ser Gly Ala Asp Val Arg Lys Pro Gly Ala
1               5                   10                  15

Ser Val Lys Val Ser Cys Lys Ala Ser Thr Tyr Ile Phe Thr Gly Tyr
            20                  25                  30
```

```
Tyr Ile His Trp Val Arg Gln Ala Pro Gly Arg Gly Leu Glu Trp Leu
        35                  40                  45

Gly Trp Ile His Pro Asn Ser Gly Gly Thr Thr Tyr Ser Gln Met Phe
    50                  55                  60

Gln Gly Arg Val Thr Met Thr Arg Asp Arg Ser Ile Thr Thr Ser Tyr
65                  70                  75                  80

Met Glu Leu Ser Arg Leu Gln Ser Asp Asp Thr Ala Ile Tyr Tyr Cys
                85                  90                  95

Ala Thr Leu Arg Phe Val Glu Tyr Ser Phe Asp Ser Trp Gly Gln Gly
            100                 105                 110

Thr Leu Val Thr Val Ser Ser
        115


<210> SEQ ID NO 162
<211> LENGTH: 357
<212> TYPE: DNA
<213> ORGANISM: Homo sapiens

<400> SEQUENCE: 162

caggtgcagc tggtgcagtc tggcgcagac gtgaggaagc caggagcctc cgtgaaggtg      60

tcttgtaagg ccagcaccta catcttcaca ggctactata tccactgggt gaggcaggca     120

ccaggaaggg gcctggagtg gctgggctgg attcacccta actctggcgg caccacatac     180

agccagatgt ttcagggcag agtgaccatg acacgggaca gatccatcac cacatcttat     240

atggagctga gccggctgca gtccgacgat accgccatct actattgcgc cacactgaga     300

ttcgtggagt attcttttga tagctggggc cagggcaccc tggtgacagt gagctcc        357


<210> SEQ ID NO 163
<211> LENGTH: 7
<212> TYPE: PRT
<213> ORGANISM: Homo sapiens

<400> SEQUENCE: 163

Thr Tyr Ile Phe Thr Gly Tyr
1               5


<210> SEQ ID NO 164
<211> LENGTH: 6
<212> TYPE: PRT
<213> ORGANISM: Homo sapiens

<400> SEQUENCE: 164

His Pro Asn Ser Gly Gly
1               5


<210> SEQ ID NO 165
<211> LENGTH: 10
<212> TYPE: PRT
<213> ORGANISM: Homo sapiens

<400> SEQUENCE: 165

Leu Arg Phe Val Glu Tyr Ser Phe Asp Ser
1               5                   10


<210> SEQ ID NO 166
<211> LENGTH: 108
<212> TYPE: PRT
<213> ORGANISM: Homo sapiens
```

<400> SEQUENCE: 166

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Ile Ser Ser Thr
20 25 30

Tyr Leu Ala Trp Tyr Gln Gln Ile Pro Gly Gln Ala Pro Arg Leu Leu
35 40 45

Ile Tyr Gly Ala Ser Ser Arg Ala Ala Gly Ile Pro Asp Arg Phe Ser
50 55 60

Gly Gly Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Arg Ser Phe Gly Gln Gly Thr Lys Leu Glu Ile Lys
100 105

<210> SEQ ID NO 167
<211> LENGTH: 324
<212> TYPE: DNA
<213> ORGANISM: Homo sapiens

<400> SEQUENCE: 167
gagatcgtgc tgacccagag cccaggcaca ctgagcctgt ccccaggaga gagggccacc 60
ctgtcctgta gagcctctca gagcatcagc tccacatacc tggcctggta tcagcagatc 120
ccaggacagg cacctaggct gctgatctac ggagcctcta gcagggcagc aggcatcccc 180
gaccgcttct ccggcggagg ctctggcacc gacttcaccc tgacaatctc tcggctggag 240
cctgaggact tcgccgtgta ctattgccag cagtatggct cctctccaag gtcctttggc 300
cagggcacaa agctggagat caag 324

<210> SEQ ID NO 168
<211> LENGTH: 12
<212> TYPE: PRT
<213> ORGANISM: Homo sapiens

<400> SEQUENCE: 168

Arg Ala Ser Gln Ser Ile Ser Ser Thr Tyr Leu Ala
1 5 10

<210> SEQ ID NO 169
<211> LENGTH: 7
<212> TYPE: PRT
<213> ORGANISM: Homo sapiens

<400> SEQUENCE: 169

Gly Ala Ser Ser Arg Ala Ala
1 5

<210> SEQ ID NO 170
<211> LENGTH: 9
<212> TYPE: PRT
<213> ORGANISM: Homo sapiens

<400> SEQUENCE: 170

Gln Gln Tyr Gly Ser Ser Pro Arg Ser
1 5

<210> SEQ ID NO 171

<211> LENGTH: 119
<212> TYPE: PRT
<213> ORGANISM: Homo sapiens

<400> SEQUENCE: 171

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Lys Thr Tyr
            20                  25                  30

Ala Met Ser Trp Val Arg Gln Val Pro Gly Lys Gly Leu Glu Trp Val
        35                  40                  45

Ser Ala Ile Ser Gly Ser Gly Thr Ala Ser Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Leu Ser Ser Leu Arg Asp Glu Asp Thr Gly Val Tyr Tyr Cys
                85                  90                  95

Ala Arg Arg Phe Leu Asp Trp Phe Gly Met Asp Val Trp Gly Leu Gly
            100                 105                 110

Thr Thr Val Thr Val Ser Ser
        115

<210> SEQ ID NO 172
<211> LENGTH: 357
<212> TYPE: DNA
<213> ORGANISM: Homo sapiens

<400> SEQUENCE: 172
gaggtgcagc tgctggagag cggcggcgcc ctggtgcagc caggaggcag cctgcggctg 60
tcctgtgccg cctctggctt cacctttaag acatacgcca tgtcctgggt gaggcaggtg 120
cctggcaagg gcctggagtg ggtgtctgcc atctccggct ctggcaccgc ctcttactat 180
gccgacagcg tgaagggcag gttcaccctg agccgcgata actccaagaa tacactgtat 240
ctgcagctga gctccctgcg ggacgaggat accggcgtgt actattgcgc ccggagattc 300
ctggactggt ttggcatgga cgtgtggggc ctgggcacca cagtgacagt gtctagc 357

<210> SEQ ID NO 173
<211> LENGTH: 7
<212> TYPE: PRT
<213> ORGANISM: Homo sapiens

<400> SEQUENCE: 173

Gly Phe Thr Phe Lys Thr Tyr
1               5

<210> SEQ ID NO 174
<211> LENGTH: 6
<212> TYPE: PRT
<213> ORGANISM: Homo sapiens

<400> SEQUENCE: 174

Ser Gly Ser Gly Thr Ala
1               5

<210> SEQ ID NO 175
<211> LENGTH: 10
<212> TYPE: PRT
<213> ORGANISM: Homo sapiens

<400> SEQUENCE: 175

Arg Phe Leu Asp Trp Phe Gly Met Asp Val
1 5 10

<210> SEQ ID NO 176
<211> LENGTH: 111
<212> TYPE: PRT
<213> ORGANISM: Homo sapiens

<400> SEQUENCE: 176

Asp Ile Val Met Thr Gln Ser Pro Leu Ser Leu Pro Val Thr Pro Gly
1 5 10 15

Glu Pro Ala Ser Ile Ser Cys Leu Ser Ser Gln Ser Leu Leu Gln Ser
20 25 30

Asn Gly Tyr Asn Tyr Val Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Val Thr
85 90 95

Leu His Pro Pro Thr Phe Gly Gln Gly Ala Lys Val Glu Ile Lys
100 105 110

<210> SEQ ID NO 177
<211> LENGTH: 333
<212> TYPE: DNA
<213> ORGANISM: Homo sapiens

<400> SEQUENCE: 177
gacatcgtga tgacccagtc ccctctgtct ctgccagtga cacccggcga gcctgcctct 60
atcagctgtc tgagctccca gagcctgctg cagtccaacg gctacaatta tgtggattgg 120
tacctgcaga agccaggcca gtccccccag ctgctgatct atctgggctc taacagggcc 180
agcggcgtgc ccgacagatt ctccggctct ggcagcggca ccgacttcac cctgaagatc 240
tctcgggtgg aggcagagga cgtgggcgtg tactattgca tggtgaccct gcacccacct 300
acattcggcc agggagccaa ggtggagatc aag 333

<210> SEQ ID NO 178
<211> LENGTH: 16
<212> TYPE: PRT
<213> ORGANISM: Homo sapiens

<400> SEQUENCE: 178

Leu Ser Ser Gln Ser Leu Leu Gln Ser Asn Gly Tyr Asn Tyr Val Asp
1 5 10 15

<210> SEQ ID NO 179
<211> LENGTH: 7
<212> TYPE: PRT
<213> ORGANISM: Homo sapiens

<400> SEQUENCE: 179

Leu Gly Ser Asn Arg Ala Ser
1 5

<210> SEQ ID NO 180

<211> LENGTH: 8
<212> TYPE: PRT
<213> ORGANISM: Homo sapiens

<400> SEQUENCE: 180

Met Val Thr Leu His Pro Pro Thr
1 5

<210> SEQ ID NO 181
<211> LENGTH: 120
<212> TYPE: PRT
<213> ORGANISM: Homo sapiens

<400> SEQUENCE: 181

Glu Gly Gln Leu Val Gln Ser Gly Gly Gly Leu Val Gln Pro Gly Gly
1 5 10 15

Ser Leu Thr Leu Ser Cys Glu Val Ser Gly Phe Thr Phe Lys Asn Tyr
20 25 30

Glu Met Asn Trp Val Arg Gln Ala Pro Gly Lys Gly Leu Glu Trp Val
35 40 45

Ser Tyr Ile Ser Ser Gly Gly Ile Ala Ile Phe His Ala Asp Ser Val
50 55 60

Lys Gly Arg Phe Thr Val Ser Arg Asp Asn Ala Lys Asn Leu Leu Tyr
65 70 75 80

Leu Gln Met Asn Ser Leu Arg Val Glu Asp Thr Ala Val Tyr Tyr Cys
85 90 95

Ala Arg Asp Glu Asn Asn Val Arg Arg Pro Phe Asp His Trp Gly Gln
100 105 110

Gly Thr Leu Val Thr Val Ser Ser
115 120

<210> SEQ ID NO 182
<211> LENGTH: 360
<212> TYPE: DNA
<213> ORGANISM: Homo sapiens

<400> SEQUENCE: 182
gagggacagc tggtgcagtc cggcggaggc ctggtgcagc caggaggctc cctgaccctg 60
tcttgtgagg tgagcggctt caccttcaag aactacgaga tgaattgggt gcggcaggca 120
cctggcaagg gcctggagtg ggtgtcttat atcagctccg gcggaatcgc aatcttccac 180
gcagattccg tgaagggcag gtttaccgtg tctcgcgaca acgccaagaa tctgctgtac 240
ctgcagatga acagcctgcg ggtggaggac acagccgtgt actattgcgc cagggatgag 300
aacaacgtgc ggcggccctt cgaccactgg ggacagggca ccctggtgac agtgtctagc 360

<210> SEQ ID NO 183
<211> LENGTH: 7
<212> TYPE: PRT
<213> ORGANISM: Homo sapiens

<400> SEQUENCE: 183

Gly Phe Thr Phe Lys Asn Tyr
1 5

<210> SEQ ID NO 184
<211> LENGTH: 6
<212> TYPE: PRT
<213> ORGANISM: Homo sapiens

<400> SEQUENCE: 184

Ser Ser Gly Gly Ile Ala
1 5

<210> SEQ ID NO 185
<211> LENGTH: 11
<212> TYPE: PRT
<213> ORGANISM: Homo sapiens

<400> SEQUENCE: 185

Asp Glu Asn Asn Val Arg Arg Pro Phe Asp His
1 5 10

<210> SEQ ID NO 186
<211> LENGTH: 109
<212> TYPE: PRT
<213> ORGANISM: Homo sapiens

<400> SEQUENCE: 186

Gln Ser Val Leu Thr Gln Pro Pro Ser Ala Ser Gly Ser Pro Gly Gln
1 5 10 15

Ser Val Thr Ile Ser Cys Thr Gly Ser Ser Ser Asp Val Gly Ala Tyr
20 25 30

Asp Phe Val Ser Trp Phe Gln Gln Tyr Pro Gly Gln Ala Pro Lys Leu
35 40 45

Ile Ile Tyr Glu Val Asn Lys Arg Pro Ser Gly Val Pro Ala Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Phe Cys Phe Ser Tyr Gly Gly Thr
85 90 95

Thr Asn Leu Arg Val Phe Gly Gly Gly Thr Lys Leu Thr
100 105

<210> SEQ ID NO 187
<211> LENGTH: 327
<212> TYPE: DNA
<213> ORGANISM: Homo sapiens

<400> SEQUENCE: 187
cagtctgtgc tgacccagcc acctagcgcc tccggctctc ccggccagag cgtgaccatc 60
tcctgtacag gcagctcctc tgacgtgggc gcctacgatt tcgtgagctg gtttcagcag 120
tatccaggcc aggcccccaa gctgatcatc tacgaggtga acaagcggcc ttccggcgtg 180
ccagccagat tcagcggctc caagtctggc aataccgcct ctctgacagt gagcggcctg 240
caggcagagg acgaggcaga ttacttctgc ttttcttatg gcggcaccac aaacctgcgg 300
gtgtttggcg gcggcaccaa gctgaca 327

<210> SEQ ID NO 188
<211> LENGTH: 14
<212> TYPE: PRT
<213> ORGANISM: Homo sapiens

<400> SEQUENCE: 188

Thr Gly Ser Ser Ser Asp Val Gly Ala Tyr Asp Phe Val Ser
1 5 10

<210> SEQ ID NO 189

<211> LENGTH: 7
<212> TYPE: PRT
<213> ORGANISM: Homo sapiens

<400> SEQUENCE: 189

Glu Val Asn Lys Arg Pro Ser
1               5

<210> SEQ ID NO 190
<211> LENGTH: 11
<212> TYPE: PRT
<213> ORGANISM: Homo sapiens

<400> SEQUENCE: 190

Phe Ser Tyr Gly Gly Thr Thr Asn Leu Arg Val
1               5                   10

<210> SEQ ID NO 191
<211> LENGTH: 122
<212> TYPE: PRT
<213> ORGANISM: Homo sapiens

<400> SEQUENCE: 191

Glu Val Gln Leu Val Glu Ser Gly Gly Asn Leu Val Gln Pro Gly Ala
1               5                   10                  15

Ser Leu Arg Leu Ser Cys Thr Ala Ser Arg Phe Asn Phe Asn Lys Tyr
            20                  25                  30

Ala Met His Trp Val Arg Gln Thr Pro Gly Lys Gly Leu Glu Trp Val
        35                  40                  45

Ser Ala Ile Ser Trp Asp Ser Thr Tyr Ile Asp Tyr Gly Asn Ser Val
    50                  55                  60

Lys Gly Arg Phe Thr Ile Ser Arg Asp Asn Thr Arg Asn Ser Leu Tyr
65                  70                  75                  80

Leu Gln Met Asn Ser Leu Thr Ala Glu Asp Thr Ala Leu Tyr Tyr Cys
                85                  90                  95

Ala Lys Cys Glu Asp Tyr Leu Arg Leu Cys Ser Ala Tyr Asp Ile Trp
            100                 105                 110

Gly His Gly Thr Met Val Thr Val Ser Ser
        115                 120

<210> SEQ ID NO 192
<211> LENGTH: 366
<212> TYPE: DNA
<213> ORGANISM: Homo sapiens

<400> SEQUENCE: 192
gaggtgcagc tggtggagag cggcggaaac ctggtgcagc caggagcctc tctgaggctg 60
agctgtaccg cctcccgctt caactttaat aagtacgcaa tgcactgggt gcggcagacc 120
cctggcaagg gcctggagtg ggtgtctgcc atcagctggg actccacata catcgattat 180
ggcaactccg tgaagggcag gttcaccatc tctcgggaca acacaagaaa tagcctgtat 240
ctgcagatga attccctgac cgccgaggat acagccctgt actattgcgc caagtgtgag 300
gactacctgc ggctgtgctc tgcctatgat atctggggcc acggcaccat ggtgacagtg 360
agctcc 366

<210> SEQ ID NO 193
<211> LENGTH: 7
<212> TYPE: PRT
<213> ORGANISM: Homo sapiens

<400> SEQUENCE: 193

Arg Phe Asn Phe Asn Lys Tyr
1 5

<210> SEQ ID NO 194
<211> LENGTH: 6
<212> TYPE: PRT
<213> ORGANISM: Homo sapiens

<400> SEQUENCE: 194

Ser Trp Asp Ser Thr Tyr
1 5

<210> SEQ ID NO 195
<211> LENGTH: 13
<212> TYPE: PRT
<213> ORGANISM: Homo sapiens

<400> SEQUENCE: 195

Cys Glu Asp Tyr Leu Arg Leu Cys Ser Ala Tyr Asp Ile
1 5 10

<210> SEQ ID NO 196
<211> LENGTH: 112
<212> TYPE: PRT
<213> ORGANISM: Homo sapiens

<400> SEQUENCE: 196

Asp Ile Val Met Thr Gln Ser Pro Leu Ser Leu Pro Val Thr Pro Gly
1 5 10 15

Glu Ser Ala Ser Ile Ser Cys Arg Ser Ser Gln Ser Leu Leu His Ser
20 25 30

Asn Gly Lys Asn Tyr Leu Ser Trp Tyr Leu Gln Lys Pro Gly Gln Ser
35 40 45

Pro Gln Leu Leu Ile Asp Leu Gly Ser Asn Arg Ala Ser Gly Val Ser
50 55 60

Asp Arg Phe Ser Gly Ser Gly Ser Gly Thr Asp Phe Thr Leu Lys Ile
65 70 75 80

Ser Arg Val Glu Ala Asp Asp Val Gly Val Tyr Tyr Cys Met Gln Ala
85 90 95

Val Gln Thr Pro Ile Thr Phe Gly Gln Gly Thr Arg Leu Ala Ile Lys
100 105 110

<210> SEQ ID NO 197
<211> LENGTH: 336
<212> TYPE: DNA
<213> ORGANISM: Homo sapiens

<400> SEQUENCE: 197
gacatcgtga tgacccagtc tcctctgagc ctgcccgtga cacctggcga gtctgccagc 60
atctcctgtc ggagctccca gagcctgctg cactccaacg gcaagaatta cctgtcttgg 120
tatctgcaga agccaggcca gagcccccag ctgctgatcg atctgggctc caacagggcc 180
tccggcgtgt ctgacagatt ctctggcagc ggctccggca ccgacttcac cctgaagatc 240
agcagggtgg aggccgacga tgtgggcgtg tactattgca tgcaggccgt gcagacccca 300
atcacattcg gccagggaac ccgcctggcc atcaag 336

<210> SEQ ID NO 198

<211> LENGTH: 16
<212> TYPE: PRT
<213> ORGANISM: Homo sapiens

<400> SEQUENCE: 198

Arg Ser Ser Gln Ser Leu Leu His Ser Asn Gly Lys Asn Tyr Leu Ser
1               5                   10                  15

<210> SEQ ID NO 199
<211> LENGTH: 7
<212> TYPE: PRT
<213> ORGANISM: Homo sapiens

<400> SEQUENCE: 199

Leu Gly Ser Asn Arg Ala Ser
1               5

<210> SEQ ID NO 200
<211> LENGTH: 9
<212> TYPE: PRT
<213> ORGANISM: Homo sapiens

<400> SEQUENCE: 200

Met Gln Ala Val Gln Thr Pro Ile Thr
1               5

<210> SEQ ID NO 201
<211> LENGTH: 123
<212> TYPE: PRT
<213> ORGANISM: Homo sapiens

<400> SEQUENCE: 201

Gln Val Gln Leu Val Gln Ser Gly Ala Glu Leu Lys Thr Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Glu Gly Leu Glu Trp Thr
        35                  40                  45

Gly Trp Ile Asn Pro Asn Ser Gly Ala Thr Arg Tyr Gly Gln Lys Phe
    50                  55                  60

Gln Gly Arg Val Thr Leu Thr Ser Asp Thr Ser Ser Ser Thr Val Tyr
65                  70                  75                  80

Met Glu Val Ser Asn Leu Thr Ser Asp Asp Ser Ala Val Tyr Tyr Cys
                85                  90                  95

Ala Arg Glu Leu Ser Tyr Ser Ile Arg Gly Thr Gly Pro Leu Gly Tyr
            100                 105                 110

Trp Gly Leu Gly Thr Leu Val Thr Val Ser Ser
        115                 120

<210> SEQ ID NO 202
<211> LENGTH: 369
<212> TYPE: DNA
<213> ORGANISM: Homo sapiens

<400> SEQUENCE: 202
caggtgcagc tggtgcagtc cggcgcagag ctgaagaccc caggagccag cgtgaaggtg      60
tcctgtaagg cctctggcta caccttcaca ggctactata tccactgggt gcggcaggca     120
ccaggagagg gcctggagtg gaccggctgg atcaacccta atagcggcgc cacaagatac     180
ggccagaagt ttcagggccg cgtgaccctg acaagcgaca ccagctcctc tacagtgtat     240

-continued

```
atggaggtgt ccaacctgac ctccgacgat tctgccgtgt actattgcgc ccgggagctg    300

tcttacagca tcagaggaac aggaccactg ggatattggg gcctgggcac cctggtgaca    360

gtgagctcc                                                            369
```

<210> SEQ ID NO 203
<211> LENGTH: 7
<212> TYPE: PRT
<213> ORGANISM: Homo sapiens

<400> SEQUENCE: 203

```
Gly Tyr Thr Phe Thr Gly Tyr
1               5
```

<210> SEQ ID NO 204
<211> LENGTH: 6
<212> TYPE: PRT
<213> ORGANISM: Homo sapiens

<400> SEQUENCE: 204

```
Asn Pro Asn Ser Gly Ala
1               5
```

<210> SEQ ID NO 205
<211> LENGTH: 14
<212> TYPE: PRT
<213> ORGANISM: Homo sapiens

<400> SEQUENCE: 205

```
Glu Leu Ser Tyr Ser Ile Arg Gly Thr Gly Pro Leu Gly Tyr
1               5                   10
```

<210> SEQ ID NO 206
<211> LENGTH: 108
<212> TYPE: PRT
<213> ORGANISM: Homo sapiens

<400> SEQUENCE: 206

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Lys
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Tyr Tyr Gly Ser Ser Pro
                85                  90                  95

Leu Thr Phe Gly Gln Gly Thr Lys Val Glu Ile Lys
            100                 105
```

<210> SEQ ID NO 207
<211> LENGTH: 324
<212> TYPE: DNA
<213> ORGANISM: Homo sapiens

<400> SEQUENCE: 207

```
gagatcgtgc tgacccagtc tccaggcaca ctgtccctgt ctccaggaga gagggccacc     60

ctgtcttgta gagccagcca gtccgtggcc agcaagtacc tggcctggta tcagcagaag    120
```

```
ccaggacagg cacctaggct gctgatctac ggagccagct ccagggcaac cggcatcccc    180

gaccgcttct ctggcagcgg ctccggcaca gacttcaccc tgacaatctc caggctggag    240

cctgaggact tcgccgtgta ctattgccag tactatggct ctagcccact gacctttggc    300

cagggcacaa aggtggagat caag                                           324


<210> SEQ ID NO 208
<211> LENGTH: 12
<212> TYPE: PRT
<213> ORGANISM: Homo sapiens

<400> SEQUENCE: 208

Arg Ala Ser Gln Ser Val Ala Ser Lys Tyr Leu Ala
1               5                   10


<210> SEQ ID NO 209
<211> LENGTH: 7
<212> TYPE: PRT
<213> ORGANISM: Homo sapiens

<400> SEQUENCE: 209

Gly Ala Ser Ser Arg Ala Thr
1               5


<210> SEQ ID NO 210
<211> LENGTH: 9
<212> TYPE: PRT
<213> ORGANISM: Homo sapiens

<400> SEQUENCE: 210

Gln Tyr Tyr Gly Ser Ser Pro Leu Thr
1               5


<210> SEQ ID NO 211
<211> LENGTH: 123
<212> TYPE: PRT
<213> ORGANISM: Homo sapiens

<400> SEQUENCE: 211

Glu Val Gln Leu Ala Glu Ser Gly Gly Gly Val Val His Pro Gly Gly
1               5                   10                  15

Ser Leu Arg Leu Ser Cys Thr Ala Ser Gly Phe Thr Phe Ser Arg His
            20                  25                  30

Ser Met His Trp Val Arg Gln Ala Pro Gly Lys Gly Leu Glu Trp Val
        35                  40                  45

Ala Val Ile Ser His Asp Gly Ser His Lys Phe Tyr Val Asp Ser Val
    50                  55                  60

Lys Gly Arg Phe Ser Ile Ser Arg Asp Asn Ala Lys Asn Thr Leu Tyr
65                  70                  75                  80

Leu Gln Met Ser Ser Leu Ser Gly Ala Asp Thr Ala Val Tyr Tyr Cys
                85                  90                  95

Val Lys Asp Ile Ser Ser Arg Ser Tyr Gly Tyr Leu Ala Gly Asp Ser
            100                 105                 110

Trp Gly Gln Gly Ser Leu Val Thr Val Ser Ser
        115                 120


<210> SEQ ID NO 212
<211> LENGTH: 369
<212> TYPE: DNA
<213> ORGANISM: Homo sapiens
```

<400> SEQUENCE: 212

```
gaggtgcagc tggccgagtc tggcggagga gtggtgcacc caggaggctc cctgaggctg     60

tcttgtaccg ccagcggctt cacattttct aggcacagca tgcactgggt gcgccaggca    120

cctggcaagg gcctggagtg ggtggccgtg atctcccacg acggctctca caagttctac    180

gtggattccg tgaagggccg gtttagcatc tccagagaca acgccaagaa taccctgtat    240

ctgcagatga gctccctgtc tggcgccgac acagccgtgt actattgcgt gaaggatatc    300

tctagcagga gctacggcta tctggcaggc gatagctggg gacagggctc cctggtgacc    360

gtgtcctct                                                            369
```

<210> SEQ ID NO 213
<211> LENGTH: 7
<212> TYPE: PRT
<213> ORGANISM: Homo sapiens

<400> SEQUENCE: 213

```
Gly Phe Thr Phe Ser Arg His
1               5
```

<210> SEQ ID NO 214
<211> LENGTH: 6
<212> TYPE: PRT
<213> ORGANISM: Homo sapiens

<400> SEQUENCE: 214

```
Ser His Asp Gly Ser His
1               5
```

<210> SEQ ID NO 215
<211> LENGTH: 14
<212> TYPE: PRT
<213> ORGANISM: Homo sapiens

<400> SEQUENCE: 215

```
Asp Ile Ser Ser Arg Ser Tyr Gly Tyr Leu Ala Gly Asp Ser
1               5                   10
```

<210> SEQ ID NO 216
<211> LENGTH: 108
<212> TYPE: PRT
<213> ORGANISM: Homo sapiens

<400> SEQUENCE: 216

```
Asp Ile Gln Met Thr Gln Ser Pro Ser Ser Leu Ser Ala Ser Val Gly
1               5                   10                  15

Asp Ile Ile Thr Ile Thr Cys Arg Ala Ser Gln Ser Val Val Thr Tyr
            20                  25                  30

Leu Asn Trp Tyr Gln Gln Lys Pro Gly Gly Ala Pro Arg Leu Leu Ile
        35                  40                  45

Tyr Thr Thr Ser Lys Leu Gln Ser Gly Val Pro Ser Arg Phe Ser Gly
    50                  55                  60

Ser Gly Ser Gly Thr Leu Phe Thr Leu Thr Ile Asn Gly Leu Arg Pro
65                  70                  75                  80

Glu Asp Phe Ala Thr Tyr Tyr Cys Gln Gln Ser Tyr Gly Thr Pro Pro
                85                  90                  95

Phe Thr Phe Gly Pro Gly Thr Arg Val Glu Ile Asn
            100                 105
```

<210> SEQ ID NO 217
<211> LENGTH: 324
<212> TYPE: DNA
<213> ORGANISM: Homo sapiens

<400> SEQUENCE: 217
gatattcaga tgactcagtc cccaagcagc ctgagcgcct ccgtgggcga catcatcacc 60
atcacatgca gggcctctca gagcgtggtg acctacctga actggtatca gcagaagcca 120
ggaggagcac ctaggctgct gatctacacc acatccaagc tgcagtctgg cgtgccatcc 180
agattctccg gctctggcag cggcaccctg tttaccctga caatcaatgg cctgcggccc 240
gaggatttcg ccacatacta ttgtcagcag agctatggaa cccccccctt tacttttgga 300
ccaggcacaa gagtggagat taac 324

<210> SEQ ID NO 218
<211> LENGTH: 11
<212> TYPE: PRT
<213> ORGANISM: Homo sapiens

<400> SEQUENCE: 218

Arg Ala Ser Gln Ser Val Val Thr Tyr Leu Asn
1 5 10

<210> SEQ ID NO 219
<211> LENGTH: 7
<212> TYPE: PRT
<213> ORGANISM: Homo sapiens

<400> SEQUENCE: 219

Thr Thr Ser Lys Leu Gln Ser
1 5

<210> SEQ ID NO 220
<211> LENGTH: 10
<212> TYPE: PRT
<213> ORGANISM: Homo sapiens

<400> SEQUENCE: 220

Gln Gln Ser Tyr Gly Thr Pro Pro Phe Thr
1 5 10

<210> SEQ ID NO 221
<211> LENGTH: 124
<212> TYPE: PRT
<213> ORGANISM: Homo sapiens

<400> SEQUENCE: 221

Gln Val His Leu Gln Gln Trp Gly Ala Gly Leu Val Lys Pro Ser Glu
1 5 10 15

Thr Leu Ser Leu Thr Cys Ala Val Gln Gly Gly Pro Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Asn Thr His Tyr Asn Pro Ser Leu Lys
50 55 60

Ser Arg Val Thr Ile Ser Val Asp Thr Ser Gly Asn Tyr Phe Ser Leu
65 70 75 80

Lys Leu Thr Ser Val Thr Ala Ala Asp Ala Ala Val Tyr Phe Cys Ala
85 90 95

Arg Gly Gln Gln Leu Leu Arg Asn Tyr Tyr Tyr Tyr Ser Gly Met Asp
100 105 110

Val Trp Gly Gln Gly Thr Thr Val Thr Val Ser Ser
115 120

<210> SEQ ID NO 222
<211> LENGTH: 372
<212> TYPE: DNA
<213> ORGANISM: Homo sapiens

<400> SEQUENCE: 222
caggtgcacc tgcagcagtg gggagcaggc ctggtgaagc catccgagac actgtctctg 60
acatgtgcag tgcagggagg acccttctct ggctactatt ggagctggat caggcagcca 120
cctggcaagg gcctggagtg gatcggcgag atcaaccaca gcggcaatac ccactacaac 180
ccctctctga agagccgggt gaccatcagc gtggacacat ccggcaatta cttctccctg 240
aagctgacct ctgtgacagc cgccgatgcc gccgtgtatt tttgcgcccg gggccagcag 300
ctgctgagaa actactatta ctattccggc atggacgtgt ggggacaggg aaccacagtg 360
acagtgagct cc 372

<210> SEQ ID NO 223
<211> LENGTH: 7
<212> TYPE: PRT
<213> ORGANISM: Homo sapiens

<400> SEQUENCE: 223

Gly Gly Pro Phe Ser Gly Tyr
1 5

<210> SEQ ID NO 224
<211> LENGTH: 5
<212> TYPE: PRT
<213> ORGANISM: Homo sapiens

<400> SEQUENCE: 224

Asn His Ser Gly Asn
1 5

<210> SEQ ID NO 225
<211> LENGTH: 16
<212> TYPE: PRT
<213> ORGANISM: Homo sapiens

<400> SEQUENCE: 225

Gly Gln Gln Leu Leu Arg Asn Tyr Tyr Tyr Tyr Ser Gly Met Asp Val
1 5 10 15

<210> SEQ ID NO 226
<211> LENGTH: 107
<212> TYPE: PRT
<213> ORGANISM: Homo sapiens

<400> SEQUENCE: 226

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Thr
20 25 30

Tyr Leu Ala Trp Tyr Gln Gln Lys Leu Gly Gln Pro Pro Arg Leu Leu
35 40 45

Ile Phe Gly Ala Ser Asn Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Arg Tyr Gly Gly Ser Ile
                85                  90                  95

Thr Phe Gly Gln Gly Thr Arg Leu Glu Ile Lys
            100                 105

<210> SEQ ID NO 227
<211> LENGTH: 321
<212> TYPE: DNA
<213> ORGANISM: Homo sapiens

<400> SEQUENCE: 227
gagatcgtgc tgacacagtc cccaggcacc ctgagcctgt ccccaggaga gcgggccaca 60
ctgtcctgta gagcctctca gagcgtgacc tctacatacc tggcctggta tcagcagaag 120
ctgggccagc cccctaggct gctgatcttc ggcgcctcta acagggccac aggcatccct 180
gaccgcttct ccggctctgg cagcggcacc gacttcaccc tgacaatcac cagactggag 240
cccgaggact tcgccgtgta ctattgccag cggtacggcg gcagcatcac atttggccag 300
ggcaccagac tggagatcaa g 321

<210> SEQ ID NO 228
<211> LENGTH: 12
<212> TYPE: PRT
<213> ORGANISM: Homo sapiens

<400> SEQUENCE: 228

Arg Ala Ser Gln Ser Val Thr Ser Thr Tyr Leu Ala
1               5                   10

<210> SEQ ID NO 229
<211> LENGTH: 7
<212> TYPE: PRT
<213> ORGANISM: Homo sapiens

<400> SEQUENCE: 229

Gly Ala Ser Asn Arg Ala Thr
1               5

<210> SEQ ID NO 230
<211> LENGTH: 8
<212> TYPE: PRT
<213> ORGANISM: Homo sapiens

<400> SEQUENCE: 230

Gln Arg Tyr Gly Gly Ser Ile Thr
1               5

<210> SEQ ID NO 231
<211> LENGTH: 126
<212> TYPE: PRT
<213> ORGANISM: Homo sapiens

<400> SEQUENCE: 231

Glu Val Gln Leu Val Gln Ser Gly Gly Gly Val Val Gln Pro Arg Arg
1               5                   10                  15

Ser Leu Arg Leu Ser Cys Ala Ala Ser Gly Phe Thr Phe Ser Asn Tyr
            20                  25                  30

```
Gly Met His Trp Val Arg Gln Val Pro Gly Lys Gly Leu Gln Trp Val
        35                  40                  45

Ala Ile Ile Trp Tyr Asp Gly Ser Asn Lys His Tyr Ala Ala Ser Val
    50                  55                  60

Gln Gly Arg Phe Arg Ile Ser Arg Asp Asn Ser Lys Asn Thr Val Tyr
65                  70                  75                  80

Leu Gln Met Asp Gly Leu Arg Ala Glu Asp Thr Gly Met Tyr Tyr Cys
                85                  90                  95

Val Arg Asp Ala Thr Thr Ala Thr Thr Glu Gly Thr Ser Gln Tyr Tyr
            100                 105                 110

Phe Asp Leu Trp Gly Gln Gly Ala Leu Val Thr Val Ser Ser
        115                 120                 125


<210> SEQ ID NO 232
<211> LENGTH: 378
<212> TYPE: DNA
<213> ORGANISM: Homo sapiens

<400> SEQUENCE: 232

gaggtgcagc tggtgcagtc cggcggagga gtggtgcagc cacggagatc tctgaggctg      60

agctgtgccg cctccggctt caccttttct aactacggaa tgcactgggt gcgccaggtg     120

cctggcaagg gcctgcagtg ggtggccatc atctggtacg acggctccaa taagcactat     180

gccgcctctg tgcagggcag gttccgcatc tctcgggata acagcaagaa taccgtgtat     240

ctgcagatgg acggcctgcg ggccgaggat acaggcatgt actattgcgt gagagacgcc     300

accacagcca ccacagaggg caccagccag tactattttg atctgtgggg acagggcgcc     360

ctggtgacag tgagctcc                                                   378


<210> SEQ ID NO 233
<211> LENGTH: 7
<212> TYPE: PRT
<213> ORGANISM: Homo sapiens

<400> SEQUENCE: 233

Gly Phe Thr Phe Ser Asn Tyr
1               5


<210> SEQ ID NO 234
<211> LENGTH: 6
<212> TYPE: PRT
<213> ORGANISM: Homo sapiens

<400> SEQUENCE: 234

Trp Tyr Asp Gly Ser Asn
1               5


<210> SEQ ID NO 235
<211> LENGTH: 17
<212> TYPE: PRT
<213> ORGANISM: Homo sapiens

<400> SEQUENCE: 235

Asp Ala Thr Thr Ala Thr Thr Glu Gly Thr Ser Gln Tyr Tyr Phe Asp
1               5                   10                  15

Leu


<210> SEQ ID NO 236
<211> LENGTH: 113
```

<212> TYPE: PRT
<213> ORGANISM: Homo sapiens

<400> SEQUENCE: 236

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Leu Tyr Thr
            20                  25                  30

Ser Asn Ser Lys Asn Tyr Leu Ala Trp Tyr Gln Gln Lys Val Gly Gln
        35                  40                  45

Pro Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Leu Ala Glu Asp Val Ala Val Tyr Tyr Cys Gln Gln
                85                  90                  95

Tyr Tyr Thr Thr Pro Leu Thr Phe Gly Gly Gly Thr Lys Val Glu Val
            100                 105                 110

Lys

<210> SEQ ID NO 237
<211> LENGTH: 339
<212> TYPE: DNA
<213> ORGANISM: Homo sapiens

<400> SEQUENCE: 237
gacatcgtga tgacccagag ccccgattcc ctggccgtgt ctctgggaga gagggcaaca     60
atcaactgta agagctccca gaccctgctg tacacatcca actctaagaa ttacctggcc    120
tggtatcagc agaaagtggg acagccacct aggctgctga tctattgggc ctctaccagg    180
gagagcggcg tgccagacag attcagcggc tccggctctg gcacagactt caccctgaca    240
atctctagcc tgctggccga ggacgtggcc gtgtactatt gccagcagta ctataccaca    300
cccctgacct tcggcggcgg cacaaaggtg gaggtgaag                           339

<210> SEQ ID NO 238
<211> LENGTH: 17
<212> TYPE: PRT
<213> ORGANISM: Homo sapiens

<400> SEQUENCE: 238

Lys Ser Ser Gln Thr Leu Leu Tyr Thr Ser Asn Ser Lys Asn Tyr Leu
1               5                   10                  15

Ala

<210> SEQ ID NO 239
<211> LENGTH: 7
<212> TYPE: PRT
<213> ORGANISM: Homo sapiens

<400> SEQUENCE: 239

Trp Ala Ser Thr Arg Glu Ser
1               5

<210> SEQ ID NO 240
<211> LENGTH: 9
<212> TYPE: PRT
<213> ORGANISM: Homo sapiens

<400> SEQUENCE: 240

Gln Gln Tyr Tyr Thr Thr Pro Leu Thr
1               5

<210> SEQ ID NO 241
<211> LENGTH: 130
<212> TYPE: PRT
<213> ORGANISM: Homo sapiens

<400> SEQUENCE: 241

Glu Val Gln Leu Val Glu Ser Gly Gly Gly Val Val His Pro Gly Lys
1               5                   10                  15

Ser Leu Thr Leu Ser Cys Glu Ala Ser Gly Phe Thr Phe Asn Asp His
            20                  25                  30

Gly Ile His Trp Val Arg Arg Ala Pro Gly Lys Gly Leu Glu Trp Leu
        35                  40                  45

Ala Leu Ile Ser Lys Asp Gly Ser Lys Glu Tyr Ser Thr Asp Ser Val
    50                  55                  60

Lys Gly Arg Phe Thr Val Ser Arg Asp Asn Ser Arg Asn Thr Val Phe
65                  70                  75                  80

Leu Gln Met Lys Ser Leu Thr Thr Glu Asp Thr Ala Ile Tyr Tyr Cys
                85                  90                  95

Ala Lys Asp Met Gly Gln Cys Ser Ser Pro Ser Cys Ser Thr Met Asp
            100                 105                 110

Ser Tyr Phe Ala Met Asp Val Trp Gly Gln Gly Thr Thr Val Ile Val
        115                 120                 125

Ser Ser
    130

<210> SEQ ID NO 242
<211> LENGTH: 390
<212> TYPE: DNA
<213> ORGANISM: Homo sapiens

<400> SEQUENCE: 242
gaggtgcagc tggtggagtc cggcggagga gtggtgcacc ctggcaagtc tctgaccctg 60
agctgtgagg ccagcggctt caccttcaac gaccacggca tccactgggt gcggagagca 120
cctggcaagg gcctggagtg gctggccctg atctctaagg acggcagcaa ggagtacagc 180
accgattccg tgaagggccg gttcacagtg tccagggata actctcgcaa taccgtgttt 240
ctgcagatga agtctctgac cacagaggac acagccatct actattgcgc caaggatatg 300
ggccagtgca gctccccctc ctgttctacc atggacagct atttcgcaat ggacgtgtgg 360
ggacagggaa ccacagtgat cgtgtctagc 390

<210> SEQ ID NO 243
<211> LENGTH: 7
<212> TYPE: PRT
<213> ORGANISM: Homo sapiens

<400> SEQUENCE: 243

Gly Phe Thr Phe Asn Asp His
1               5

<210> SEQ ID NO 244
<211> LENGTH: 6
<212> TYPE: PRT
<213> ORGANISM: Homo sapiens

<400> SEQUENCE: 244

Ser Lys Asp Gly Ser Lys
1 5

<210> SEQ ID NO 245
<211> LENGTH: 21
<212> TYPE: PRT
<213> ORGANISM: Homo sapiens

<400> SEQUENCE: 245

Asp Met Gly Gln Cys Ser Ser Pro Ser Cys Ser Thr Met Asp Ser Tyr
1 5 10 15

Phe Ala Met Asp Val
20

<210> SEQ ID NO 246
<211> LENGTH: 113
<212> TYPE: PRT
<213> ORGANISM: Homo sapiens

<400> SEQUENCE: 246

Asp Ile Val Met Thr Gln Ser Pro Leu Ser Leu Pro Val Thr Pro Gly
1 5 10 15

Glu Pro Ala Ser Ile Ser Cys Arg Ser Ser Gln Asn Leu Arg His Asn
20 25 30

Asn Gly Tyr Asn Tyr Leu Asn Trp Tyr Leu Gln Lys Pro Gly Gln Ser
35 40 45

Pro Gln Leu Leu Ile Tyr Leu Gly Ser Ile Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Pro Trp Thr Phe Gly Gln Gly Thr Lys Val Asp Phe
100 105 110

Lys

<210> SEQ ID NO 247
<211> LENGTH: 339
<212> TYPE: DNA
<213> ORGANISM: Homo sapiens

<400> SEQUENCE: 247
gacatcgtga tgacccagtc ccctctgtct ctgccagtga cacccggcga gcctgcctct 60
atcagctgtc ggagctccca gaacctgaga cacaacaatg gctacaacta tctgaattgg 120
tacctgcaga agccaggcca gtctccccag ctgctgatct atctgggcag catcagggcc 180
tccggcgtgc ccgaccgctt ctccggctct ggcagcggca ccgacttcac cctgaagatc 240
agccgggtgg aggcagagga cgtgggcgtg tactattgca tgcaggccct gcagaccccc 300
ccttggacat tcggccaggg caccaaggtg gacttcaag 339

<210> SEQ ID NO 248
<211> LENGTH: 16
<212> TYPE: PRT
<213> ORGANISM: Homo sapiens

<400> SEQUENCE: 248

Arg Ser Ser Gln Asn Leu Arg His Asn Asn Gly Tyr Asn Tyr Leu Asn
1               5                   10                  15

<210> SEQ ID NO 249
<211> LENGTH: 7
<212> TYPE: PRT
<213> ORGANISM: Homo sapiens

<400> SEQUENCE: 249

Leu Gly Ser Ile Arg Ala Ser
1               5

<210> SEQ ID NO 250
<211> LENGTH: 10
<212> TYPE: PRT
<213> ORGANISM: Homo sapiens

<400> SEQUENCE: 250

Met Gln Ala Leu Gln Thr Pro Pro Trp Thr
1               5                   10

<210> SEQ ID NO 251
<211> LENGTH: 118
<212> TYPE: PRT
<213> ORGANISM: Homo sapiens

<400> SEQUENCE: 251

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Ile Ile Ser Pro Thr Gly Asp Phe Thr Asn Tyr Ala Gln Lys Phe
    50                  55                  60

Gln Gly Arg Val Thr Leu Thr Arg Asp Thr Ser Thr Ser Thr Asp Tyr
65                  70                  75                  80

Met Glu Val Thr Ser Leu Arg Ser Glu Asp Thr Ala Val Tyr Tyr Cys
                85                  90                  95

Ala Arg Asp Cys Ser Ala Trp Ala Pro Asp Tyr Trp Gly Gln Gly Thr
            100                 105                 110

Leu Val Thr Val Ser Ser
        115

<210> SEQ ID NO 252
<211> LENGTH: 354
<212> TYPE: DNA
<213> ORGANISM: Homo sapiens

<400> SEQUENCE: 252
caggtgcagc tggtgcagtc cggcgcagag gtgaagaagc caggagccag cgtgaaggtg     60
tcctgtaagg cctctggcta caccttcaca tctcactata tgcactgggt gcggcaggca    120
ccaggacagg gcctggagtg gatgggcatc atcagcccta caggcgactt caccaactac    180
gcccagaagt ttcagggccg ggtgaccctg acaagagaca cctctacaag caccgattat    240
atggaggtga catccctgag gtctgaggat accgccgtgt actattgcgc aagggactgt    300
tccgcctggg cccccgatta ctggggacag ggcacactgg tgaccgtgag ctcc          354

<210> SEQ ID NO 253
<211> LENGTH: 7
<212> TYPE: PRT
<213> ORGANISM: Homo sapiens

<400> SEQUENCE: 253

Gly Tyr Thr Phe Thr Ser His
1               5

<210> SEQ ID NO 254
<211> LENGTH: 6
<212> TYPE: PRT
<213> ORGANISM: Homo sapiens

<400> SEQUENCE: 254

Ser Pro Thr Gly Asp Phe
1               5

<210> SEQ ID NO 255
<211> LENGTH: 9
<212> TYPE: PRT
<213> ORGANISM: Homo sapiens

<400> SEQUENCE: 255

Asp Cys Ser Ala Trp Ala Pro Asp Tyr
1               5

<210> SEQ ID NO 256
<211> LENGTH: 108
<212> TYPE: PRT
<213> ORGANISM: Homo sapiens

<400> SEQUENCE: 256

Gln Ser Ala Leu Thr Arg Pro Pro Ser Val Ser Arg Cys Pro Gly Gln
1               5                   10                  15

Ser Ile Thr Ile Ser Cys Ser Gly Thr Ser Ser Asp Val Gly His Asp
            20                  25                  30

Asn His Val Ser Trp Tyr Gln Gln His Pro Gly Arg Ala Pro Lys Leu
        35                  40                  45

Met Val Tyr Glu Val Arg Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Thr Tyr Tyr Cys Cys Ser Tyr Thr Thr Thr
                85                  90                  95

His Arg Tyr Ile Phe Gly Gly Gly Thr Lys Leu Thr
            100                 105

<210> SEQ ID NO 257
<211> LENGTH: 324
<212> TYPE: DNA
<213> ORGANISM: Homo sapiens

<400> SEQUENCE: 257
cagtctgccc tgacaaggcc cccttctgtg agccgctgcc ctggacagag catcacaatc      60
tcctgttctg gcaccagctc cgacgtgggc cacgataacc acgtgtcctg gtaccagcag     120
cacccaggaa gggcacccaa gctgatggtg tatgaggtgc ggaacagacc aagcggcgtg     180
tccgacaggt tcagcggctc caagtctggc aatacagcct ctctgaccat cagcggcctg     240
caggcagagg atgaggcaac ctactattgc tgttcttaca ccacaaccca ccggtatatc 300
tttggcggcg gcacaaagct gacc 324

<210> SEQ ID NO 258
<211> LENGTH: 14
<212> TYPE: PRT
<213> ORGANISM: Homo sapiens

<400> SEQUENCE: 258

Ser Gly Thr Ser Ser Asp Val Gly His Asp Asn His Val Ser
1 5 10

<210> SEQ ID NO 259
<211> LENGTH: 7
<212> TYPE: PRT
<213> ORGANISM: Homo sapiens

<400> SEQUENCE: 259

Glu Val Arg Asn Arg Pro Ser
1 5

<210> SEQ ID NO 260
<211> LENGTH: 10
<212> TYPE: PRT
<213> ORGANISM: Homo sapiens

<400> SEQUENCE: 260

Cys Ser Tyr Thr Thr Thr His Arg Tyr Ile
1 5 10

<210> SEQ ID NO 261
<211> LENGTH: 123
<212> TYPE: PRT
<213> ORGANISM: Homo sapiens

<400> SEQUENCE: 261

Gln Val Gln Leu Leu Gly Ser Gly Pro Gly Leu Val Lys Pro Ser Glu
1 5 10 15

Thr Leu Ser Leu Thr Cys Thr Val Ser Gly Ala Ser Ile Ser Ser Pro
20 25 30

Gly Tyr Tyr Trp Gly Phe Ile Arg Gln Ser Pro Gly Lys Gly Leu Glu
35 40 45

Trp Ile Gly Ser Met Val Ser Gly Gly Thr Thr Tyr Tyr Asn Pro Ser
50 55 60

Leu Lys Ser Arg Val Thr Ile Ser Met Asp Met Ser Asn Asn Gln Phe
65 70 75 80

Ser Leu Arg Leu Asn Ser Val Thr Ala Ala Asp Thr Ala Leu Tyr Tyr
85 90 95

Cys Ala Arg Gly Ser Arg Gln Leu Val Arg Arg Ala Thr Ile Asp Tyr
100 105 110

Trp Gly Gln Gly Ala Leu Phe Thr Val Ser Pro
115 120

<210> SEQ ID NO 262
<211> LENGTH: 369
<212> TYPE: DNA
<213> ORGANISM: Homo sapiens

<400> SEQUENCE: 262
caggtgcagc tgctgggcag cggcccaggc ctggtgaagc cttctgagac actgagcctg 60
acctgtacag tgtctggcgc cagcatcagc tccccaggct actattgggg cttcatcagg 120
cagagcccag gcaagggcct ggagtggatc ggctccatgg tgtctggcgg caccacatac 180
tataacccta gcctgaagtc ccgggtgaca atctccatgg acatgtctaa caatcagttc 240
agcctgaggc tgaattccgt gaccgccgcc gatacagccc tgtactattg cgcaaggggc 300
tcccgccagc tggtgcggag agcaaccatc gactactggg gacagggcgc cctgtttaca 360
gtgtctccc 369

<210> SEQ ID NO 263
<211> LENGTH: 9
<212> TYPE: PRT
<213> ORGANISM: Homo sapiens

<400> SEQUENCE: 263

Gly Ala Ser Ile Ser Ser Pro Gly Tyr
1 5

<210> SEQ ID NO 264
<211> LENGTH: 5
<212> TYPE: PRT
<213> ORGANISM: Homo sapiens

<400> SEQUENCE: 264

Val Ser Gly Gly Thr
1 5

<210> SEQ ID NO 265
<211> LENGTH: 13
<212> TYPE: PRT
<213> ORGANISM: Homo sapiens

<400> SEQUENCE: 265

Gly Ser Arg Gln Leu Val Arg Arg Ala Thr Ile Asp Tyr
1 5 10

<210> SEQ ID NO 266
<211> LENGTH: 108
<212> TYPE: PRT
<213> ORGANISM: Homo sapiens

<400> SEQUENCE: 266

Gln Ser Val Leu Thr Gly Pro Pro Ser Val Ser Ala Gly Pro Gly Gln
1 5 10 15

Gln Val Phe Ile Ser Cys Ser Gly Asn Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Ser Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Ser Ser Leu
85 90 95

Ser Ala Gly Val Phe Gly Gly Gly Thr Lys Leu Thr
100 105

<210> SEQ ID NO 267
<211> LENGTH: 324
<212> TYPE: DNA
<213> ORGANISM: Homo sapiens

<400> SEQUENCE: 267
cagtctgtgc tgaccggacc accttccgtg tctgccggac caggacagca ggtgttcatc 60
agctgttccg gcaacagctc caatatcggc aacaattacg tgtcttggta tcagcagctg 120
ccaggcacag cccccaagct gctgatctac gactctaaca agcggcctag cggcatccca 180
gatagattct ctggcagcaa gtccggcacc agcgccacac tgggcatcac cggcctgcag 240
acaggcgacg aggcagatta ctattgcgga acctgggact ctagcctgtc cgccggcgtg 300
tttggaggag gaaccaagct gaca 324

<210> SEQ ID NO 268
<211> LENGTH: 13
<212> TYPE: PRT
<213> ORGANISM: Homo sapiens

<400> SEQUENCE: 268

Ser Gly Asn Ser Ser Asn Ile Gly Asn Asn Tyr Val Ser
1 5 10

<210> SEQ ID NO 269
<211> LENGTH: 7
<212> TYPE: PRT
<213> ORGANISM: Homo sapiens

<400> SEQUENCE: 269

Asp Ser Asn Lys Arg Pro Ser
1 5

<210> SEQ ID NO 270
<211> LENGTH: 11
<212> TYPE: PRT
<213> ORGANISM: Homo sapiens

<400> SEQUENCE: 270

Gly Thr Trp Asp Ser Ser Leu Ser Ala Gly Val
1 5 10

<210> SEQ ID NO 271
<211> LENGTH: 124
<212> TYPE: PRT
<213> ORGANISM: Homo sapiens

<400> SEQUENCE: 271

Glu Val Gln Leu Val Glu Ser Gly Gly Gly Leu Val Lys Pro Gly Glu
1 5 10 15

Ser Leu Arg Leu Ser Cys Ala Ala Ser Gly Phe Thr Phe Ser Ser Tyr
20 25 30

Ser Met Ser Trp Val Arg Gln Ala Pro Gly Lys Gly Leu Glu Trp Val
35 40 45

Ser Cys Ile Thr Ser Ser Gly His Thr Tyr Tyr Ala Asp Ser Val Lys
50 55 60

Gly Arg Phe Ala Ile Ser Arg Asp Asn Gly Lys Asn Ser Leu Tyr Leu
65 70 75 80

Gln Met Asn Asn Leu Arg Ala Glu Asp Thr Ala Val Tyr Phe Cys Ala
85 90 95

Lys Glu Leu Gly Ala His Ser Gly Leu Phe Tyr Asn Gly Val Phe Asp
100 105 110

Tyr Trp Gly Gln Gly Asn Pro Val Thr Val Ser Ser
115 120

<210> SEQ ID NO 272
<211> LENGTH: 372
<212> TYPE: DNA
<213> ORGANISM: Homo sapiens

<400> SEQUENCE: 272
gaggtgcagc tggtggagtc cggcggaggc ctggtgaagc caggcgagtc tctgaggctg 60
agctgtgccg cctccggctt cacctttagc tcctacagca tgtcctgggt gcgccaggca 120
cctggcaagg gcctggagtg ggtgtcctgc atcacctcta gcggccacac atactatgcc 180
gactctgtga agggccggtt cgccatcagc cgggataacg gcaagaatag cctgtacctg 240
cagatgaaca atctgcgggc cgaggacacc gccgtgtatt tttgtgcaaa ggagctggga 300
gcacactctg gcctgttcta caacggcgtg tttgattatt ggggccaggg caatcccgtg 360
acagtgtcct ct 372

<210> SEQ ID NO 273
<211> LENGTH: 7
<212> TYPE: PRT
<213> ORGANISM: Homo sapiens

<400> SEQUENCE: 273

Gly Phe Thr Phe Ser Ser Tyr
1 5

<210> SEQ ID NO 274
<211> LENGTH: 5
<212> TYPE: PRT
<213> ORGANISM: Homo sapiens

<400> SEQUENCE: 274

Thr Ser Ser Gly His
1 5

<210> SEQ ID NO 275
<211> LENGTH: 16
<212> TYPE: PRT
<213> ORGANISM: Homo sapiens

<400> SEQUENCE: 275

Glu Leu Gly Ala His Ser Gly Leu Phe Tyr Asn Gly Val Phe Asp Tyr
1 5 10 15

<210> SEQ ID NO 276
<211> LENGTH: 108
<212> TYPE: PRT
<213> ORGANISM: Homo sapiens

<400> SEQUENCE: 276

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

```
Met Ile Tyr Glu Val Ser Asn Arg Pro Ser Gly Val Ser Asn Arg Phe
    50                  55                  60

Ser Gly Ser Lys Gly Asn Thr Ala Ser Leu Thr Ile Ser Gly Leu Arg
65                  70                  75                  80

Gly Glu Asp Glu Ala Asp Tyr Tyr Cys Ser Ser Tyr Thr Ser Ser Ser
                85                  90                  95

Thr Leu Val Val Phe Gly Gly Gly Thr Lys Leu Thr
            100                 105


<210> SEQ ID NO 277
<211> LENGTH: 324
<212> TYPE: DNA
<213> ORGANISM: Homo sapiens

<400> SEQUENCE: 277

cagtccgccc tgacccagcc agcctccgtg tctggcagcc ccggccagtc tatcacaatc      60

agctgtaccg gcacaagctc cgacgtgggc ggctacaact acgtgagctg gtaccagcag     120

cacccaggca aggcacctaa gctgatgatc tatgaggtgt ccaacaggcc aagcggcgtg     180

tccaatagat tctccggctc taagggcaat accgcctccc tgacaatctc tggcctgagg     240

ggagaggacg aggcagatta ctattgctct agctacacct cctctagcac actggtggtg     300

tttggcggcg gcaccaagct gaca                                            324


<210> SEQ ID NO 278
<211> LENGTH: 14
<212> TYPE: PRT
<213> ORGANISM: Homo sapiens

<400> SEQUENCE: 278

Thr Gly Thr Ser Ser Asp Val Gly Gly Tyr Asn Tyr Val Ser
1               5                   10


<210> SEQ ID NO 279
<211> LENGTH: 7
<212> TYPE: PRT
<213> ORGANISM: Homo sapiens

<400> SEQUENCE: 279

Glu Val Ser Asn Arg Pro Ser
1               5


<210> SEQ ID NO 280
<211> LENGTH: 11
<212> TYPE: PRT
<213> ORGANISM: Homo sapiens

<400> SEQUENCE: 280

Ser Ser Tyr Thr Ser Ser Ser Thr Leu Val Val
1               5                   10


<210> SEQ ID NO 281
<211> LENGTH: 124
<212> TYPE: PRT
<213> ORGANISM: Homo sapiens

<400> SEQUENCE: 281

Gln Val His Leu Gln Gln Trp Gly Ala Gly Leu Val Lys Pro Ser Glu
1               5                   10                  15

Thr Leu Ser Leu Thr Cys Ala Val Gln Gly Gly Pro Phe Ser Gly Tyr
            20                  25                  30
```

```
Tyr Trp Ser Trp Ile Arg Gln Pro Pro Gly Lys Gly Leu Glu Trp Ile
        35                  40                  45

Gly Glu Ile Asn His Ser Gly Asn Thr His Tyr Asn Pro Ser Leu Lys
    50                  55                  60

Ser Arg Val Thr Ile Ser Val Asp Thr Ser Gly Asn Tyr Phe Ser Leu
65                  70                  75                  80

Lys Leu Thr Ser Val Thr Ala Ala Asp Ala Ala Val Tyr Phe Cys Ala
                85                  90                  95

Arg Gly Gln Gln Leu Leu Arg Asn Tyr Tyr Tyr Tyr Ser Gly Met Asp
            100                 105                 110

Val Trp Gly Gln Gly Thr Thr Val Thr Val Ser Ser
        115                 120
```

<210> SEQ ID NO 282
<211> LENGTH: 372
<212> TYPE: DNA
<213> ORGANISM: Homo sapiens

<400> SEQUENCE: 282

```
caggtgcacc tgcagcagtg gggagcaggc ctggtgaagc catccgagac actgtctctg      60

acatgtgcag tgcagggagg acccttctct ggctactatt ggagctggat caggcagcca     120

cctggcaagg gcctggagtg gatcggcgag atcaaccaca gcggcaatac ccactacaac     180

ccctctctga agagccgggt gaccatcagc gtggacacat ccggcaatta cttctccctg     240

aagctgacct ctgtgacagc cgccgatgcc gccgtgtatt tttgcgcccg gggccagcag     300

ctgctgagaa actactatta ctattccggc atggacgtgt ggggacaggg aaccacagtg     360

acagtgagct cc                                                         372
```

<210> SEQ ID NO 283
<211> LENGTH: 7
<212> TYPE: PRT
<213> ORGANISM: Homo sapiens

<400> SEQUENCE: 283

```
Gly Gly Pro Phe Ser Gly Tyr
1               5
```

<210> SEQ ID NO 284
<211> LENGTH: 5
<212> TYPE: PRT
<213> ORGANISM: Homo sapiens

<400> SEQUENCE: 284

```
Asn His Ser Gly Asn
1               5
```

<210> SEQ ID NO 285
<211> LENGTH: 16
<212> TYPE: PRT
<213> ORGANISM: Homo sapiens

<400> SEQUENCE: 285

```
Gly Gln Gln Leu Leu Arg Asn Tyr Tyr Tyr Tyr Ser Gly Met Asp Val
1               5                   10                  15
```

<210> SEQ ID NO 286
<211> LENGTH: 108
<212> TYPE: PRT
<213> ORGANISM: Homo sapiens

<400> SEQUENCE: 286

Gln Ser Ala Leu Thr Gln Pro Ala Ser Val Ser Gly Ser Pro Gly Gln
1 5 10 15

Ser Ile Thr Ile Ser Cys Thr Glu Thr Ser Arg Asp Val Gly Asp Tyr
20 25 30

Asn Tyr Val Ser Trp Tyr Gln Gln His Pro Gly Pro Ala Pro Lys Leu
35 40 45

Ile Met Tyr Glu Val His Lys Arg Pro Ser Gly Ile Ser Asn Arg Phe
50 55 60

Ser Gly Ser Lys Ser Gly Thr Thr Ala Ser Leu Thr Ile Ser Gly Leu
65 70 75 80

Gln Ala Asp Asp Glu Gly Asp Tyr Tyr Cys Ser Ser Tyr Thr Asp Lys
85 90 95

Asn Thr Tyr Val Phe Gly Ser Gly Thr Gln Val Thr
100 105

<210> SEQ ID NO 287
<211> LENGTH: 324
<212> TYPE: DNA
<213> ORGANISM: Homo sapiens

<400> SEQUENCE: 287
cagtctgccc tgacccagcc agcctctgtg agcggctccc ctggccagtc catcacaatc 60
tcttgtaccg agacatctcg ggacgtgggc gattacaact atgtgagctg gtaccagcag 120
cacccaggac ctgcaccaaa gctgatcatg tatgaggtgc acaagcggcc ctctggcatc 180
agcaatagat tctctggcag caagtccggc accacagcca gcctgaccat ctccggcctg 240
caggcagacg atgagggcga ctactattgc agctcctaca ccgataagaa cacatacgtg 300
ttcggcagcg gcacccaggt gaca 324

<210> SEQ ID NO 288
<211> LENGTH: 14
<212> TYPE: PRT
<213> ORGANISM: Homo sapiens

<400> SEQUENCE: 288

Thr Glu Thr Ser Arg Asp Val Gly Asp Tyr Asn Tyr Val Ser
1 5 10

<210> SEQ ID NO 289
<211> LENGTH: 7
<212> TYPE: PRT
<213> ORGANISM: Homo sapiens

<400> SEQUENCE: 289

Glu Val His Lys Arg Pro Ser
1 5

<210> SEQ ID NO 290
<211> LENGTH: 10
<212> TYPE: PRT
<213> ORGANISM: Homo sapiens

<400> SEQUENCE: 290

Ser Ser Tyr Thr Asp Lys Asn Thr Tyr Val
1 5 10

<210> SEQ ID NO 291

<211> LENGTH: 447
<212> TYPE: PRT
<213> ORGANISM: Homo sapiens

<400> SEQUENCE: 291

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Asp
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Arg Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380
```

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His
405 410 415

Lys Val Ile Phe Ser Lys Ala Pro Gly Ser Gly Leu Asn Asp Ile Phe
420 425 430

Glu Ala Gln Lys Ile Glu Trp His Glu His His His His His His
435 440 445

<210> SEQ ID NO 292
<211> LENGTH: 1341
<212> TYPE: DNA
<213> ORGANISM: Homo sapiens

<400> SEQUENCE: 292
gaagctgccc tgctcgtgtg ccagtacacc atccagagcc tgatccacct gaccggcgag 60
gaccccggct tcttcaacgt ggaaatcccc gagttcccct tctaccctac ctgcaacgtg 120
tgcaccgccg acgtgaacgt gaccatcaac ttcgacgtgg gcggcaagaa gcaccagctg 180
gacctggatt tcggccagct gacccctcac accaaggccg tgtatcagcc cagaggcgcc 240
tttggcggca gcgagaacgc caccaatctg tttctgctgg aactcctagg cgccggcgag 300
ctggccctga ccatgagaag caagaaactg cccatcaatg tgaccacagg cgaggaacag 360
caggtgtccc tggaaagcgt ggacgtgtac tttcaagacg tgttcggcac catgtggtgc 420
caccacgccg agatgcagaa ccccgtgtac ctgatccccg agacagtgcc ctacatcgat 480
tgggacaact gcaacagcac caacatcacc gccgtcgtgc gggcccaggg actggatgtg 540
acactgcctc tgagcctgcc taccagcgcc caggacagca acttcagcgt gaaaaccgag 600
atgctgggca acgagatcga catcgagtgc atcatggaag atggcgagat cagccaggtg 660
ctgcccggcg acaacaagtt caacatcaca tgcagcggct acgagagcca cgtgccatct 720
ggcggcatcc tgaccagcac aagcccagtg gccacaccca tccctggcac aggctacgcc 780
tacagcctga gactgacccc cagacccgtg tccagattcc tgggcaacaa cagcatcctg 840
tacgtgttct acagcggcaa cggccccaag gcctctggcg gccggtactg tatccagagc 900
aacatcgtgt tcagcgacga gatccccgcc agccaggaca tgcccaccaa taccaccgac 960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc accccctagcg gctgcgagaa tatcagcgga 1140
gccttcgcca gcaaccggac cttcgatatc accgtgtctg gcctgggcac cgcccccaag 1200
accctgatca tcaccagaac cgccacaaat gccaccacca caacccacaa agtgatcttc 1260
agcaaggccc ccggctctgg cctgaacgac atttttgagg cccagaagat tgagtggcat 1320
gaacatcacc accaccacca t 1341

<210> SEQ ID NO 293
<211> LENGTH: 5118
<212> TYPE: DNA
<213> ORGANISM: Homo sapiens

<400> SEQUENCE: 293
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

-continued

```
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtacacgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
ccagtctgcc ctgactcagc ctccctctgt gtctgggtct cctggacagt cggtcaccat   1500
ctcctgcact ggaaccagca gtgacgttga tggttataac tatgtctcct ggtaccaaca   1560
acatccaggc aaagccccca aactcatgat ttatggtgtc agcaatcggc cctcaggggt   1620
ctctgatcgc ttctctggct ccaagtctgg caacacggcc tccctgacca tctctgggct   1680
ccaggctgag gacgaggctg attattactg ttgttcatct acaaccagtt acacttacat   1740
cttcggaact gggaccaagg tcacagtact aggtcagccc aaggctgccc cctcggtcac   1800
tctcttcccg ccctcctctg aggagcttca agccaacaag gccacactag tgtgtctgat   1860
cagtgacttc tacccgggag ccgtggaagt ggcctggaag gcagatggca gcgctgtcaa   1920
cgcgggagtg gagaccacca aaccctccaa acagagcaac aacaagtacg cggccagcag   1980
ctacctgagc ctgacgtccg accagtggaa gtcccacaag agctacagct gccaggtcac   2040
gcacgaaggg agcaccgtgg agaagacagt ggcccctgca gaatgttcat agggatccag   2100
atctgctgtg ccttctagtt gccagccatc tgttgtttgc ccctcccccg tgccttcctt   2160
gaccctggaa ggtgccactc ccactgtcct ttcctaataa aatgaggaaa ttgcatcgca   2220
ttgtctgagt aggtgtcatt ctattctggg gggtggggtg gggcaggaca gcaaggggga   2280
ggattgggaa gacaatagca ggcatgctgg ggatgcggtg ggctctatgg gtacccaggt   2340
gctgaagaat tgacccggtt cctcctgggc cagaaagaag caggcacatc cccttctctg   2400
tgacacaccc tgtccacgcc cctggttctt agttccagcc ccactcatag gacactcata   2460
gctcaggagg gctccgcctt caatcccacc cgctaaagta catggagcgg tctctccctc   2520
```

-continued

```
cctcatcagc ccaccaaacc aaacctagcc tccaagagtg ggaagaaatt aaagcaagat   2580
aggctattaa gtgcagaggg agagaaaatg cctccaacat gtgaggaagt aatgagagaa   2640
atcatagaat tttaaggcca tgatttaagg ccatcatggc cttaatcttc cgcttcctcg   2700
ctcactgact cgctgcgctc ggtcgttcgg ctgcggcgag cggtatcagc tcactcaaag   2760
gcggtaatac ggttatccac agaatcaggg gataacgcag gaaagaacat gtgagcaaaa   2820
ggccagcaaa aggccaggaa ccgtaaaaag gccgcgttgc tggcgttttt ccataggctc   2880
cgcccccctg acgagcatca caaaaatcga cgctcaagtc agaggtggcg aaacccgaca   2940
ggactataaa gataccaggc gtttccccct ggaagctccc tcgtgcgctc tcctgttccg   3000
accctgccgc ttaccggata cctgtccgcc tttctccctt cgggaagcgt ggcgctttct   3060
catagctcac gctgtaggta tctcagttcg gtgtaggtcg ttcgctccaa gctgggctgt   3120
gtgcacgaac cccccgttca gcccgaccgc tgcgccttat ccggtaacta tcgtcttgag   3180
tccaacccgg taagacacga cttatcgcca ctggcagcag ccactggtaa caggattagc   3240
agagcgaggt atgtaggcgg tgctacagag ttcttgaagt ggtggcctaa ctacggctac   3300
actagaagaa cagtatttgg tatctgcgct ctgctgaagc cagttacctt cggaaaaaga   3360
gttggtagct cttgatccgg caaacaaacc accgctggta gcggtggttt ttttgtttgc   3420
aagcagcaga ttacgcgcag aaaaaaagga tctcaagaag atcctttgat cttttctacg   3480
gggtctgacg ctcagtggaa cgaaaactca cgttaaggga ttttggtcat gagattatca   3540
aaaaggatct tcacctagat ccttttaaat taaaaatgaa gttttaaatc aatctaaagt   3600
atatatgagt aaacttggtc tgacagttac caatgcttaa tcagtgaggc acctatctca   3660
gcgatctgtc tatttcgttc atccatagtt gcctgactcg gggggggggg gcgctgaggt   3720
ctgcctcgtg aagaaggtgt tgctgactca taccaggcct gaatcgcccc atcatccagc   3780
cagaaagtga gggagccacg gttgatgaga gctttgttgt aggtggacca gttggtgatt   3840
ttgaactttt gctttgccac ggaacggtct gcgttgtcgg gaagatgcgt gatctgatcc   3900
ttcaactcag caaaagttcg atttattcaa caaagccgcc gtcccgtcaa gtcagcgtaa   3960
tgctctgcca gtgttacaac caattaacca attctgatta gaaaaactca tcgagcatca   4020
aatgaaactg caatttattc atatcaggat tatcaatacc atatttttga aaaagccgtt   4080
tctgtaatga aggagaaaac tcaccgaggc agttccatag gatggcaaga tcctggtatc   4140
ggtctgcgat tccgactcgt ccaacatcaa tacaacctat taatttcccc tcgtcaaaaa   4200
taaggttatc aagtgagaaa tcaccatgag tgacgactga atccggtgag aatggcaaaa   4260
gcttatgcat ttctttccag acttgttcaa caggccagcc attacgctcg tcatcaaaat   4320
cactcgcatc aaccaaaccg ttattcattc gtgattgcgc ctgagcgaga cgaaatacgc   4380
gatcgctgtt aaaaggacaa ttacaaacag gaatcgaatg caaccggcgc aggaacactg   4440
ccagcgcatc aacaatattt tcacctgaat caggatattc ttctaatacc tggaatgctg   4500
ttttcccggg gatcgcagtg gtgagtaacc atgcatcatc aggagtacgg ataaaatgct   4560
tgatggtcgg aagaggcata aattccgtca gccagtttag tctgaccatc tcatctgtaa   4620
catcattggc aacgctacct ttgccatgtt tcagaaacaa ctctggcgca tcgggcttcc   4680
catacaatcg atagattgtc gcacctgatt gcccgacatt atcgcgagcc catttatacc   4740
catataaatc agcatccatg ttggaattta atcgcggcct cgagcaagac gtttcccgtt   4800
gaatatggct cataacaccc cttgtattac tgtttatgta agcagacagt tttattgttc   4860
```

-continued

| | |
|---|---|
| atgatgatat atttttatct tgtgcaatgt aacatcagag attttgagac acaacgtggc | 4920 |
| tttccccccc cccccattat tgaagcattt atcagggtta ttgtctcatg agcggataca | 4980 |
| tatttgaatg tatttagaaa aataaacaaa taggggttcc gcgcacattt ccccgaaaag | 5040 |
| tgccacctga cgtctaagaa accattatta tcatgacatt aacctataaa aataggcgta | 5100 |
| tcacgaggcc ctttcgtc | 5118 |